United States Patent [19]
Guiremand

[11] Patent Number: 5,841,959
[45] Date of Patent: Nov. 24, 1998

[54] ROBOTIC INTERFACE

[75] Inventor: Harry A. Guiremand, Halfmoon Bay, Calif.

[73] Assignee: P.E. Applied Biosystems, Inc., Foster City, Calif.

[21] Appl. No.: 598,188

[22] Filed: Dec. 6, 1994

Related U.S. Application Data

[63] Continuation of Ser. No. 423,785, Oct. 17, 1989, abandoned.

[51] Int. Cl.$^6$ ..................................................... G06F 15/00
[52] U.S. Cl. ............................................................ 395/140
[58] Field of Search ..................................... 395/140, 348, 395/349, 350, 351

[56] References Cited

U.S. PATENT DOCUMENTS

| | | | |
|---|---|---|---|
| 4,601,003 | 7/1986 | Yonegama et al. | 395/160 |
| 4,821,211 | 4/1989 | Torres | 395/160 |
| 4,860,204 | 8/1989 | Gendron et al. | 364/300 |
| 4,893,256 | 1/1990 | Rutherfoord et al. | 364/518 |
| 4,970,664 | 11/1990 | Kaiser et al. | 364/521 |
| 5,065,347 | 11/1991 | Pajak et al. | 395/159 |
| 5,122,972 | 6/1992 | Richard et al. | 395/157 |

OTHER PUBLICATIONS

Visual Programming—Toward Realization of User–Friendly Programming Environments by Tadao Ichikawa and Masahito Hirakawa of Hiroshima University. Proceedings 1987 Fall Joint Computer Conference—Exploring Technology: Today and Tomorrow Oct. 25–29, 1987, Dallas, Texas, USA pp. 129–137.

*Primary Examiner*—Phu K. Nguyen
*Attorney, Agent, or Firm*—Donald R. Boys

[57] ABSTRACT

An automated apparatus is programmed to perform a process by arranging a sequence of first icons on a display in the order of the process, wherein the first icons represent functions of the apparatus, and wherein at least one of the first icons provides a visual representation of a function of the apparatus. Said at least one of the first icons can be expanded to show second icons that comprise the function of said at least one of the first icons, and at least one of the second icons provides a visual representation of a subfunction of the apparatus. In a preferred mode, when said at least one of the first icons is expanded, said at least one of the first icons maintains its same sequential relationship on the display to the other of the first icons in the sequence as before it was expanded.

54 Claims, 17 Drawing Sheets

Fig. 19

Group Samples:

|   | 1 | 2 | 3 | 4 | 5 | 6 | 7 | 8 | 9 | 10 | 11 | 12 |
|---|---|---|---|---|---|---|---|---|---|----|----|----|
| A | o | o | o | o | o | o | o | o | o | o  | o  | o  |
| B |   |   |   |   |   |   |   |   |   |    |    |    |
| C |   |   |   |   |   |   |   |   |   |    |    |    |
| D |   |   |   |   |   |   |   |   |   |    |    |    |
| E |   |   |   |   |   |   |   |   |   |    |    |    |
| F |   |   |   |   |   |   |   |   |   |    |    |    |
| G |   |   |   |   |   |   |   |   |   |    |    |    |
| H |   |   |   |   |   |   |   |   |   |    |    |    |

☐ Group 1    Sickle Cell
☐ Group 2    Beta Thalasemia
☐ Group 3    Low Alcohol Tolerance
☐ Group 4    Hodgkin's Disease
☐ Unused
☐ Unused ( OK )    ( Cancel )

Select Restriction Group

Sample Groups

1. Sickle Cell Anemia
2. Beta Thalasemia
3. Low Alcohol Tolerance
4. Huntington'e Disease Enzyme Hin C II
Hin D III
Hin F I
Hin P I
Hpa II
Hpa 1
Hph I
Kpn II
Mbo II Flourescent Oligo AG Orange
GC Green Ligaid AG Orange
GC Green Cut Pattern

:: AAGCTT ::
:: TTCGAA ::

Buffer

Sal 5

Adapter Molecule

None

OK
Cancel

Fig. 20

ROBOTIC INTERFACE

CROSS REFERENCE TO RELATED APPLICATIONS

This is a continuation of application Ser. No. 07/423,785 filed Oct. 17, 1989, now abandoned.

FIELD OF THE INVENTION

The present invention is in the area of user interfaces for computers, and has particular application to the programming of automated processing equipment.

BACKGROUND OF THE INVENTION

Programming computers of all sorts has become a very sophisticated art, and computerized techniques for building other programs and for accomplishing such tasks as altering program flow and changing values of variables in a program are commonplace. One area of computer application where such techniques have found considerable application is in the area of controlling automated processing equipment.

It is often true in controlling automated processes that there are several steps in a process, and that one or more of the several steps might be done in a variety of ways, or under a variety of conditions. It is also true that a particular step might be performed more than once at different times in the overall process flow. For example, consider a machine for performing chemical procedures automatically that are ordinarily performed by hand. Such a machine might have a robotic system for moving chemicals to specific stations on the machine, where specific kinds of procedures might be performed, and storage areas where containers of various chemicals, solvents, reagents, and other supplies might be stored. One station could be used for heating substances in the containers to facilitate or precipitate chemical reactions. There could be another station for stirring. Yet another station might be devoted to diluting the contents of a container by addition of a particular solvent or other chemical. There are many other procedures that could be dedicated to specific stations, or even performed in a single station.

In the performance of chemical procedures with a machine such as described above, it would be an advantage if the order of procedures could be quickly and easily altered. In one case for example, a user might wish to select a particular sample material from one position in a storage matrix of test tubes, and then move it through a sequence of process steps. He might wish to heat the sample, stir it, add an enzyme solution, stir again, heat again, add another chemical, allow time for a reaction, then replace the sample in the storage matrix at a different position from the original position, afterwards retrieving a different sample for an entirely different procedure.

A machine with the robotic ability to alter the sequence of steps as described has special requirements that are necessary for its flexibility in use. Not only must the sequence of steps be programmable, but the conditions under which each step is performed need to be programmable as well. For example, at a heating station, the researcher needs to be able to choose the temperature to which a sample is heated, and perhaps the length of time that the chosen temperature is maintained as well. At a stirring station an operator may want to control the vigor with which a mixture is stirred and the time duration for the stirring action. There are a number of variables at each station in such a machine that an operator might want to control.

The value of such a machine is determined in large part by its flexibility and the ease and accuracy with which changes in the order of procedures and the magnitude of process variables may be altered. To provide a computerized operating system for such a machine is no simple task. If a program is written in which the subroutines to perform the various steps are sequentially entered and there is no way to send the program flow from one to any other subroutine at a signal, then the ability to alter the sequence of steps is sacrificed. A program for such a machine must be modular in the sense that control subroutines must be callable and arrangeable in almost any order for program flow. Also within each control subroutine corresponding to a definable task, there needs to be a way for an operator to alter the variables for each type of activity, for example: temperature at a heating station.

In addition to modularity and facility in entering variable values, there needs to be an interface for the operator that allows the operator to choose steps in a sequence with reference to other steps and to maintain a sense of position in the program. Without the position sense, an operator might, for example, easily enter variable values for one step that were meant for another.

Although it is possible to enter steps and variable values for such a program by reading storage media that can be programmed off-line, such as floppy disks or recording tape, it is generally desirable to alter step sequence and enter variable values on-line through an operator interface. By providing on-line interaction, an operator may make corrections and adjustments quickly and easily. An operator interface, however, is needed whether the programming is done on-line or off-line.

Typically, an operator interface for such a control program is an interactive display on the screen of a monitor, where an operator may reorder the steps and enter values for variables in one or a combination of ways. One way is for the program to ask printed or audible questions and then go to an input mode for an operator to enter a sequence number, a choice from a list, or a value from a keyboard, which input the computer program will store in a particular memory location to be accessed at a later time during execution of the sequence being programmed.

Another interface mechanism is called menu-driven, in which the program presents lists of choices on the display, and the operator may select by operating a cursor with the aid of a device called a mouse, providing a signal by pressing a button on the mouse. In a menu-driven interface text fields may also be presented for entry of information from the keyboard.

In other kinds of interfaces, a process flow may be simulated on a display device by the program as graphic symbols for various processes with the symbols connected by lines representing continuity in the process flow. In some cases an operator can move symbols from one position to another in the flow chart and may enter information for variables at the position of a symbol representing a process.

A problem with presenting a process flow schematic on a CRT or other computer display is that the area for display is limited. If a process flow schematic has a relatively large number of nodes, a node being a symbol or other notation representing a specific activity, it may not be possible to present all of the nodes on the screen. Presenting all of the nodes becomes particularly difficult if there are text fields involved or menus to allow entry of process variables at some or all of the nodes.

One manner in which the space problem has been addressed is by dedicating separate screens to separate parts of a program, with a portion of an overall process flow presented on each screen. In this implementation of a process flow schematic, there has to be a menu or other device for an operator to select a screen.

A node in a process flow schematic for machine control is typically a box, triangle, or other polygon symbol with identifying text. A node may also have one or more text fields for entering information. A text field is a field identified on the display that can be selected to become active, and will then accept keyboard input. The input is typically displayed in the text field by the computer program as well as stored at an assigned memory address for later reference. If nodes in such a program contain text fields, then the display space problem is more critical, fewer nodes may be displayed, and more screens are required for display of an entire process flow schematic.

The relationship of nodes to one another in a process flow is generally sequential, with alternative (parallel) paths sometimes encountered. The relationship of information at a node, however, is typically hierarchical, i.e. a conceptual, logical ordering of the information at each node, to condense content, and to more directly relate the primary concepts from one paragraph to those of another. One way of handling hierarchical information on a display to save space is typified by outline programs such as Thinktank, MaxThink, and More, marketed by Living Videotext Co., Inc. of Mountain View, Calif. In an outline program, an outline may be collapsed so that only major headings are shown.

From a collapsed outline entered in a program like Thinktank, a user may, with an appropriate signal, e.g. positioning a cursor on a heading and pressing a pushbutton, cause entries at a next level to be displayed while the original level is still on the display. The next lower level is typically shown indented one position from a next higher level. Further expansion is accomplished in the same manner, and, as is typical with an outline, the lowest level may be paragraphs of text rather than a heading. One may then view the outline in various states of expansion and collapse, accessing those parts of the outline needed at any particular time.

A similar mechanism to the collapsing and expanding outline is provided by a windows ability which is common to programs for Apple Computers such as the Macintosh line. By "clicking" on a graphic symbol, a window is displayed. Window type programs, e.g. Microsoft Windows and X Windows, are also becoming increasingly popular for other computers such as IBM Personal Computer compatible systems and for larger systems such as systems using a UNIX operating environment.

"Clicking" is short terminology for positioning a cursor on the symbol and pressing a button. A window is a screen area, like a smaller display, positioned over the original display seemingly at another level, as another layer. A window seems to float on the original. Lower order windows in a hierarchy may be floated over other windows. In the Macintosh Finder system and many applications, windows may be moved from one apparent level to another, and moved to different positions on a display by a process called dragging, which is similar to clicking. Microsoft Windows for IBM compatible machines is marketed by MicroSoft Corporation of Redmond, Wash.

Windows may be programmed to have text fields, menus, check boxes for selection, and other interactive features. A serious disadvantage is that with windows the relationship of a node to other nodes in a process flow is lost when a window is opened. There is no visual link to a flow schematic when the window is opened.

There are, then, several distinct shortcomings in interactive operator interfaces for creating process schematics and other sequential programs, and for editing node-specific variables and other hierarchical information at a node. One, as mentioned earlier is an inability to display entire complicated schematics on a single screen. Another is a loss of relational information with expanding and collapsing techniques such as windows. Still another is a sameness in the look of nodes, requiring reference to numbers or written descriptions for identification, which may easily lead to error. Yet another is a typical requirement to collapse nodes before choosing different screens to see other parts of an extensive process flow schematic.

What is clearly needed is an interactive interface with nodes represented by descriptive graphic symbols so specific activities and activity strings may be easily recognized. Such an interface should retain relational information of one node to surrounding nodes in a process flow regardless of state of expansion or collapse hierarchically. Also, to avoid the problem of calling other screens, the program should provide a display that is at all times a window on a full process schematic, allowing a user to pan to other parts of the schematic without changing screens. Lastly, for applications involving robotic process control, the interface should not be just a process flow visualization means, but should be keyed directly to the apparatus it is related to, so that the apparatus is operated via the interface.

SUMMARY OF THE INVENTION

In accordance with preferred embodiments of the invention a powerful and flexible robotic control language is disclosed which frees the user from the characteristic dialects used in computer programming. The language provides an advanced user interface for programming the function of complex equipment, e.g. such as laboratory robots. The interface facilitates rapid learning as well as a convenient day-to-day tool for use by experts. This is achieved for robots through the use of an iconic programming language for the description of robot operations, and an intuitive interactive enviroment for creating, editing, and executing programs. The iconic programming language primarily differs from traditional text-based ones in that its symbols are icons rather than words, with the advantage that icons are immediately recongnizable, independent of natural language, cannot be misspelled, and a single symbol can represent many interconnected functions. The function of syntax, the formal relationships between symbols, is fulfilled in this visual programming language via ordered, and enforced, ways of placing symbols in relationship to one another.

According to a method of the invention, an automated apparatus is programmed to perform a process by arranging a sequence of first icons on a display in the order of the process, wherein the first icons represent functions of the apparatus, and wherein at least one of the first icons provides a visual representation of a function of the apparatus. Said at least one of the first icons can be expanded to show second icons that comprise the function of said at least one of the first icons, and at least one of the second icons provides a visual representation of a subfunction of the apparatus. In a preferred mode, when said at least one of the first icons is expanded, said at least one of the first icons maintains its same sequential relationship on the display to the other of the first icons in the sequence as before it was expanded.

BRIEF DESCRIPTION OF THE DRAWINGS

FIG. 19 shows a window for selecting Group samples.

FIG. 20 shows a shows a window for selecting Restriction Groups.

DESCRIPTION OF THE PREFERRED EMBODIMENTS

This invention is related to an interactive user interface for programming process equipment and handling and storing other relational and hierarchical information. Hence, its description will be put in the context of a specific application to illustrate its use and power. Those skilled in the art will appreciate that the context is used merely for illustration and that other examples of automated equipment could also be used.

Figure 1:
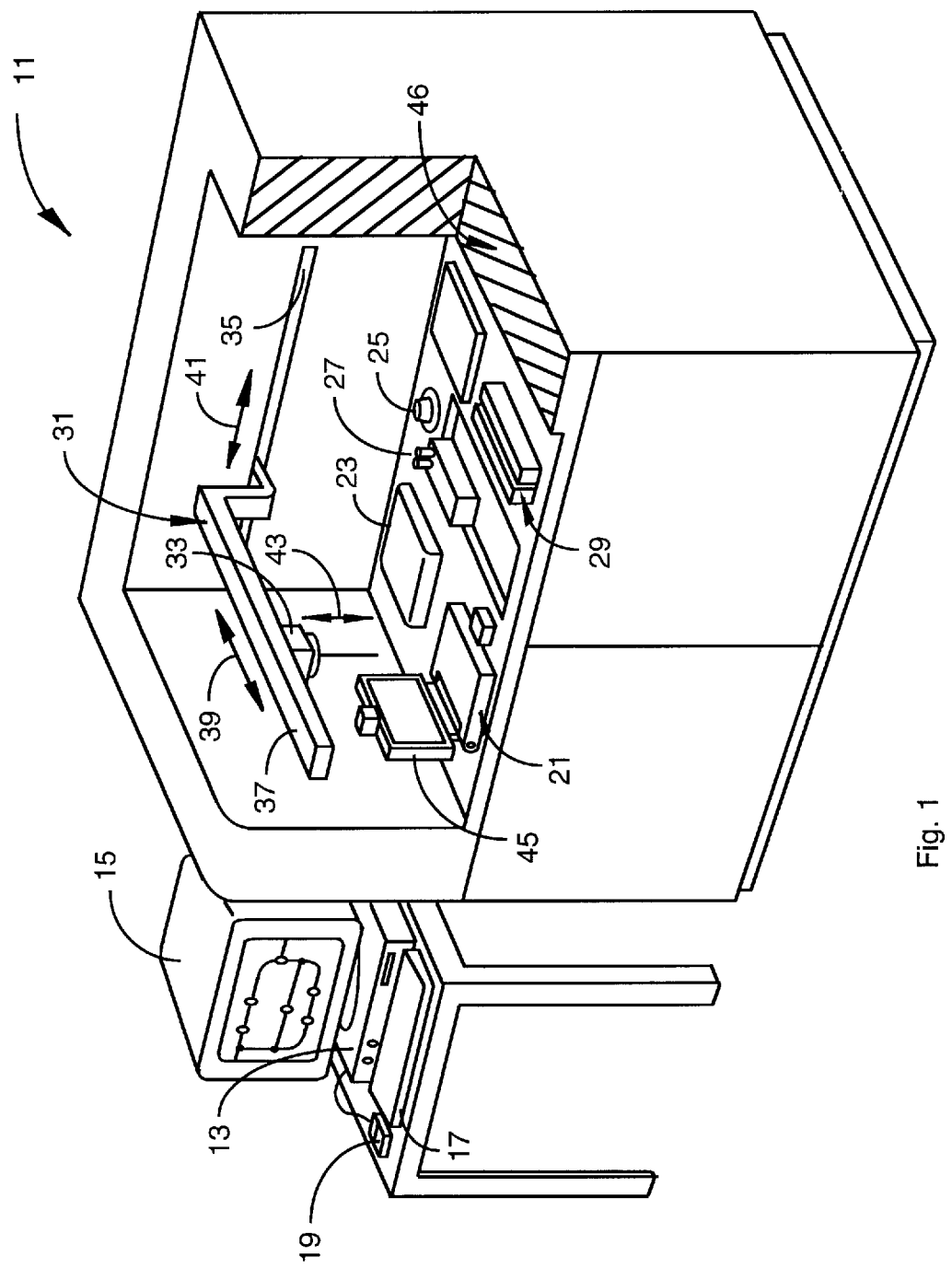
FIG. 1 is a perspective view of an automated laboratory for perfoming chemical processes.

FIG. 1 is a perspective view of an automated laboratory (AL) 11 for performing chemical processes, e.g. such as those involved in molecular biology. A computer 13 with a CRT monitor 15, a keyboard 17 and a mouse device 19 is connected to the AL. The computer, CRT display, mouse, and keyboard are hardware components of an operator interface for programming the AL to perform sequences of activities, for starting and stopping processes and sequences of processes and for entering and altering process variables for specific activities. In the preferred embodiment the computer is a Macintosh II computer made by Apple Computer of Cupertino, Calif., but other computers may also be used.

The AL has a closed heating station 21, a cold storage station 23, a wash station 25, a storage position 27 for storing and presenting frequently used fluids such a DI water and solvents, and a separation station 29 for separating materials in suspension in sample fluids. A transport apparatus 31 carries a needle 33 of a pipette system for aspirating fluids from containers at the various stations and dispensing the same fluids into containers at the same or other stations. The pipette system includes two syringe pumps (not shown) in the preferred embodiment. One pump is for relatively course transfer, and the other is transfer of precise amounts of fluids. There are also actuators, motors, sensors, printed circuit boards, power supplies, and other devices (not shown) typical of such equipment. One end of the AL at region 46 is shown cut away so internal details may be seen.

Heating station 21 has positions for placing a plurality of vials for holding samples and mixtures of fluids, and lid 45 is automatically closed to seal the tops of all the vials in the station during heating. Cold storage station 23 has an array of vial positions in the preferred embodiment similar to the array at station 21, except the lid thereon does not open. The lid has holes through which the needle of the pipette may pass to aspirate or dispense fluids. Storage position 27 is an indented area where a user may place carriers holding a number of tubes of frequently used fluids. Separation station 29 has two rows of positions for vials for sepating materials that are suspended in solutions by performing an extraction process. The separation station also has a resistance heater for maintaining heat of fluids at the station and water cooled passages, also for temperature control.

Transport apparatus 31 moves along slot 35 passing over the storage and activity stations. The pipette needle is movable along arm 37 of the transport device in the direction of arrow 39 and the transport is movable along slot 35 in the direction of arrow 41 to position the pipette over any container position at an activity station. The pipette needle is translatable vertically as well in the direction of arrow 43 so the transport apparatus is an XYZ mechanism capable of placing the pipette in any container on the AL.

The pipette is for aspirating fluid from any one container and dispensing it into any another container. With the pipette, mixtures of various chemicals and other fluids may be made, diluted, and concentrated, and transported to any vial or other container on the AL. The pipette system may also serve to agitate fluids in a container to perform mixing, by repeated aspirating and dispensing of the fluid in a container. Wash station 25 is used for washing and backflowing the pipette tip after a transfer of fluid to avoid cross-contamination.

Figure 2:
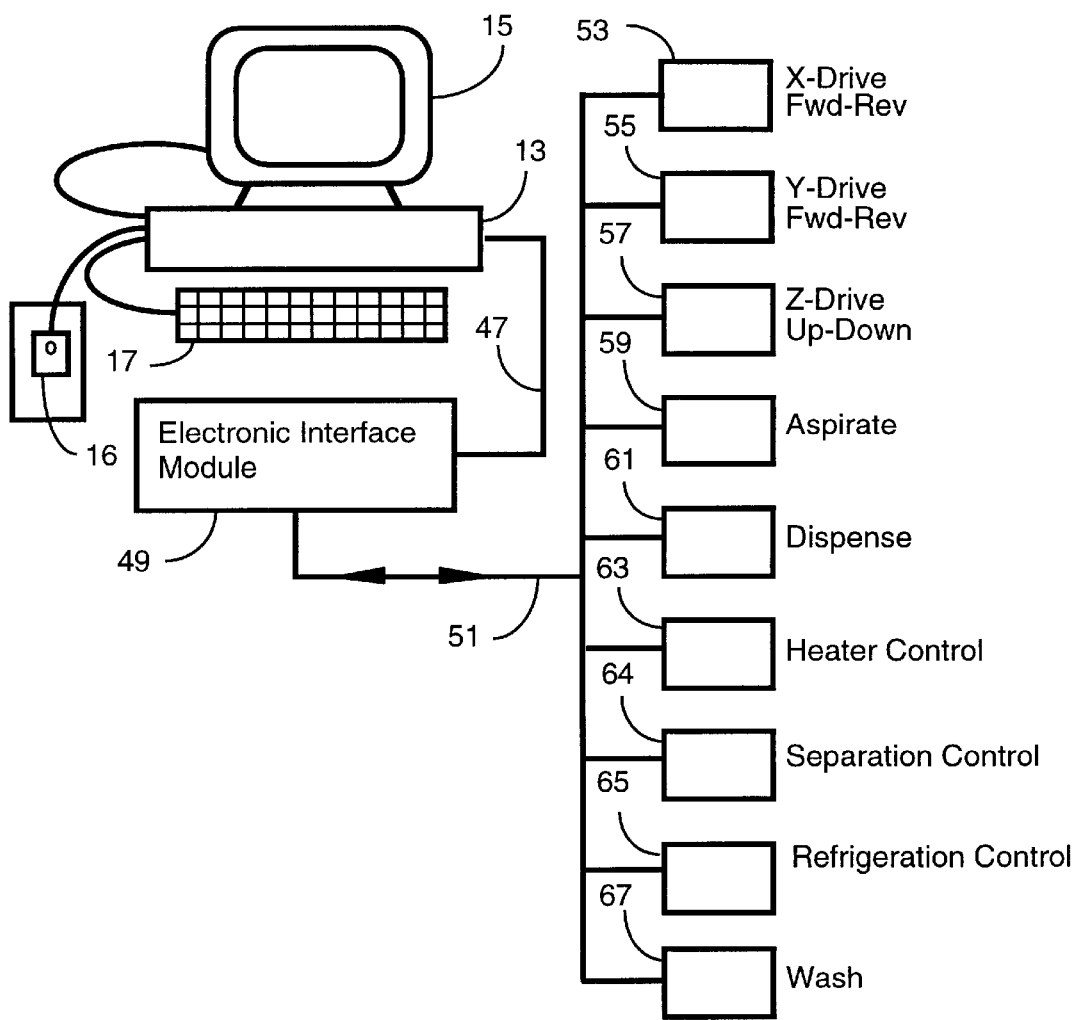
FIG. 2 is a block diagram of a control interface for the automated laboratory of FIG. 1.

Computer 13, CRT 15, mouse 19 and keyboard 17 are used with a unique program, hereinafter called Proto, to prepare control sequences and establish specific characteristics for the various activities that make up a complete control sequence, as well as to initiate and terminate specific strings of activities. FIG. 2 is a block diagram showing control activities and modules.

Computer 13, keyboard 17, mouse 16, and display 15 are connected together in the usual way, and the computer is connected by a communication line 47 to an electronic interface module 49. A variety of communications protocols can be used. However, since the system is implemented using the Apple Macintosh, the Appletalk protocol is preferred. As is customary in the art, module 49 includes switching elements for converting low-level signals to voltages and currents capable of running the actuators and motors of the AL, power supplies, analog-to-digital converters and digital-to-analog converters, among other equipment needed to translate low-level signals from the computer to levels sufficient to drive the activities of the AL. Line 51 represents multiple circuitry to carry both communication and power between module 49 and specific drives, actuators and sensors on the AL.

X-Drive 53, Y-Drive 55 and Z-Drive 57 are the three dimension drives for transport apparatus, and each of these drives also includes position sensors that send signals back to the computer via module 49 so the computer has updated information relative to the position of the transport elements. Aspirate actuator 59 causes the travelling pipette to aspirate fluid from a container after the pipette is positioned, and dispense actuator 61 causes fluid to be dispensed from the pipette. In the case of both aspirate and dispense there are timers and sensors (not shown) that control the rate and amount of fluid aspirated or dispensed.

Heater control 63 is for heat at the heater station, and includes thermal sensing elements to inform the computer of the effect of heating. Separation control 64 manipulates assemblies at the separation station. Refrigeration control 65 is for maintaining temperature at cold-storage station 23, and includes temperature sensing. Wash actuator 67 operates the washing action at the wash station to wash the pipette between transfer procedures that use the pipette. Mixing actions in the preferred embodiment are accomplished in vials and other containers, if needed, by repeated aspiration and dispensing of fluid.

As indicated earlier, a unique program, Proto, is run on the computer in the preferred embodiment to create control programs, enter and edit variable values, and initiate and terminate process sequences. Proto is an iconic program, employing graphic symbols called icons to represent processes, process steps, and other activities. Proto provides a unique user interface that is useful for handling hierarchical information and for controlling many kinds of process machines and equipment.

Proto has a set of routines allowing a user to select icons representing various activities and to organize the icons into flow schematics representing process flow, with the icons connected on the display with lines. The icons may also be nested such that a relatively complex sequence of activities may be represented by a single icon, and the single icon may be expanded in place to show a connected sequence of icons representing steps in the more complex sequence. The second level icons may also consist of sequences of other icons, also expandable in place, until, at the lowest level, icon sequences consist of icons representing fundamental process steps. The fundamental steps in the preferred embodiment are typically themselves sequences of even more basic activities. For example, a fundamental step may be a direction by the program to the AL to send the transport to the Home position. The control system through sensors tracks the real-time position of the transport apparatus and the Home position is a known position to the computer, so the computer would then operate the X-drive and the Y-drive in the appropriate directions to attain the home position. Fundamental steps, however, could be as basic as to move the z-drive in one direction by a specific amount.

Figure 3:
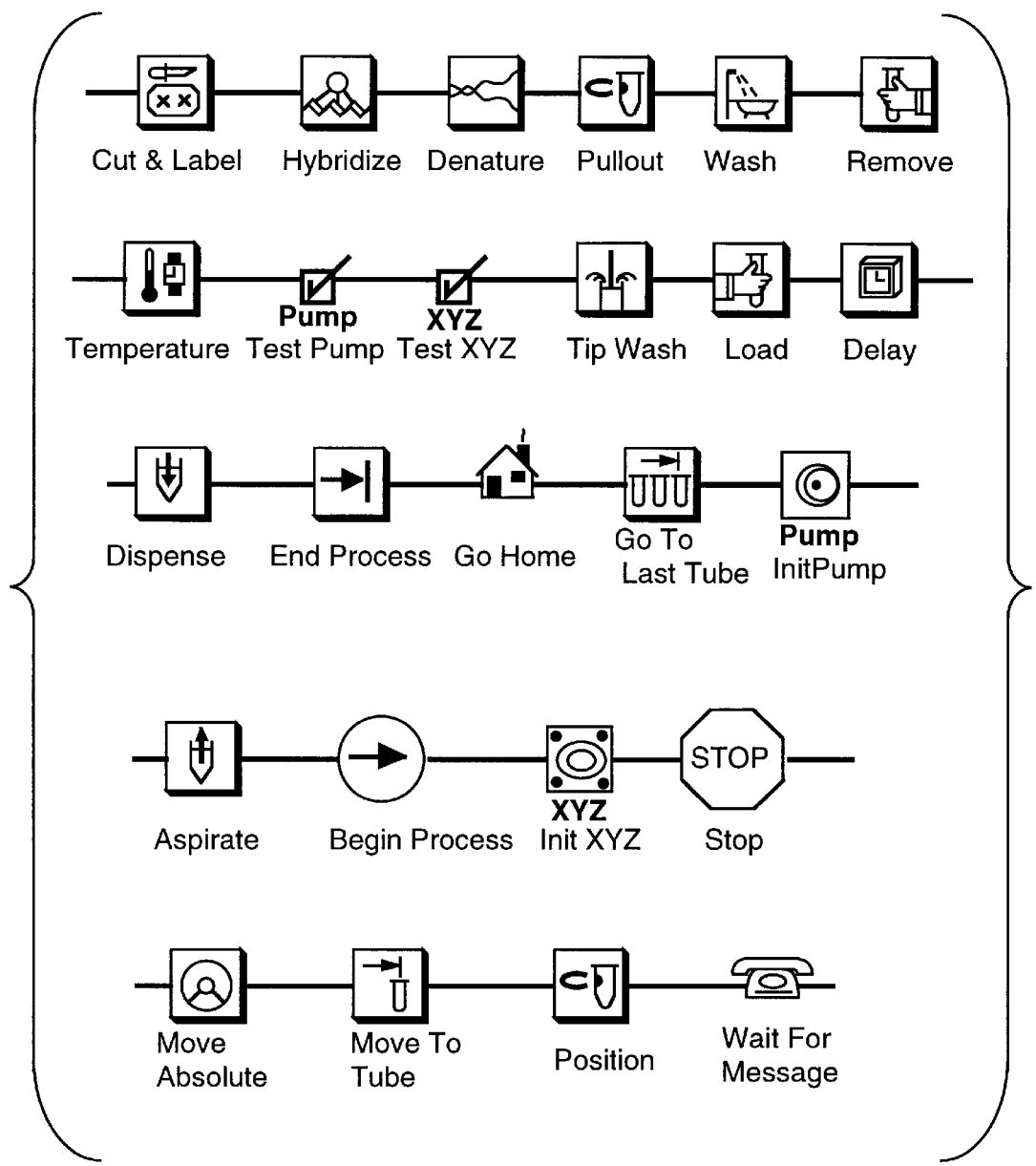
FIG. 3 shows a sample of exemplary icons that can be used with the automated laboratory for different laboratory functions.

FIG. 3 is a sampler showing a number of the icons provided with the Proto program for use in building and operating control programs to operate the AL. The icons shown are labeled as to their function, and only a selection of the implemented icons is shown. Proto provides an ability for a user to define new icons and to specify the relationship to function of new icons in a program; that is, what code is to be inserted into a program and what signal string is to be generated and sent when an icon is activated.

A fundamental icon is typically expandable in the preferred embodiment to display an input window which allows an operator to enter or edit variable values for the fundamental process step represented by an icon. In addition, the graphic icons are drawn to uniquely represent the steps, sequences of steps, or complete processes that they denote. The icons are verbs in this sense. As an example, an icon for Disepense is a small picture of a test tube showing the direction of flow of materials into the tube. This icon can then be expanded to illustrate the fundamental processes that are used in the dispense function.

In programs other than Proto, such as programs prepared in Apple Computer's Hypercard application or in Microsoft's Windows program, expanding a symbol results in a window floating over the icon, and the network representation, if any, appears as though the window is in a separate graphic layer on the screen. Indeed, such windows may often be repositionable on the screen by an operator and caused to show in a different layer, in front of or behind other such windows. Hence, the relationship of the symbol to the rest of the elements on the screen is lost.

In Proto, the icons are expandable in place, and the new network or control panel displayed by expansion of an icon is shown still connected to the network sequence on both sides. Moreover, the previous icon, though no longer visible, is still represented as a border of a box, surrounding the lower order network, relaying the continuing relationship to the user. The expansion in place allows a user to maintain an accurate sense of place in a network of icons, and reduces the probability of costly error in placing and removing icons to alter a process sequence, as well as in entering and editing variables for specific activities. Moreover, even though expansion creates greater competition for screen space, as in other programs, Proto does not resort to separate screens, breaking the relational continuity, but provides for scrolling (panning) of a single screen in the expanded state so a user may view the entire process network in any expanded or collapsed state.

Figure 4:
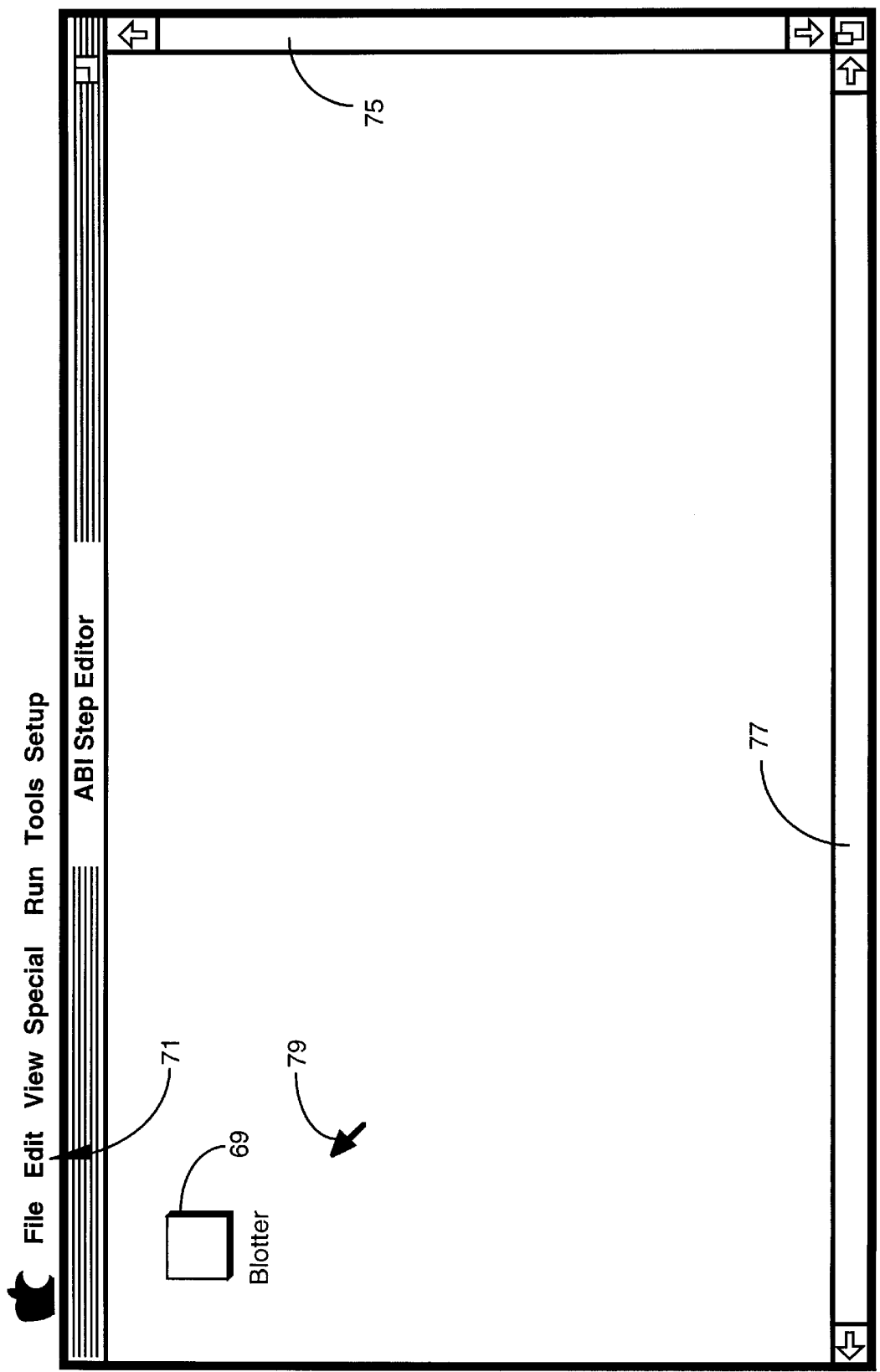
FIG. 4 shows a screen of a Proto program according to the invention for a DNA labelling and hybridization process called Blotter.

FIG. 4 is a screen of an actual program, called Blotter, prepared in Proto for controlling the AL to perform a process for labeling selected DNA sequences. In the screen of FIG. 4, the process network is in its most collapsed state, reduced to a single blank icon 69 named Blotter. A menu bar 71 contains labels that are selectable to activate programming functions for creating and editing programs in Proto. Blotter icon 69 is the icon for the fully collapsed Blotter control program to operate the AL or other processing equipment. There is a vertical scroll bar 75 and a horizontal scroll bar 77 for scrolling the screen. In the fully collapsed state, as in FIG. 4 the scroll bars are shown blank because the screen does not need to scroll. Single icon 69 represents the entire control program.

A cursor 79, showing on the display as an arrow at a slight angle, is movable throughout the display area in response to movement of mouse 19 (FIG. 1). Cursor movement may be accomplished by other devices as well, such as a joy stick, a palm ball, a puck, and by keys on the keyboard. Selection on the display is by positioning the cursor at a particular point and momentarily pressing a button on the mouse. This combined action, as indicated earlier, is termed "clicking" in the art, such as "click on the Blotter icon". This terminology will be used hereinafter in the present specification. A different action is initiated in some instances by "double clicking", which is positioning the cursor and pressing the button twice in rapid succession.

By clicking on the Blotter icon, a user may select the Blotter process for some action or editing. Typically, in Proto, the item clicked is then shown highlighted in the display, and any menu function chosen and activated will act upon the highlighted process. Double clicking in Proto will expand an icon in place to reveal subprocesses arranged in an order that make up the process represented by the icon, or in the case of an icon at the fundamental level, will display a variable entry box, called the control panel for the particular icon, for making choices and entering variables to alter the characteristics of an action initiated by the icon.

Figure 5:
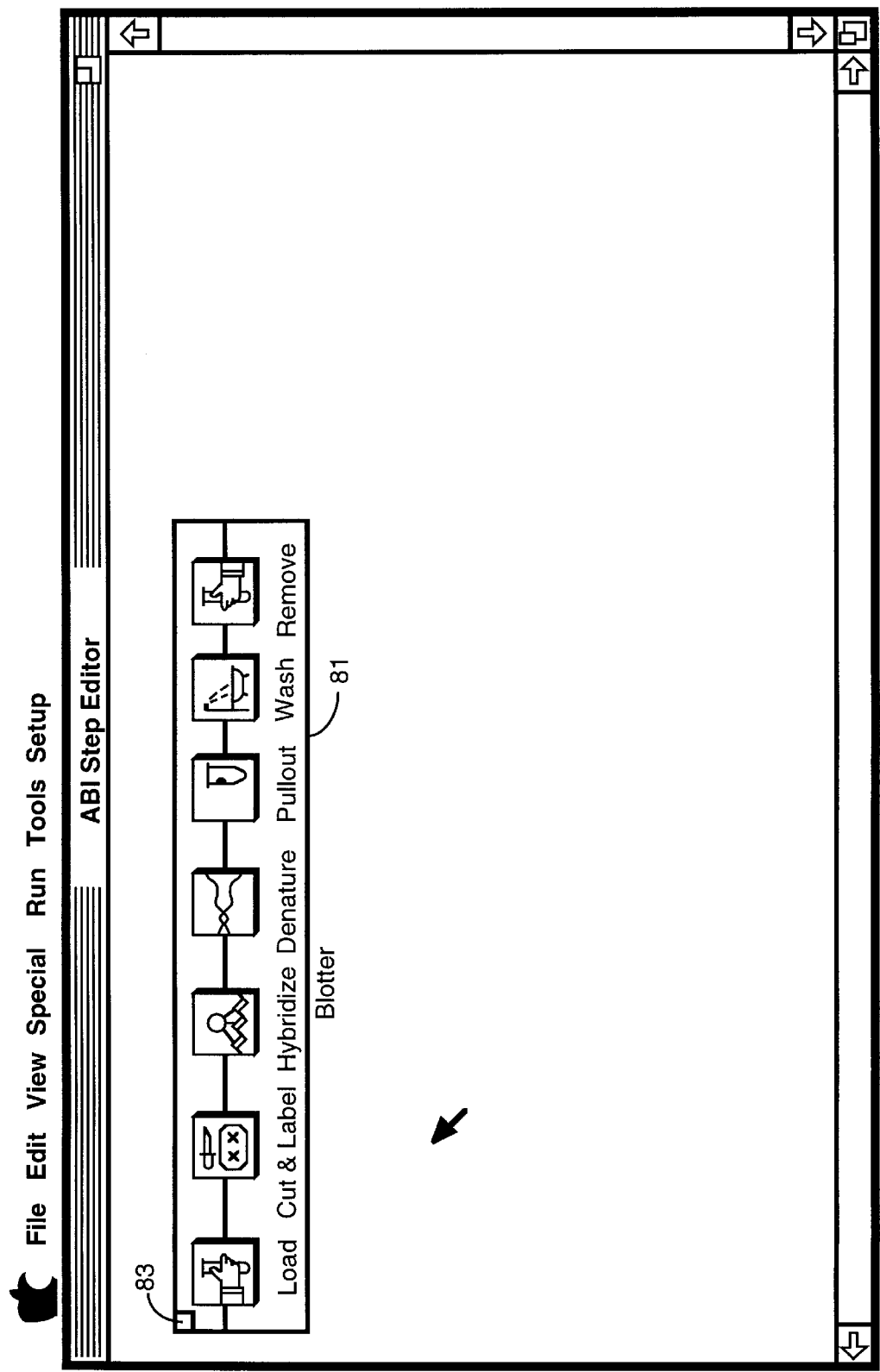
FIG. 5 shows a display of a first level expansion of the icon representing the Blotter process.

A first level expansion is shown in FIG. 5, which is the display after double clicking the Blotter icon. In FIG. 5 rectangle 81 represents the Blotter process that was represented in FIG. 4 by icon 69. Within rectangle 81 there is a sequence of seven subprocesses: Load, Cut and Label, Hybridize, Denature, Pullout, Wash, and Remove; connected by lines, indicating clearly to a user that the Blotter process is made up of these seven subprocesses in the order shown with the convention from left to right for time sequence. The relationship of one process to another and the hierarchical relationship are clearly apparent.

Rectangle 81 representing the Blotter process has a small rectangle 83 in the upper left corner that is known as the close box. Clicking on the close box collapses the representation of the network shown in FIG. 5 back to the single icon as shown in FIG. 4. Every expansion box has a close box for expedient closing to collapse to a higher order display. Typically, collapsing, i.e. closing, may also be accomplished by highlighting the box and choosing a close command from the file menu in the menu bar, or by highlighting and a keystroke combination.

A user may click on any one of the seven subprocess icons of FIG. 5 to highlight that icon for editing or other action, or double click on any one to open that subprocess to a next lower level of detail. Clicking once inside rectangle 81, but with the cursor not on any one of the seven subprocess icons will highlight the Blotter rectangle, which is functionally equivalent to highlighting the Blotter icon in FIG. 4.

Figure 6:
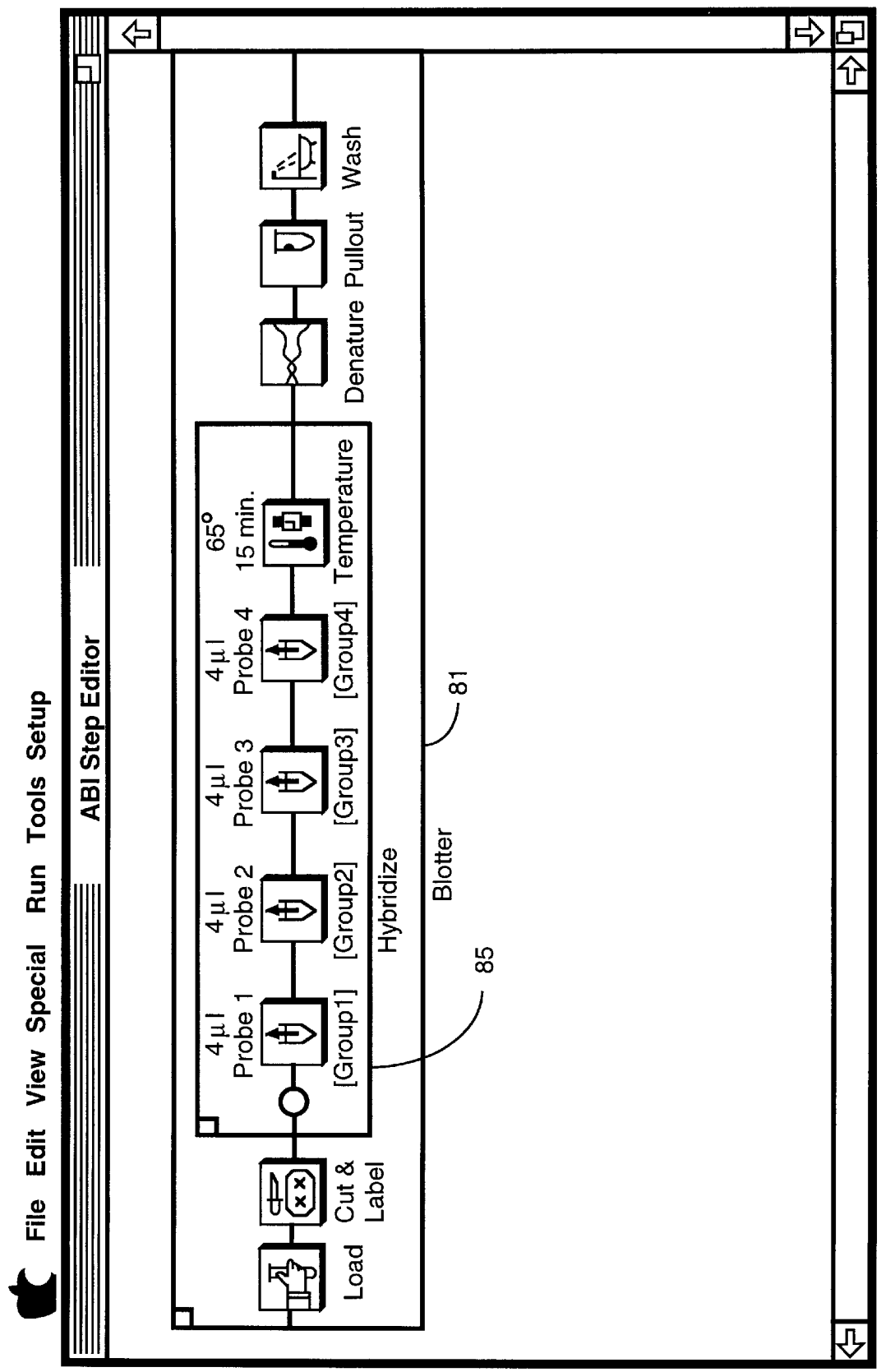
FIG. 6 shows a display of a second level expansion of the Blotter icon, which illustrates the Hybridize subprocess.

FIG. 6 shows a new display, the result of double clicking the Hybridize subprocess to open it. This is a second level expansion. Now there are two rectangles on the screen, rectangle 85 representing the Hybridize subprocess and rectangle 81 representing the Blotter process. Rectangle 85 is shown nested within rectangle 81 along with the other six subprocesses that make up the Blotter process. The relationship of the Hybridize subprocess to the other six subprocesses is clearly represented by connecting lines, and now the Hybridize subprocess has been expanded in place to reveal a sequence of five lower order activities that make up the hybridize subprocess: Probe 1, Probe 2, Probe 3, Probe 4, and Temperature.

In the expanded state of FIG. 6 not all the network may be seen on the monitor screen, because the two expansions have taken more than the full horizontal dimension of the screen. The complete network in its expanded state is still apparent on the single display, however, because the display can be panned to the left and right by use of the horizontal scroll bar. The display may also be panned by a process called dragging. The user can position the cursor at a point outside any icon and press and hold the mouse button while moving the mouse. The image on the screen will move as though a document bigger than the screen is being moved behind the screen. The screen operates as a movable window on a document larger than the screen.

Although it is not shown in FIG. 6, other icons could be expanded without closing the Hybridize icon, and the others would also expand in place without losing any sense of relationship to the rest of the network. By panning, the entire network could still be moved into view.

Figure 7:
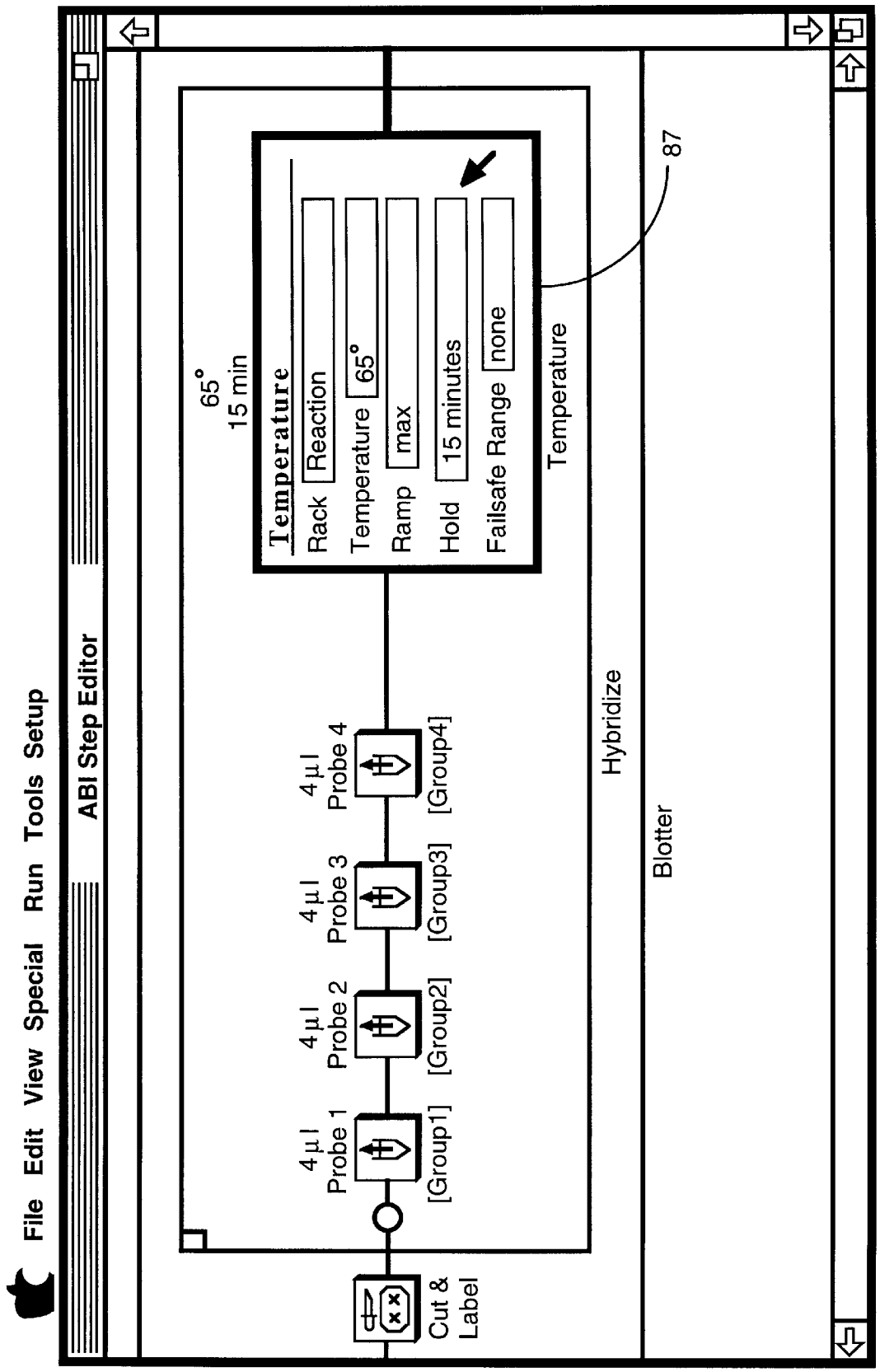
FIG. 7 shows a display of a third level expansion of the Blotter icon, which illustrates the Temperature subprocess within the Hybridize subprocess.

FIG. 7 shows the result of double clicking the Temperature icon of FIG. 6, which displays control panel 87 for allowing a user to input and edit characteristics for temperature control. The Temperature control panel in this case has text fields for Rack, Temperature, Ramp Hold, and Failsafe range. For the entries as shown, when the Temperature icon is activated in the process flow, the temperature of a rack known as the Reaction rack will be cycled to a temperature of sixty-five degrees centigrade at a maximum ramp (as quickly as possible), and the temperature will be held for fifteen minutes. There is also a text box to enter a failsafe range, which is none in the instant case. A control panel has a close box like a process rectangle, and a user may close the temperature control panel after making or editing entries, collapsing the display back to the display of FIG. 6.

Figure 8:
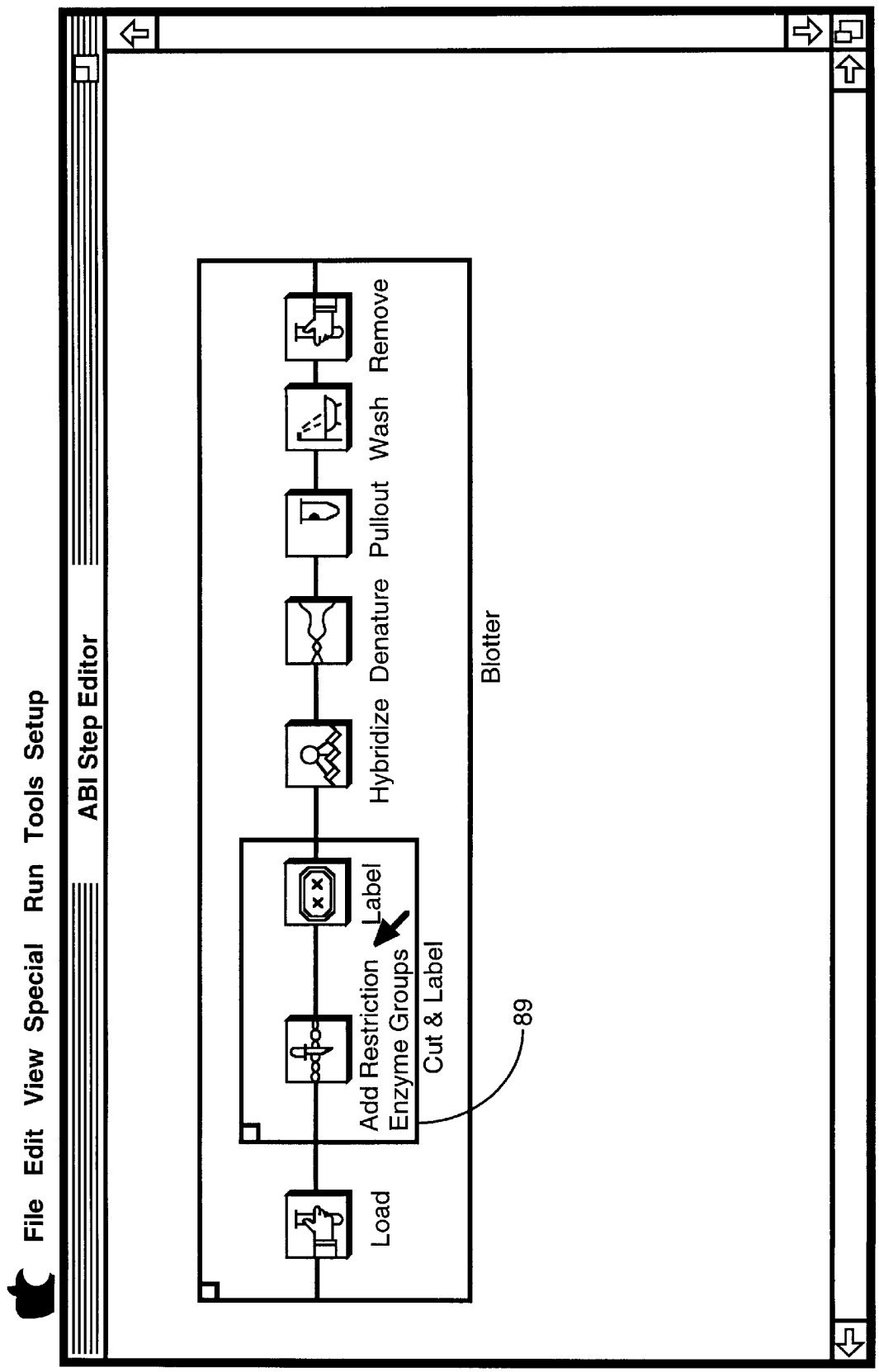
FIG. 8 shows a display of a second level expansion of the Blotter icon, which illustrates the Cut and Label subprocess.

It is not required that each subprocess have the same number of nested levels. FIG. 8 shows the network with the Hybridize subprocess collapsed to the Hybridize icon, and the Cut and Label subprocess expanded to the next level. Rectangle 89 represents the Cut and Label subprocess, which in FIG. 7 is seen to consist of two other subprocesses: Add Restriction Enzyme Groups and Label. Adding restriction enzymes is a part of the chemical procedure by which DNA molecules are cut.

Figure 9:
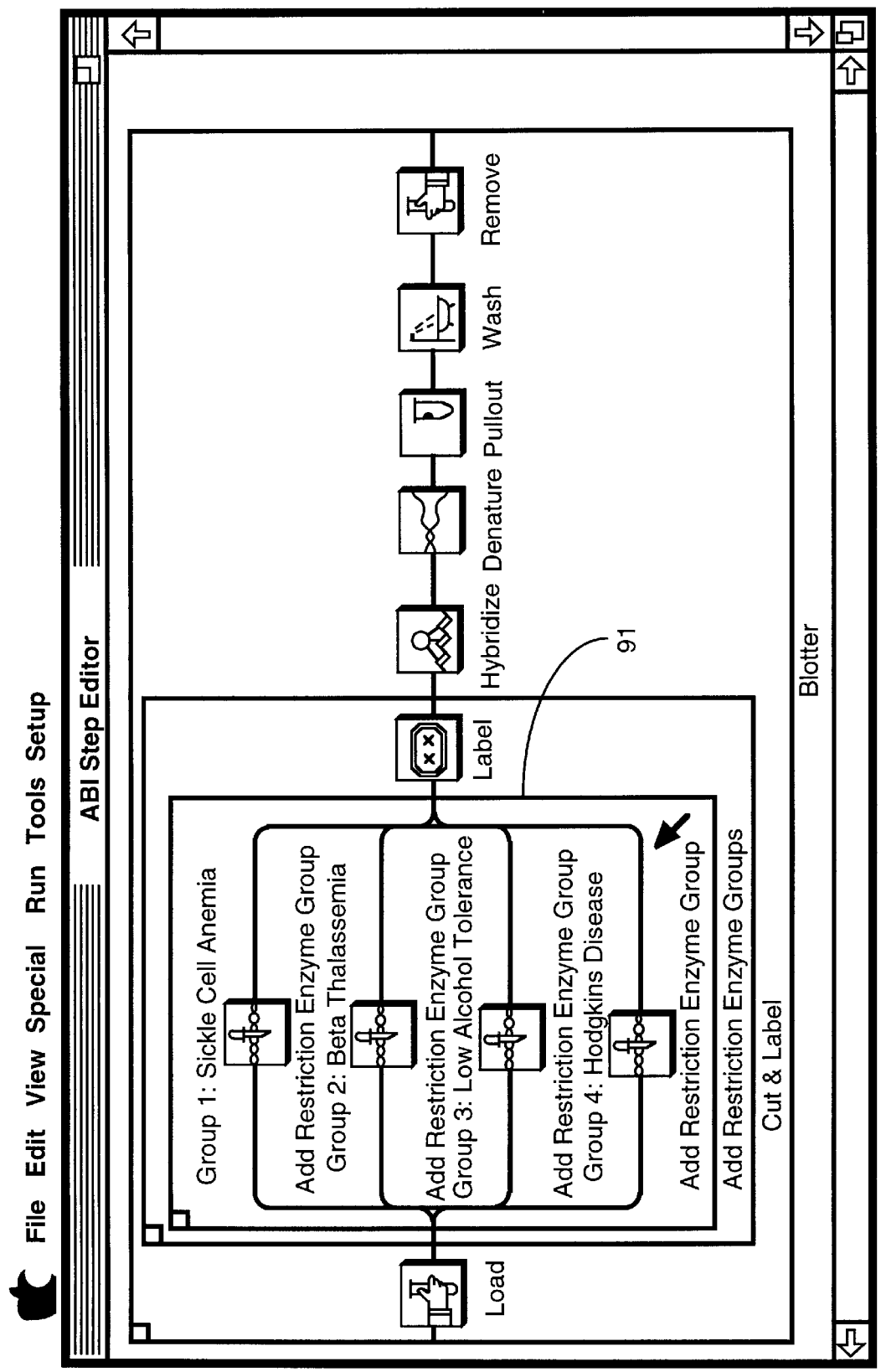
FIG. 9 shows a third level expansion of the Blotter icon, which illustrates the Add Restriction Enzymes subprocess of the Cut and Label subprocess.

FIG. 9 shows the display after double clicking on the Add Restriction Enzymes subprocess, which is represented in FIG. 9 by rectangle 91. The Add Restriction Enzyme subprocess is revealed to be a choice of one of four parallel paths, depending upon which restriction enzyme group a user elects for a particular Blotter process. This permits changes in the chemistry to be made for any particular path.

Figure 10:
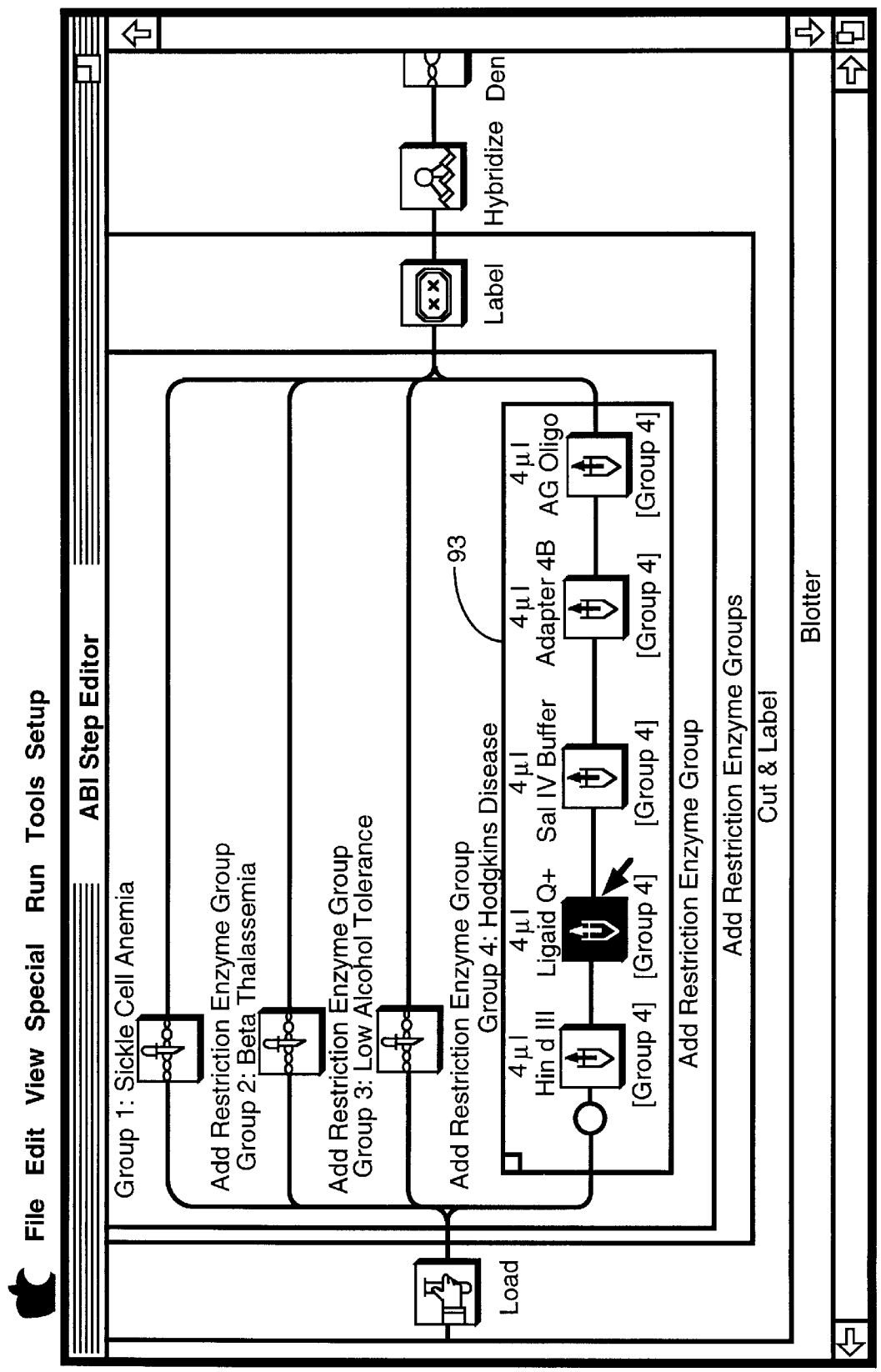
FIG. 10 shows a fourth level expansion of the Blotter icon, which illustrates the Group 4: Hodgkins Disease subprocess within the Add Restriction Enzymes subprocess.
Figure 11:
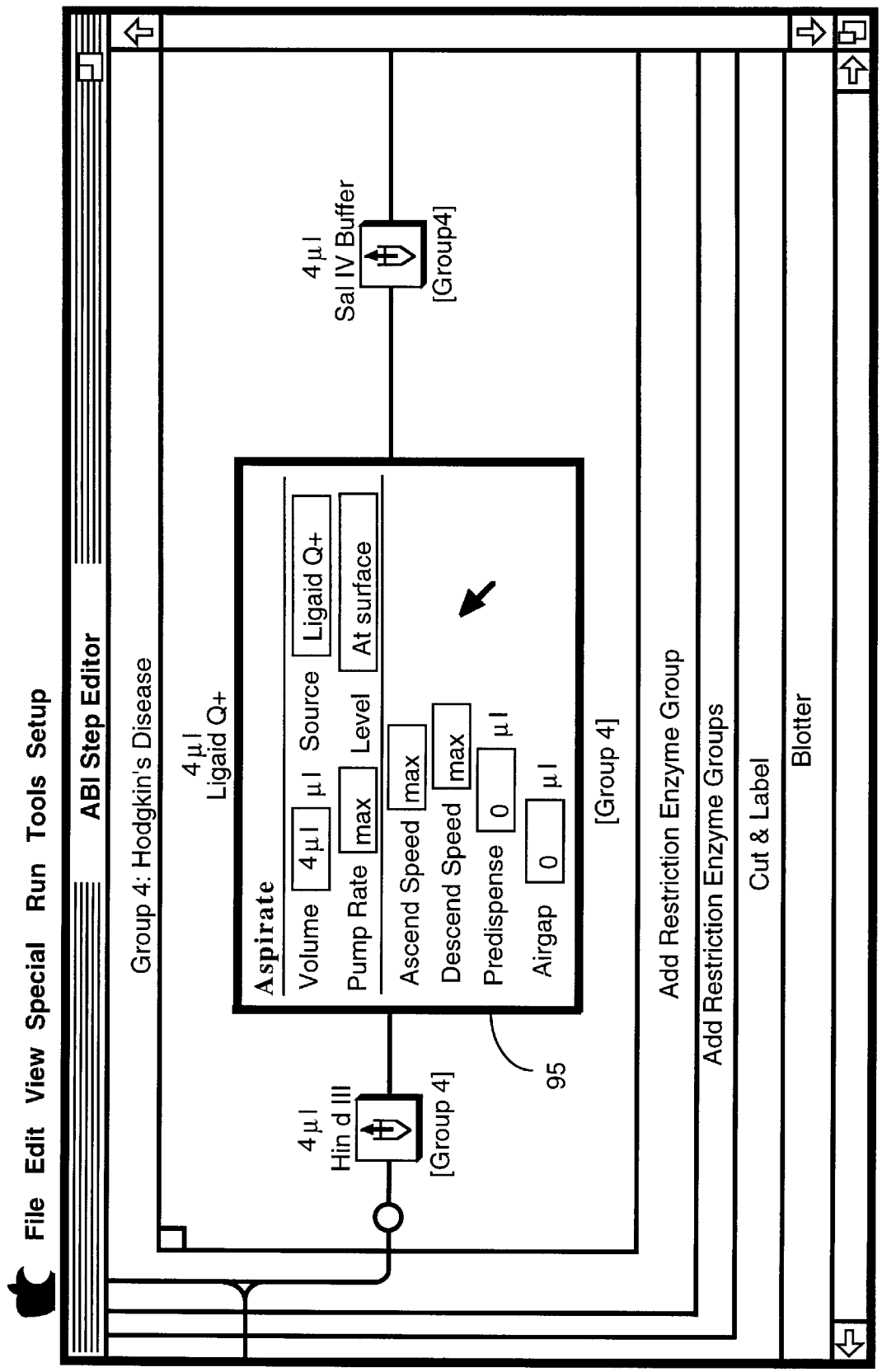
FIG. 11 shows a fifth level expansion of the Blotter icon, which illustrates the Ligaid Q+ subprocess.

FIG. 10 shows a further expansion as the result of double clicking on the icon of Group 4, Hodgkins Disease, in the Add Restriction Enzyme Groups rectangle. Rectangle 93 in FIG. 10 represents the Hodgkins Disease icon of FIG. 9. FIG. 10 shows that there is a sequence of 5 restriction enzymes to be added for the Hodgkins Disease group. FIG. 11 shows the result of double clicking on the Ligaid Q+ icon in FIG. 10. Control panel 95 is for setting control variables for aspiration of Ligaid Q+ by the pipette in the Blotter process. FIG. 11 shows text fields for setting the volume, choosing the source, adjusting the Dump rate, choosing the level at the source at which to aspirate, setting the ascend and descend speeds for the pipette drive, and setting an airgap and a predispense volume.

To completely define a process, a user opens the necessary icons, expanding to the level needed, enters the necessary values to define the process, and then collapses the network again. A Blotter program thus defined can be saved to be used as needed to control the same process.

Proto includes tools, accessible in menu bar 71, for altering the sequence of icons, entering new icons, deleting icons, changing names, and doing all functions necessary to build programs. By clicking on a choice in the menu bar an operator causes a menu to appear. The operator may then drag the cursor down the menu to a listed function, and the function will be activated when the operator releases the mouse button. This operation is a well known procedure in menu-driven programs.

Some of the menus in Proto are common to many Apple programs, and will be recognizable to a programmer with skill in the art. For example, choosing the Apple logo in the menu bar displays a menu of functions that are loaded as desk accessories, such as Chooser, Scrapbook and others.

Figure 12:
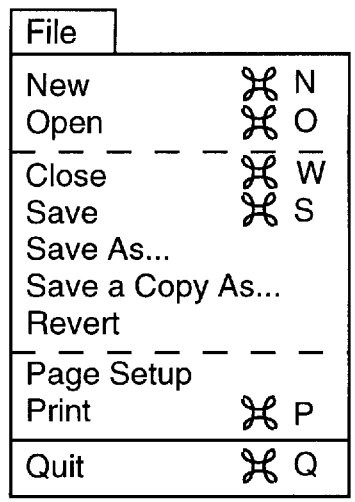
FIG. 12 shows a Files menu.

The Files menu, shown in FIG. 12, is for activating functions that relate to such activities as opening, closing, saving and printing files in Proto. In many cases a function may be activated from the keyboard by a key combination without clicking on the choice in the menu bar. If so, the shortcut key combination is shown next to the function label in the function list. In the Files menu, choosing New presents a new window on the screen which may be used to create a new control program by the use of other functions from the menus, described in further detail below. Open presents a scrolling window by which an operator may access each storage device, usually disk drives, that are operating for the computer, may list the Proto programs on each storage medium, and may select a program for display and editing. In the preferred embodiment, the scrolling window presented and the listings are similar to those familiar to Macintosh users.

Close removes the display of a Proto program from the screen. Save causes an edited program being displayed to be saved to a storage medium, where it will be available to be loaded (opened) at a later time. Save as . . . allows an operator to save an open program to a storage medium under a different name, and provides a dialog window for the operator to enter the new name. The Save as . . . function makes it possible for a user to start with an existing program to edit when creating a new program that will be similar to the existing program. Save a Copy as . . . is a similar function to Save as . . . except the old program is left displayed on the screen after using the function rather than the new.

Revert in the Files menu causes the Proto program displayed to revert to the form that was last saved. Page Setup is a function familiar to Mac users that allows the user to specify for the Mac what sort of page layout will be used for printing; such as A size, legal size, C size, etc. Print is the command function to send the current file to the printer specified in the Chooser function for hardcopy output. Quit is a function that closes the current file and closes the Proto program to the Macintosh desktop in the preferred embodiment. All of the File functions are functions familiar to Macintosh users.

Figure 13:
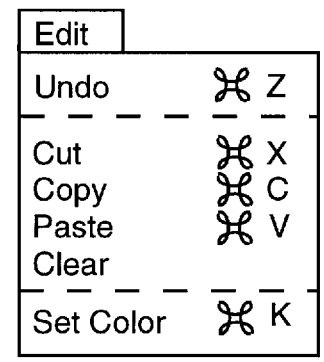
FIG. 13 shows an Edit menu.

The Edit choice from the menu bar presents a menu list of functions that are useful for editing Proto programs. The Edit menu is shown in FIG. 13. These functions are also familiar to Macintosh users, as they are used in other programs written for the Macintosh Copy, for example, used with a word processing program, will typically copy a selection of text into a memory location reserved for that purpose, where it may be accessed to be pasted into an open document at a different position. In graphics programs Copy is used to copy a selected region of pixels, or a selected vector or group of vectors, which may then be accessed to be pasted back into a picture at a different location, without removing or altering the original selection. Copy in Proto operates differently. In Proto Copy copies not only a selected icon, but all nested icons at a lower level in the network order that hold at the time of the copy, all control panels associated with icons, and, critically, the programming code associated with each of the icons and control panels. A Paste function after a Copy, then, will paste into a process network the copied icon, the lower order elements, and all the associated program code.

Undo from the Edit menu is a function that cancels the result of the last function performed. It is used typically to correct the results of a mistake. Cut removes a highlighted icon, all lower order icons associated with the highlighted icon, all control panels associated with lower order icons, and all the code associated with the icons and control panels.

The network is rejoined where the highlighted icon is removed. With Cut a copy of the elements removed is stored in the memory location reserved for Paste, so the elements removed may be reinserted at another point in the program network.

Copy was described above, as was Paste. Paste may be used to insert a copy of elements as a result of either a Cut or a Copy function. Clear removes a highlighted icon, lower order icons and control panels associated with the highlighted icon, and code associated with the other elements, without saving a copy for Paste. Clear is a functional eraser. Set Color allows a user to control the color of elements displayed in the Proto program, such as the background color of a process rectangle or an icon.

Figure 14:
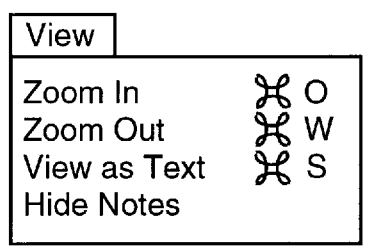
FIG. 14 shows a View menu.

The View menu shown in FIG. 14 offers functions that control the way that a user may view displays of a Proto program. Zoom In allows a user to magnify a display and Zoom Out allows a user to return a display to normal, or smaller, from a magnified view. View as Text works by displaying elements in the display as text rather than as graphic symbols. Hide Notes allows a user to display a program without text notes on the display.

Figure 15:
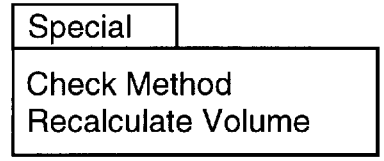
FIG. 15 shows a Special menu.

Special has a two-item menu list: Check Method and Recalculate Volume. The Special menu is shown in FIG. 15.

Check Method checks that the entire network of icons is internally consistent, and executable within the limitation of the designated hardware. Recalculate volumes calculates volumes of fluids needed to perform the method and updates the load steps within those volume amounts.

Figure 16:
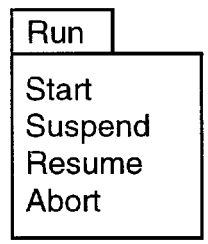
FIG. 16 shows a Run menu.

The Run menu shown in FIG. 16 provides menu functions to control the starting and stopping of process flow performance according to a Proto process network. Start causes a process sequence to begin at the first step, which then proceeds through the steps represented by the icons in the Proto network. Suspend causes a process sequence to halt at the time and at the position in the process flow when and where a Suspend function is activated by a user. Resume causes a suspended process flow to resume. Abort causes the process flow to cease, and control to return to the beginning of the process flow. After Abort, Resume has no effect.

Figure 17:
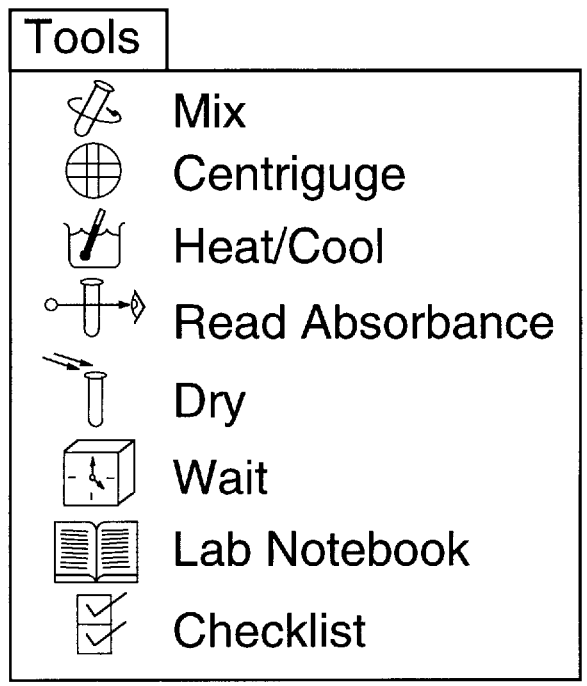
FIG. 17 shows a Tools menu.

The Tools menu shown in FIG. 17 provides icons representing system functions. By highlighting an icon in a process network displayed in a Proto program, then selecting an icon from Tools, the icon, any nested functionality and control panels, and associated code for the elements represented, are inserted into the process flow network at a position immediately following the highlighted icon. The Tools function allows a user to build programs beginning with a blank screen with no icons to copy.

The icons of the Tools menu are the "lowest-level" icons, which represent the last level of expansion before a control panel. For reasons of complexity, these icons are provided in the program by coding in the computer language used to implement the Proto program. In the preferred embodiment, the language is the well known C-language.

Figure 18:
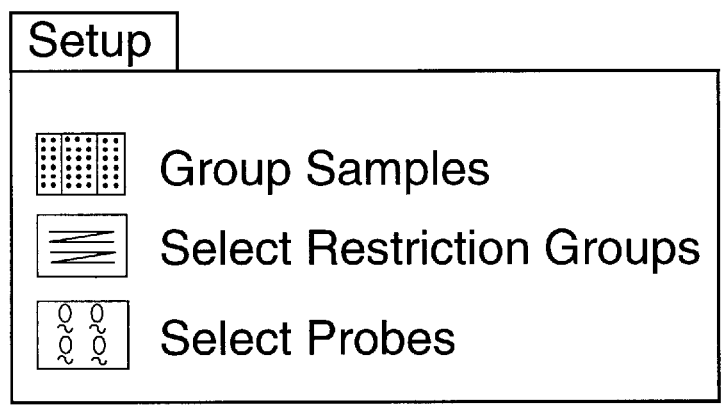
FIG. 18 shows a Setup menu.

Other aspects of the system can be implemented in the iconic language as well. For example, a Setup menu shown in FIG. 18 can be used to provide an ability to easily specify using the keyboard or mouse certain arrangements for the equipment of the AL controlled by a Proto program such as Blotter. Similar setup functions could be programmed for a Proto program operating an entirely different piece of automated equipment, such as a machine tool. Also, the system can be programmed so that by selecting Group Samples from the Setup menu, the system displays the dialog window of FIG. 19. This is an example of a window that is used to represent physical features of the apparatus. For example, the 8 by 12 array of positions in FIG. 19, identified by numbered columns and letters for rows, can be used to represent a 96 position vial tray that is used in the AL for samples. A user can change the groupings in the graphic array and also the labels for the groupings by the text fields. Clicking on OK can be used to save changes. The designations thus provided tell the system where to look for sample groups when called by icons in a process flow.

Similarly, the system can be programmed such that selecting Restriction Groups in the preferred embodiment displays the dialog window of FIG. 20. The text fields in the window are for an operator to use to identify certain groups of chemicals and enzymes to be used in a process sequence and to be available for loading from various positions in the AL. Four of the fields in the dialog window of FIG. 20 have scroll bars at one side. These fields are known as scrolling fields, and one can use the arrows and scroll bars to scroll through lists too long to display in the field in their entirety.

Figure 21:
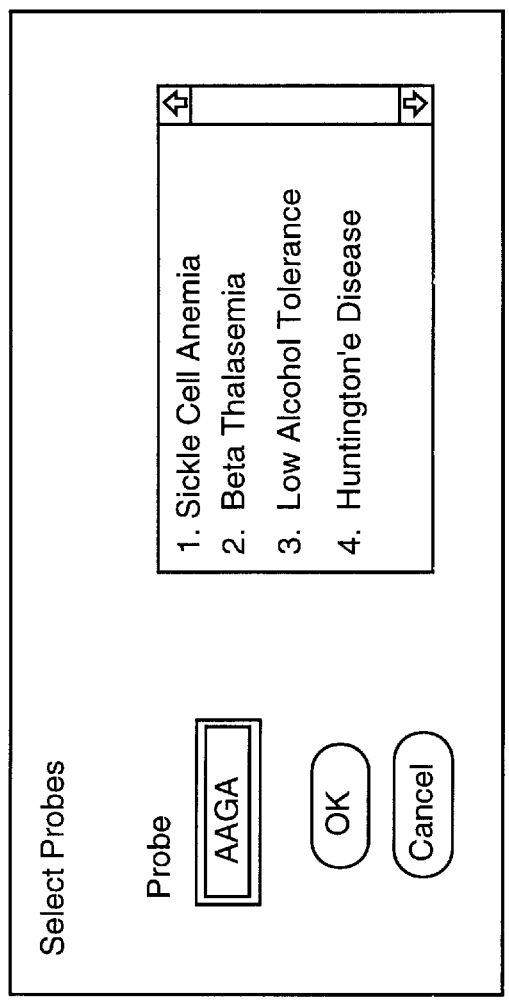
FIG. 21 shows a window for selecting Probes.

Similarly, the system can be programmed so that selecting Select Probes in the preferred embodiment displays the dialog window of FIG. 21. The Select Probes dialog window is for a user to identify probes relative to sample groups.

Figure 22:
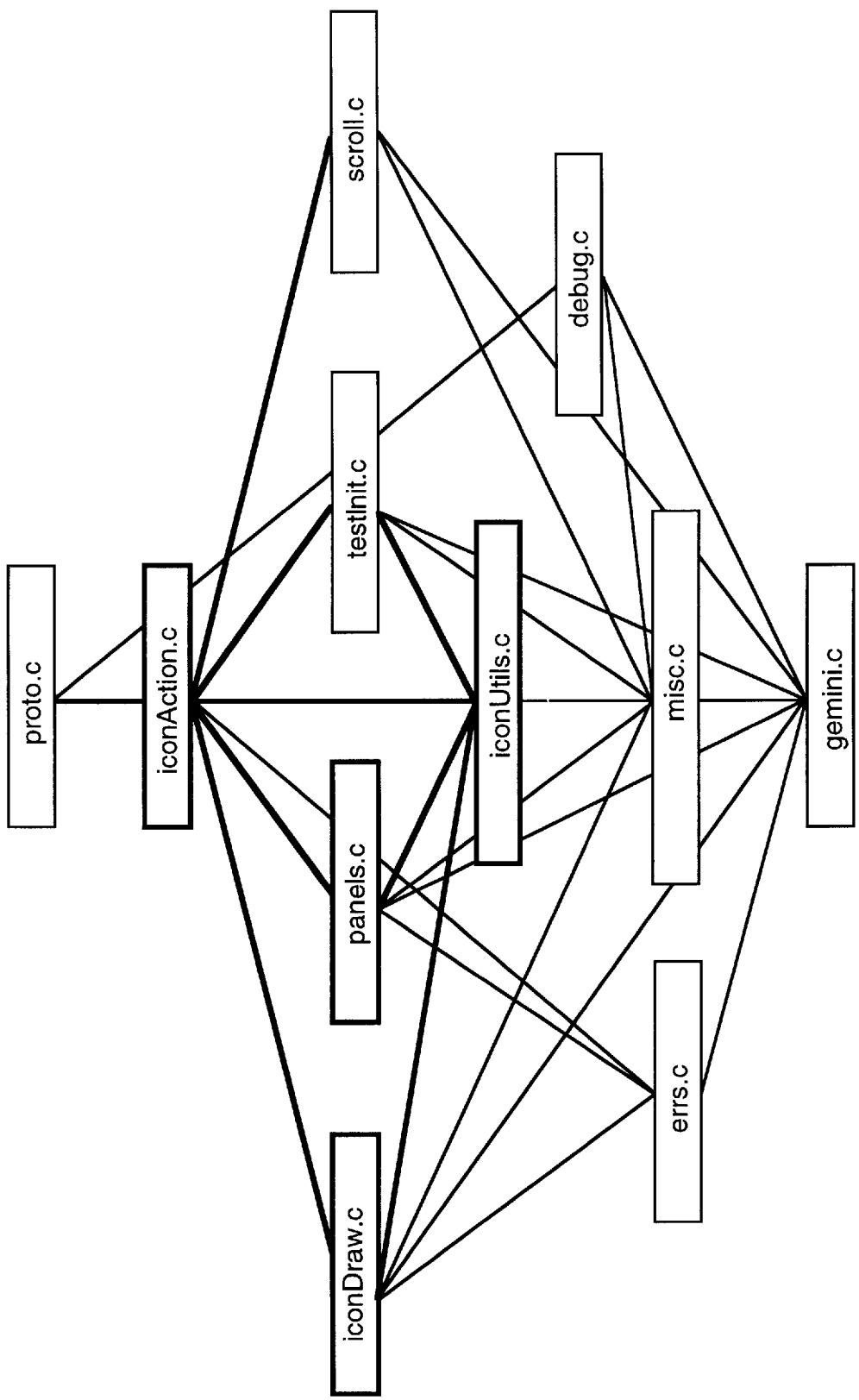
FIG. 22 shows a diagram of the code structure for the Proto programming language.

Appendix A provides an index to Proto with a brief explanation of each subroutine. Appendix B provides a listing of each of the implemented subroutines. FIG. 22 shows a diagram illustrating the Proto code structure.

It will be clear to one with skill in the art that although the many functions in the preferred embodiment have been described with reference to the Blotter process, many different chemical processes could be programmed for the AL in a similar way. It will be clear, too, that similar functions would be useful for automatic control of various other kinds of processes amenable to control by Proto. For example, in applying Proto to an NC milling machine, one could provide functions for relating certain tool bits with different tool holders and for plotting speeds and feeds for operation.

It will be apparent to one with skill in the art that there are many changes that may be made without departing from the spirit and scope of the invention. A software application program according to the invention may be programmed for any of a large number of different computers, so the invention is not restricted to the Apple Macintosh machines that will run the preferred embodiment described herein. Proto programs may also be prepared for a very large number of different kinds of process equipment, not just for the AL machine described herein as being operated by Proto. There are many, many kinds of icons that can be drawn, and the icons may or may not have text associated with them. There are similarly many ways one might implement and initiate specific functions in Proto, and still maintain the essentials of the invention. For example, the pull-dowm menus in the menu bar are not essential, but merely convenient. Pop Up menus that appear in response to keyboard commands, and other types, could also be used. There are a large variety of similar kinds of changes that could be made without departing from the spirit and scope of the invention.

APPENDIX A

Index to Proto

The source code is divided into the following sections:

| UNIT | FUNCTION |
|---|---|
| 1. Gemini.c | Gemini enables this source code to be used by either of two compilation systems, Macintosh Programmer's Workshop C and Think C. |
| 2. Misc.c | Misc supplies miscelleaneous low-level functions used frequently in other sections of the program. These utilties are generic C functions and macros which are not unique to this program. |
| 3. Debug.c | Debug supplies some debugging tools used elsewhere in the code. |
| 4. Scroll.c | Scroll provides utilities for handling scrolling and resizing of standard Macintosh windows. These scrolling routines are generic and not unique to this program. |
| 5. IconUtils.c | IconUtils provides utilities for creating, copying, deleting and building into hierarchically structured lists the underlying data structures for expandable nested icons. These utilities are used by the other PopFrames code modules. |
| 6. Panels.c | Panels provides the functions needed to draw and respond to user actions in control panels, the type of view which is created when a step icon is expanded. |
| 7. IconDraw.c | IconDraw is the code which draws the expandable nested icons within their windows. Care has been taken in IconDraw to make it execute quickly by doing the least amount of work necessary each time drawing is required. These efficiencies are essential to the responsiveness needed to make the use of the program gratifying. |
| 8. IconAction.c | IconAction handles events initiated by the user: mouse presses, key presses, and menu commands such as cut, copy, and paste. IconAction also uses special techniques to ensure responsiveness to the user's actions. |
| 9. TestInit.c | TestInit enables the program to read a file of data in the form of indented text and parse the text to create from it a network of expandable nested icons. |
| 10. Proto.c | Proto provides the the basic functions that all Macintosh programs must have, doing initializations, handling menus, dispatching key and mouse events to other portions of the |

1 program, handling cut, copy and paste commands, and shutting down.

Module: gemini

Function: Other modules which include this file of C preprocessor directives can be compiled with either the MPW 3.0 C compiler or the Think 3.2 C compilers. Each of these compilers has features and conveniences for the programmer that the other does not and so it is desirable to make one's code usable via either compilation system.

Module: misc

Function: As the name implies, misc is a collection of miscellaneous functions and macros which are used throughout the remainder of the code. These functions and macros include those to find the height or width of a rectangle, the minimum or maximum of two numbers, and determine which color the user has selected for highlighting selection objects, among others.

Module:    errs

Function:  The functions in this module are used to test for error conditions and display to the user error codes generated by the Macintosh Operating System.

Module: scroll

Function: The scroll module contains code to handle resizeable scrolling windows based upon the Macintosh Window Manager. The functions provided by the scroll module include the creation, updating, sizing, panning, and zooming of windows.

Module:     iconUtils

Function:   The data structures and functions in the iconUtils module are the
            basic organization data and operations needed to make PopFrames
            work. The data structures defined in this module include:
            iconNode, the collection of data required to give an icon its place within
            its network, and to maintain its screen drawing dimensions, color,
            highlighting information, it's open or closed state and to link the icon with
            the programming function it represents.

iconData, the data structure which is used to contain the information
            which is unique to step icons (primitives) and process icons (macros
            containing other primitives and macros).

process, the data structure which contains information unique to
            process icons, their color, whether they represent a parallel or serial
            process, and the beginning and ending of a range of selected
            subprocesses, if any.

cPanel, the data structure which contains the information relevant to
            display and handle user interactions with control panels, the view
            presented to a user when a step icon is in the open state.

cItem, the data structure which contains information about the various
            control items contained within a control panel: pictures, editable and
            non-editable blocks of text, and popup menus.

The functions defined in iconUtils perform the actions of building and
            destroying networks of iconNodes and maintaining the context of the
            currently active icon window.

The functions set_context and restore_context enable quick
            access to essential data about the active ( topmost) icon window.

Icon network maintenance functions:
            new_node creates a new iconNode;
            attach_after appends an iconNode or network of iconNodes after a
                 specific node in a network;
            add_node creates an iconNode and splices it into a network of nodes.
            detach_node removes an iconNode from the network.
            kill_node destroys an iconNode and its associated data structures.
            kill_list destroys a network of iconNodes;
            copy_list duplicates a network of iconNodes.

Module: panels

Function: The code contained in the panels module defines the behavior of control panels, the opened state of those iconNodes which represent steps. These functions include initialization, parsing of panel description resources, drawing the control panel and responding to mouse clicks and keystrokes destined for control panels.

Module: iconAction

Function: The iconAction module coordinates all icon related functions and provides a high-level interface to icon windows.

`new_icon_window` creates a new window and associates with it information unique to windows which contain icon networks.

`do_content` takes a Macintosh event, such as a mouse movement or a key press and causes the correct action to occur within the icon window, such as opening or closing an icon or typing into a text editing field of a control panel.

The editing functions `cut_icon`, `copy_icon`, `paste_icon`, and `clear_icon` execute the standard Macintosh editing commands on iconNodes and networks of iconNodes.

`set_color` sets the background color of a process icon according to a user's preference.

`new_icon_node` appends a new iconNode of the indicated type after topmost highlighted icon in the network.

Module: testInit

Function: The testInit module parses a file of text and generates from it a network of icons. This enables descriptions of icon networks to be easily edited with text editor during the program development phase.

The function `test_init` takes the name of a icon description text file returns the icon network that can be generated from it and an error code indicating the success or failure of the operation.

Module: proto

Function: The proto module comprises the high-level activities common to all Macintosh applications. These are dispatching events such as mouse movements, keystrokes and menu selections to the parts of the program that can make use of them.

APPENDIX B

11/14/88 6:06 PM                    includes.h                                  Page 1

```
 1  /*
 2   * File Includes.h
 3   *
 4   * Header file for Proto, the User Interface Prototype
 5   *
 6   */
 7
 8  #ifndef __INCLUDES__
 9  #define __INCLUDES__
10
11  /* Allow Mac II features */
12  #ifndef __ALLNU__
13  #define __ALLNU__
14  #endif
15
16  #include "gemini.h"
17
18  #endif
```

12/21/88 4:01 PM                         gemini.h                                  Page 1

```
  1  /*******************************************************************************
  2      Copyright ©1988 by Applied Biosystems, Inc. All rights reserved.
  3  ********************************************************************************
  4  *
  5  *        File Name: gemini.h
  6  *
  7  *     Description: MPW & LSC Universal Source routines
  8  *
  9  *        Caveats: None.
 10  *
 11  *    Edit History: 88/ 8   Created by JHS.
 12  *                  88/11/10 Updated by HG
 13  *
 14  *******************************************************************************/
 15  #ifndef __GEMINI__
 16  #define __GEMINI__
 17
 18  #define NIL 0L
 19  #define CANCEL 2
 20
 21  /* define "pointers" to Pascal-, C-type strings: */
 22  #define PCHAR char
 23  #define CCHAR char
 24  /* usage:    PCHAR *s  /* s is intended to be a Pascal string (s[0] is length byte).  */
 25  /*           CCHAR *s  /* s is intended to be a C string (s[length] is null terminator). */
 26
 27
 28  #ifndef THINK_C
 29
 30  /*******************************************************************************
 31  *  M P W
 32  */
 33
 34  #define OK 1
 35  #define QD qd.
 36  #define PtoCstr p2cstr
 37  #define CtoPstr c2pstr
 38  #define DEBUGPSTR cDebugStr
 39  #define DEBUGCSTR  DebugStr
 40  #define STR255 Str255
 41  #define STRINGPTR StringPtr
 42  #define STRINGHANDLE StringHandle
 43  #define PT(p) (&(p))
 44  #define BITFIELD
 45  #define scrnActive  screenActive
 46
 47
 48  /*******************************************************************************
 49  *       MPW Includes
 50  */
 51
 52  /*==   #include <CType.h>  ==*/
 53  #include <Controls.h>
 54  #include <Desk.h>
 55  #include <Dialogs.h>
 56  #include <Errors.h>
 57  #include <Events.h>
 58  #include <Files.h>
 59  #include <Fonts.h>
 60  #include <Memory.h>
 61  #include <Menus.h>
 62  #include <OSUtils.h>
 63  #include <Palette.h>
 64  #include <Picker.h>
```

```
 65   #include <Quickdraw.h>
 66   #include <Resources.h>
 67   #include <Retrace.h>
 68   #include <Scrap.h>
 69   #include <SegLoad.h>
 70   #include <Serial.h>
 71   #include <Strings.h>
 72   #include <Textedit.h>
 73   #include <Toolutils.h>
 74   #include <Traps.h>
 75   #include <Types.h>
 76   #include <Windows.h>
 77
 78
 79   #else
 80
 81   /*******************************************************************************
 82    *   Lightspeed C
 83    */
 84
 85   #include <strings.h>
 86   #include <SerialDvr.h>
 87   #include <color.h>
 88
 89   #define p2cstr PtoCstr
 90   #define c2pstr CtoPstr
 91   #define iBeamCursor 1
 92   #define QD
 93   #define DEBUGPSTR DebugStr
 94   #define DEBUGCSTR(s) CtoPstr(s);DebugStr(s);PtoCstr(s);
 95   #define PT(p) (p)
 96   #define BITFIELD short
 97   #define screenActive scrnActive
 98
 99   #define nil 0L
100   #define false 0
101   #define true 1
102
103   #define String(size) struct {unsigned char length; unsigned char text[size];}
104   typedef String(255) STR255,*STRINGPTR,**STRINGHANDLE;
105
106       /* All Cap Routines in MPW avoid glue; define them here for LightSpeed: */
107
108   /* from Controls.h */
109   #define FINDCONTROL FindControl
110   #define TRACKCONTROL TrackControl
111
112   /* from Files.h */
113   #define GETVOL   GetVol
114   #define SETVOL   SetVol
115   #define FSOPEN FSOpen
116   #define CREATE Create
117   #define GETFINFO GetFInfo
118   #define SETFINFO SetFInfo
119
120   /* from Fonts.h (complete) */
121   #define GETFONTNAME GetFontName
122   #define GETFNUM     GetFNum
123   /* from Dialogs.h */
124   #define SETITEXT       SetIText
125   #define GETITEXT       GetIText
126   #define PARAMTEXT      ParamText
127
128   /* from Quickdraw.h */
```

12/21/88 4:01 PM　　　　　　　　　　　gemini.h　　　　　　　　　　　Page 3

```
129   #define DRAWSTRING  DrawString
130   #define STRINGWIDTH StringWidth
131   #define GETCOLOR GetColor
132   #define PTINRECT    PtInRect
133
134   /* from Packages.h */
135   #define SFGETFILE   SFGetFile
136   #define SFPUTFILE   SFPutFile
137   #define NUMTOSTRING NumToString
138   #define STRINGTONUM StringToNum
139
140   /* from Menus.h  (complete) */
141   #define APPENDMENU  AppendMenu
142   #define NEWMENU     NewMenu
143   #define SETITEM     SetItem
144   #define GETITEM     GetItem
145   #define INSMENUITEM InsMenuItem
146   #define MENUSELECT  MenuSelect
147
148   /* from ToolUtils.h */
149   #define SETSTRING        SetString
150   #define NEWSTRING        NewString
151   #define GETINDSTRING     GetIndString
152   #define OPENDESKACC      OpenDeskAcc
153
154   /* from Windows.h */
155   #define GROWWINDOW       GrowWindow
156   #define DRAGWINDOW       DragWindow
157   #define TRACKGOAWAY      TrackGoAway
158   #define FINDWINDOW       FindWindow
159   #define DRAGGRAYRGN      DragGrayRgn
160   #define TRACKBOX         TrackBox
161
162   /* from TextEdit.h */
163   #define TECLICK          TEClick
164
165
166   #endif
167   #endif
```

12/19/88 3:43 PM  misc.h  Page 1

```
1   /**************************************************************************
2       Copyright ©1988 by Applied Biosystems, Inc. All rights reserved.
3   ***************************************************************************
4   *
5   *       File Name: misc.h
6   *
7   *       Description: Header for misc.c, miscellaneous routines for Mac Applications.
8   *
9   *       Caveats: None.
10  *
11  *       Edit History: 88/8/1 Created by HG
12  *
13  ***************************************************************************/
14
15
16  /**************************************************************************
17  *   Preprocessor Directives
18  */
19  #ifndef __MISC__
20  #define __MISC__
21
22  /* Character codes */
23  #define CR       13
24  #define ENTER    3
25  #define TAB      9
26  #define SPACE    32
27
28
29  /**************************************************************************
30  *   Include Files
31  */
32  #include "includes.h"
33
34
35  /**************************************************************************
36  *   Macros
37  */
38  #define HIWORD(aLong)       (((aLong) >> 16) & 0xFFFF)
39  #define LOWORD(aLong)       ((aLong) & 0xFFFF)
40  #define ABS(n)              (((n) < 0) ? (-(n)) : (n))
41  #define MIN(n, m)           (((n) < (m)) ? (n) : (m))
42  #define MAX(n, m)           (((n) > (m)) ? (n) : (m))
43  #define WIDTH(rectangle)    ((rectangle).right - (rectangle).left)
44  #define HEIGHT(rectangle)   ((rectangle).bottom - (rectangle).top)
45  #define HCENTER(rectangle)  (((rectangle).left + (rectangle).right) / 2)
46  #define VCENTER(rectangle)  (((rectangle).top + (rectangle).bottom) / 2)
47
48  /* Inline SetRect() macro, efficient when (rectp) is a constant.
49   * Must not be used if (rectp) has side effects.
50   */
51  #define SETRECT(rectp, _left, _top, _right, _bottom)    \
52      (rectp)->left = (_left), (rectp)->top = (_top),     \
53      (rectp)->right = (_right), (rectp)->bottom = (_bottom)
54
55
56  /**************************************************************************
57  *   Structures and Typedefs
58  */
59
60
61  /**************************************************************************
62  *   Scope
63  */
64  extern SysEnvRec    environs;
```

12/19/88 3:43 PM                                misc.h                                    Page 2

```
65
66
67  /**********************************************************************************
68   *   Prototypes
69   */
70  short   init_environs(void);
71  void    global_rect(Rect *r);
72  void    offset_point(Point *p, short h, short v);
73  Boolean bright(RGBColor *rgb);
74  void    hilightcolor(WindowPtr wPtr, RGBColor *rgb);
75  void    set_text(Handle t, STR255 *s);
76  void    set_Str255(StringHandle h, STR255 *s);
77  Boolean shallow_depth(WindowPtr wPtr);
78  void    get_origin(Point *p);
79
80
81  #endif
```

11/8/88 3:56 PM                               misc.c                                    Page 1

```
 1  /******************************************************************************
 2      Copyright ©1988 by Applied Biosystems, Inc. All rights reserved.
 3  ******************************************************************************
 4  *
 5  *       File Name: misc.c
 6  *
 7  *    Description: Miscellaneous routines for Mac Applications.
 8  *
 9  *        Caveats: None.
10  *
11  *    Edit History: 88/8/1 Created by HG
12  *
13  ******************************************************************************/
14
15
16  /******************************************************************************
17  *   Preprocessor Directives
18  */
19
20
21  /******************************************************************************
22  *   Include Files
23  */
24  #include "misc.h"
25
26
27  /******************************************************************************
28  *   External References
29  */
30
31
32  /******************************************************************************
33  *   Structures and Typedefs
34  */
35
36
37  /******************************************************************************
38  *   Static Objects
39  */
40  SysEnvRec    environs;
41
42
43
```

11/8/88 3:56 PM                               misc.c                                    Page 2

```
44   /*******************************************************************************
45    * Function name:    init_environs -- Initializes the environs global struct.
46    *
47    *   Description:    Gets a version one system environment record.
48    *
49    *        Inputs:    none
50    *
51    *       Outputs:    SysEnvRec   Fills out this record.
52    *
53    *        Return:    short       an error code, noErr means we got an environment record
54    *
55    *******************************************************************************/
56
57   short init_environs()
58
59   {
60       OSErr   err;
61
62       /* The 1 passed to SysEnvirons means we're requesting the environs record
63        * for the Mac II era, circa 1988.
64        */
65       err = SysEnvirons(1, &environs);
66
67       /* It's not an error if a newer, larger environment record is available, because
68        * the portion we're concerned with will be returned regardless of whatever
69        * new versions are created in the future.
70        */
71       if (err == envSelTooBig)
72           err = noErr;
73
74       return err;
75   }
76
77
78
```

```
11/8/88 3:56 PM                           misc.c                                    Page 3

79   /*******************************************************************************
 80    * Function name:    global_rect -- changes a rect from local to global coordinates.
 81    *
 82    *   Description:    GlobalRect does to rects what LocalToGlobal does to points.
 83    *                   Just like LocalToGlobal, GlobalRect uses the current grafPort
 84    *                   as the reference to the local coordiate system.
 85    *
 86    *       Inputs:     r           Rect to be put into global coordinates
 87    *
 88    *       Outputs:    r           Ditto.
 89    *
 90    *       Return:     void
 91    *
 92    *******************************************************************************/
 93
 94   void global_rect(r)
 95
 96   Rect    *r;
 97
 98   {
 99
100       GrafPtr         gp;     /* The current port for local coordinates. */
101       Rect            bounds; /* portbits.bounds for converting to global coordinates. */
102
103       GetPort(&gp);
104
105       /* Determine the offset to use to convert to global coordinates. */
106       if ((gp->portBits.rowBytes) && 0xC000)                        /* Color grafPort ? */
107           bounds = (*(((CGrafPtr)gp)->portPixMap))->bounds;         /* Use the PixMap */
108       else
109           bounds = gp->portBits.bounds;                             /* Use the BitMap */
110
111       OffsetRect(r, -bounds.left, -bounds.top);   /* Equivalent to a LocalToGlobal on a rect. */
112       return;
113   }
114
115
116
117
```

```
118  /************************************************************************
119   * Function name:    offset_point -- offsets a point in both X and Y directions.
120   *
121   *   Description:    Like OffsetRect except for points.
122   *
123   *       Inputs:     p          a pointer to a Point
124   *                   h          horizontal offset to apply to point pointed to by p
125   *                   v          vertical offset to apply to point pointed to by p
126   *
127   *       Outputs:    p          point pointed by p is changed
128   *
129   *       Return:     void
130   *
131   ************************************************************************/
132
133  void offset_point(p,h,v)
134
135  Point   *p;
136  short   h;
137  short   v;
138
139  {
140       p->h += h;
141       p->v += v;
142       return;
143  }
144
145
146
```

```
11/8/88 3:56 PM                         misc.c                                    Page 5

147  /*****************************************************************************
148   * Function name:    bright - determines if an RGB color is bright.
149   *
150   *   Description:    Bright returns true iff the passed RGBColor is as bright or
151   *                   brighter than 50% gray.
152   *
153   *       Inputs:     rgb         a pointer to a Point
154   *                   h           horizontal offset to apply to point pointed to by p
155   *                   v           vertical offset to apply to point pointed to by p
156   *
157   *       Outputs:    p           point pointed by p is changed
158   *
159   *       Return:     Boolean
160   *
161   *****************************************************************************/
162
163  Boolean bright(rgb)
164
165  RGBColor        *rgb;
166
167  {
168      HSVColor    hsv;
169
170      RGB2HSV(rgb,&hsv);              /* Let the color picker convert to hue, saturation, brightness */
171      return(hsv.value && 0x8000);    /* high bit set means more than 50% brightness */
172  }
```

```
177  /*******************************************************************************
178   * Function name:    hilightcolor - returns highlight color as chosen by user.
179   *
180   *   Description:    Hilightcolor is needed to find out which color the user prefers to use
181   *                   for hilighting. The hilight color is stored in the grafVars of the
182   *                   grafport belonging to the window pointed to by wPtr.
183   *
184   *       Inputs:     wPtr        Pointer to the window in question
185   *
186   *       Outputs:    rgb         RGBColor pointed to by rgb
187   *
188   *       Return:     void
189   *
190   *******************************************************************************/
191
192  void hilightcolor(wPtr,rgb)
193
194  WindowPtr   wPtr;
195  RGBColor    *rgb;
196
197  {
198      CGrafPtr    cg;
199      GrafVars    **gv;
200
201      cg = (CGrafPtr) wPtr;           /* Get the windows color graf port. */
202      gv = cg->grafVars;              /* Get the grafport's graf variables. */
203      *rgb = (*gv)->rgbHiliteColor;   /* Get the hilite color from the grafvars. */
204
205      return;
206  }
207
208
209
```

```
210  /*******************************************************************************
211   * Function name:    set_text - Sets a text handle to the contents of a Str255.
212   *
213   *   Description:    Set_text sets a previously allocated text handle to the
214   *                   Pascal string passed in s.
215   *
216   *       Inputs:     t         an allocated handle containing zero or more bytes
217   *                   s         an Str255
218   *
219   *       Outputs:    t         the contents of handle t are changed
220   *
221   *       Return:     void
222   *
223   *******************************************************************************/
224
225  void set_text(t, s)
226
227  Handle    t;
228  Str255    *s;
229
230  {
231      long    len;
232
233      len = s->length;
234      SetHandleSize(t, len);
235      HLock(t);
236          BlockMove(s->text, *t, len);
237      HUnlock(t);
238  }
239
240
241
```

11/8/88 3:56 PM misc.c Page 8

```
242   /****************************************************************************
243    * Function name:    shallow_depth - returns true iff window intersects a b&w only GDevice.
244    *
245    *   Description:    shallow_depth returns true if the environs indicate that
246    *                   color QuickDraw isn't available on this machine, or if the current
247    *                   window's CGrafPort intersects a GDevice with only one bit of color
248    *                   depth. This is basically a kludge to circumvent a difficulty with
249    *                   mapping RGBcolors to their correct Black or White values on one
250    *                   bit devices.
251    *
252    *       Inputs:     wPtr       an icon window
253    *
254    *       Outputs:    Boolean    true if any GDevice used by the window has a depth of one.
255    *
256    *   Side Effects:              May cause heap objects to be moved.
257    *
258    *       Return:     Boolean
259    *
260    ****************************************************************************/
261
262   Boolean shallow_depth(wPtr)
263
264   WindowPtr wPtr;
265
266   {
267       Rect            wRect;
268       Rect            gdRect;
269       GDHandle        gdh;
270       Boolean         singleBit;
271       PixMapHandle    gdpm;
272       PixMapHandle    wpm;
273       Rect            bounds;
274       long            n;
275
276       if (!environs.hasColorQD)       /* If it's not a color machine... */
277           singleBit = true;           /* ...then it can't have a depth greater than one. */
278       else
279           {
280           wRect = wPtr->portRect;
281           wpm = ((CGrafPtr)wPtr)->portPixMap;
282           bounds = (*wpm)->bounds;
283           OffsetRect(&wRect, -bounds.left, -bounds.top);  /* Align to multiscreen coordinates. */
284
285           /* Step through the device list and compare the window's aligned portrect */
286           /* to each of the devices. When the device's rectangle and the window's rectangle */
287           /* overlap check to see if the device has a depth of one. If any device has a depth */
288           /* of one, then do all drawing in black and white. This is simply a kludge, because */
289           /* Palette Manager seems to be not performing to spec when it comes to mapping */
290           /* color calls to one-bit deep devices. (Circa System 6.0.2) */
291
292           gdh = GetDeviceList();
293           singleBit = false;
294           do{
295               if ((TestDeviceAttribute(gdh, screenDevice)) && (TestDeviceAttribute(gdh, screenActive)))
296                   {
297                   gdRect = (*gdh)->gdRect;
298                   gdpm = (*gdh)->gdPMap;
299                   n = (*gdpm)->pixelSize;              /* Device's color depth */
300
301                   if (SectRect(&wRect,&gdRect,&gdRect))   /* Device used by this window? */
302                       singleBit = (n == 1);
303                   }
304               gdh = GetNextDevice(gdh);
              }while((gdh) && (!singleBit));
```

```
11/8/88 3:56 PM                       misc.c                                    Page 9
306              }
307     return(singleBit);
308
309  }
310
311
312
```

11/18/88 12:02 PM                       errs.h                              Page 1

```
1  /**********************************************************************************
2   *    Copyright ©1988 by Applied Biosystems, Inc. All rights reserved.
3   **********************************************************************************
4   *
5   *      File Name: errs.h
6   *
7   *      Description: Header for errs.c
8   *
9   *      Caveats: None.
10  *
11  *    Edit History: 11 Nov 88 Created by HG
12  *
13  **********************************************************************************/
14
15 #ifndef __ERRS__
16 #define __ERRS__
17
18 /**********************************************************************************
19  *   Preprocessor Directives
20  */
21
22 #define WARNALRT 666
23
24
25 /**********************************************************************************
26  *   Include Files
27  */
28 #include "includes.h"
29
30
31 /**********************************************************************************
32  *   External References
33  *   none
34  */
35
36
37 /**********************************************************************************
38  *   Structures and Typedefs
39  *   none
40  */
41
42
43 /**********************************************************************************
44  *   Static Objects
45  *   none
46  */
47
48
49 /**********************************************************************************
50  *   Function Prototypes
51  */
52 #ifdef THINK_C
53 void warn(OSErr err);
54 void failnil(char* p);
55 #endif
56
57 #endif
```

10/21/88 4:57 PM　　　　　　　　　　　errs.c　　　　　　　　　　　　　　　　Page 1

```
 1  /******************************************************************************
 2        Copyright ©1988 by Applied Biosystems, Inc. All rights reserved.
 3  *******************************************************************************
 4  *
 5  *       File Name: errs.c
 6  *
 7  *       Description: Simple error handling functions for Mac Applications.
 8  *
 9  *          Caveats: None.
10  *
11  *       Edit History: 21 Oct 88 Created by HG
12  *
13  ******************************************************************************/
14
15
16  /******************************************************************************
17   *   Preprocessor Directives
18   */
19
20  #define WARNALRT 666
21
22
23  /******************************************************************************
24   *   Include Files
25   */
26  #include <types.h>
27  #include <errors.h>
28  #include <dialogs.h>
29
30
31  /******************************************************************************
32   *   External References
33   *   none
34   */
35
36
37  /******************************************************************************
38   *   Structures and Typedefs
39   *   none
40   */
41
42
43  /******************************************************************************
44   *   Static Objects
45   *   none
46   */
47
48
49
```

10/21/88 4:57 PM                              errs.c                              Page 2

```
50  /************************************************************************************
51   * Function name:    warn -- puts up an Alert with an error number.
52   *
53   *   Description:    Warns the user via an Alert if the error code passed in err
54   *                   is non-zero.
55   *
56   *        Inputs:    err         an error code of type OSErr
57   *
58   *       Outputs:    none
59   *
60   *        Return:    void
61   *
62   ************************************************************************************/
63
64  void warn(err)
65
66  OSErr       err;
67
68  {
69      short       n;
70      Str255      s;
71
72      if (err)
73          {
74              NumToString(err,&s);
75              PARAMTEXT(&s,"\p","\p","\p");
76              n = CautionAlert(WARNALRT,NULL);
77          };
78  }
79
80
81
82
```

10/21/88 4:57 PM                           errs.c                                          Page 3

```
 83  /*******************************************************************************
 84   * Function name:    failnil -- warns if a handle or pointer is nil.
 85   *
 86   *   Description:    Warns the user via an Alert if the handle or pointer code passed in p
 87   *                   is zero.
 88   *
 89   *       Inputs:     p           a pointer or handle
 90   *
 91   *       Outputs:    none
 92   *
 93   *       Return:     void
 94   *
 95   *******************************************************************************/
 96
 97  void failnil(p)
 98
 99  Ptr     p;
100
101  {
102      if (!p)
103          {
104          warn(memFullErr);
105          /* ExitToShell; */
106          };
107  }
108
109
```

11/18/88 5:27 PM debug.h Page 1

```
1   /************************************************************************
2       Copyright ©1988 by Applied Biosystems, Inc. All rights reserved.
3   ************************************************************************
4   *
5   *   File Name: debug.h
6   *
7   *   Description: Debugging utilities.
8   *
9   *   Caveats: None.
10  *
11  *   Edit History: 21 Oct 88 Converted from Pascal by HG
12  *
13  ************************************************************************/
14
15
16  /************************************************************************
17  *   Preprocessor Directives
18  */
19  #ifndef __DEBUG__
20  #define __DEBUG__
21
22  #define MODEMOUT -7
23  #define MODEMIN -6
24
25
26  /************************************************************************
27  *   Include Files
28  */
29  #include <strings.h>
30  #include "includes.h"
31  #include "misc.h"
32
33
34  /************************************************************************
35  *   Structures and Typedefs
36  *   none
37  */
38
39
40  /************************************************************************
41  *   Macros
42  *   none
43  */
44
45
46  /************************************************************************
47  *   Function Prototypes
48  */
49  OSErr open_debug_serial(void);
50  OSErr open_debug_file(void);
51  void opendebug(void);
52  void closedebug(void);
53  void debugwrite(Str255 *s);
54
55
56
57  #endif
```

10/25/88 10:09 AM  debug.c  Page 1

```
1   /******************************************************************************
2    *  Copyright ©1988 by Applied Biosystems, Inc. All rights reserved.
3    *******************************************************************************
4    *
5    *      File Name: debug.c
6    *
7    *      Description: Simple debugging functions for Mac Applications.
8    *
9    *      Caveats: None.
10   *
11   *      Edit History: 21 Oct 88 Converted from Pascal by HG
12   *
13   ******************************************************************************/
14
15
16  /******************************************************************************
17   *  Preprocessor Directives
18   */
19
20
21  /******************************************************************************
22   *  Include Files
23   */
24  #include "debug.h"
25
26
27  /******************************************************************************
28   *  External References
29   *  none
30   */
31
32
33  /******************************************************************************
34   *  Structures and Typedefs
35   *  none
36   */
37
38
39  /******************************************************************************
40   *  Static Objects
41   */
42  static short    debugFRef;  /* reference number for debugging file */
43  static OSErr    debugErr;   /* error code returned by file manager */
44
45
46
```

10/25/88 10:09 AM                              debug.c                                              Page 2

```
47   /*******************************************************************************
48    * Function name:    open_debug_serial -- Opens the modem port for debugging information
49    *
50    *   Description:    Modem port is opened to handle debugging information. Useful when
51    *                   a terminal is connected to the development Macintosh.
52    *
53    *       Inputs:     none
54    *
55    *       Outputs:    none
56    *
57    *       Return:     OSErr   First non-zero error code encountered.
58    *
59    *******************************************************************************/
60
61   OSErr open_debug_serial()
62
63   {
64       OSErr       err;
65       SerShk      flags;
66
67       debugFRef = MODEMOUT;              /* Modem (port A) output */
68       err = RAMSDOpen(sPortA);
69       if (!err)
70           {
71               err = SerReset(debugFRef, data8+baud9600+noParity+stop10);
72               if (!err)
73                   {
74                       err = SerReset(MODEMIN, data8+baud9600+noParity+stop10);
75                       if (!err)
76                           {
77                               flags.fXOn  = 1;        /* Xon/Xoff enabled */
78                               flags.fCTS  = 0;        /* Clear to Send disabled */
79                               flags.xOn   = (char) 11; /* Xon = vertical tab */
80                               flags.xOff  = (char) 13; /* Xoff = return */
81                               flags.errs  = 0;
82                               flags.evts  = 0;
83                               flags.fInX  = 1;        /* enables xOn/xOff */
84                               flags.fDTR  = 0;
85                               err = SerHShake(debugFRef, &flags);
86                               if (!err)
87                                   err = SerHShake(MODEMIN, &flags);
88                           }
89                   }
90           }
91       return(err);
92   }
93
94
95
```

10/25/88 10:09 AM　　　　　　　　　　　　　　　　debug.c　　　　　　　　　　　　　　　　　　　　Page 3

```
 96   /******************************************************************************
 97   * Function name:    open_debug_file -- Opens the debugging file for output
 98   *
 99   *   Description:    The debugging file is opened and reset and the first error encountered
100   *                   or noErr is returned.
101   *
102   *       Inputs:     none
103   *
104   *       Outputs:    none
105   *
106   *       Return:     OSErr
107   *
108   ******************************************************************************/
109
110   OSErr open_debug_file()
111
112   {
113
114       OSErr       err;
115       short       vRefNum;
116       long        len;
117       Str255      name;
118
119       vRefNum = 0;
120
121       strcpy((char*)&name, "\pdebug.out");       /* Hard coded file name: "debug.out" */
122
123       err = CREATE(&name, vRefNum, 'MPS ', 'TEXT');
124
125       if ((!err) || (err == dupFNErr))           /* No need to create it if it already exists. */
126           {
127               err = FSOPEN(&name, vRefNum, &debugFRef);
128               if (err == opWrErr)                /* If it was left open, close it and reopen it. */
129                   {
130                       err = FSClose(debugFRef);
131                       if (!err)
132                           err = FSOPEN(&name, vRefNum, &debugFRef);
133                   }
134
135               if (!err)
136                   err = SetFPos(debugFRef, fsFromStart, 0);   /* Reset pointer to beginning of the file. */
137
138               if (!err)
139                   err = SetEOF(debugFRef, 0);                 /* Reset the EOF to zero. */
140           }
141
142       return(err);
143   }
144
145
146
```

10/25/88 10:09 AM    debug.c    Page 4

```
147  /********************************************************************************
148   * Function name:    opendebug -- Opens the debugging file or serial port
149   *
150   *   Description:    If SERIAL is true then the modem port is opened for receiving
151   *                   debugging information, otherwise the debugging file is opened and
152   *                   reset.
153   *
154   *     Inputs:       none
155   *
156   *     Outputs:      none
157   *
158   *     Return:       void
159   *
160   ********************************************************************************/
161
162  void opendebug()
163
164  {
165  #ifdef DEBUG
166
167  #ifdef SERIAL
168
169          /* Debugging messages go to the modem port. */
170          debugErr = open_debug_serial();
171  #else
172
173          /* Debugging messages go to a file. */
174          debugErr = open_debug_file();
175
176  #endif
177
178          /* For either serialport or file output warn if errors are encountered. */
179          warn(debugErr);
180
181  #endif
182  }
183
184
185
```

10/25/88 10:09 AM	debug.c	Page 5

```
186  /**********************************************************************************
187   * Function name:    closedebug -- Closes the debugging file or serial port
188   *
189   *   Description:    If SERIAL is true then the modem port is closed,
190   *                   otherwise the debugging file is closed.
191   *
192   *       Inputs:     none
193   *
194   *       Outputs:    none
195   *
196   *       Return:     void
197   *
198   **********************************************************************************/
199
200  void closedebug()
201
202  {
203  #ifdef DEBUG
204  #ifdef SERIAL
205          RAMSDClose(sPortA);
206  #else
207          debugErr = FSClose(debugFRef);
208          debugFRef = 0;                  /* Set file ref num to a harmless value. */
209  #endif
210  #endif
211  }
212
213
214
```

10/25/88 10:09 AM                              debug.c                                    Page 6

```
215  /********************************************************************************
216   * Function name:   debugwrite -- Closes the debugging file or serial port
217   *
218   *   Description:    If SERIAL is true then the modem port is closed,
219   *                   otherwise the debugging file is closed.
220   *
221   *       Inputs:     none
222   *
223   *       Outputs:    none
224   *
225   *       Return:     void
226   *
227   ********************************************************************************/
228
229  void debugwrite(s)
230
231  Str255  *s;
232
233  {
234
235  #ifdef DEBUG
236
237      Str255      ss;         /* Local copy of the string, so the passed one isn't changed. */
238      long        count;
239      char        c;
240
241      ss = *s;                            /* copy the string */
242      count = strlen(p2cstr(&ss));        /* convert from pascal string and get the length */
243
244      debugErr = FSWrite(debugFRef, &count, &ss);
245      if (!debugErr)                      /* Add a return character for readibility. */
246          {
247          c = CR;                         /* CR = carriage return = 13 */
248          count = 1;
249          debugErr = FSWrite(debugFRef, &count, &c);
250          }
251  #endif
252
253  }
254
255
```

11/16/88 6:26 PM                            scroll.h                                    Page 1

```
1   /******************************************************************************
2        Copyright ©1988 by Applied Biosystems, Inc. All rights reserved.
3   *******************************************************************************
4   *
5   *       File Name: scroll.h
6   *
7   *    Description: Header file for scroll.c. Support routines for scrollable, resizeable windows.
8   *
9   *       Caveats: None.
10  *
11  *    Edit History: 88/7/25 Converted from Pascal by HG
12  *
13  ******************************************************************************/
14
15
16  /******************************************************************************
17   *   Preprocessor Directives
18   */
19  #ifndef __SCROLL__
20  #define __SCROLL__
21
22  /* These constants serve as Control Refcons to differentiate between horiz. & vert.
23   * scrollbars as well as the option indicators for the MakeWindow function.
24   */
25  #define VSCROLL     1
26  #define HSCROLL     2
27  #define GROWBOX     4
28
29  /* pixels to scroll on mousedown in up/down arrows of scroll bars */
30  #define LINE_INC    48
31
32
33  /******************************************************************************
34   *   Include Files
35   */
36  #include "includes.h"
37  #include "misc.h"
38
39
40  /******************************************************************************
41   *   Structures and Typedefs
42   */
43
44  typedef struct wData{               /* Window's scrolling and sizing data structure */
45      Rect        usableArea;         /* Content region not occupied by controls */
46      Rect        imageRect;          /* Bounding rect for entire image, not just shown part. */
47      Point       curOrigin;          /* Current offset for scrolled windows. */
48      Boolean     growable;           /* False for fixed-size windows. */
49      Handle      more;               /* A handle for additional data structures. */
50  } wData, *wDataPtr, **wDataHdl;
51
52
53  /******************************************************************************
54   *   Macros
55   *     none
56   */
57
58
59  /******************************************************************************
60   *   Prototypes
61   */
62  void GetWindowData(WindowPtr wPtr, Rect *imageRect, Rect *usableArea, Point *curOrigin, Handle *more);
    void ScrollTheWindow(WindowPtr wPtr, short dh, short dv);
    void GrowTheWindow(WindowPtr wPtr, Point downPt, Rect *growRect);
```

11/16/88 6:26 PM                            scroll.h                                    Page 2

```
65    void ZoomTheWindow(WindowPtr wPtr);
66    void DoControls(WindowPtr wPtr, EventRecord *event);
67    WindowPtr MakeWindow(short id, short options, short kind, Handle more);
68    void HomeWindow(WindowPtr wPtr);
69    void SetImageArea(WindowPtr wPtr, Rect* newArea);
70    void DrawGrow(WindowPtr wPtr);
71    void UpdateTheWindow(WindowPtr  wPtr);
72    void DragImage(WindowPtr wPtr, EventRecord *event);
73    void InitScroll(void);
74
75    #endif
```

10/19/88 4:36 PM　　　　　　　　　　　　　　scroll.c　　　　　　　　　　　　　　　　Page 1

```
1   /***************************************************************************
2        Copyright ©1988 by Applied Biosystems, Inc. All rights reserved.
3   ****************************************************************************
4   *
5   *     File Name: scroll.c
6   *
7   *     Description: Support routines for scrollable, resizeable windows.
8   *
9   *        Caveats: None.
10  *
11  *     Edit History: 88/7/25 Converted from Pascal by HG
12  *
13  ****************************************************************************/
14
15
16  /***************************************************************************
17  *   Preprocessor Directives
18  *   see also scroll.h
19  */
20  /* mBarHeight is a low memory global pointing to a short containing current height
21   * of the menu bar.
22   */
23  #define MBARHEIGHT 0x0BAA
24
25  /* DRAGSLOP indicates the number of pixels of slop allowed before accepting that
26   * a drag has begun.
27   */
28  #define DRAGSLOP        5
29
30
31  /***************************************************************************
32  *   Include Files
33  */
34  #include "scroll.h"
35
36
37  /***************************************************************************
38  *   External References
39  */
40  /* Draw is a dispatcher to the drawing routines employed by
41   * each of the windows using the scroll routines.
42   */
43  extern void Draw(WindowPtr, Rect*);
44
45
46  /***************************************************************************
47  *   Structures and Typedefs
48  *   see also scroll.h
49  */
50  typedef struct twoRect{            /* Window's zooming data structure */
51      Rect        small;             /* Zoom in to this size */
52      Rect        big;               /* Zoom out to this size */
53  } twoRect, *twoRectPtr, **twoRectHdl;
54
55
56  /***************************************************************************
57  *   Static Objects
58  */
59  static short    start_part;        /* Globals needed to control scroll bars */
60  static short    page_inc;          /* Pixels to scroll on click in scrollbar's gray area. */
61  static short    **kinds = NULL;    /* A handle to the list of known windowKinds */
62
63
64
```

10/19/88 4:36 PM                                scroll.c                                Page 2

```
65   /*******************.   ***********************************.   ************************
66    * Function name:    fix_clip -- fixes clip region so that pictures may be saved
67    *
68    *   Description:    Sets the clipRgn of a window equal to the window's portrect to
69    *                   circumvent a bug in OpenPicture that causes a saved picture to be
70    *                   invisible. SeeTechNote #59.
71    *
72    *       Inputs:     wPtr           a pointer to the window with the clipRgn to be fixed.
73    *
74    *       Outputs:    wPtr->clipRgn  set to a rectangular region equal to wPtr->portRect
75    *
76    *       Return:     void
77    *
78    ********************************************************************************/
79
80   void fix_clip(wPtr)
81
82   WindowPtr    wPtr;
83
84   {
85       GrafPtr gp;        /* temporary storage for the current grafPort */
86
87       GetPort(&gp);
88       SetPort(wPtr);
89       ClipRect(&wPtr->portRect);
90       SetPort(gp);
91       return;
92   }
93
94
95
```

```
10/19/88 4:36 PM                              scroll.c                                    Page 3

96  /********************************************************************************
 97   * Function name:    get_type_control -- gets handle to a control of a particular type
 98   *
 99   *    Description:   Checks a window's entire control list for a control with a CRefCon field
100   *                   equal to cType. Returns control's ControlHandle and a function result
101   *                   of true if the control is found; nil and false otherwise.
102   *
103   *    Inputs:        wPtr          a pointer to the window in question
104   *                   cType         a control type identifier
105   *
106   *    Outputs:       ctrl *        a pointer to the ControlHandle or nil
107   *
108   *    Return:        Boolean       true iff the specified type of control was found
109   *
110   ********************************************************************************/
111
112  Boolean get_type_control(wPtr, cType, ctrl)
113
114  WindowPtr       wPtr;
115  short           cType;
116  ControlHandle   *ctrl;      /* pointer to found control or null */
117
118  {
119      Boolean              foundIt;    /* found the control in the window's control list */
120      register ControlHandle  c;       /* local copy of the ControlHandle for speed */
121
122      foundIt = false;
123      c = (ControlHandle) ((WindowPeek) wPtr)->controlList;
124
125      /* The statement below is equivalent to, and a bit faster than:
126       *
127       * while ((c != NULL) && !foundIt)
128       * {
129       *     if (GetCRefCon(c) == cType)
130       *         foundIt = true;
131       *     else
132       *         c = (*c)->nextControl;
133       * }
134       */
135
136      while ((c) && !(foundIt = (GetCRefCon(c) == cType)))
137          c = (*c)->nextControl;
138
139      *ctrl = c;
140      return(foundIt);
141  }
142
143
144
```

10/19/88 4:36 PM                                scroll.c                                            Page 4

```
145  /*******************************************************************************
146   * Function name:    GetWindowData -- returns the window's scrolling information
147   *
148   *   Description:    Function returns the image-bounding
149   *                   rectangle for a window.
150   *
151   *       Inputs:     wPtr            a pointer to the window in question
152   *
153   *       Outputs:    imageRect       Entire image, in image's own coordinates
154   *                   usableArea      Bounds of window's usable area, in window's coordinates
155   *                   curOrigin       Offset of two coordinate systems
156   *                   more            additional data for window
157   *
158   *       Return:     void
159   *
160   *******************************************************************************/
161
162  void GetWindowData(wPtr, imageRect, usableArea, curOrigin, more)
163
164  WindowPtr       wPtr;           /* Window in question */
165  Rect            *imageRect;
166  Rect            *usableArea;
167  Point           *curOrigin;
168  Handle          *more;
169
170  {
171      register wDataPtr    wdp;   /* Make it quick */
172
173      wdp = *((wDataHdl) GetWRefCon(wPtr));   /* get local copies of the rects */
174      *imageRect = wdp->imageRect;
175      *usableArea = wdp->usableArea;
176      *curOrigin = wdp->curOrigin;
177      *more = wdp->more;
178      return;
179  }
180
181
182
```

```
10/19/88 4:36 PM                              scroll.c                                    Page 5

183  /*******************************************************************************
184   * Function name:   move_scroll_bars -- adjusts window's scroll bars after a resize
185   *
186   *   Description:   Aligns either or both vertical and horizontal scroll bars to the edge
187   *                  of the window. Does nothing if the window has no scroll bars.
188   *
189   *      Inputs:     wPtr          a pointer to the window in question
190   *
191   *      Outputs:    contrlRect    bounding rectangles of window's scroll bars
192   *
193   *      Return:     void
194   *
195   *******************************************************************************/
196
197  void move_scroll_bars(wPtr)
198  WindowPtr     wPtr;
199
200  {
201      ControlHandle  ctrl;       /* control being resized */
202      Rect           pr;         /* window's current portrect*/
203      Rect           crect;      /* bounds of the scrollbar */
204      short          w, h;       /* control's width & height */
205
206      pr = wPtr->portRect;
207
208      /* Note the "magic numbers" in this routine assume a standard grow box
209       * of 13 pixels.
210       */
211
212      /* Resize the vertical scroll bar, if present. */
213      if (get_type_control(wPtr, VSCROLL, &ctrl))
214          {
215          HideControl(ctrl);
216          crect = (*ctrl)->contrlRect;
217          w = WIDTH(crect); /*crect.right - crect.left */
218          MoveControl(ctrl, pr.right - w + 1, pr.top - 1);   /* overlap window by one pixel. */
219          SizeControl(ctrl, w, HEIGHT(pr) - 13);             /* 13 is height of growbox */
220          ShowControl(ctrl);
221          }
222
223      /* Resize horizontal scroll bar, if present. */
224      if (get_type_control (wPtr, HSCROLL, &ctrl))
225          {
226          HideControl(ctrl);
227          crect = (*ctrl)->contrlRect;
228          h = HEIGHT(crect); /* crect.bottom - crect.top; */
229          MoveControl(ctrl, pr.left - 1, pr.bottom - h + 1); /* overlap window by one pixel. */
230          SizeControl(ctrl, WIDTH(pr) - 13, h);              /* 13 is width of grow box */
231          ShowControl(ctrl);
232          }
233      return;
234  }
235
236
237
```

```
10/19/88 4:36 PM                         scroll.c                                    Page 6

238  /**********************************************************************************
239   * Function name:    get_w_rects -- get the usableArea and imageRect for a window.
240   *
241   *   Description:    Fetches the usableArea and imageRect for a window.
242   *
243   *       Inputs:     wPtr       a pointer to the window in question
244   *
245   *       Outputs:    usable     window's usableArea field
246   *                   image      window's imageRect field
247   *
248   *       Return:     void
249   *
250   **********************************************************************************/
251
252  void get_w_rects(wPtr, image, usable)
253
254  WindowPtr       wPtr;
255  Rect            *image;
256  Rect            *usable;
257
258  {
259      register    wDataPtr        wdp;        /* pointer to window's data */
260
261      wdp = *((wDataHdl) GetWRefCon(wPtr));   /* get local copies of the rects */
262      *image = wdp->imageRect;
263      *usable = wdp->usableArea;
264      return;
265  }
266
267
268
```

10/19/88 4:36 PM                    scroll.c                                    Page 7

```
269  /*****************************************************************************
270   * Function name:    set_scroll_max -- adjusts window's scroll bars' maximum value
271   *
272   *   Description:    Sets the maximum value for the vertical and horizontal scroll bars,
273   *                   if present. Used after a window is resized. Causes the scroll bars
274   *                   to be redrawn.
275   *
276   *       Inputs:     wPtr        a pointer to the window in question
277   *
278   *       Outputs:    contrlMax   max values for horizontal an vertical scroll bars
279   *
280   *       Return:     void
281   *
282  *****************************************************************************/
283
284  void set_scroll_max(wPtr)
285
286  WindowPtr      wPtr;
287
288  {
289      short           v_or_h;    /* selects control type */
290      short           max;       /* new maximum value */
291      ControlHandle   ctrl;      /* affected control */
292      RgnHandle       clip;      /* temporary storage for window's clipRgn */
293      Rect            image;     /* local copy of window's imageRect */
294      Rect            usable;    /* local copy of window's usableArea */
295
296      clip = NewRgn();           /* clip to whole port */
297      GetClip(clip);
298      ClipRect(&wPtr->portRect);
299
300      get_w_rects(wPtr, &image, &usable);
301
302      /* If a vertical scroll bar is present, set its max value. */
303      if (get_type_control(wPtr, VSCROLL, &ctrl))
304          {
305          max = HEIGHT(image) - HEIGHT(usable);
306          SetCtlMax(ctrl, (max < 0 ? 0 : max));
307          }
308
309      /* If a horizontal scroll bar is present, then set its max value */
310      if (get_type_control(wPtr ,HSCROLL, &ctrl))
311          {
312          max = WIDTH(image) - WIDTH(usable);
313          SetCtlMax(ctrl, (max < 0 ? 0 : max));
314          }
315
316      /* Now reset the clip region */
317      SetClip(clip);
318      DisposeRgn(clip);
319      return;
320  }
321
322
323
```

10/19/88 4:36 PM　　　　　　　　　　　　　　　　scroll.c　　　　　　　　　　　　　　　　　　　Page 8

```
324  /******************************************************************************
325   * Function name: scroll_control -- scrolls a window to match the setting of a scrollbar
326   *
327   *   Description:  Scrolls the window to match the setting of one of its scroll bars.
328   *                 Used after a scrollbar has processed a mousedown event.
329   *
330   *   Inputs:    ctrl        a scrollbar
331   *
332   *   Outputs:   contrlMax   max values for horizontal an vertical scroll bars
333   *
334   *   Return:    void
335   *
336   ******************************************************************************/
337
338  void scroll_control(ctrl)
339
340  ControlHandle       ctrl;      /* a vertical or horizontal scroll bar */
341
342  {
343      WindowPtr       wPtr;       /* the window which owns the scroll bar */
344      GrafPtr         gp;         /* temp storage for current grafport */
345      short           delta_h;    /* scrolling distance in the X dimension */
346      short           delta_v;    /* scrolling distance in the Y dimension */
347      wDataHdl        wdh;        /* handle to window's data */
348      wData           wd;         /* local copy of window's data */
349      RgnHandle       scrolledRgn; /* scrolled area needing updating */
350      short           cVal;       /* control's current value */
351      RgnHandle       updateRgn;  /* window's update region before scrolling begins */
352
353      wPtr = (*ctrl)->contrlOwner;   /* extract needed control information */
354      cVal = GetCtlValue(ctrl);
355
356      wdh = (wDataHdl) GetWRefCon(wPtr);
357      wd = **wdh;
358      GetPort(&gp);
359      SetPort(wPtr);
360
361      if (GetCRefCon(ctrl) == VSCROLL)        /* Derive the delta and new origin values. */
362          {
363          delta_h = 0;
364          delta_v = wd.curOrigin.v - cVal;
365          wd.curOrigin.v = cVal;
366          }
367      else
368          {
369          delta_v = 0;
370          delta_h = wd.curOrigin.h - cVal;
371          wd.curOrigin.h = cVal;
372          }
373
374      /* Scroll the visible portion of the screen */
375      scrolledRgn = NewRgn();
376      ScrollRect(&wd.usableArea, delta_h, delta_v, scrolledRgn);
377
378      /* Offset the UpdateRgn to match if it's not empty. */
379      updateRgn = ((WindowPeek)wPtr)->updateRgn;
380      if (!EmptyRgn(updateRgn))
381          OffsetRgn(updateRgn, delta_h, delta_v);
382
383      InvalRgn(scrolledRgn);     /* Now add the new stuff to the updateRgn */
384      DisposeRgn(scrolledRgn);
385
386      (*wdh)->curOrigin = wd.curOrigin;   /* save the new origin */
387      SetPort(gp);                        /* restore the current port */
```

```
388        return;
389    }
390
391
392
```

10/19/88 4:36 PM						scroll.c						Page 10

```
393   /*****************************************************************************
394   * Function name:    scroll_it -- changes a scrollbar's value and scrolls the screen
395   *
396   *   Description:    Takes a scroll bar type and a delta value; adjusts the scroll bar
397   *                   by the delta value and scrolls the window to the new value. To
398   *                   prevent annoying and unnessary redrawing of the control, values which
399   *                   are out of range for the control are filtered by this routine rather
400   *                   than letting SetCtrlValue do the filtering.
401   *
402   *       Inputs:     wPtr            Window that owns the control
403   *                   v_or_h          scrollbar type (VSCROLL or HSCROLL)
404   *                   delta           change in controls value
405   *
406   *       Outputs:    contrlVal       values for the scroll bar
407   *                                   causes screen to be updated
408   *
409   *       Return:     void
410   *
411   *****************************************************************************/
412
413   void scroll_it(wPtr, v_or_h, delta)
414
415   WindowPtr   wPtr;
416   short       v_or_h;
417   short       delta;
418
419   {
420       ControlHandle       ctrl;       /* the scroll bar */
421       short               cMin;       /* its minimum */
422       short               cVal;       /* its starting value */
423       short               cMax;       /* its maximum */
424       short               newVal;     /* its new value */
425
426       if (delta != 0)
427           {
428           if (get_type_control(wPtr, v_or_h, &ctrl))
429               {
430               cMin = GetCtlMin(ctrl);
431               cVal = GetCtlValue(ctrl);
432               cMax = GetCtlMax(ctrl);
433               newVal = cVal + delta;
434               newVal = ( (newVal > cMax) ? cMax : newVal);
435               newVal = ( (newVal < cMin) ? cMin : newVal);
436
437               if (newVal != cVal)
438                   {
439                   SetCtlValue(ctrl, newVal);
440                   scroll_control(ctrl);
441                   }
442               }
443           }
444       return;
445   }
446
447
448
```

```
10/19/88 4:36 PM                            scroll.c                                     Page 11
449  /**********************************************************************************
450   * Function name: ScrollTheWindow -- changes a scrollbar's value and scrolls the screen
451   *
452   *   Description:    Scrolls the window by the amounts dh and dv.
453   *
454   *       Inputs:     wPtr            Window to be scrolled
455   *                   dh              horizontal delta
456   *                   dv              vertical delta
457   *
458   *       Outputs:    scrollbars      may change values for the window's scroll bars
459   *                                   may cause window to be updated
460   *
461   *       Return:     void
462   *
463   **********************************************************************************/
464
465  void ScrollTheWindow(wPtr, dh, dv )
466
467  WindowPtr       wPtr;
468  short           dh;
469  short           dv;
470
471  {
472      scroll_it(wPtr, HSCROLL, dh);
473      scroll_it(wPtr, VSCROLL, dv);
474      return;
475  }
476
477
478
```

```
10/19/88 4:36 PM                              scroll.c                                    Page 12

479  /****************************************************************************
480   * Function name:    backpedal -- scrolls image to fill window's bottom right hand corner
481   *
482   *   Description:    Backpedal scrolls the image down and to the right if the window's
483   *                   usableArea extends beyond the image in these directions and the image
484   *                   is not already fully scrolled in these directions. Used by resize
485   *                   to ensure that the viewing area of the window contains as much of the
486   *                   image as possible.
487   *
488   *   Inputs:         wPtr            Window to be scrolled
489   *
490   *   Outputs:        scrollbars
491   *                   curOrigin       scrolls imageRect with respect to usableArea
492   *
493   *   Return:         void
494   *
495   ****************************************************************************/
496
497  void backpedal(wPtr)
498
499  WindowPtr       wPtr;
500
501  {
502      wDataHdl        wdh;    /* Handle to window's data */
503      wData           wd;     /* local copy of window's data */
504      ControlHandle   ctrl;   /* a scroll bar */
505      short           gap;    /* gap to be corrected by backpedling */
506
507      wdh = (wDataHdl) GetWRefCon(wPtr);
508      wd = **wdh;
509
510      if (get_type_control(wPtr, VSCROLL, &ctrl)) /* Backpedal downwards, if needed. */
511          {
512          gap = HEIGHT(wd.imageRect) - (wd.curOrigin.v + HEIGHT(wd.usableArea));
513          if (gap < 0)
514              {
515              SetCtlValue(ctrl, GetCtlMax(ctrl));
516              scroll_control(ctrl);
517              }
518          }
519
520      if (get_type_control(wPtr, HSCROLL, &ctrl)) /* Backpedal to the right, if needed. */
521          {
522          gap = WIDTH(wd.imageRect) - (wd.curOrigin.h + WIDTH(wd.usableArea));
523          if (gap < 0)
524              {
525              SetCtlValue(ctrl, GetCtlMax(ctrl));
526              scroll_control(ctrl);
527              }
528          }
529      return;
530  }
531
532
533
```

10/19/88 4:36 PM                    scroll.c                                    Page 13

```
534  /*******************************************************************************
535   * Function name:    resize -- resizes a window
536   *
537   * Description:      Resizes a window to a new width and height. Updates the window's
538   *                   usableArea rects, resizes controls, backpedals image if needed.
539   *                   Updates the window with minimal redrawing.
540   *
541   *   Inputs:         wPtr            Window to be scrolled
542   *
543   *   Outputs:        scrollbars      resized, get new values
544   *                   curOrigin       may scroll imageRect with respect to usableArea
545   *                   usableArea      resized
546   *                                   may cause update of image
547   *
548   *   Return:         void
549   *
550   *******************************************************************************/
551
552  void resize(wPtr, w, h)
553
554  WindowPtr       wPtr;
555  short           w;
556  short           h;
557
558  {
559      wDataHdl        wdh;        /* handle to window's data */
560      Rect            r;          /* scratch rectangle */
561      Rect            oldpr;      /* original portrect */
562      Rect            newpr;      /* resized portrect */
563      Rect            usable;     /* usableArea */
564      GrafPtr         gp;         /* to restore thePort */
565      RgnHandle       scrollRgn;  /* old scroll bars and grow icon to be invalidated */
566      ControlHandle   ctrl;       /* vert or horiz scrollbars */
567
568      GetPort(&gp);
569      SetPort(wPtr);
570      wdh = (wDataHdl) GetWRefCon(wPtr);
571
572      /* Get rid of old scroll bars and grow icon. */
573      oldpr = wPtr->portRect;
574      usable = (*wdh)->usableArea;
575      r = oldpr;
576      r.left = usable.right;
577      InvalRect(&r);              /* Invalidate vert. scroll & grow box */
578      r = oldpr;
579      r.top = usable.bottom;
580      InvalRect(&r);              /* Invalidate horiz. scroll bar & (redundantly) grow box */
581
582      /* Now resize the window*/
583      SizeWindow(wPtr, w, h, true);
584      fix_clip(wPtr);
585      newpr = wPtr->portRect;
586
587      /* Reset usable area rectangle in window data. */
588      usable.right = newpr.right;
589      usable.bottom = newpr.bottom;
590
591      /* Test for presence of scrollbars and set usable area accordingly. */
592      if (get_type_control(wPtr, VSCROLL, &ctrl))
593          r = (**ctrl).contrlRect,
594          usable.right -= WIDTH(r) - 1;
595
596      if (get_type_control(wPtr, HSCROLL, &ctrl))
597          r = (**ctrl).contrlRect,
```

```
10/19/88 4:36 PM                          scroll.c                              Page 14
598             usable.bottom -= HEIGHT(r) - 1;
599
600     (**wdh).usableArea = usable;    /* save the new value of usableArea */
601
602     /* adjust scroll bars and backpedal image, if needed. */
603     set_scroll_max(wPtr);
604     move_scroll_bars(wPtr);
605     backpedal(wPtr);
606
607     /* Force a redraw on the new grow box. */
608     r = newpr;
609     r.top = r.bottom - 15; /* height of growbox */
610     r.left = r.right - 15; /* width of growbox */
611     InvalRect(&r);
612
613     SetPort(gp);
614     return;
615  }
616
617
618
```

```
10/19/88 4:36 PM                          scroll.c                              Page 15

619  /*******************************************************************************
620   * Function name: set_user_zoom -- sets the smaller of the zoom rects for a window
621   *
622   *   Description:   A function to reset the user-selected zoom size
623   *                  to the window's current size and position.
624   *
625   *      Inputs:     wPtr           Window to be scrolled
626   *
627   *      Outputs:    small zoom rect Window's small zoom rect is found in the windowPeek
628   *                                  dataHandle
629   *
630   *      Return:     void
631   *
632   *******************************************************************************/
633
634  void set_user_zoom(wPtr)
635
636  WindowPtr      wPtr;
637
638  {
639      twoRectHdl     tr;    /* a construct to reference a window's zoom rectangles */
640      Rect           r;     /* scratch rectangle */
641
642      tr = (twoRectHdl)(((WindowPeek) wPtr)->dataHandle);
643      if (tr != NULL)
644          {
645          r = wPtr->portRect;
646          global_rect(&r);   /* Equivalent to a LocalToGlobal on a rect. */
647
648          (*tr)->small = r;
649
650          }
651      return;
652  }
653
654
655
```

```
10/19/88 4:36 PM                          scroll.c                                Page 16

656  /***********************************************************************************
657   * Function name:    set_default_zoom -- Sets the default zoom rectangle for a window.
658   *
659   *   Description:    A function to reset the user-selected zoom size
660   *                   to the window's current size and position.
661   *
662   *       Inputs:     wPtr            Window to be affected
663   *
664   *       Outputs:    big zoom rect   Window's big zoom rect is found in the windowPeek
665   *                                   dataHandle
666   *
667   *       Return:     void
668   *
669   ***********************************************************************************/
670
671  void set_default_zoom(wPtr)
672
673  WindowPtr       wPtr;
674
675  {
676      Rect        r;              /* scratch rectangle */
677      twoRectHdl  tr;             /* a construct to reference a window's zoom rectangles */
678      RgnHandle   grayRgn;        /* all of the Mac's desktop, may span multiple screens */
679      GDHandle    maxGD;          /* a handle to the deepest (most colors) screen device */
680      short       *mBarHeight;    /* a pointer to low-memory global mBarHeight */
681      short       n;
682
683      /* Set default zoom to be the full screen on the deepest monitor, (color only.) */
684      if (environs.hasColorQD)
685          {
686          grayRgn = GetGrayRgn();     /* color version */
687          r = (*grayRgn)->rgnBBox;
688          maxGD = GetMaxDevice(&r);   /* default to using the screen with the most colors */
689          r = (*maxGD)->gdRect;
690          }
691      else
692          r = qd.screenBits.bounds;   /* B & W version */
693
694      /* Find out how tall the menu bar is on this machine. */
695      mBarHeight = (short *) MBARHEIGHT;
696
697      r.top += *mBarHeight + 20;  /* 20 is height of titlebar on a document window. */
698      InsetRect(&r, 4, 4);        /* Inset by 4 pixels on all sides */
699
700      tr = (twoRectHdl)(((WindowPeek) wPtr)->dataHandle);
701      if (tr != NULL)
702          (*tr)->big = r;
703
704      return;
705  }
706
707
708
```

```
709  /******************************************************************************
710  * Function name: GrowTheWindow -- Handles a mouseDown in the growBox.
711  *
712  *   Description:    A procedure to resize a window in response to a
713  *                   mouseDown event in its growBox. Tracks the user's dragging of the
714  *                   grayed window outline and calls resize to do all the housekeeping
715  *                   to reset the window's data to the new size.
716  *
717  *   Inputs:     wPtr            Window to be scrolled
718  *
719  *   Outputs:                    Alter's grafport, window data record, window's zoom
720  *                               rects;
721  *
722  *   Return:     void
723  *
724  ******************************************************************************/
725
726  void GrowTheWindow(wPtr, downPt, growRect)
727
728  WindowPtr       wPtr;
729  Point           downPt;
730  Rect            *growRect;      /* pointer to window's growing/shrinking limits rectangle */
731
732  {
733
734      long        newsize;    /* size code returned by GrowWindow */
735      short       w;          /* new width */
736      short       h;          /* new height */
737
738      newsize = GrowWindow(wPtr, &downPt, growRect);     /* Tracks the mousedown, returns new size. */
739      w = LOWORD(newsize);
740      h = HIWORD(newsize);
741      resize(wPtr, w, h);             /* Handles all resizing, redrawing, invalidating. */
742      set_user_zoom(wPtr);            /* Sets the user's zoom selection to the new size. */
743      return;
744  }
745
746
747
```

```
10/19/88 4:36 PM                        scroll.c                              Page 18

748  /******************************************************************************
749   * Function name: ZoomTheWindow -- Responds to click of Window's zoom box.
750   *
751   *   Description:    A procedure to toggle between the window's two
752   *                   zoom levels. The system call ZoomWindow will resize the
753   *                   window's grafPort, this procedure finishes the task
754   *                   by updating all the information affected by a resize of a window.
755   *
756   *   Inputs:     wPtr        Window to be zoomed
757   *
758   *   Outputs:                Alters all the data structures affected by a resize.
759   *
760   *   Return:     void
761   *
762   ******************************************************************************/
763
764  void ZoomTheWindow(wPtr)
765
766  WindowPtr     wPtr;
767
768  {
769      Rect          r;        /* newly zoomed size */
770
771      r = wPtr->portRect;
772
773      resize(wPtr, WIDTH(r), HEIGHT(r));
774      return;
775  }
776
777
778
```

```
779  /**********************************************************************************
780   * Function name: line_scroll -- handles mousedowns in arrows and gray bands of scrollbars.
781   *
782   *   Description:   line_scroll is called in response to a mousedown in a
783   *                  a scrollbar arrow button or page up/down areas. Changes the
784   *                  controls value by the appropriate amount, and scrolls the window.
785   *
786   *   Inputs:    ctrl          a vertical or horizontal scrollbar
787   *              part          the clicked-upon part of that scrollbar
788   *
789   *   Outputs:                 Alters all the data structures affected by a scroll.
790   *
791   *   Return:    void
792   *
793   *   Warning:   Called by a procPtr.
794   *
795   **********************************************************************************/
796
797  void line_scroll (ctrl, part)
798
799  ControlHandle     ctrl;
800  short             part;
801
802  {
803      short        was;     /* the scrollbar's original value. */
804      short        delta;   /* change in scrollbar's value */
805      Boolean      updir;   /* true iff up or left direction was pressed */
806      short        cmin;    /* control minimum */
807      short        cmax;    /* control maximum */
808      extern void UpdateTheWindow(WindowPtr); /* forward reference to window updating routine */
809
810      updir = ((part == inUpButton) || (part == inPageUp));
811      was = GetCtlValue(ctrl);
812      cmin = GetCtlMin(ctrl);
813      cmax = GetCtlMax(ctrl);
814
815      /* If it makes sense to change this control at all... */
816      if (((updir && (was > cmin)) || (!updir && (was < cmax))) && (part == start_part))
817          {
818          switch (part)
819              {
820              case (inUpButton) :
821                  delta = -LINE_INC;
822                  break;
823              case (inDownButton) :
824                  delta = LINE_INC;
825                  break;
826              case (inPageUp) :
827                  delta = -page_inc;
828                  break;
829              case (inPageDown) :
830                  delta = page_inc;
831                  break;
832              default :
833                  break;
834              } /* endswitch */
835
836          SetCtlValue(ctrl, (was + delta));
837          scroll_control(ctrl);
838
839          UpdateTheWindow((*ctrl)->contrlOwner); /* External reference to update mechanism. */
840          }
841      return;
842  }
```

10/19/88 4:36 PM  scroll.c  Page 20

```
843
844
845
```

10/19/88 4:36 PM     scroll.c     Page 21

```c
846  /*******************************************************************************
847   * Function name: DoControls -- handles events destined for window's scrollbars.
848   *
849   *   Description:    A procedure to handle events which belong to the
850   *                   scrollbars of a window.
851   *
852   *       Inputs:     wPtr            window in question
853   *                   event           pointer to event destined for a control of the window
854   *
855   *       Outputs:                    May alters all the data structures affected by a scroll.
856   *
857   *       Return:     void
858   *
859   *******************************************************************************/
860
861  void DoControls(wPtr, event)
862
863  WindowPtr       wPtr;
864  EventRecord     *event;  /* pointer to the event to be processed */
865
866  {
867      ControlHandle   ctrl;       /* scroll bar affected */
868      short           part;       /* part of scroll bar */
869      short           cKind;      /* type of control */
870      wDataHdl        wdh;        /* window's data handle */
871      Rect            u;          /* local copy of window's usableArea field */
872      Point           where;      /* where mousedown occurred in local coordinates */
873      extern void UpdateTheWindow(WindowPtr); /* forward reference to window updating routine */
874
875      if (event->what == mouseDown)
876          {
877          where = event->where;
878          GlobalToLocal(&where);
879          part = FINDCONTROL(where, wPtr, &ctrl);
880          start_part = part;                      /* static global for line_scroll */
881
882          if (part != 0)
883              {
884              cKind = GetCRefCon(ctrl);
885              if ((cKind == VSCROLL) || (cKind == HSCROLL))  /* A scrollbar? */
886                  {
887                  wdh = (wDataHdl) GetWRefCon(wPtr);
888                  u = (*wdh)->usableArea;
889
890                  /* Set the page increment to half the width or height according to scrollbar. */
891                  page_inc = ((cKind == VSCROLL) ? HEIGHT(u) : WIDTH(u)) / 2;
892
893                  if (part == inThumb)
894                      {
895                      if (TRACKCONTROL(ctrl, where, NULL) != 0)
896                          {
897                          scroll_control(ctrl);
898                          UpdateTheWindow(wPtr);
899                          }
900                      }
901                  else
902                      TRACKCONTROL(ctrl, where, line_scroll);  /* function pointer */
903                  }
904              }
905          }
906      return;
907  }
908
```

910

10/19/88 4:36 PM　　　　　　　　　　　　　　　scroll.c　　　　　　　　　　　　　　　　　　Page 23

```
911   /******************************************************************************
912    * Function name: w_make -- creates a window, allocates its data structures.
913    *
914    *   Description:    Takes a WIND resource identifier, gets a window, sets its
915    *                   windowKind field, allocates its window data structure
916    *
917    *   Inputs:     id          WIND resource id
918    *               kind        window's windowKind identifier
919    *               more        like a refCon field, more data for application's use
920    *
921    *   Outputs:                allocates a new window
922    *
923    *   Return:     WindowPtr
924    *
925    ******************************************************************************/
926
927   WindowPtr w_make(id, kind, more)
928
929   short       id;     /* window's WIND resource id */
930   short       kind;   /* window's windowKind field */
931   Handle      more;   /* additional window-specific data for the application's use. */
932
933   {
934       WindowPtr       wPtr;       /* newly created window */
935       wDataHdl        wdh;        /* handle to window's data */
936       wData           wd;         /* local copy of window's data */
937       Rect            r;          /* scratch rectangle */
938
939       wPtr = (environs.hasColorQD ? GetNewCWindow(id,NULL,(Ptr)-1L) : GetNewWindow(id,NULL,(Ptr)-1L));
940
941       fix_clip(wPtr);
942       ((WindowPeek) wPtr)->windowKind = kind;
943
944       wdh = (wDataHdl) NewHandle(sizeof(wData));
945       SetWRefCon(wPtr, (long) wdh);
946
947       /* Usable area is assumed to be whole port until scroll bars are added. */
948       wd.usableArea = wPtr->portRect;
949
950       SetRect(&r,0,0,0,0);            /* No image yet, so image rect is empty. */
951       wd.imageRect = r;
952
953       wd.growable = false;            /* Assume window isn't growable. */
954
955       wd.more = more;                 /* Store the additional data. */
956
957       wd.curOrigin.h = 0;             /* Current origin is assumed to be 0,0 */
958       wd.curOrigin.v = 0;
959
960       (**wdh) = wd;
961
962       set_default_zoom(wPtr);
963
964       return wPtr;
965
966   }
967
968
969
```

```
970  /**********************************************************************
971   * Function name: make_ctls -- creates scrollbars for a new window.
972   *
973   *   Description:    Adds scrollbars to a new window, adjusts usable area,
974   *                   marks scrollbars as vertical and horizontall.
975   *
976   *   Inputs:     wPtr            Window to receive scrollbars
977   *               h               if true, window gets a horizontal scroll bar
978   *               v               if true, window gets a vertical scroll bar
979   *
980   *   Outputs:                    Allocates new scrollbars, adds them to window's
981   *                               controlList.
982   *
983   *   Return:     void
984   *
985   **********************************************************************/
986
987  void make_ctls(wPtr, h, v)
988
989  WindowPtr       wPtr;
990  Boolean         h;
991  Boolean         v;
992
993  {
994      wDataHdl        wdh;    /* handle to window's data */
995      wData           wd;     /* local copy of window's data */
996      Rect            r;      /* scratch rectangle */
997      ControlHandle   ctrl;   /* a scroll bar */
998
999      wdh = (wDataHdl) GetWRefCon(wPtr);
1000     wd = **wdh;
1001
1002     /* Setup horizontal scroll bar */
1003     if (h)
1004         {
1005         r = wPtr->portRect;
1006         r.right -= 14;          /* overlap growbox by one pixel */
1007         r.left -= 1;            /* overlap window frame by one pixel */
1008         r.bottom += 1;          /* overlap bottom pixel */
1009         r.top = r.bottom - 16;  /* 16 is standard scrollbar width */
1010         ctrl = NewControl(wPtr, &r, "", true, 0, 0, 0, scrollBarProc, HSCROLL);
1011
1012         wd.usableArea.bottom -= 15; /* room for horiz. scroll */
1013         }
1014
1015     /* Set up vertical scroll bar */
1016     if (v)
1017         {
1018         r = wPtr->portRect;
1019         r.top -= 1;             /* overlap top pixel */
1020         r.right += 1;           /* overlap right pixel */
1021         r.left = r.right -16;   /* 16 pixels is standard scrollbar width */
1022         r.bottom -= 14;         /* overlap growbox by one pixel */
1023         ctrl = NewControl(wPtr, &r, "", true, 0, 0, 0, scrollBarProc, VSCROLL);
1024
1025         wd.usableArea.right -= 15;  /* room for vert scroll */
1026         }
1027
1028     (**wdh).usableArea = wd.usableArea;
1029
1030     set_scroll_max(wPtr);       /* Adjust the new scroll to window's image size */
1031
1032     return;
1033  }
```

10/19/88 4:36 PM            scroll.c                    Page 25

```
1034
1035
1036
```

10/19/88 4:36 PM	scroll.c	Page 26

```
1037  /*******************************************************************************
1038   * Function name: make_w_growable -- set the growable attribute for this window.
1039   *
1040   *    Description:    Sets the growable attribute for a window.
1041   *
1042   *        Inputs:     wPtr            Window in question
1043   *                    growable        true iff window is to be made growable
1044   *
1045   *        Outputs:                    sets growable field of window's data
1046   *
1047   *        Return:     void
1048   *
1049   *******************************************************************************/
1050
1051  void make_w_growable(wPtr, growable)
1052
1053  WindowPtr       wPtr;
1054  Boolean         growable;           /* growable attribute */
1055
1056  {
1057      wDataHdl        wdh;            /* handle to window's data */
1058
1059      wdh = (wDataHdl) GetWRefCon(wPtr);
1060      (*wdh)->growable = growable;
1061
1062      return;
1063  }
1064
1065
1066
```

10/19/88 4:36 PM                                    scroll.c                                         Page 27

```
1067   /*******************************************************************************
1068   * Function name:    my_kind -- tells if a windowKind is known to the scroll routines
1069   *
1070   *   Description:    Compares target windowKind value to a list of all windowKinds
1071   *                   used by MakeWindow. Result is true iff target is on the list
1072   *
1073   *       Inputs:     target        the windowKind we're wondering about
1074   *
1075   *       Outputs:    none
1076   *
1077   *       Return:     Boolean       true iff the specified windowKind was found
1078   *
1079   *******************************************************************************/
1080
1081   Boolean my_kind(target)
1082
1083   short       target;         /* target window's windowKind */
1084
1085   {
1086       short       *p;         /* pointer to list of window kinds */
1087       long        n;          /* number of windowKinds in the array. */
1088       Boolean     found;      /* true when a matching windowKind is found. */
1089       int         i;
1090
1091       n = GetHandleSize(kinds) / sizeof(short); /*Let the array do the scaling for us. */
1092       found = false;
1093       p = *kinds;
1094       for (i = 0; ((i < n) && !found); i++)
1095           found = (p[i] == target);
1096
1097       return(found);
1098   }
1099
1100
1101
```

```
10/19/88 4:36 PM                          scroll.c                                    Page 28

1102  /******************************************************************************
1103   * Function name:    register_window_kind -- registers a windowKind in list of windowKinds
1104   *
1105   *   Description:    If the value passed in wKind does not yet exist in the list of
1106   *                   known windowKinds contained in handle kinds, then its appended
1107   *                   to that list.
1108   *
1109   *   Inputs:     wKind       the windowKind value to be recorded.
1110   *
1111   *   Outputs:    kinds       static handle containing all known windowKinds
1112   *
1113   *   Return:     void
1114   *
1115   ******************************************************************************/
1116
1117  void register_window_kind(wKind)
1118
1119  short       wKind;      /* window's windowKind field. */
1120
1121  {
1122      long    n;      /* Size of kinds Handle */
1123      short   *p;     /* A pointer that looks at kinds as an array of 2-byte ints. */
1124      int     i;      /* Index to last element of kinds array. */
1125
1126      if (!my_kind(wKind))                /* Do we know about this kind already? */
1127      {
1128          if (kinds == NULL)              /* Is this the first kind to be registered? */
1129          {
1130              kinds = (Handle) NewHandle(sizeof(short));
1131              p = *kinds;
1132              *p = wKind;
1133          }
1134          else
1135          {
1136              n = GetHandleSize(kinds);
1137              SetHandleSize(kinds, n + sizeof(short));    /* Make room for it. */
1138              p = *kinds;
1139              i = n / sizeof(short) - 1;
1140              p[i] = wKind;                           /* Record the new windowKind. */
1141          }
1142      }
1143  }
1144
1145
1146
```

10/19/88 4:36 PM                           scroll.c                                    Page 29

```
1147  /*******************************************************************************
1148   * Function name: MakeWindow -- Creates a new window and sets it's data fields.
1149   *
1150   *    Description:    Creates a window with optional vertical
1151   *                    and horizontal scrollbars and growbox.
1152   *
1153   *    Inputs:     id          WIND resource id
1154   *                kind        windowKind identifier
1155   *
1156   *    Outputs:    wPtr        newly created window
1157   *
1158   *    Return:     WindowPtr
1159   *
1160   *******************************************************************************/
1161
1162  WindowPtr MakeWindow(id, options, kind, more)
1163
1164  short           id;             /* WIND resource id */
1165  short           options;        /* Optional parts: scrollbars, and growbox */
1166  short           kind;           /* windowKind field */
1167  Handle          more;           /* more data for window-specific information */
1168
1169  {
1170      wDataHdl        wdh;        /* handle to window's data */
1171      WindowPtr       w;          /* local copy of window pointer */
1172      Boolean         h;          /* true if window is to be horizontally scrollable. */
1173      Boolean         v;          /* true if window is to be vertically scrollable. */
1174
1175      w = w_make(id, kind, more);     /* Allocate the window */
1176
1177      register_window_kind(kind); /* Record that a window of this kind has been made. */
1178
1179      h = (options & HSCROLL);    /* Add it's scroll bars */
1180      v = (options & VSCROLL);
1181      make_ctls(w, h, v);
1182
1183      make_w_growable(w,(options & GROWBOX)); /* Add a resize box, if needed */
1184
1185      ShowWindow(w);              /* The Big Debut */
1186      return(w);
1187  }
```

```
10/19/88 4:36 PM                           scroll.c                                    Page 30

1191  /************************************************************************************
1192   * Function name: HomeWindow -- Restores a window to home position (scrolled to (0,0)).
1193   *
1194   *    Description:   Scrolls a window so that the top
1195   *                   left corner of its image is showing.
1196   *
1197   *    Inputs:     wPtr          Window in question
1198   *
1199   *    Outputs:                  affects all field affected by a scroll
1200   *
1201   *    Return:     void
1202   *
1203   ************************************************************************************/
1204
1205  void HomeWindow(wPtr)
1206
1207  WindowPtr       wPtr;
1208
1209  {
1210       ControlHandle   ctrl;
1211
1212       /* Reset the vertical scroll bar to 0. */
1213       if (get_type_control(wPtr, VSCROLL, &ctrl))
1214           {
1215           SetCtlValue(ctrl, 0);
1216           scroll_control(ctrl);
1217           };
1218
1219       /* Reset the horizontal scroll bar to 0. */
1220       if (get_type_control(wPtr, HSCROLL, &ctrl))
1221           {
1222           SetCtlValue(ctrl, 0);
1223           scroll_control(ctrl);
1224           };
1225       return;
1226  }
1227
1228
1229
```

10/19/88 4:36 PM　　　　　　　　　　　　　　　scroll.c　　　　　　　　　　　　　　　　　　Page 31

```
1230  /**********************************************************************************
1231   * Function name: SetImageArea -- Changes a window's image area.
1232   *
1233   *   Description:    Changes a window's imageRect to the
1234   *                   rectangle supplied. Use SetImageArea to let the window know
1235   *                   when the content it's displaying has changed shape.
1236   *
1237   *   Inputs:     wPtr            Window in question
1238   *               newArea         New rectangle to be used as the image rect
1239   *
1240   *   Outputs:    imageRect
1241   *
1242   *   Return:     void
1243   *
1244   **********************************************************************************/
1245
1246  void SetImageArea(wPtr, newArea)
1247
1248  WindowPtr       wPtr;
1249  Rect            *newArea;
1250
1251  {
1252      wDataHdl    wdh;        /* handle to window's data */
1253
1254      wdh = (wDataHdl) GetWRefCon(wPtr);
1255      (*wdh)->imageRect = *newArea;
1256
1257      set_scroll_max(wPtr);       /* scroll maximums may have changed. */
1258      backpedal(wPtr);            /* image may need backpedaling */
1259      return;
1260  }
1261
1262
1263
```

10/19/88 4:36 PM                              scroll.c                                    Page 32

```
1264  /******************************************************************************
1265   * Function name: DrawGrow -- Draws a window's grow icon.
1266   *
1267   *   Description:    Procedure to draw a window's grow icon if the window is marked as
1268   *                   growable.
1269   *
1270   *     Inputs:       wPtr            Window in question
1271   *
1272   *    Outputs:                       causes drawing to occur on the screen
1273   *
1274   *     Return:       void
1275   *
1276   ******************************************************************************/
1277
1278  void DrawGrow(wPtr)
1279
1280  WindowPtr       wPtr;
1281
1282  {
1283      if ((*(wDataHdl)GetWRefCon(wPtr))->growable)
1284          DrawGrowIcon(wPtr);
1285      return;
1286  }
1287
1288
1289
1290
```

10/19/88 4:36 PM　　　　　　　　　　　　　　　　　scroll.c　　　　　　　　　　　　　　　　　　　　Page 33

```
1291  /******************************************************************************
1292   * Function name:    draw_window -- draws scrolled windows
1293   *
1294   *   Description:    Draw_window prepares a window's grafport for the drawing of its
1295   *                   contents, then calls the external Draw routine to do the actual,
1296   *                   window-specific drawing, and finally resets the grafport to its
1297   *                   default state and draws growbox and scrollbars as appropriate.
1298   *
1299   *       Inputs:     wPtr            the window to be drawn
1300   *                   updateArea      bounding rectangle of the area to be redrawn
1301   *
1302   *       Outputs:    -               changes the on-screen appearance of a window
1303   *
1304   *       Return:     void
1305   *
1306   ******************************************************************************/
1307
1308  void draw_window(wPtr, updateArea)
1309
1310  WindowPtr       wPtr;           /* Window to be drawn. */
1311  Rect            *updateArea;    /* Bounding rectangle of update region in window's coordinates. */
1312
1313  {
1314      int             kind;       /* Window's windowKind field. */
1315      Point           curOrigin;  /* Current amount of scrolling in x and y dimensions. */
1316      Rect            useRect;    /* Window's useable area in window's coordinates. */
1317      Rect            update;     /* Local copy of the updateArea rectangle. */
1318      ControlHandle   ctrl;       /* A scrollbar's control handle */
1319      register wDataPtr wdp;      /* Make it quick */
1320
1321      wdp = *((wDataHdl) GetWRefCon(wPtr));       /* Acquire the relevant information. */
1322      curOrigin = wdp->curOrigin;
1323      useRect = wdp->usableArea;
1324      update = *updateArea;
1325
1326      SetOrigin(curOrigin.h, curOrigin.v);        /* Go to Image coordinates temporarily. */
1327      OffsetRect(&useRect, curOrigin.h, curOrigin.v);
1328      OffsetRect(&update, curOrigin.h, curOrigin.v);
1329      ClipRect(&useRect);                         /* Restrict drawing to the usable area. */
1330
1331      Draw(wPtr, &update);                        /* Call the general draw routine. */
1332
1333      SetOrigin(0,0);                             /* Return to screen coordinates. */
1334      ClipRect(&(wPtr->portRect));                /* Allow scrollbars to be drawn */
1335
1336      DrawGrow(wPtr);                             /* Draw the grow icon, if needed. */
1337
1338      if (get_type_control(wPtr, VSCROLL, &ctrl)) /* Drow the scrollbars, if they exist. */
1339          DrawlControl(ctrl);
1340
1341      if (get_type_control(wPtr, HSCROLL, &ctrl))
1342          DrawlControl(ctrl);
1343  }
1344
1345
1346
```

```
10/19/88 4:36 PM                            scroll.c                                        Page 34

1347    /*******************************************************************************
1348     * Function name:    UpdateTheWindow -- call in response to an update event for a window.
1349     *
1350     *   Description:    UpdateTheWindow does all action necessary for handling an update event
1351     *                   for a window created by MakeWindow. Eventually calls Draw, an external
1352     *                   routine that dispatches the drawing task to the drawing routines
1353     *                   appropriate for the particular window being updated.
1354     *
1355     *       Inputs:     wPtr            the window to be drawn
1356     *
1357     *       Outputs:    -               changes the on-screen appearance of a window
1358     *
1359     *       Return:     void
1360     *
1361     *******************************************************************************/
1362
1363    void UpdateTheWindow(wPtr)
1364
1365    WindowPtr   wPtr;                       /* Window in question. */
1366
1367    {
1368        Rect        r;                      /* A copy of the update region's bounding rectangle. */
1369
1370        BeginUpdate(wPtr);
1371        if (my_kind(((WindowPeek)wPtr)->windowKind))    /* If it was created by MakeWindow.. */
1372        {
1373            r = (*(wPtr->visRgn))->rgnBBox;             /* Get update rect for optimization. */
1374            draw_window(wPtr, &r);                      /* then draw it. */
1375        }
1376        EndUpdate(wPtr);
1377    }
1378
1379
1380
```

10/19/88 4:36 PM  scroll.c  Page 35

```c
1381  /***********************************************************************
1382   * Function name: DragImage -- Drags a window's contents.
1383   *
1384   *   Description:    Procedure to handle an event which is to be
1385   *                   interpreted as dragging the image within the usable area of the
1386   *                   window.
1387   *
1388   *   Inputs:     wPtr            Window in question
1389   *
1390   *   Outputs:                    causes drawing to occur on the screen
1391   *
1392   *   Return:     void
1393   *
1394   ***********************************************************************/
1395
1396  void DragImage(wPtr,event)
1397
1398  WindowPtr       wPtr;
1399  EventRecord     *event;
1400
1401  {
1402      Point           pt1, pt2;       /* begining and ending points of a drag */
1403      Boolean         moved;          /* true iff mouse moves more than 5 pixels */
1404      short           dh, dv;         /* deltas of a drag */
1405      ControlHandle   hctrl, vctrl;   /* scroll bars */
1406      short           hmax, vmax;     /* scroll bar max values */
1407      Rect            r;              /* local copy of usableArea */
1408
1409      r = (*(wDataHdl) GetWRefCon(wPtr))->usableArea;
1410      if (get_type_control(wPtr, VSCROLL, &vctrl) && get_type_control(wPtr, HSCROLL, &hctrl))
1411          {
1412          hmax = GetCtlMax(hctrl);
1413          vmax = GetCtlMax(vctrl);
1414
1415          pt1 = event->where;         /* place of original mouseDown */
1416          GlobalToLocal(&pt1);
1417
1418          moved = false;
1419          while (StillDown() && !moved)   /* check for dragging */
1420              {
1421              GetMouse(&pt2);
1422              moved = (ABS(pt2.h - pt1.h) > DRAGSLOP) || (ABS(pt2.v - pt1.v) > DRAGSLOP);
1423              }
1424
1425          if (moved)
1426              while (StillDown())     /* If user is dragging, then start moving image. */
1427                  {
1428                  GetMouse(&pt2);
1429                  dh = pt1.h - pt2.h;
1430                  dv = pt1.v - pt2.v;
1431
1432                  if (!PtInRect(&pt2,&r))     /* Autoscroll if user drags out of the window */
1433                      {
1434                      if (pt2.v < r.top)          /* test for vertical out-of-bounds */
1435                          dv = LINE_INC;
1436                      else if (pt2.v > r.bottom)
1437                          dv = -LINE_INC;
1438                      if (pt2.h < r.left)         /* test for horizontal out-of-bounds */
1439                          dh = LINE_INC;
1440                      else if (pt2.h > r.right)
1441                          dh = -LINE_INC;
1442                      }
1443                  if ((vmax != 0) && (dv != 0))
1444                      SetCtlValue(vctrl, (GetCtlValue(vctrl) + dv)),
```

```
10/19/88 4:36 PM                        scroll.c                              Page 36
1445                    scroll_control(vctrl);
1446
1447                if ((hmax != 0) && (dh != 0))
1448                    SetCtlValue(hctrl, (GetCtlValue(hctrl) + dh)),
1449                    scroll_control(hctrl);
1450
1451                pt1 = pt2;
1452                UpdateTheWindow(wPtr);
1453                }
1454            }
1455        return;
1456    }
1457
1458
```

```
10/19/88 4:36 PM                             scroll.c                                  Page 37

1459   /***********************************************************************************
1460   * Function name:    InitScroll -- Initializes the scrolling unit.
1461   *
1462   *   Description:    Calls init_evirons to set up the environs record.
1463   *
1464   *
1465   *      Inputs:     wPtr           Window in question
1466   *
1467   *      Outputs:                   causes drawing to occur on the screen
1468   *
1469   *      Return:     void
1470   *
1471   ***********************************************************************************/
1472
1473   void InitScroll()
1474   {
1475       short   err;
1476       err = init_environs();
1477       return;
1478   }
```

```
12/22/88 1:33 PM                         iconutils.h                              Page 1

1   /****************************************************************************
2       Copyright ©1988 by Applied Biosystems, Inc. All rights reserved.
3   ****************************************************************************
4   *
5   *       File Name: iconUtils.h
6   *
7   *       Description: Header for iconUtils.c, Utilities for icon editor windows.
8   *
9   *       Caveats: None.
10  *
11  *       Edit History: 25 October 88 Created by HG
12  *
13  ****************************************************************************/
14
15
16  /****************************************************************************
17  *   Preprocessor Directives
18  */
19  #ifndef __ICONUTILS__
20  #define __ICONUTILS__
21
22  /* Resource IDs */
23  /* Hand cursor */
24  #define HANDCURS 500
25
26  /* DEFAULT_ICON is substituted for any icon that can't be located. */
27  #define DEFAULT_ICON 2000
28
29  /* step icon id's fall in the range 1000 to 1999 */
30  #define STEP_ICON_RANGE    1000
31
32  /* process icon id's fall in the range 2000 to 2999 */
33  #define PROC_ICON_RANGE    2000
34
35  /* structural icon id's fall in the range 3000 to 3999 */
36  #define STRUC_ICON_RANGE   3000
37
38  /* Icon window kind identifier. */
39  #define ICONWKIND   128
40
41  /* Icon attributes */
42  #define KOPEN   1
43  #define KHILITE 2
44
45  /* Dimensions for drawing */
46  /* Inter-icon spacing constant, could be a user-controlled variable. */
47  #define MARGIN  12
48
49  /* Pixel dimensions of an opened frame's close box. */
50  #define CLOSEBOXSIZE    10
51
52  /* Width of hilight frame for opened icons. */
53  #define HILITEWIDTH    10
54
55  /* */
56  #define OPEN   1
57  #define CLOSE  2
58
59  /* Cursor key keycodes. */
60  #define DOWNKEY    0x1F
61  #define UPKEY      0x1E
62  #define LEFTKEY    0x1C
63  #define RIGHTKEY   0x1D
64
```

12/22/88 1:33 PM                           iconutils.h                                              Page 2

```
65
66  /*******************************************************************************
67   *   Include Files
68   */
69  #include "includes.h"
70
71
72  /*******************************************************************************
73   *   Macros
74   *   none
75   */
76
77
78
```

```
 79  /*******************************************************************************
 80   *   Structures and Typedefs
 81   */
 82  enum itemType { itemControl, itemEditText, itemStaticText, itemMenu, itemList, itemPict };
 83  enum iconType { iconStep, iconProcess };
 84
 85
 86  typedef struct editItemData {
 87        StringHandle    prelabel;
 88        StringHandle    theText;
 89        StringHandle    postlabel;
 90        Rect            editBox;
 91        TEHandle        teh;
 92  } editItemData;
 93
 94
 95  typedef struct menuItemData {
 96        MenuHandle      menu;
 97        short           selected;
 98        short           titlewidth;
 99        short           menuwidth;
100  } menuItemData;
101
102
103  /* Union cItemData contains some flavor of control panel item data. */
104  typedef union cItemData{
105        PicHandle       iPic;       /* picture */
106        editItemData    iEdit;      /* Edit text data */
107        menuItemData    iMenu;      /* Menu item's menu handle */
108        StringHandle    iText;      /* Static text */
109  } cItemData;
110
111
112  /* Control panel items. */
113  typedef struct cItem{
114        struct cItem    **next;     /* next item in list or null if this is the last one. */
115        struct cPanel   **panel;    /* panel to which this item belongs */
116        Rect            iBox;       /* controls position relative to topleft of frame */
117        long            iType;      /* control, editText, staticText, menu, list, pict */
118        cItemData       iData;      /* storage for the item itself (ControlHandle, MenuHandle etc.) */
119  } cItem, *cItemPtr, **cItemHdl;
120
121
122  /* Control panels are shown when a step icon is opened. */
123  typedef struct cPanel{
124        Rect            pBox;       /* bounds of a the panel, normalized to (0,0) */
125        StringHandle    name;       /* name of this step = text view step name */
126        cItemHdl        items;      /* list of panel's items */
127        struct iconNode **iNode;    /* it's parent node */
128  } cPanel, *cPanelPtr, **cPanelHdl;
129
130
131  /* procedure nodes contain this extra information */
132  typedef struct process {
133        RGBColor        backColor;  /* background color for opened state */
134        Boolean         split;      /* true if this node contains divergent paths */
135        short           selStart;   /* position of first selected descendent node */
136        short           selEnd;     /* position of last selected descendent node */
137  } process, *processPtr, **processHdl;
138
139
140  /* Union iData contains either control panel handles or process handles. */
141  typedef union iconData{
142        processHdl      proc;       /* process information of procedure nodes */
```

```
143        cPanelHdl       panel;      /* control panel information for step nodes */
144  } iconData;
145
146
147  /* Every step and procedure icon is represented in memory via the iconNode struct. */
148  typedef struct iconNode {
149        struct iconNode **next;     /* next node at this level */
150        struct iconNode **prev;     /* previous node at this level */
151        struct iconNode **desc;     /* descendent list or null if none */
152        struct iconNode **moma;     /* parent node or null if root level */
153        Rect            frame;      /* bounds of the icon (closed state) or the control panel (open) */
154        Rect            outLine;    /* bounds of icon and its top and bottom notes */
155        Boolean         hilite;     /* true when this node is selected */
156        Boolean         open;       /* true when this icon is open */
157        Handle          icon;       /* b/w copy of this node's icon */
158        CIconHandle     cicn;       /* color copy of this node's icon (not yet implemented) */
159        Handle          tNote;      /* legend on top of the icon */
160        Handle          bNote;      /* legend beneath the icon */
161        short           stepID;     /* stepId is equal to the resource number of the icon */
162        short           iKind;      /* type of data contained within this icon */
163        iconData        data;       /* icon's control panel or process information */
164  } iconNode, *iconNodePtr, **iconNodeHdl;
165
166
167  typedef struct iconWInfo {
168        iconNodeHdl     iList;      /* Root of one window's icon list. */
169        /* iconNodeHdl   topHilited; /* Topmost hilited icon in icon list. */
170        Boolean         remeasure;  /* true when the icon list needs to be remeasured */
171  } iconWInfo, *iconWInfoPtr, **iconWInfoHdl;
172
173
174  /***********************************************************************
175  *   Scope
176  */
177  extern  iconNodeHdl     iScrap;     /* Root to icon list scrap or NULL if scrap is empty. */
178  extern  WindowPtr       theWPtr;    /* Window currently in use */
179  extern  Rect            image;      /* Its image rectangle. */
180  extern  Rect            usable;     /* Its usable area. */
181  extern  Point           curOrigin;  /* Its current origin. */
182  extern  iconWInfoHdl    iconWData;  /* Window's copy of the following two variables. */
183  extern  iconNodeHdl     iList;      /* Root of one window's icon list. */
184  extern  Boolean         remeasure;  /* true when the icon list needs to be remeasured */
185
186
187  /***********************************************************************
188  *   Function Prototypes
189  */
190  void          set_context(WindowPtr aWPtr);
191  void          restore_context(void);
192  iconNodeHdl   new_node(void);
193  void          attach_after(iconNodeHdl a, iconNodeHdl b);
194  iconNodeHdl   add_node(short iKind, iconNodeHdl after);
195  void          detach_node(iconNodeHdl iNode);
196  void          kill_node(iconNodeHdl iNode);
197  void          kill_list(iconNodeHdl *iNode);
198  iconNodeHdl   copy_list(iconNodeHdl iNode);
199
200
201  #endif
```

```
12/14/88 12:31 PM                         iconutils.c                                      Page 1

1   /*******************************************************************************
2    *   Copyright ©1988 by Applied Biosystems, Inc. All rights reserved.
3    ********************************************************************************
4    *
5    *   File Name: iconUtils.c
6    *
7    *   Description: Data structures and utilities for handling icon editor windows
8    *
9    *   Caveats: None.
10   *
11   *   Edit History: 25 October 88 Converted from Pascal by HG
12   *
13   *******************************************************************************/
14
15
16   /*******************************************************************************
17    *   Preprocessor Directives
18    *   none
19    */
20
21   /*******************************************************************************
22    *   Include Files
23    */
24   #include "iconUtils.h"
25
26
27   /*******************************************************************************
28    *   External References
29    *   none
30    */
31
32
33   /*******************************************************************************
34    *   Structures and Typedefs
35    *   none
36    */
37
38
39   /*******************************************************************************
40    *   Globals
41    */
42   iconNodeHdl      iScrap;         /* Root to icon list scrap or NULL if scrap is empty. */
43   WindowPtr        theWPtr;        /* Window currently in use */
44   Rect             image;          /* Its image rectangle. */
45   Rect             usable;         /* Its usable area. */
46   Point            curOrigin;      /* Its current origin. */
47   iconWInfoHdl     iconWData;      /* Window's copy of the following two variables. */
48   iconNodeHdl      iList;          /* Root of one window's icon list. */
49   Boolean          remeasure;      /* true when the icon list needs to be remeasured */
50
51
52   /*******************************************************************************
53    *   Static Objects
54    */
55       static  GrafPtr saveport;      /* port to be restored after a setcontext call */
56
57
58   /*******************************************************************************
59    *   Function Prototypes - functions used within this file only
60    */
61   static cPanelHdl   new_panel(void);
62   static processHdl  new_process(void);
63   static void duplicate_list(iconNodeHdl iNode, iconNodeHdl parent, iconNodeHdl *newList);
64
```

12/14/88 12:31 PM iconutils.c Page 2

65
66

12/14/88 12:31 PM                           iconutils.c                                    Page 3

```
 67  /*******************************************************************************
 68   * Function name:    set_context -- Makes an icon window the current one.
 69   *
 70   *   Description:    Takes a pointer to an icon window and makes it the current window.
 71   *                   Copies information about the icon window to local variables for faster
 72   *                   access.
 73   *
 74   *        Inputs:    wPtr        an icon window
 75   *
 76   *       Outputs:    none
 77   *
 78   *  Side Effects:    theWPtr     Global pointer to the current window
 79   *                   image       Global copy of window's imageRect
 80   *                   usable      Global copy of window's usableArea Rect
 81   *                   curOrigin   Global copy of window's current origin
 82   *                   iList       Global Handle to it's icon node list
 83   *                   remeasure   Global flag indicating whether remeasuring is needed
 84   *
 85   *        Return:    void
 86   *
 87   *******************************************************************************/
 88
 89  void set_context(aWPtr)
 90
 91  WindowPtr   aWPtr;
 92
 93  {
 94      register iconWInfoPtr    iwp;    /* Dereferenced pointer to more window info. */
 95
 96      GetPort(&saveport);
 97      SetPort(aWPtr);
 98      theWPtr = aWPtr;        /* Set global pointer to current window now. */
 99
100      GetWindowData(aWPtr, &image, &usable, &curOrigin, &iconWData);
101
102      iwp = *iconWData;       /* Set the globals to the right values for this window. */
103      iList = iwp->iList;
104      remeasure = iwp->remeasure;
105  }
106
107
108
```

12/14/88 12:31 PM                                iconutils.c                                          Page 4

```
109   /*******************************************************************************
110   * Function name:    restore_context -- restores active grafport.
111   *
112   *   Description:    Restores the active grafport in effect at the time of the last
113   *                   setcontext.
114   *
115   *   Inputs:         none
116   *
117   *   Outputs:        none
118   *
119   *   Side Effects:   thePort     System Global thePort is set to contents of
120   *                               Application Global saveport
121   *
122   *   Return:         void
123   *
124   *******************************************************************************/
125
126   void restore_context()
127
128   {
129
130       register   iconWInfoPtr    iwp;    /* For quickness */
131
132       SetPort(saveport);
133       iwp = *iconWData;
134       iwp->iList = iList;
135       iwp->remeasure = remeasure;
136   }
137
138
139
```

```
12/14/88 12:31 PM                          iconutils.c                                         Page 5

140   /*******************************************************************************************
141    * Function name:     new_node -- creates a new icon node.
142    *
143    *   Description:     Creates a new icon node but doesn't initialize it.
144    *
145    *       Inputs:       none
146    *
147    *      Outputs:       none
148    *
149    *  Side Effects:              Allocates memory; heap objects may move.
150    *
151    *       Return:       void
152    *
153    *******************************************************************************************/
154
155   iconNodeHdl new_node()
156
157   {
158        iconNodeHdl     iNode;
159
160        iNode = (iconNodeHdl) NewHandle(sizeof(iconNode));
161        failnil((char*)iNode);                              /* Make sure memory was available. */
162        return(iNode);
163   }
164
165
166
```

```
167  /******************************************************************************
168  * Function name:    attach_after -- splices a node into an existing list.
169  *
170  *   Description:    Attach node b after node a. Both nodes must be allocated and
171  *                   initialized before calling attach_after.
172  *
173  *        Inputs:    a          the icon node which will preceed node b
174  *                   b          the icon node to be added to the list
175  *
176  *       Outputs:    none
177  *
178  *  Side Effects:    <iconList>  changes the pointers in the nodes surrounding b
179  *
180  *        Return:    void
181  *
182  ******************************************************************************/
183
184  void attach_after(a,b)
185
186  iconNodeHdl a;
187  iconNodeHdl b;
188
189  {
190       (*b)->prev = a;
191       (*b)->next = (*a)->next;
192       (*(*b)->next)->prev = b;
193       (*a)->next = b;
194       (*b)->moma = (*a)->moma;
195  }
196
197
198
```

```
12/14/88 12:31 PM                       iconutils.c                                      Page 7

199  /*******************************************************************************
200   * Function name:   new_panel -- allocates and initializes a new control panel structure.
201   *
202   *   Description:   Allocates, initializes a control panel for a step icon.
203   *
204   *        Inputs:   none
205   *
206   *       Outputs:   none
207   *
208   *  Side Effects:              Allocates memory; heap objects may move.
209   *
210   *        Return:   a handle to the new control panel
211   *
212   *******************************************************************************/
213
214  cPanelHdl new_panel()
215
216  {
217
218      cPanelHdl       ph;         /* temporary storage for the control panel */
219      cPanelPtr       pp;         /* quick access */
220
221      ph = (cPanelHdl) NewHandle(sizeof(cPanel));
222      failnil((char*)ph);
223
224      pp = *ph;
225      pp->name = nil;             /* name not determined yet */
226      pp->items = nil;            /* items not detemined yet */
227
228      return(ph);
229  }
230
231
232
```

```
233   /*******************************************************************************
234    * Function name:   new_process -- allocates and initializes a new process structure.
235    *
236    *   Description:    Allocates and initializes a process structure for a process icon.
237    *
238    *       Inputs:     none
239    *
240    *       Outputs:    none
241    *
242    *   Side Effects:               Allocates memory; heap objects may move.
243    *
244    *       Return:     process     a handle to the new process
245    *
246    *******************************************************************************/
247
248   processHdl new_process()
249
250   {
251
252       processHdl    proc;    /* temporary storage for the control panel */
253       processPtr    pp;      /* for quick access */
254
255       proc = (processHdl) NewHandle(sizeof(process));
256       failnil((char*)proc);
257
258       pp = *proc;
259       pp->backColor.red   = 0xFFFF;    /* default to RGB White */
260       pp->backColor.green = 0xFFFF;
261       pp->backColor.blue  = 0xFFFF;
262
263       pp->split = false;
264       pp->selStart = 0;
265       pp->selEnd = 0;
266
267       return(proc);
268   }
269
270
271
```

```
272  /******************************************************************************
273  * Function name:   add_node -- allocates, initializes and splices a new node.
274  *
275  *    Description:   Allocates, initializes and splices a new node into place after the
276  *                   node passed in the parameter called after. If after is nil, the new
277  *                   node is initialized as a list of one.
278  *
279  *         Inputs:   iKind     the type of this icon (iconStep or iconProcess)
280  *                   after     the icon node which will preceed the new node
281  *
282  *        Outputs:   none
283  *
284  *   Side Effects:   <iconList> changes the pointers in the nodes surrounding the new node
285  *
286  *         Return:   iconNodeHdl a handle to the newly created node
287  *
288  ******************************************************************************/
289
290  iconNodeHdl add_node(iKind, after)
291
292  short           iKind;
293  iconNodeHdl     after;
294
295  {
296               Handle       ht, hb;  /* temporary storage for text handles */
297               iconNodeHdl  iNode;   /* temporary storage for the function result */
298      register iconNodePtr  p;       /* For quickness when memory can't move. */
299               cPanelHdl    panel;   /* temporary storage for a new panel */
300               processHdl   proc;    /* temporary storage for a new process */
301               iconData     data;    /* temporary storage to avoid dereferencing while allocating */
302
303      iNode = new_node();             /* Allocate space for the new node. */
304      failnil((char*)iNode);                    /* Give up if we're out of memory. */
305
306      p = *iNode;                     /* Dereference once for initializations that don't move memory *
307      p->desc = nil;
308      p->moma = nil;
309      SetRect(&(p->frame),0,0,0,0);
310      SetRect(&(p->outLine),0,0,0,0);
311      p->hilite = false;
312      p->icon = nil;
313      p->cicn = nil;
314      p->stepID = 0;
315      p->open = false;
316      p->iKind = iKind;
317
318      switch (iKind) {
319         case iconStep:
320              data.panel = nil; /* new_panel();        /* Steps need a control panel object */
321              break;
322         case iconProcess:
323              data.proc = new_process();  /* Procedures need a process object */
324              break;
325      } /* end switch */
326
327      ht = (Handle) NewHandle(0);
328      failnil((char*)ht);
329      hb = (Handle) NewHandle(0);
330      failnil((char*)hb);
331
332      p = *iNode;       /* Dereference again */
333      p->data = data;
334      p->tNote = ht;
335      p->bNote = hb;
```

```
336
337     if (!after)                     /* If we have nothing to attach to, then... */
338         {                           /* ...make the node into a list of one. */
339         p->prev = iNode;
340         p->next = iNode;
341         }
342     else
343         attach_after(after, iNode); /* Splice it into the list. */
344
345     return(iNode);
346 }
347
348
349
```

12/14/88 12:31 PM                              iconutils.c                                              Page 11

```
350  /****************************************************************************
351   * Function name:   detach_node -- detaches and deallocates an icon node.
352   *
353   *   Description:    Removes an icon node from a list by detaching it, and freeing the
354   *                   memory that it occupies.
355   *
356   *   Inputs:     iNode       The node to be detached
357   *
358   *   Outputs:    none
359   *
360   * Side Effects:             can cause memory to move
361   *
362   *   Return:     void
363   *
364   ****************************************************************************/
365
366  void detach_node(iNode)
367
368  iconNodeHdl    iNode;
369
370  {
371      register iconNodePtr    ip;
372
373      ip = *iNode;
374
375      /* Notify next-of-kin. */
376      if ((*ip->moma)->desc == iNode)     /* If this node is the first descendent... */
377          if (ip->next == iNode)          /* If this is the only node remaining at this level... */
378              (*ip->moma)->desc = nil;    /* ...then notify the parent that it no longer has descendents.*/
379          else
380              (*ip->moma)->desc = ip->next;   /* Let the parent point to sibling. */
381
382      (*ip->next)->prev = ip->prev;       /* Notify siblings. */
383      (*ip->prev)->next = ip->next;
384
385      /* Fix the detached node. */
386      ip->moma = nil;
387      ip->next = iNode;
388      ip->prev = iNode;
389  }
390
391
392
```

```
12/14/88 12:31 PM                      iconutils.c                              Page 12

393  /*******************************************************************************
394   * Function name:   kill_node -- disposes of a node and sets its handle to nil.
395   *
396   *   Description:   Removes an icon node from a list by detaching it, and freeing the
397   *                  memory that it occupies.
398   *
399   *       Inputs:    iNode      the type of this icon (iStep or iProcess)
400   *
401   *       Outputs:   none
402   *
403   *   Side Effects:             May cause heap objects to be moved.
404   *
405   *       Return:    void
406   *
407   *******************************************************************************/
408
409  void kill_node(iNode)
410
411  iconNodeHdl iNode;
412
413  {
414      Handle      ht,hb;           /* Temporary storage for handles to be disposed. */
415      short       iKind;
416      iconData    data;
417      cItemHdl    items;
418      register    iconNodePtr ip;
419
420      detach_node(iNode);          /* Take it out of the list. */
421      ip = *iNode;
422      ht = ip->tNote;
423      ht = ip->tNote;
424      iKind = ip->iKind;
425      data = ip->data;
426
427      switch (iKind) {
428          case iconStep:
429              {
430                  items = (*data.panel)->items;
431                  if (items != nil)
432                      DisposHandle(items);
433                  DisposHandle((Handle) data.panel);
434              }
435              break;
436          case iconProcess:
437              {
438                  DisposHandle((Handle) data.proc);
439              }
440              break;
441      } /* endswitch */
442
443      DisposHandle(ht);
444      DisposHandle(hb);
445      DisposHandle((Handle)iNode);
446  }
447
448
449
```

```
450  /*****************************************************************************
451   * Function name:    kill_list -- disposes of an entire list.
452   *
453   *   Description:    Detaches the node passed in iNode and disposes of it and all of its
454   *                   descendents.
455   *
456   *        Inputs:    iNode       an icon node
457   *
458   *       Outputs:    none
459   *
460   *  Side Effects:                May cause heap objects to be moved.
461   *                               Alters the list containing iNode.
462   *
463   *        Return:    void
464   *
465   *****************************************************************************/
466
467  void kill_list(iNode)
468
469  iconNodeHdl *iNode;
470
471  {
472      iconNodeHdl    aNode;
473      iconNodeHdl    nextNode;
474      iconNodeHdl    desc;
475      Boolean        stop;
476
477      aNode = *iNode;
478      do {
479          nextNode = (*aNode)->next;
480          stop = (aNode == nextNode);
481
482          desc = (*aNode)->desc;
483          if (!desc)
484              kill_node(aNode);
485          else
486              {
487                  kill_list(&desc);
488                  kill_node(aNode);
489              }
490          aNode = nextNode;
491      }while(!stop);
492      iNode = nil;
493  }
494
495
496
```

12/14/88 12:31 PM                           iconutils.c                                    Page 14

```
497  /*********************************************************************************
498   * Function name:    duplicate_list -- copies an entire list.
499   *
500   *   Description:    DuplicateList recursively makes a copy of the list pointed to by iNode.
501   *                   To use, set parent to nil. The new copy of the list is passed in newList.
502   *
503   *      Inputs:      iNode         an icon node
504   *
505   *      Outputs:     *newList      a copy of the iNode & its descendents
506   *
507   *   Side Effects:                 May cause heap objects to be moved.
508   *
509   *      Return:      void
510   *
511   *********************************************************************************/
512
513  void duplicate_list(iNode, parent, newList)
514
515  iconNodeHdl     iNode;
516  iconNodeHdl     parent;
517  iconNodeHdl     *newList;
518
519  {
520      OSErr           err;
521      Handle          ht, hb;
522      iconNodeHdl     sourceHdl;      /* Node being copied on this pass. */
523      iconNodeHdl     q;              /* The clone of sourceHdl, above. */
524      register iconNodePtr    qp;
525      iconNodeHdl     sibling;
526      iconNodeHdl     son;
527      iconNodeHdl     desc;
528      Boolean         top;
529
530      top = (parent == nil);          /* On topmost invocation, don't copy siblings. */
531      *newList = nil;
532      sourceHdl = iNode;
533      sibling = nil;                  /* First iteration of repeat loop makes an only child.*/
534      son = nil;
535
536      /* Execute loop at least once, and until we've complete _ */
537      /* _ this level or there are no higher levels */
538
539      do {
540              q = new_node();         /* Allocate a new node. */
541              **q = **sourceHdl;      /* Make the contents identical_ */
542              qp = *q;
543              qp->next = q;           /* except for the pointers. */
544              qp->prev = q;
545              qp->desc = nil;
546              qp->moma = nil;
547              ht = (*sourceHdl)->tNote;
548              hb = (*sourceHdl)->bNote;
549
550              err = HandToHand(&ht);  /* Duplicate the text handles. */
551              warn(err);
552              err = HandToHand(&hb);
553              warn(err);
554              qp = *q;                /* Dereference anew. */
555              qp->tNote = ht;
556              qp->bNote = hb;
557
558              if (!(*newList))        /* On the first time through, make sure the */
559                  *newList = q;       /* list's handle points at the first node. */
560
```

```
561         if (sibling)            /* nil sibling means we're making the first sibling at this */
562             attach_after(sibling, q);  /* level. If not, Connect the new node after it's sibling. */
563         (*q)->moma = parent;
564
565         desc = (*sourceHdl)->desc;
566         if (desc)               /* Now that we've made the node let's */
567             (                   /* make it's descendents, if any. */
568                 duplicate_list(desc, q, &son);
569                 (*q)->desc = son;
570             )
571         sibling = q;            /* Next sibling will attach to sibling. */
572         sourceHdl = (*sourceHdl)->next;
573     } while ((sourceHdl != iNode) && !top);
574 }
575
576
577
```

```
578  /*******************************************************************
579   * Function name:   copy_list -- copies an entire list with a single parameter.
580   *
581   *   Description:   Calls duplicate list, above, to handle the recursive traversing
582   *                  of the icon node tree.
583   *
584   *       Inputs:    iNode       an icon node
585   *
586   *      Outputs:    none
587   *
588   *  Side Effects:               can cause memory to move
589   *
590   *       Return:    iconNodeHdl a copy of iNode and its descendents
591   *
592   *******************************************************************/
593
594  iconNodeHdl copy_list(iNode)
595
596  iconNodeHdl     iNode;
597
598  {
599      iconNodeHdl    newList;
600
601      duplicate_list(iNode, nil, &newList);
602
603      return(newList);
604  }
605
606
```

| 12/22/88 3:08 PM | panels.h | Page 1 |

```
1   /******************************************************************************
2       Copyright ©1988 by Applied Biosystems, Inc. All rights reserved.
3   *******************************************************************************
4   *
5   *      File Name: panels.h
6   *
7   *      Description: Header for panels.c, control panel handling routines
8   *
9   *      Caveats: None.
10  *
11  *   Edit History: 13 December 88 Created by HG
12  *
13  ******************************************************************************/
14
15
16  /******************************************************************************
17  *   Preprocessor Directives
18  */
19  #ifndef __PANELS__
20  #define __PANELS__
21
22  #define panelType 'Panl'
23
24
25  /******************************************************************************
26  *   Include Files
27  */
28  #include "includes.h"
29  #include "misc.h"
30  #include "errs.h"
31  #include "iconUtils.h"
32
33
34  /******************************************************************************
35  *   Macros
36  *   none
37  */
38
39
40  /******************************************************************************
41  *   Structures and Typedefs
42  *   none
43  */
44
45
46  /******************************************************************************
47  *   Scope Declarations
48  */
49  extern TEHandle gTEH;
50
51
52  /******************************************************************************
53  *   Function Prototypes
54  */
55
56  void init_panels(void);
57  void load_panel(short id, cPanelHdl *newPanel, iconNodeHdl iNode);
58  void draw_panel(cPanelHdl panel);
59  void do_panel_mouse_down(cPanelHdl panel, EventRecord *event);
60  void do_panel_key(EventRecord *event);
61  void panel_idle(WindowPtr wPtr);
62
63
64  #endif
``` panels.c                                                                     Page 1

```
1  /*************************************************************************
2   *    Copyright ©1988 by Applied Biosystems, Inc. All rights reserved.
3   *************************************************************************
4   *
5   *    File Name: panels.c
6   *
7   *    Description: Control panel handling routines
8   *
9   *       Caveats: None.
10  *
11  *    Edit History: 13 December 88 Created by HG
12  *
13  *************************************************************************/
14
15
16 /*************************************************************************
17  *    Preprocessor Directives
18  */
19
20
21 /*************************************************************************
22  *    Include Files
23  */
24 #include "panels.h"
25
26
27 /*************************************************************************
28  *    Macros
29  *        none
30  */
31
32
33 /*************************************************************************
34  *    Structures and Typedefs
35  *        none
36  */
37
38
39 /*************************************************************************
40  *    Static variables
41  */
42 static  cPanelHdl    thePanel;
43 static  Handle       theTemplate;
44 static  short        index;
45 static  RgnHandle    savedClip;
46 static  Point        savedOrigin;
47 static  short        txFont;
48 static  short        txFace;
49 static  short        txSize;
50 static cItemHdl gActiveEditItem = nil;
51
52 TEHandle gTEH;
53
54
55
```

1. 88 3:47 PM                                         panels.c                                                    Page 2

```
 56  /******************  ****************************************************************
 57   *   Function Prototype
 58   */
 59  static void align_word(void);
 60  static void next_byte(char *b);
 61  static void next_word (short *w);
 62  static void next_long (long *l);
 63  static void next_rect (Rect *r);
 64  static void next_pstring(STR255 *s);
 65  static void next_Picture (cItemHdl item);
 66  static void next_Menu (cItemHdl item);
 67  static void next_EditText(cItemHdl item);
 68  static void next_Text (cItemHdl item);
 69  static void parse_panel (Handle template, cPanelHdl *newPanel, iconNodeHdl  iNode);
 70  static void draw_picture_item(cItemHdl item);
 71  static void draw_rect_item(cItemHdl item);
 72  static void draw_menu_item(cItemHdl item);
 73  static void draw_edit_item(cItemHdl item);
 74  static void draw_text_item(cItemHdl item);
 75  static void draw_item(cItemHdl item);
 76  static Boolean find_item(Point *p, cPanelHdl panel, cItemHdl *item);
 77  static void do_menu_item(Point *p, cPanelHdl panel, cItemHdl item, EventRecord *event);
 78  static void start_edit(cPanelHdl panel, cItemHdl item);
 79  static void complete_edit(cItemHdl item);
 80  static void do_edit_item(Point *p, cPanelHdl panel, cItemHdl item, EventRecord *event);
 81  static void do_item(Point *p, cPanelHdl panel, cItemHdl item, EventRecord *event);
 82
 83
 84
```

```
12/22/88 3:47 PM                            panels.c                                  page 3

85  /*******************************************************************************
 86   * Function name:    init_panels - initializes the control panel handling unit
 87   *
 88   *   Description:    Allocates a region handle to hold window's clip region during
 89   *                   while focussing.
 90   *
 91   *       Inputs:     none
 92   *
 93   *      Outputs:     none
 94   *
 95   *  Side Effects:            Allocates memory; heap objects may move.
 96   *
 97   *       Return:     void
 98   *
 99   *******************************************************************************/
100
101  void init_panels()
102
103  {
104  }
105
106
107
108
```

```
12/22/8  3:47 PM                       panels.c                                              Page 4
109   /*******************************************************************************
110    * Function name:   save_text_info - Saves a grafport's text drawing mode for later.
111    *
112    *   Description:   Keeps a temporary copy of the current grafport's text drawing
113    *                  information.
114    *
115    *       Inputs:    none
116    *
117    *      Outputs:    none
118    *
119    *  Side Effects:   none
120    *
121    *       Return:    void
122    *
123    *******************************************************************************/
124
125   void save_text_info()
126
127   {
128       GrafPtr gp;
129
130       GetPort(&gp);
131       txFont = gp->txFont;
132       txFace = gp->txFace;
133       txSize = gp->txSize;
134   }
135
136
137
```

```
12/22/88 3:47 PM                            panels.c                                    Page 138  /************************************************************************************
139   * Function name:   restore_text_info - Restores a saved text drawing info.
140   *
141   *    Description:   Restores the grafport's text drawing info from static vars.
142   *
143   *         Inputs:   none
144   *
145   *        Outputs:   none
146   *
147   *   Side Effects:              Alter's current grafport.
148   *
149   *         Return:   void
150   *
151   ************************************************************************************/
152
153  void restore_text_info()
154
155  {
156      TextFont(txFont);
157      TextFace(txFace);
158      TextSize(txSize);
159  }
160
161
162
163
```

```
164    /******************************************************************************
165     * Function name:    focus - focusses drawing to a control panel
166     *
167     *   Description:
168     *
169     *        Inputs:    none
170     *
171     *        Outputs:   none
172     *
173     *   Side Effects:            May allocate memory; heap objects may move.
174     *
175     *        Return:    void
176     *
177     ******************************************************************************/
178
179    void focus(panel)
180
181    cPanelHdl   panel;
182
183    {
184        Point       p2;
185        Rect        contents;
186        short       h, v;
187        iconNodeHdl iNode;
188
189        get_origin(&savedOrigin);                      /* Save origin and clip region. */
190        p2 = savedOrigin;
191        savedClip = NewRgn();
192        failnil((char*)savedClip);
193        GetClip(savedClip);
194
195        iNode = (*panel)->iNode;
196        contents = (*iNode)->frame;
197        InsetRect(&contents, HILITEWIDTH, HILITEWIDTH);
198        h = contents.left;
199        v = contents.top;
200        OffsetRect(&contents, -h, -v);
201        offset_point(&p2, -h, -v);
202        ClipRect(&contents);              /* Clip to content area. */
203        SetOrigin(p2.h, p2.v);            /* Move origin to topleft corner of content area. */
204    }
205
206
207
```

```
12/22/88 3:47 PM                         panels.c                                        Page 208   /***********  ******************************************************************
209   * Function name:   unfocus - focusses drawing to an entire window.
210   *
211   *   Description:   Undoes a focus on a control panel.
212   *
213   *        Inputs:   none
214   *
215   *       Outputs:   none
216   *
217   * Side Effects:              May allocate memory; heap objects may move.
218   *
219   *        Return:   void
220   *
221   ********************************************************************************/
222
223   void unfocus()
224
225   {
226       SetOrigin(savedOrigin.h, savedOrigin.v);   /* Move origin to topleft corner of content area. */
227       SetClip(savedClip);
228       DisposeRgn(savedClip);
229       savedClip = nil;
230   }
231
232
233
```

```
234  /************************************************************************
235   * Function name:    window2panel_point
236   *
237   *   Description:    Converts a point in the window's local coordinate system to
238   *                   the panel's local coordinate system. A panel must be in focus for
239   *                   window2panel_point to be meaningful.
240   *
241   *        Inputs:    index      an index into theTemplate
242   *
243   *       Outputs:    none
244   *
245   *   Side Effects:   index      may be incremented by one
246   *
247   *        Return:    void
248   *
249   ************************************************************************/
250
251  void window2panel_point(p)
252
253  Point   *p;
254
255  {
256      Point   pt;
257
258      offset_point(p, -curOrigin.h, -curOrigin.v);       /* Image coordinates. */
259      get_origin(&pt);
260      offset_point(p, pt.h, pt.v);                       /* Panel coordinates */
261  }
262
263
```

```
12/22/88 3:47 PM                         panels.c                                    Pa( 264   /***************************************************************************
265    * Function name:   window2panel_rect
266    *
267    *   Description:    Converts a rectangle in the window's local coordinate system to
268    *                   the panel's local coordinate system. A panel must be in focus for
269    *                   window2panel_rect to be meaningful.
270    *
271    *       Inputs:     index       an index into theTemplate
272    *
273    *       Outputs:    none
274    *
275    *   Side Effects:   index       may be incremented by one
276    *
277    *       Return:     void
278    *
279    ***************************************************************************/
280
281   void window2panel_rect(r)
282
283   Rect    *r;
284
285   {
286       Point   pt;
287
288       OffsetRect(r, -curOrigin.h, -curOrigin.v);      /* Image coordinates. */
289       get_origin(&pt);
290       OffsetRect(r, pt.h, pt.v);                      /* Panel coordinates */
291   }
292
293
294
295
```

```
12/22/88 3:47                              panels.c                                    Page 10

296  /***********************************************************************************
297   * Function name:    align_word
298   *
299   *   Description:    Advances the index to the next word boundary if it's not currently on
300   *                   a word boundary.
301   *
302   *        Inputs:    index      an index into theTemplate
303   *
304   *       Outputs:    none
305   *
306   *  Side Effects:    index      may be incremented by one
307   *
308   *        Return:    void
309   *
310   ***********************************************************************************/
311
312  void align_word ()
313
314  {
315      if ((index & 1) != 0)
316          index++;
317  }
318
319
320
```

```
12/22/88 3:47 PM                        panels.c                                        Page 321   /*******************************************************************************
322   * Function name:    next_byte
323   *
324   *   Description:    Extracts a byte from the current position in the panel resource
325   *                   template. Advances the index to the panel template.
326   *
327   *       Inputs:     theTemplate a handle to the panel's template resource
328   *                   index       an index into theTemplate
329   *                   thePanel    a handle to the panel being built
330   *
331   *       Outputs:    *b          the byte
332   *
333   * Side Effects:     none
334   *
335   *       Return:     void
336   *
337   *******************************************************************************/
338
339   void next_byte (b)
340
341   char    *b;
342
343   {
344       *b = *((*theTemplate) + index++);
345   }
346
347
348
```

```
349  /******************************************************************************
350  * Function name:   next_word
351  *
352  *   Description:   Extracts a word (short) from the current position in the panel resource
353  *                  template. Advances the index to the panel template.
354  *
355  *        Inputs:   theTemplate a handle to the panel's template resource
356  *                  index       an index into theTemplate
357  *                  thePanel    a handle to the panel being built
358  *
359  *       Outputs:   *w          the word
360  *
361  * Side Effects:    none
362  *
363  *        Return:   void
364  *
365  ******************************************************************************/
366
367  void next_word (w)
368
369  short   *w;
370
371  {
372      char    hi;
373      char    lo;
374
375      next_byte(&hi);
376      next_byte(&lo);
377
378      *w = ( ((hi & 0x00FF) << 8) | (lo & 0x00FF));
379  }
380
381
382
```

```
383  /********************************************************************************
384   * Function name:   next_long
385   *
386   *   Description:   Extracts a long from the current position in the panel resource
387   *                  template. Advances the index to the panel template.
388   *
389   *        Inputs:   theTemplate a handle to the panel's template resource
390   *                  index       an index into theTemplate
391   *                  thePanel    a handle to the panel being built
392   *
393   *       Outputs:   *l          the long
394   *
395   *  Side Effects:   none
396   *
397   *        Return:   void
398   *
399   ********************************************************************************/
400
401  void next_long (l)
402
403  long    *l;
404
405  {
406      short   hi;
407      short   lo;
408      long    bighi;
409
410      next_word(&hi);
411      next_word(&lo);
412
413      bighi = (hi & 0xFFFF);
414      *l = ( (bighi << 16) | (lo & 0xFFFF));
415  }
416
417
418
```

```
12/22/88 3:47 PM                      panels.c                                       Page 14

419    /*******************************************************************************
420    * Function name:    next_rect
421    *
422    *   Description:    Extracts a rectangle from the current position in the panel resource
423    *                   template. Advances the index to the panel template.
424    *
425    *       Inputs:     theTemplate a handle to the panel's template resource
426    *                   index       an index into theTemplate
427    *                   thePanel    a handle to the panel being built
428    *
429    *       Outputs:    *r          the Rectangle
430    *
431    *  Side Effects:    none
432    *
433    *       Return:     void
434    *
435    *******************************************************************************/
436
437    void next_rect (r)
438
439    Rect    *r;
440
441    {
442        next_word(&(r->top));
443        next_word(&(r->left));
444        next_word(&(r->bottom));
445        next_word(&(r->right));
446    }
447
448
449
```

```
12/22/88 3:47 PM                        panels.c                                  Page 15

450   /******************************************************************************
451   * Function name:    next_pstring
452   *
453   *   Description:    Extracts a Pascal string from the current position in the panel resource
454   *                   template. Advances the index to the panel template.
455   *
456   *       Inputs:     theTemplate a handle to the panel's template resource
457   *                   index       an index into theTemplate
458   *                   thePanel    a handle to the panel being built
459   *
460   *       Outputs:    *s          the String
461   *
462   * Side Effects:     none
463   *
464   *       Return:     void
465   *
466   ******************************************************************************/
467
468   void next_pstring(s)
469
470   STR255  *s;
471
472   {
473       short   len;
474       short   sIndex = 0;
475       char    c;
476
477       next_byte(&c);
478       ((char*)s)[0] = c;
479
480       len = c;
481       for (sIndex = 1; sIndex <= len; sIndex++)
482           {
483               next_byte(&c);
484               ((char*)s)[sIndex] = (char) c;
485           }
486
487       align_word();
488   }
489
490
491
```

```
/****************************************************************************
 * Function name:   next_Picture
 *
 *   Description:   Extracts the item record of type 'pict' from the data in the current
 *                  panel template. If successful, appends an item handle to the
 *                  current panel's item list.
 *
 *        Inputs:   theTemplate  a handle to the panel's template resource
 *                  index        an index into theTemplate
 *                  thePanel     a handle to the panel being built
 *
 *       Outputs:   thePanel     the panel's item list is updated with the new text item
 *
 *  Side Effects:                May cause heap objects to be moved.
 *
 *        Return:   void
 *
 ****************************************************************************/ void next_Picture (item)

cItemHdl    item;

{ short       id;
    PicHandle   pic;

next_word(&id);

pic = GetPicture(id);
    (*item)->iData.iPic = pic;
}
```

```
529  /*********************************************************************************
530   * Function name:   next_Menu
531   *
532   *   Description:   Extracts the item record of type 'menu' from the data in the current
533   *                  panel template. If successful, appends an item handle to the
534   *                  current panel's item list.
535   *
536   *        Inputs:   theTemplate  a handle to the panel's template resource
537   *                  index        an index into theTemplate
538   *                  thePanel     a handle to the panel being built
539   *
540   *       Outputs:   thePanel     the panel's item list is updated with the new text item
541   *
542   *  Side Effects:                May cause heap objects to be moved.
543   *
544   *        Return:   void
545   *
546   *********************************************************************************/
547
548  void next_Menu (item)
549
550  cItemHdl    item;
551
552  {
553      short           id;
554      MenuHandle      menu;
555      menuItemData    mid;
556      STR255          title;
557      long            len;
558      Rect            r;
559
560      next_word(&id);
561
562      menu = GetMenu(id);
563      mid.menu = menu;
564      mid.selected = 1;          /* nothing has been selected yet. */
565
566      /* Copy the title string. */
567      len = *((char*)&((*menu)->menuData)) + 1;
568      BlockMove(&((*menu)->menuData), &title, len);
569
570      mid.titlewidth = STRINGWIDTH(&title) + 4; /**** 4 should be a constant ****/
571      r = (*item)->iBox;
572      mid.menuwidth = WIDTH(r) - mid.titlewidth;
573      (*item)->iData.iMenu = mid;
574  }
575
576
577
```

12/22/88 3:47 PM                                                 panels.c                                              Page 19

```
578   /************************************************************************
579   * Function name:   next_EditText
580   *
581   *   Description:   Extracts the item record of type 'edit' from the data in the current
582   *                  panel template. If successful, appends an item handle to the
583   *                  current panel's item list.
584   *
585   *       Inputs:    theTemplate  a handle to the panel's template resource
586   *                  index        an index into theTemplate
587   *                  thePanel     a handle to the panel being built
588   *
589   *       Outputs:   thePanel     the panel's item list is updated with the new text item
590   *
591   * Side Effects:                 May cause heap objects to be moved.
592   *
593   *       Return:    void
594   *
595   ************************************************************************/
596
597   void next_EditText(item)
598
599   cItemHdl    item;
600
601   {
602       STR255          str;
603       StringHandle    sh;
604       editItemData    eid;
605       Rect            editBox;
606       short           preWidth;
607       short           postWidth;
608
609
610       next_pstring(&str);        /* prelabel */
611       preWidth = STRINGWIDTH(&str);
612       sh = NEWSTRING(&str);
613       failnil((char*)sh);
614       eid.prelabel = sh;
615
616       next_pstring(&str);        /* initial value of theText */
617       sh = NEWSTRING(&str);
618       failnil((char*)sh);
619       eid.theText = sh;
620
621       next_pstring(&str);        /* postlabel */
622       postWidth = STRINGWIDTH(&str);
623       sh = NEWSTRING(&str);
624       failnil((char*)sh);
625       eid.postlabel = sh;
626
627       editBox = (*item)->iBox;   /* let the edit text occupy the remaining space. */
628       editBox.left += (preWidth + 4);
629       editBox.right -= (postWidth + 4);
630
631       eid.editBox = editBox;
632       eid.teh = nil;     /* No text edit handle allocated means this isn't the active TE item. */
633
634       (*item)->iData.iEdit = eid;
635   }
636
637
638
```

```
12/22/88 3:47 PM                         panels.c                                   Page 19

639   /****************************************************************************
640   * Function name:    next_Text
641   *
642   *   Description:    Extracts the item-specific information for items of type 'text'
643   *                   from the data in the current panel template.
644   *
645   *        Inputs:    theTemplate  a handle to the panel's template resource
646   *                   index        an index into theTemplate
647   *
648   *        Outputs:   newItem      the current item
649   *
650   * Side Effects:                  May cause heap objects to be moved.
651   *
652   *        Return:    void
653   *
654   ****************************************************************************/
655
656   void next_Text (item)
657
658   cItemHdl    item;
659
660   {
661       STR255          str;
662       StringHandle    strHdl;
663
664       next_pstring(&str);
665       strHdl = NewString(&str);
666       failnil((char*)strHdl);
667       (*item)->iData.iText = strHdl;
668   }
669
670
671
```

```
672  /************************************************************************
673   * Function name:    parse_panel
674   *
675   *   Description:    Takes a Panl resource and converts it into a panelHandle and an itemlist.
676   *
677   *       Inputs:     template    a handle to a resource of type 'PANL'
678   *                   *panel      a pointer to space reserved for a panel handle
679   *                   iNode       handle to the panel's parent icon node
680   *
681   *       Outputs:    *newPanel   the handle to the new panel or nil
682   *
683   *   Side Effects:               May cause heap objects to be moved.
684   *
685   *       Return:     void
686   *
687   ************************************************************************/
688
689  void parse_panel (template, newPanel, iNode)
690
691  Handle       template;
692  cPanelHdl    *newPanel;
693  iconNodeHdl  iNode;
694
695  {
696      Rect            r;
697      STR255          str;
698      short           i;
699      short           itemCount;
700      StringHandle    strHdl;
701      long            l;
702      cItemHdl        newItem;
703      cItemHdl        lastItem;   /* Keep a copy of the last item around for list-building. */
704      short           opCode;
705      short           resID;
706
707      lastItem = nil;
708      newItem = nil;
709      theTemplate = template; /* Make a copy of the template global to the subroutines. */
710      index = 0;              /* Reset the index into the resource data. */
711
712      /* Create a new panel handle. */
713      *newPanel = (cPanelHdl) NewHandle(sizeof(cPanel));
714      failnil((char*)*newPanel);
715
716      /* Get the panel bounds rectangle. */
717      next_rect(&r);
718      (**newPanel)->pBox = r;
719
720      /* Parent icon node. */
721      (**newPanel)->iNode = iNode;
722
723      /* Get the panel name string. */
724      next_pstring(&str);
725      strHdl = NEWSTRING(&str);
726      failnil((char*)strHdl);
727      (**newPanel)->name = strHdl;
728
729      next_word(&opCode);
730      next_word(&resID);
731
732      /* Get the number of items for this control panel.*/
733      next_word(&itemCount);
734
735      /* For each item, get it's characteristics. */
```

```
736         for (i = 1; i <= itemCount; i++)
737         {
738             /* Create storage for a new item. */
739             newItem = (cItemHdl) NewHandle(sizeof(cItem));
740             failnil((char*)newItem);
741
742             (*newItem)->next = nil;
743             (*newItem)->panel = *newPanel;
744
745             /* Get it's boundary rectangle. */
746             next_rect(&r);
747             (*newItem)->iBox = r;
748
749             /* Get it's type. */
750             next_long(&l);
751             (*newItem)->iType = l;
752
753             /* Get the type-specific data. */
754             switch (l) {
755                 case 'pict':
756                     next_Picture(newItem);
757                     break;
758
759                 case 'rect':
760                     break;
761
762                 case 'edit':
763                     next_EditText(newItem);
764                     break;
765
766                 case 'text':
767                     next_Text(newItem);
768                     break;
769
770                 case 'menu':
771                     next_Menu(newItem);
772                     break;
773
774             }; /* end switch */
775
776             /* Attach the item to the end of the panel's item list. */
777             if (lastItem == nil)
778                 (**newPanel)->items = newItem;
779             else
780                 (*lastItem)->next = newItem;
781
782             lastItem = newItem;
783         }
784     }
785
786
```

```
12/22/88 3:47 PM                           panels.c                                    Page 22

787  /**********************************************************************************
788   * Function name:    default_panel
789   *
790   * Description:      Takes a Panl resource and converts it into a panelHandle and an itemlist.
791   *
792   *        Inputs:    template   a handle to a resource of type 'PANL'
793   *                   *panel     a pointer to space reserved for a panel handle
794   *                   iNode      the control panel's parent icon node
795   *
796   *        Outputs:   *newPanel  the handle to the new panel or nil
797   *
798   * Side Effects:                May cause heap objects to be moved.
799   *
800   *        Return:    void
801   *
802   **********************************************************************************/
803
804  void default_panel(id, newPanel, iNode)
805
806  short         id;
807  cPanelHdl     *newPanel;
808  iconNodeHdl   iNode;
809
810  {
811      Rect         r;
812      PicHandle    pic;
813      cItemHdl     item;
814      OSErr        err;
815
816      *newPanel = (cPanelHdl) NewHandle(sizeof(cPanel));
817      failnil((char*)*newPanel);
818
819      SetRect(&r, 0, 0, 48, 48); /* default panel dimensions. */
820      (**newPanel)->pBox = r;
821      (**newPanel)->name = NEWSTRING("\pdefault");
822      (**newPanel)->iNode = iNode;
823      (**newPanel)->items = nil;
824
825      pic = GetPicture(id);
826      err = ResError();
827      if ((err == noErr) && (pic != nil))
828          {
829              item = (cItemHdl) NewHandle(sizeof(cItem));
830              (**newPanel)->items = item;
831              failnil((char*)item);
832              (*item)->next = nil;
833              (*item)->panel = *newPanel;
834              (*item)->iType = 'pict';
835              (*item)->iData.iPic = pic;
836
837              r = (*pic)->picFrame;
838              OffsetRect(&r, -r.left, -r.top);
839              (**newPanel)->pBox = r;
840              (*item)->iBox = r;
841          }
842  }
843
844
```

```
845  /*******************************************************************************
846   * Function name:   load_panel
847   *
848   *  Description:    Loads a panel template resource and, if succcesful, parses the panel
849   *                  template and creates a new panel and item list.
850   *
851   *      Inputs:     id          id of a resource of type 'PANL'
852   *                  *panel      a pointer to space reserved for a panel handle
853   *                  iNode       parent icon node for the panel
854   *
855   *      Outputs:    *panel      the handle to the new panel or nil
856   *
857   *  Side Effects:               May cause heap objects to be moved.
858   *
859   *      Return:     void
860   *
861   *******************************************************************************/
862
863  void load_panel (id, newPanel, iNode)
864
865  short        id;
866  cPanelHdl    *newPanel;
867  iconNodeHdl  iNode;
868
869  {
870      Handle      template;
871      OSErr       err;
872
873      *newPanel = nil;
874
875      template = GetResource(panelType, id);
876      err = ResError();
877
878      save_text_info();
879      TextFont(systemFont);
880      TextFace(0);
881      TextSize(0);
882
883      if ((template != nil) && (err == noErr))
884          parse_panel(template, newPanel, iNode);
885      else
886          default_panel(id, newPanel, iNode);
887
888      restore_text_info();
889
890  }
891
892
893
894
```

```
12/22/88 3:47 PM                       panels.c                              Page 24

895   /****************************************************************************
896    * Function name:   draw_picture_item - draws a picture.
897    *
898    *   Description:    Draws a control panel picture item within its rectangle.
899    *
900    *       Inputs:     cItemHdl    a handle to an control panel item
901    *
902    *       Outputs:    none
903    *
904    *   Side Effects:               May cause heap objects to be moved.
905    *                               Draws to current grafport.
906    *
907    *       Return:     void
908    *
909    ****************************************************************************/
910
911   void draw_picture_item(item)
912
913   cItemHdl    item;
914
915   {
916       register cItemPtr cip;
917       Rect            iBox, r;
918       cItemData       iData;
919       PicHandle       pic;
920
921       cip   = *item;
922       iBox  = cip->iBox;
923       iData = cip->iData;
924
925       pic = iData.iPic;
926       LoadResource(pic);              /* Make sure it's there before you draw it. */
927       r = (*pic)->picFrame;
928
929       OffsetRect(&r, -r.left, -r.top);
930       OffsetRect(&r, iBox.left, iBox.top);
931       DrawPicture(pic, &r);
932   }
933
934
935
```

```
12/22/88 3:47 PM                       panels.c                                 Page 25

936   /*****************************************************************************
937   * Function name:   draw_rect_item - draws a rectangle.
938   *
939   *    Description:   Draws a control panel rectangle item by framing the rectangle in
940   *                   the curent drawing mode (pensize, forecolor).
941   *
942   *    Inputs:        cItemHdl    a handle to an control panel item
943   *
944   *    Outputs:       none
945   *
946   * Side Effects:                 May cause heap objects to be moved.
947   *                               Draws to current grafport.
948   *
949   *    Return:        void
950   *
951   *****************************************************************************/
952
953   void draw_rect_item(item)
954
955   cItemHdl    item;
956
957   {
958       Rect        iBox;
959
960       iBox  = (*item)->iBox;
961
962       FrameRect(&iBox);
963   }
964
965
966
967
```

```
12/22/88 3:47 PM                          panels.c                                    Page 26

968  /******************************************************************************
969   * Function name:   truncate_string - chops chars off a string until it fits
970   *
971   *   Description:    truncate_string takes a pascal string and chops characters off of it
972   *                   until it fits with a trailing elipsis within the width supplied.
973   *                   The trailing elipsis is also added by this routine.
974   *
975   *       Inputs:     str        a pointer to a Pascal string
976   *                   width      the desired width for the string + elipsis
977   *
978   *       Outputs:    str        the string will be altered, if it's too long
979   *
980   *   Side Effects:              May cause heap objects to be moved.
981   *
982   *       Return:     void
983   *
984   ******************************************************************************/
985  void    truncate_string(str, width)
986
987  char*   str;            /* This is really a Pascal string! */
988  short   width;
989
990  {
991      short   strwidth;
992      short   len;
993
994      strwidth = STRINGWIDTH(str);
995
996      while ((str[0] > 2) && (strwidth > width))
997          {
998          len = --str[0];
999          strwidth = STRINGWIDTH(str);
1000         str[len] = '_';
1001         }
1002 }
1003
1004
1005
```

```
12/22/88 3:47 PM                            panels.c                                       Page 27

1006  /******************************************************************************
1007   * Function name:    draw_menu_item - draws a menu.
1008   *
1009   *   Description:    Draws a control panel picture item within its rectangle.
1010   *
1011   *       Inputs:     cItemHdl    a handle to an control panel item
1012   *
1013   *       Outputs:    none
1014   *
1015   *   Side Effects:              May cause heap objects to be moved.
1016   *                              Draws to current grafport.
1017   *
1018   *       Return:     void
1019   *
1020   ******************************************************************************/
1021
1022  void draw_menu_item(item)
1023
1024  cItemHdl    item;
1025
1026  {
1027      register cItemPtr cip;
1028      Rect            iBox, r, stringRect;
1029      menuItemData    mid;
1030      MenuHandle      menu;
1031      STR255          str;
1032      long            len;
1033      RgnHandle       clip;
1034
1035      cip = *item;
1036      iBox = cip->iBox;
1037      mid = cip->iData.iMenu;
1038      menu = mid.menu;
1039      LoadResource((Handle) menu);
1040
1041      /* Draw the title string. */
1042      len = *((char*)&((*menu)->menuData)) + 1;
1043      BlockMove(&((*menu)->menuData), &str, len);
1044      MoveTo(iBox.left+2, iBox.top + 12 );
1045      DRAWSTRING(&str);
1046
1047      r = iBox;
1048      r.left = r.left + mid.titlewidth;
1049      r.right = r.left + mid.menuwidth;
1050      r.bottom = r.top + 18;
1051      FrameRect(&r);
1052      MoveTo(r.left + 2, r.bottom);
1053      LineTo(r.right, r.bottom);
1054      LineTo(r.right, r.top + 2);
1055
1056      clip = NewRgn();          /* Clip string drawing to the menu's rect */
1057      failnil((char*)clip);
1058      GetClip(clip);
1059      ClipRect(&r);
1060
1061      /* Draw the current value string. */
1062      stringRect = r;
1063      stringRect.left += 12;        /* Match the standard text menu's item offset */
1064      MoveTo( stringRect.left, stringRect.bottom - 6);
1065      GETITEM(menu, mid.selected, &str);
1066      truncate_string(&str, WIDTH(stringRect)); /* Chop long strings to fit. */
1067      DRAWSTRING(&str);
1068
1069      SetClip(clip);
```

```
12/22/88 3:47 PM                    panels.c                        Page 28
   1070         DisposeRgn(clip);
   1071   }
   1072
   1073
   1074
```

```
12/22/88 3:47 PM                            panels.c                                    Page 29

1075    /**********************************************************************************
1076     * Function name:    draw_edit_item - draws an edit text item.
1077     *
1078     * Description:      Draws a control panel edit text item within its rectangle.
1079     *
1080     *      Inputs:       cItemHdl    a handle to an control panel item
1081     *
1082     *      Outputs:      none
1083     *
1084     * Side Effects:                  May cause heap objects to be moved.
1085     *                                Draws to current grafport.
1086     *
1087     *      Return:       void
1088     *
1089     **********************************************************************************/
1090
1091    void draw_edit_item(item)
1092
1093    cItemHdl     item;
1094
1095    {
1096        register cItemPtr cip;
1097        Rect            iBox;
1098        editItemData    eid;
1099        FontInfo        fi;
1100        STR255          str;
1101        short           baseline;
1102        RgnHandle       clip;
1103
1104        cip = *item;
1105        iBox = cip->iBox;
1106        eid = cip->iData.iEdit;
1107
1108        GetFontInfo(&fi);
1109        baseline = iBox.bottom - fi.descent - 4; /* 4 is a guess for offsetting for editbox */
1110
1111        set_Str255(eid.prelabel, &str);    /* Draw the leading label. */
1112        MoveTo(iBox.left, baseline);
1113        DRAWSTRING(&str);
1114
1115        set_Str255(eid.postlabel, &str);   /* Draw the leading label. */
1116        MoveTo(iBox.right - STRINGWIDTH(&str), baseline);
1117        DRAWSTRING(&str);
1118
1119        FrameRect(&eid.editBox);
1120
1121        clip = NewRgn();                   /* Clip string drawing to the viewrect */
1122        failnil((char*)clip);
1123        GetClip(clip);
1124        ClipRect(&eid.editBox);
1125
1126        /**** the following will be changed when real text edit is incorporated. ****/
1127        set_Str255(eid.theText, &str);
1128        MoveTo(eid.editBox.left + 4, baseline);
1129        DRAWSTRING(&str);
1130
1131        SetClip(clip);
1132        DisposeRgn(clip);
1133    }
1134
1135
1136
```

12/22/88 3:47 PM                          panels.c                                      Page 30

```
1137  /*******************************************************************************
1138   * Function name:   draw_text_item - draws a static text item.
1139   *
1140   * Description:     Draws a control panel text item within its rectangle.
1141   *
1142   *     Inputs:      cItemHdl    a handle to a control panel item
1143   *
1144   *     Outputs:     none
1145   *
1146   * Side Effects:                May cause heap objects to be moved.
1147   *                              Draws to current grafport.
1148   *
1149   *     Return:      void
1150   *
1151   *******************************************************************************/
1152
1153  void draw_text_item(item)
1154
1155  cItemHdl    item;
1156
1157  {
1158      register cItemPtr cip;
1159      Rect        iBox;
1160      cItemData   iData;
1161      FontInfo    fi;
1162      STR255      str;
1163      short       baseline;
1164      short       width;
1165
1166      cip = *item;
1167      iBox  = cip->iBox;
1168      iData = cip->iData;
1169
1170      GetFontInfo(&fi);
1171      baseline = iBox.bottom - fi.descent - 4; /* 4 is a guess for offsetting for editbox */
1172
1173      set_Str255(iData.iText, &str);  /* Draw the leading label. */
1174      width = STRINGWIDTH(&str);
1175      MoveTo(iBox.right - (width + 4), baseline);
1176      DRAWSTRING(&str);
1177
1178  }
1179
1180
1181
```

```
12/22/88 3:47 PM                        panels.c                                Page 31

1182   /****************************************************************************
1183    * Function name:   draw_item - draws a control panel item within it's rectangle.
1184    *
1185    *   Description:    Draws a control panel at 0,0.
1186    *
1187    *       Inputs:     cItemHdl    a handle to an control panel item
1188    *
1189    *       Outputs:    none
1190    *
1191    * Side Effects:                 May cause heap objects to be moved.
1192    *                               Draws to current grafport.
1193    *
1194    *       Return:     void
1195    *
1196    ****************************************************************************/
1197
1198   void draw_item(item)
1199
1200   cItemHdl    item;
1201
1202   {
1203       long        iType;
1204
1205       iType = (*item)->iType;
1206
1207       /* Choose the right drawing routine. */
1208       switch (iType) {
1209           case 'pict':
1210               draw_picture_item(item);
1211               break;
1212
1213           case 'rect':
1214               draw_rect_item(item);
1215               break;
1216
1217           case 'edit':
1218               draw_edit_item(item);
1219               break;
1220
1221           case 'text':
1222               draw_text_item(item);
1223               break;
1224
1225           case 'menu':
1226               draw_menu_item(item);
1227               break;
1228       }; /* end switch */
1229
1230   }
1231
1232
1233
```

12/22/88 3:47 PM                    panels.c                                  Page 32

```
1234   /************************************************************************
1235    * Function name:    draw_panel - draws a control panel.
1236    *
1237    *   Description:    Draws a control panel at 0,0.
1238    *
1239    *       Inputs:     panel       a panel handle
1240    *
1241    *       Outputs:    none
1242    *
1243    *   Side Effects:               May cause heap objects to be moved.
1244    *                               Draws to the screen
1245    *
1246    *       Return:     void
1247    *
1248    ************************************************************************/
1249
1250   void draw_panel(panel)
1251
1252   cPanelHdl   panel;
1253
1254   {
1255
1256       cItemHdl    item;
1257       Rect        r;
1258
1259       if (panel != nil)           /* Be sure the panel exists. */
1260           {
1261           save_text_info();
1262           TextFont(systemFont);
1263           TextFace(0);
1264           TextSize(0);
1265           focus(panel);
1266
1267           r = (*panel)->pBox;     /* Erase the background. */
1268           EraseRect(&r);
1269
1270           item = (*panel)->items; /* Get the first item. */
1271           while (item != nil)     /* Draw the entire item list. */
1272               {
1273               draw_item(item);
1274               item = (*item)->next;
1275               };
1276
1277           restore_text_info();
1278           unfocus();
1279           }
1280   }
1281
1282
1283
1284
```

12/22/88 3:47 PM                                panels.c                                       Page 33

```
1285  /*****************************************************************************
1286   * Function name:    find_item - finds the first item that encloses the point.
1287   *
1288   *   Description:    Finds the item corresponding to a mouseDown point or nil
1289   *                   if the point is contain in no item's bounding rectangle.
1290   *
1291   *       Inputs:     p           Mouse down point in image coordinates
1292   *                   panel       the control panel
1293   *                   *item       the item containing the point
1294   *
1295   *       Outputs:    none
1296   *
1297   *   Side Effects:               May cause heap objects to be moved.
1298   *
1299   *       Return:     Boolean     true if the point was in an item
1300   *
1301   *****************************************************************************/
1302
1303  Boolean find_item(p, panel, item)
1304
1305  Point      *p;
1306  cPanelHdl  panel;
1307  cItemHdl   *item;
1308
1309  {
1310      cItemHdl   ih;
1311      Boolean    found;
1312      Rect       r;
1313
1314      found = false;
1315      ih = (*panel)->items;           /* Get the first item. */
1316
1317      while ((ih != nil) && (!found))
1318          {
1319          r = (*ih)->iBox;
1320          if (PTINRECT(*p, &r))
1321              found = true;
1322          else
1323              ih = (*ih)->next;
1324          }
1325
1326      *item = (found ? ih : nil);
1327      return found;
1328  }
1329
1330
1331
```

```
12/22/88 3:47 PM                          panels.c                                    Page 34

1332  /******************************************************************************
1333   * Function name:   do_menu_item - handles a mousedown event for a menu item.
1334   *
1335   *   Description:    Crates a popup menu, tracks mouse movements, finds the new selection,
1336   *                   if any and disposes of the popup menu.
1337   *
1338   *       Inputs:     p           a pointer to a point
1339   *                   panel       a handle to a control panel
1340   *                   item        a handle to the item
1341   *                   *event      a pointer to an event
1342   *
1343   *       Outputs:    none
1344   *
1345   *   Side Effects:           May cause heap objects to be moved.
1346   *                           May cause the current selection of the menu item to change.
1347   *
1348   *       Return:     void
1349   *
1350   ******************************************************************************/
1351
1352  void do_menu_item(p, panel, item, event)
1353
1354  Point           *p;
1355  cPanelHdl       panel;
1356  cItemHdl        item;
1357  EventRecord     *event;
1358
1359  {
1360      Rect            menuRect;
1361      Rect            titleRect;
1362      MenuHandle      mh;
1363      long            l;
1364      short           width;
1365      menuItemData    mid;
1366      Point           menuPt;
1367
1368      menuRect = (*item)->iBox;
1369
1370      mid = (*item)->iData.iMenu;
1371      mh = mid.menu;
1372      width = mid.titlewidth;
1373
1374      LoadResource((Handle) mh);
1375      InsertMenu(mh, -1);
1376      titleRect = menuRect;
1377      titleRect.right = titleRect.left + width;
1378      titleRect.bottom = titleRect.top + 16;          /**** need a constant ***/
1379      InvertRect(&titleRect);
1380
1381      /* Erase the old menu image, as the popup may not completely overlap it. */
1382      menuRect.left += width;     /* don't erase the title */
1383      menuRect.right += 1;        /* overlap the drop shadow */
1384      EraseRect(&menuRect);
1385
1386      menuPt.h = menuRect.left;
1387      menuPt.v = menuRect.top;
1388      LocalToGlobal(&menuPt);     /* PopUpMenuSelect needs Global coordinates */
1389      l = PopUpMenuSelect(mh, menuPt.v, menuPt.h, mid.selected);
1390      InvertRect(&titleRect);
1391
1392      /* Record the new selection. */
1393      if (HIWORD(l) != 0)         /* 0 in the high word means nothing was selected */
1394          (*item)->iData.iMenu.selected = LOWORD(l);
1395
```

12/22/88 3:47 PM                              panels.c                                        Page 35

```
1396        DeleteMenu(235);         /* Let our only popup menu slot become available again. */
1397        InvalRect(&menuRect);    /* Redraw the menu box with the new selection. */
1398   }
1399
1400
1401
```

```
1402   /******************************************************************************
1403    * Function name:   start_edit - opens a text edit record for a textedit item
1404    *
1405    *   Description:
1406    *
1407    *       Inputs:     panel       a handle to a control panel
1408    *                   item        a handle to the item
1409    *
1410    *       Outputs:    none
1411    *
1412    *   Side Effects:               May cause heap objects to be moved.
1413    *
1414    *       Return:     void
1415    *
1416    ******************************************************************************/
1417
1418   void start_edit(panel, item)
1419
1420   cPanelHdl       panel;
1421   cItemHdl        item;
1422
1423   {
1424       editItemData    eid;
1425       Rect            destRect;
1426       Rect            viewRect;
1427       STR255          str;
1428       char            *s;
1429       TEHandle        teh;
1430
1431       eid = (*item)->iData.iEdit;         /* Get the width of the leading label. */
1432       viewRect = eid.editBox;             /* Get the editing rectangles. */
1433       InsetRect(&viewRect, 2, 0);
1434       viewRect.bottom -= 1;
1435       destRect = viewRect;
1436       InsetRect(&destRect, 3, 3);
1437
1438       teh = TENew(&destRect, &viewRect);  /* Create a text edit handle. */
1439       TEActivate(teh);
1440
1441       failnil((char*)teh);
1442       eid.teh = teh;
1443       (*item)->iData.iEdit = eid;
1444
1445       s = (char*)&str;                    /* Make a C string pointer for easy indexing. */
1446       set_Str255(eid.theText, &str);      /* Copy the string and insert it. */
1447       TESetText(&s[1], s[0], teh);
1448
1449       InvalRect(&viewRect);
1450       gActiveEditItem = item;             /* This is now the active edit item for this window. */
1451       gTEH = teh;
1452   }
1453
1454
1455
```

```
12/22/88 3:47 PM                        panels.c                                Page 37

1456  /*******************************************************************************
1457   * Function name:    save_edit -
1458   *
1459   *   Description:
1460   *
1461   *       Inputs:     p           a pointer to a point
1462   *                   panel       a handle to a control panel
1463   *                   item        a handle to the item
1464   *                   *event      a pointer to an event
1465   *
1466   *       Outputs:    none
1467   *
1468   *   Side Effects:               May cause heap objects to be moved.
1469   *                               May cause the values of the panels controls to change.
1470   *
1471   *       Return:     void
1472   *
1473   *******************************************************************************/
1474
1475  void save_edit(item)
1476
1477  cItemHdl        item;
1478
1479  {
1480      editItemData    eid;
1481      Handle          t;
1482      STR255          str;
1483
1484      eid = (*item)->iData.iEdit;
1485
1486      t = (*(eid.teh))->hText;            /* Save the edited text. */
1487      GETITEXT(t, &str);                  /* This odd use of GetIText is recommended IM I-381. */
1488      SETSTRING(eid.theText, &str);
1489
1490      (*item)->iData.iEdit = eid;         /* Update the item's data record. */
1491  }
1492
1493
1494
```

12/22/88 3:47 PM    panels.c    Page 38

```
1495   /*******************************************************************************
1496    * Function name:     complete_edit -
1497    *
1498    *   Description:
1499    *
1500    *       Inputs:      p           a pointer to a point
1501    *                    panel       a handle to a control panel
1502    *                    item        a handle to the item
1503    *                    *event      a pointer to an event
1504    *
1505    *       Outputs:     none
1506    *
1507    *   Side Effects:                May cause heap objects to be moved.
1508    *                                May cause the values of the panels controls to change.
1509    *
1510    *       Return:      void
1511    *
1512    *******************************************************************************/
1513
1514   void complete_edit(item)
1515
1516   cItemHdl       item;
1517
1518   {
1519       editItemData    eid;
1520
1521       eid = (*item)->iData.iEdit;
1522
1523       save_edit(item);
1524
1525       TEDispose(eid.teh);              /* Throw away the edit record. */
1526       eid.teh = nil;                   /* And rememeber that it's gone. */
1527       gTEH = nil;
1528
1529       (*item)->iData.iEdit = eid;      /* Update the item's data record. */
1530       gActiveEditItem = nil;           /* No active edit items any more. */
1531   }
1532
1533
1534
1535
```

```
12/22/88 3:47 PM                          panels.c                                 Page 39

1536   /****************************************************************************
1537   * Function name:    do_edit_item - handles a mousedown event for an edit text item.
1538   *
1539   *   Description:    Activates an inactive text edit item, or changes its selection
1540   *                   range.
1541   *
1542   *       Inputs:     p           a pointer to a point
1543   *                   panel       a handle to a control panel
1544   *                   item        a handle to the item
1545   *                   *event      a pointer to an event
1546   *
1547   *       Outputs:    none
1548   *
1549   *   Side Effects:               May cause heap objects to be moved.
1550   *                               May cause the values of the panels controls to change.
1551   *
1552   *       Return:     void
1553   *
1554   ****************************************************************************/
1555
1556   void do_edit_item(p, panel, item, event)
1557
1558   Point          *p;
1559   cPanelHdl      panel;
1560   cItemHdl       item;
1561   EventRecord    *event;
1562
1563   {
1564       editItemData    eid;
1565
1566       /* If another item is currently being edited, close that edit before starting the new one. */
1567       if ((gActiveEditItem != nil) && (gActiveEditItem != item))
1568           complete_edit(gActiveEditItem);
1569
1570       /* If this item isn't already the active edit item, make it so. */
1571       if ((*item)->iData.iEdit.teh == nil)
1572           start_edit(panel, item);
1573
1574       eid = (*item)->iData.iEdit;
1575
1576       TECLICK(*p, (event->modifiers & shiftKey), eid.teh);
1577
1578   }
1579
1580
```

```
12/22/88 3:47 PM                         panels.c                                    Page 40

1581  /*******************************************************************************
1582   * Function name:    do_no_item - handles a mousedown in a panel's background.
1583   *
1584   *   Description:    Currently just unselects the active edit item, if any.
1585   *
1586   *        Inputs:    panel       a handle to a control panel
1587   *                   *event      a pointer to an event
1588   *
1589   *        Outputs:   none
1590   *
1591   * Side Effects:                 May cause heap objects to be moved.
1592   *                               May cause the values of the panels controls to change.
1593   *
1594   *        Return:    void
1595   *
1596   *******************************************************************************/
1597
1598  void do_no_item(panel, event)
1599
1600  cPanelHdl   panel;
1601  EventRecord *event;
1602
1603  {
1604      if (gActiveEditItem != nil)
1605          {
1606          InvalRect(&((*gActiveEditItem)->iData.iEdit.editBox));
1607          complete_edit(gActiveEditItem);
1608          }
1609
1610  }
1611
1612
1613
```

12/22/88 3:47 PM                          panels.c                                          Page 41

```
1614   /******************************************************************************
1615    * Function name:    do_item - handles a mousedown event for an item.
1616    *
1617    *   Description:    Dispatches mouse down events to handler routines by item type.
1618    *
1619    *       Inputs:     p           a pointer to a point
1620    *                   panel       a handle to a control panel
1621    *                   item        a handle to the item
1622    *                   *event      a pointer to an event
1623    *
1624    *       Outputs:    none
1625    *
1626    *   Side Effects:               May cause heap objects to be moved.
1627    *                               May cause the values of the panels controls to change.
1628    *
1629    *       Return:     void
1630    *
1631    ******************************************************************************/
1632
1633   void do_item(p, panel, item, event)
1634
1635   Point       *p;
1636   cPanelHdl   panel;
1637   cItemHdl    item;
1638   EventRecord *event;
1639
1640   {
1641       long        iType;
1642
1643       iType = (*item)->iType;
1644
1645       /* Choose the right drawing routine. */
1646       switch (iType) {
1647           case 'pict':
1648               break;
1649
1650           case 'rect':
1651               break;
1652
1653           case 'edit':
1654               do_edit_item(p, panel, item, event);
1655               break;
1656
1657           case 'text':
1658               break;
1659
1660           case 'menu':
1661               do_menu_item(p, panel, item, event);
1662               break;
1663       }; /* end switch */
1664   }
1665
1666
1667
1668
```

```
12/22 88 3.47 PM                               panels.c                                    Page 42

1669  /*******************************************************************************
1670   * Function name:   do_panel_mouse_down - Handles an event destined for a control panel.
1671   *
1672   *   Description:   Performs whatever action is necessary to process an event
1673   *                  for a control panel.
1674   *
1675   *        Inputs:   panel     the handle to the panel in question
1676   *                  *event    a pointer to an event
1677   *
1678   *       Outputs:   none
1679   *
1680   *  Side Effects:             May cause heap objects to be moved.
1681   *                            May cause the values of the panels controls to change.
1682   *
1683   *        Return:   void
1684   *
1685   *******************************************************************************/
1686
1687  void do_panel_mouse_down(panel, event)
1688
1689  cPanelHdl    panel;
1690  EventRecord  *event;
1691
1692  {
1693      Point     p;
1694      cItemHdl  item;
1695      Rect      use;
1696
1697      save_text_info();
1698      TextFont(systemFont);   /* Always use the system font inside a panel. */
1699      TextFace(0);
1700      TextSize(0);
1701
1702      use = usable;
1703      SetOrigin(curOrigin.h, curOrigin.v);        /* Go to Image coordinates temporarily. */
1704      OffsetRect(&use, curOrigin.h, curOrigin.v);
1705      ClipRect(&use);                             /* Offset the clip. */
1706
1707      p = event->where;             /* Global coordinates. */
1708      GlobalToLocal(&p);            /* Window's coordinates. */
1709      focus(panel);                 /* Set local coordinate system to panel's coordinates. */
1710      window2panel_point(&p);
1711
1712      if (find_item(&p, panel, &item))
1713          do_item(&p, panel, item, event);
1714      else
1715          do_no_item(panel, event);
1716
1717      unfocus();
1718      restore_text_info();
1719
1720      SetOrigin(0,0);                             /* Return to screen coordinates. */
1721      ClipRect(&(theWPtr->portRect));             /* Allow scrollbars to be drawn */
1722  }
1723
1724
```

12/22/88 3:47 PM                             panels.c                                      Page 46

```
1725  /******************************************************************************
1726   * Function name:   do_panel_key - Handles an keyDown event for a control panel
1727   *
1728   *   Description:
1729   *
1730   *       Inputs:     panel       the handle to the panel in question
1731   *                   *event      a pointer to an event
1732   *
1733   *       Outputs:    none
1734   *
1735   *       Side Effects:           May cause heap objects to be moved.
1736   *                               May cause the values of the panels controls to change.
1737   *
1738   *       Return:     void
1739   *
1740   ******************************************************************************/
1741
1742  void do_panel_key(event)
1743
1744  EventRecord *event;
1745
1746  {
1747      Rect        use;
1748      cPanelHdl   panel;
1749
1750      if (gActiveEditItem != nil)
1751          {
1752          save_text_info();
1753          TextFont(systemFont);    /* Always use the system font inside a panel. */
1754          TextFace(0);
1755          TextSize(0);
1756
1757          use = usable;
1758          SetOrigin(curOrigin.h, curOrigin.v);        /* Go to Image coordinates temporarily. */
1759          OffsetRect(&use, curOrigin.h, curOrigin.v);
1760          ClipRect(&use);                             /* Offset the clip. */
1761
1762          panel = (*gActiveEditItem)->panel;
1763          focus(panel);                   /* Set local coordinate system to panel's coordinates. */
1764
1765          TEKey((event->message & charCodeMask), (*gActiveEditItem)->iData.iEdit.teh);
1766
1767          unfocus();
1768          restore_text_info();
1769
1770          SetOrigin(0,0);                             /* Return to screen coordinates. */
1771          ClipRect(&(theWPtr->portRect));             /* Allow scrollbars to be drawn */
1772
1773          save_edit(gActiveEditItem);
1774          }
1775  }
1776
1777
1778  void panel_idle(wPtr)
1779
1780  WindowPtr wPtr;
1781
1782  {
1783      Rect        use;
1784      cPanelHdl   panel;
1785
1786      if (gActiveEditItem != nil)
1787          {
1788          use = usable;
```

12/22/88 3:47 PM                              panels.c                                    Page 44

```
1789        SetOrigin(curOrigin.h, curOrigin.v);           /* Go to Image coordinates temporarily. */
1790        OffsetRect(&use, curOrigin.h, curOrigin.v);
1791        ClipRect(&use);                                /* Offset the clip. */
1792
1793        panel = (*gActiveEditItem)->panel;
1794        focus(panel);               /* Set local coordinate system to panel's coordinates. */
1795
1796        TEIdle((*gActiveEditItem)->iData.iEdit.teh);
1797
1798        unfocus();
1799        restore_text_info();
1800
1801        SetOrigin(0,0);                                 /* Return to screen coordinates. */
1802        ClipRect(&(theWPtr->portRect));                 /* Allow scrollbars to be drawn */
1803
1804        }
1805  }
1806
1807
```

```
1  /****************************************************************************
2   *    Copyright ©1988 by Applied Biosystems, Inc. All rights reserved.
3   ****************************************************************************
4   *
5   *     File Name: iconDraw.h
6   *
7   *     Description: Header for iconDraw.c, Drawing routines for icon editor windows.
8   *
9   *     Caveats: None.
10  *
11  *     Edit History: 26 October 88 Converted from Pascal by HG
12  *
13  ****************************************************************************/
14
15
16 /****************************************************************************
17  *    Preprocessor Directives
18  */
19 #ifndef __ICONDRAW__
20 #define __ICONDRAW__
21
22 #ifdef MPW
23 #define HiliteMode  0x0938
24 #endif
25
26 #define pHiliteBit  0
27
28 /****************************************************************************
29  *    Include Files
30  */
31 #include "includes.h"
32 #include "misc.h"
33 #include "iconUtils.h"
34
35
36 /****************************************************************************
37  *    Macros
38  *    none
39  */
40
41
42 /****************************************************************************
43  *    Structures and Typedefs
44  */
45
46 typedef BitMap  *BitMapPtr;
47
48 typedef long iconBits[32];
49
50 typedef struct iconList {
51     iconBits    icon;
52     iconBits    mask;
53 } iconList, *iconListPtr, **iconListHdl;
54
55
56 /****************************************************************************
57  *    Scope
58  */
59 extern RGBColor RGBWhite;
60 extern RGBColor RGBBlack;
61 extern RGBColor RGBGray;
62
63
64 /****************************************************************************
```

11/18/88 10:22 AM iconDraw.h Page 2

```
65  *   Function Prototypes
66  */
67  void remeasure_icons(void);
68  void draw_icons(WindowPtr wPtr, Rect *area);
69
70  #endif
```

11/23/88 5:56 PM                          iconDraw.c                                  Page 1

```
1   /*******************************************************************************
2      Copyright ©1988 by Applied Biosystems, Inc. All rights reserved.
3   ********************************************************************************
4   *
5   *      File Name: iconDraw.c
6   *
7   *      Description: Drawing routines for icon editor windows
8   *
9   *      Caveats: None.
10  *
11  *      Edit History: 26 October 88 Converted from Pascal by HG
12  *
13  *******************************************************************************/
14
15
16  /*******************************************************************************
17  *   Preprocessor Directives
18  *   none
19  */
20
21
22  /*******************************************************************************
23  *   Include Files
24  */
25  #include "iconDraw.h"
26
27
28  /*******************************************************************************
29  *   External References
30  */
31
32
33  /*******************************************************************************
34  *   Structures and Typedefs
35  *   none
36  */
37
38
39  /*******************************************************************************
40  *   Static Objects
41  */
42  RGBColor    RGBWhite;
43  RGBColor    RGBBlack;
44  RGBColor    RGBGray;
45  static Boolean oneBit;  /* true whenever current window intersects a one-bit deep grafport */
46
47
48  /*******************************************************************************
49  *   Function Prototypes -- functions local to this file
50  */
51  static void     measure_note(Handle t, Rect *box);
52  static void     measure_panel(iconNodeHdl iNode, Rect *bounds);
53  static void     measure_icon (iconNodeHdl iNode, Rect *bounds);
54  static void     measure_icon_list(iconNodeHdl  iNode, Rect *bounds);
55  static void     offset_descendents(iconNodeHdl iNode, short *offset);
56  static void     center_icons(iconNodeHdl iNode, Rect *bounds);
57  static void     draw_a_note(Rect *r, Handle t);
58  static Boolean  bright_node(iconNodeHdl iNode);
59  static void     draw_notes(iconNodeHdl iNode);
60  static RgnHandle back_rgn(iconNodeHdl iNode);
61  static void     draw_frame(iconNodeHdl iNode);
62  static void     draw_centerline(iconNodeHdl iNode);
63  static void     draw_open_icon(iconNodeHdl  iNode);
64  static void     draw_closed_icon(iconNodeHdl iNode);
```

```
65  static void    draw_icon_node(iconNodeHdl iNode);
66  static void    draw_icon_list(Rect *area, iconNodeHdl iNode);
67
68
69
70
```

11/23/88 5:56 PM                                iconDraw.c                                        Page 3

```
71   /********************************************************************************
72   * Function name:    measure_note -- returns bounding rectangle for text passed in t
73   *
74   *   Description:    Using the window's default text size font face and style, measure_note
75   *                   computes the smallest rectangle that will enclose the text pa
76   *
77   *        Inputs:    t           a Handle to text
78   *
79   *       Outputs:    Rect        the bounding rectangle for the text normalized to (0,0)
80   *
81   * Side Effects:                 May cause heap objects to be moved.
82   *
83   *        Return:    void
84   *
85   ********************************************************************************/
86
87   void measure_note(t, box)
88
89   Handle     t;
90   Rect       *box;
91
92   {
93       short      width;       /* width of text */
94       short      newWidth;    /* width of latest line to be measured */
95       short      height;      /* height of text */
96       short      fHeight;     /* total height for a line of text */
97       FontInfo   f;           /* basic metrics for grafport's font */
98       long       p;           /* Munger's result */
99       long       start;       /* start of most recent Munger search for a CR */
100      long       last;        /* last character in the text */
101      long       count;       /* last char in current line. */
102      char       c;           /* a place for our search string, a CR */
103
104  #ifdef DEBUG
105      /* debugwrite("\pmeasure_note"); */
106  #endif
107
108      width = 0;
109      height = 0;
110      GetFontInfo(&f);
111      fHeight = f.ascent + f.descent + f.leading;
112
113      c = CR;
114      start = 0;
115      last = GetHandleSize(t);
116      p = 0;
117      while (p >= 0)    /* Fall out when Munger returns a negative when it can't find another CR. */
118          {
119          p = Munger(t, start, &c, 1, nil, 0);
120          if ((p > 0) || (start < last))
121              {
122              /* If p > 0 then a carriage return terminated line was found. */
123              /* Last line in text might not be terminated with a return. */
124              count = ((p > 0) ? p : last) - start;
125
126              /* Expand the dimensions to include the new line. */
127              height += fHeight;
128              HLock(t);
129              newWidth = TextWidth(*t, start, count);
130              width = MAX(width, newWidth);
131              HUnlock(t);
132
133              }
134          start = p + 1;   /* Start searching again after the last found return character. */
```

```
11/23/88 5:56 PM                          iconDraw.c                              Page 4
135          }
136
137       SetRect(box, 0, 0, width, height);  /* L T R B */
138  }
139
140
141
```

```
11/23/8  5:56 PM                          iconDraw.c                                      Page 5

142  /*******************************************************************************
143   * Function name:     measure_panel -- measures a control panel
144   *
145   *   Description:     Returns a control panel's rectangle offset to bounds.topleft;
146   *
147   *         Inputs:     iNode      a Handle to an icon node
148   *                     bounds     topleft point of the control panel rect is passed in bounds
149   *
150   *        Outputs:     bounds     bottom right point is returned.
151   *
152   *   Side Effects:                May cause heap objects to be moved.
153   *
154   *         Return:     void
155   *
156   *******************************************************************************/
157
158  void measure_panel(iNode, bounds)
159
160  iconNodeHdl    iNode;
161  Rect           *bounds;
162
163  {
164      Rect       r;
165
166  #ifdef DEBUG
167      /* debugwrite("\pmeasure_panel"); */
168  #endif
169
170      r = (*((*iNode)->data.panel))->pBox;
171      OffsetRect(&r, bounds->left, bounds->top);
172      *bounds = r;
173
174  }
175
176
177
```

11/23/88 5:56 PM                        iconDraw.c                                    Page 6

```
178  /********************************************************************************
179   * Function name:   measure_icon -- sets the size of an icon's bounding rect.
180   *
181   *   Description:   Measure_icon detemines the size of an icon's bounding rect
182   *                  based upon its cicn size or a standard icon size and the top
183   *                  left point of the rectangle as passed in bounds.
184   *
185   *        Inputs:   iNode      a Handle to an icon node
186   *                  bounds     top left point of the rectangle is preserved
187   *
188   *       Outputs:   bounds     bottom right point is changed
189   *
190   *  Side Effects:              May cause heap objects to be moved.
191   *
192   *        Return:   void
193   *
194   ********************************************************************************/
195
196  void measure_icon (iNode, bounds)
197
198  iconNodeHdl       iNode;
199  Rect              *bounds;
200
201  {
202
203  CIconHandle       cicn;
204  Rect              r;
205
206  cicn = (*iNode)->cicn;
207
208  if (cicn)                                 /* Use the color icon if there is one. */
209      {
210      r = (*cicn)->iconPMap.bounds;         /* Color icons can be other than 32x32. */
211      bounds->right = bounds->left + WIDTH(r);
212      bounds->bottom = bounds->top + HEIGHT(r);
213      }
214  else
215      {
216      bounds->right = bounds->left + 32;    /* Regular icons are always 32x32. */
217      bounds->bottom = bounds->top + 32;
218      }
219  }
220
221
222
223
```

11/23/88 5:56 PM                    iconDraw.c                                    Page 7

```
224   /*******************************************************************************
225    * Function name:    measure_icon_list -- adjust frames & outlines for an icon list
226    *
227    *   Description:    Recursively adjusts all frames and outlines for the icon list
228    *                   indicated by iNode. Includes iNode and all of iNode's descendents.
229    *                   Returns the bounding rectangle for the entire icon list.
230    *
231    *       Inputs:     iNode       a Handle to an icon node
232    *                   bounds      topleft point is used as starting point for this iconlist
233    *
234    *       Outputs:    bounds      bottom right point is set based upon topleft and size of bounds
235    *
236    * Side Effects:                 May cause heap objects to be moved.
237    *
238    *       Return:     void
239    *
240    *******************************************************************************/
241
242   void measure_icon_list(iNode, bounds)
243
244   iconNodeHdl iNode;
245   Rect        *bounds;
246
247   {
248       iconNodeHdl aNode;
249       iconNodeHdl desc;
250       iconNodeHdl next;
251       iconNodePtr ip;            /* to dereference the handle for quickness. */
252       Rect        r;             /* a scratchpad for Rects */
253       Rect        tNoteRect;     /* top note */
254       Rect        bNoteRect;     /* bottom note */
255       Rect        frame;         /* a local copy of the icon's frame */
256       Point       offset;        /* offset from upper left corner of this node */
257       short       v;             /* a vertical offset for placing notes */
258       short       maxNoteDepth;  /* depth of deepest note */
259       short       maxFrameDepth; /* depth of deepest frame */
260       short       noteDepth;     /* deepest note for this icon */
261       short       noteWidth;     /* widest note for this icon */
262       short       maxWidth;      /* widest point at this level */
263       Boolean     split;         /* if true, represent descendent nodes as divergent paths. */
264       Boolean     open;
265       short       kind;
266       Handle      tNote;
267       Handle      bNote;
268       Rect        outLine;
269
270
271   #ifdef DEBUG
272       debugwrite("\pmeasure_icon_list");
273   #endif
274
275       /* Icons are arranged vertically if parent of this generation is a divergent path node. */
276       split = false;
277       ip = *iNode;
278       /* Don't dereference root's (non-existant) parent and ... */
279       /* ... only look at process icons. */
280       if ((ip->moma) && (ip->iKind == iconProcess))
281           split = (*((*(ip->moma))->data.proc))->split;
282
283       /* Repeat the measurement process for each node at the same level. */
284       aNode = iNode;
285
286       /* On entering, leave a margin at the topleft corner. */
287       offset.h = bounds->left + MARGIN;
```

11/23/88 5:56 PM iconDraw.c Page 8

```
288        if (split)              /* Leave extra margin for split nodes */
289            offset.h += MARGIN;
290        offset.v = bounds->top + MARGIN;
291
292        maxNoteDepth = 0;       /* No notes have been measured yet at this level. */
293        maxFrameDepth = 0;      /* No frames have been measured yet either. */
294        maxWidth = 0;           /* No widths have been recorded yet. */
295
296        do {
297
298 #ifdef DEBUG
299        /* debugwrite("\pone more"); */
300 #endif
301            ip = *aNode;         /* Grab some values from the current node. */
302            kind = ip->iKind;
303            tNote = ip->tNote;
304            bNote = ip->bNote;
305            open = ip->open;
306            frame = ip->frame;
307            outLine = ip->outLine;
308            desc = ip->desc;
309            next = ip->next;
310
311            /* Find the width and depth of the notes for this icon. */
312            measure_note(tNote, &tNoteRect);
313            measure_note(bNote, &bNoteRect);
314
315            /* Save the new maximum note depth. */
316            noteDepth = MAX(tNoteRect.bottom, bNoteRect.bottom);
317            maxNoteDepth = MAX(maxNoteDepth, noteDepth);
318
319            v = offset.v + maxNoteDepth - HEIGHT(tNoteRect);   /* Place the tNote rect vertically. */
320            OffsetRect(&tNoteRect, 0, v);
321
322            ip = *aNode;                /* Dereference aNode again as memory may have moved. */
323            frame.top = tNoteRect.bottom;
324            frame.left = offset.h;
325            outLine.top = tNoteRect.top;   /* Record the topleft point of the outline. */
326            outLine.left = offset.h;
327
328            /* Set frame's bottom right point according to it's size. */
329            if (!open)                  /* If it's closed, just measure it's icon. */
330                measure_icon(aNode, &frame);   /* Find the bottom right corner of the frame. */
331            else
332                switch (kind){          /* Currently only two kinds: steps and processes. */
333                    case iconStep:      /* For step icons, measure the control panel. */
334                        measure_panel(aNode, &frame);
335                        break;
336                    case iconProcess:   /* For processes, measure sublist recursively. */
337                        if (desc)       /* Be sure the descendents are there! */
338                        {
339                            measure_icon_list(desc, &frame);   /* Recursion here */
340                            /* Add an extra margin for split descendent nodes. */
341                            if ((*((*aNode)->data.proc))->split)
342                                frame.right += MARGIN;
343                        }
344                        break;
345                } /*end switch*/
346
347            /* Find the bottomRight corner of the outline. */
348            outLine.bottom = frame.bottom + HEIGHT(bNoteRect);
349            noteWidth = MAX(tNoteRect.right, bNoteRect.right);
350            outLine.right = MAX(frame.right, frame.left + noteWidth);
351
```

```
352            ip = *aNode;            /* Dereference again as memory may have moved. */
353            ip->frame = frame;      /* Record new frame size. */
354            ip->outLine = outLine;  /* Record new outline. */
355
356            /* Locate the bottomRight corner of the bounds rect. */
357            maxFrameDepth = MAX(maxFrameDepth, frame.bottom);
358            bounds->bottom = maxFrameDepth + maxNoteDepth + MARGIN;
359            maxWidth = MAX(maxWidth, ip->outLine.right);
360            bounds->right = maxWidth + MARGIN;
361
362            /* Prepare for another sibling node. */
363            if (split)
364                offset.v = bounds->bottom;  /* Offset split nodes vertically */
365            else
366                offset.h = bounds->right;   /* Offset regular nodes horizontally */
367
368            aNode = next;
369        }while (aNode != iNode);
370
371    }
372
373
374
375
```

11/23/88 5:56 PM                    iconDraw.c                              Page 10

```
376   /******************************************************************************
377    * Function name:    offset_descendents -- horizontally offsets both frames and outlines
378    *
379    *   Description:    Horizontally offsets both the frames and the outlines of iNode
380    *                   its siblings, and all of their descendents.
381    *
382    *        Inputs:    iNode       a Handle to an icon node
383    *                   offset      offset to apply to iNode & Sons
384    *
385    *       Outputs:    bounds      a pointer to a rect, the bounding rect of the entire list
386    *
387    *  Side Effects:                May cause heap objects to be moved.
388    *
389    *        Return:    void
390    *
391    ******************************************************************************/
392
393   void offset_descendents(iNode, offset)
394
395   iconNodeHdl     iNode;
396   short           *offset;
397
398   {
399       iconNodeHdl aNode;              /* the node currently operated upon. */
400       register iconNodePtr    ap;     /* To dereference node for quick access. */
401       Boolean     open;
402       iconNodeHdl desc;
403
404   #ifdef DEBUG
405       debugwrite("\poffset_descendents");
406   #endif
407
408       aNode = iNode;
409       do {
410               ap = *aNode;        /* Grab some values. */
411               desc = ap->desc;
412               open = ap->open;
413
414               /* Offset both the frame and the outLine. */
415               OffsetRect(&(ap->frame), *offset, 0);
416               OffsetRect(&(ap->outLine), *offset, 0);
417
418               /* Offset any open sub-descendents */
419               if ((open) && (desc))
420                   offset_descendents(desc, offset);
421
422               aNode = (*aNode)->next;
423           }while(aNode != iNode);
424   }
425
426
427
```

11/23/88 5:56 PM iconDraw.c Page 11

```
428  /*****************************************************************************
429   * Function name:    center_icons -- center icons within the bounds of the list
430   *
431   *   Description:    Vertically centers outlines within the bounds rect and horizontally
432   *                   centers the icon frame with within the outline. center_icons is needed
433   *                   to center the icons after measure_icon_list measures the icons.
434   *
435   *       Inputs:     iNode      a Handle to an icon node
436   *
437   *       Outputs:    bounds     a pointer to a rect, the bounding rect of the entire list
438   *
439   * Side Effects:                May cause heap objects to be moved.
440   *
441   *       Return:     void
442   *
443   *****************************************************************************/
444
445  void center_icons(iNode, bounds)
446
447  iconNodeHdl    iNode;
448  Rect           *bounds;
449
450  {
451
452      Point       offset;
453      iconNodeHdl aNode;
454      Rect        descBounds;
455      Rect        allFrames;
456      Boolean     split;
457      short       frameHOffset;
458      Rect        prevFrame;
459      register iconNodePtr   ip;
460      Boolean     open;
461      iconNodeHdl desc;
462      iconNodeHdl moma;
463
464  #ifdef DEBUG
465      /*debugwrite("\pcenter_icons"); */
466  #endif
467
468      /* Icons are arranged vertically if parent of this generation is a divergent path node. */
469      split = false;
470      ip = *iNode;
471      moma = ip->moma;
472
473      /* Don't dereference root's (non-existant) parent and _ */
474      /* _ only look at process icons. */
475      if ((moma) && (ip->iKind == iconProcess))
476          split = (*((*moma)->data.proc))->split;
477
478      aNode = iNode;
479      offset.v = 0;
480      offset.h = 0;
481
482      /* Determine the rectangle that encloses all frames at this level. */
483      allFrames = ip->frame;
484      prevFrame = (*(ip->prev))->frame;
485      allFrames.bottom = prevFrame.bottom;
486      allFrames.right = prevFrame.right;
487
488      /* Split paths need to be centered as a special case. */
489      if (split)
490          /* Center all frames as a group within their parent frame. */
491          offset.v = VCENTER(*bounds) - VCENTER(allFrames);
```

11/23/88 5:56 PM　　　　　　　　　　　　　　　iconDraw.c　　　　　　　　　　　　　　　Page

```
492
493         do {
494                 /* Center each icon frame vertically within its parent's bounds. */
495                 if (!split)
496                     offset.v = VCENTER(*bounds) - VCENTER((*aNode)->frame);
497
498                 /* Center icon frame and its descendents horizontally within outline. */
499                 ip = *aNode;
500                 open = ip->open;
501                 desc = ip->desc;
502                 frameHOffset = HCENTER(ip->outLine) - HCENTER(ip->frame);
503
504                 if (frameHOffset)
505                     {
506                         OffsetRect(&(ip->frame), frameHOffset, 0);
507                         if ((open) && (desc))
508                             offset_descendents(desc, &frameHOffset);
509                     }
510
511                 ip = *aNode;
512                 OffsetRect(&(ip->frame), 0, offset.v);
513                 OffsetRect(&(ip->outLine), 0, offset.v);
514
515                 if ((open) && (desc))
516                     {
517                         descBounds = ip->frame;
518                         center_icons(desc, &descBounds);
519                     }
520
521                 aNode = (*aNode)->next;
522         } while (aNode != iNode);
523
524     }
525
526
527
```

11/23/88 5:56 PM  iconDraw.c  Page 13

```
528   /*******************************************************************************
529    * Function name:   draw_a_note -- Draws one note in place
530    *
531    *  Description:    Draw_a_note draws the carriage-return-separated text passed in t
532    *                  starting at point pt, using the default font for the current
533    *                  grafport.
534    *
535    *       Inputs:    r        the bounding rectangle for the note
536    *                  t        the handle to the text of the note
537    *
538    *       Outputs:   none
539    *
540    *  Side Effects:            May cause heap objects to be moved.
541    *
542    *       Return:    void
543    *
544    *******************************************************************************/
545
546   void draw_a_note(r, t)
547
548   Rect    *r;
549   Handle  t;
550
551   {
552       short       depth;
553       short       fHeight;
554       short       w;
555       FontInfo    f;
556       long        p;
557       long        start;
558       long        last;
559       long        count;
560       char        c;
561
562   #ifdef DEBUG
563       /* debugwrite("\pdraw_a_note");*/
564   #endif
565
566       GetFontInfo(&f);
567       fHeight = f.ascent + f.descent + f.leading;
568       depth = r->top + f.ascent;
569       MoveTo(r->left, depth);
570
571       c = CR;
572       start = 0;
573       last = GetHandleSize(t);
574       p = 0;
575       while (p >= 0)
576           {
577               p = Munger(t, start, &c, 1, nil, 0);
578               if ((p > 0) || (start < last))
579                   {
580                       /* If p > 0 then a carriage return terminated line was found. */
581                       /* Last line in text might not be terminated with a return. */
582                       count = ((p > 0) ? p : last) - start;
583
584                       HLock(t);
585                       w = TextWidth(*t, start, count);
586                       Move(((r->right - r->left) - w) / 2, 0);    /* Center text horizontally within outli
587                       DrawText(*t, start, count); /* Draw the line using default text characteristics. */
588                       depth += fHeight;           /* Move the pen into position for the next line. */
589                       MoveTo(r->left, depth);
590                       HUnlock(t);
591                   }
```

11/23/88 5:56 PM                iconDraw.c                                Page 14

```
592                start = p + 1;
593            }
594    }
595
596
597
```

11/23/88 5:56 PM                            iconDraw.c                                   Page 15

```
598  /***********************************************************************
599   * Function name:    bright_node -- returns true if node's backcolor >= 50% brightness.
600   *
601   *   Description:    Determines whether the node in it's current hilite state
602   *                   is brighter than 50% gray. Used to select color for foreground text.
603   *
604   *        Inputs:    iNode       an icon Node
605   *
606   *       Outputs:    none
607   *
608   * Side Effects:                 May cause heap objects to be moved.
609   *
610   *        Return:    void
611   *
612   ***********************************************************************/
613
614  Boolean bright_node(iNode)
615
616  iconNodeHdl iNode;
617
618  {
619      RGBColor     c;
620      Boolean      brilliant;
621      iconNodeHdl  moma;
622
623  #ifdef  DEBUG
624      /* debugwrite("\pbright_node"); */
625  #endif
626
627      if (!(environs.hasColorQD))
628          {
629          SysBeep(1);
630          brilliant = true;           /* background is white for B&W machines */
631          }
632      else
633          {
634          moma = (*iNode)->moma;
635          if (!moma)                  /* Root node means background is */
636              GetBackColor(&c);       /* window's background (erase) color. */
637          else
638              if ((*moma)->hilite)
639                  hilightcolor(theWPtr, &c);
640              else
641                  c = (*(*moma)->data.proc)->backColor;
642          brilliant = bright(&c);
643          }
644
645      return brilliant;
646  }
647
648
649
```

11/23/88 5:56 PM                                iconDraw.c                                         Page 16

```
650   /*******************************************************************************
651    * Function name:    draw_notes -- draws top and bottom notes.
652    *
653    *   Description:    Draws both the top and bottom notes for an iconNode in either
654    *                   black or white, depending upon the background's luminance value.
655    *
656    *       Inputs:     iNode      an icon Node
657    *
658    *       Outputs:    none
659    *
660    *   Side Effects:              May cause heap objects to be moved.
661    *
662    *       Return:     void
663    *
664    *******************************************************************************/
665
666   void draw_notes(iNode)
667
668   iconNodeHdl     iNode;
669
670   {
671       Rect        r;
672       Rect        frame;
673       Rect        outLine;
674       iconNodePtr ip;
675       Handle      t, b;
676       short       center;
677
678   #ifdef  DEBUG
679       /* debugwrite("\pdraw_notes"); */
680   #endif
681
682       if (environs.hasColorQD)
683           if (bright_node(iNode))
684               TextMode(srcOr);     /* Black text over bright background. */
685           else
686               TextMode(srcBic);    /* White text over dark background. */
687
688       SysBeep(1);
689
690       ip = *iNode;            /* Copy some information from the icon node struct */
691       t = ip->tNote;
692       b = ip->bNote;
693       frame = ip->frame;
694       outLine = ip->outLine;
695
696       /* Draw the top notes starting at the top left corner of the icon's overall outline. */
697       if (GetHandleSize(t) != 0)
698           {
699               r = outLine;
700               r.bottom = frame.top;
701               draw_a_note(&r, t);
702           }
703
704       /* Draw the bottom notes starting at the bottom left corner of the icon's frame rectangle. */
705       if (GetHandleSize(b) != 0)
706           {
707               r = outLine;
708               r.top = frame.bottom;
709               draw_a_note(&r, b);
710           }
711
712       TextMode(srcOr);
713   }
```

11/23/88 5:56 PM  iconDraw  Page 17

```
714
715
716
```

11/23/88 5:56 PM iconDraw

```
717   /**************************************************************************
718    * Function name:    back_rgn - give a region of background sans objects on top.
719    *
720    *   Description:    BackRgn returns a region containing the background region of
721    *                   the node passed in i, or an empty region, if the node is not open.
722    *                   The background region will exclude any the descendent frames.
723    *
724    *       Inputs:     iNode       an icon Node
725    *
726    *       Outputs:    RgnHandle   the newly created region
727    *
728    * Side Effects:                 May cause heap objects to be moved.
729    *
730    *       Return:     RgnHandle
731    *
732    **************************************************************************/
733
734   RgnHandle back_rgn(iNode)
735
736   iconNodeHdl iNode;
737
738   {
739       iconNodeHdl dl;      /* First descendent node. */
740       iconNodeHdl dn;      /* Current descendent node. */
741       RgnHandle   rgn;
742       Rect        r;
743       register iconNodePtr  ip;
744       Rect        frame;
745       iconNodeHdl next;
746
747   #ifdef DEBUG
748       debugwrite("\p back_rgn");
749   #endif
750
751       rgn = NewRgn();
752       failnil((char*)rgn);
753       ip = *iNode;        /* Grab some values for the parent node. */
754       frame = ip->frame;
755       dl = ip->desc;
756
757       if (ip->open)       /* If the icon isn't open, just leave with an empty rgn. */
758           {
759           InsetRect(&frame, 1, 1);    /* Leave space for the frame. */
760           OpenRgn();
761               FrameRect(&frame);
762
763               dn = dl;              /* Go down a level, if there's one there. */
764               if (dl)               /* Make sure we're not going to never-never land. */
765                   do{
766                       ip = *dn;     /* Grab some values for the current descendent node. */
767                       frame = ip->frame;
768                       next = ip->next;
769
770                       /* Cut holes in the back rgn for the opened descendent nodes. */
771                       if (ip->open)
772                           FrameRect(&frame);
773
774                       dn = next;
775                   } while (dn != dl);
776           CloseRgn(rgn);
777           }
778       return(rgn);
779   }
780
```

11/23/8c 5:56 PM                    iconDraw.c                                 age 19

781
782
783

```
/23/88 5:56 PM                          iconDraw.c                                        Page 20

784   /***********************************************************************************
785   * Function name:   draw_frame - draws the frame and close box for an open icon node
786   *
787   *   Description:   draw_frame draws the frame and close box in medium gray.
788   *
789   *       Inputs:    iNode       an icon Node
790   *
791   *       Outputs:   none
792   *
793   *   Side Effects:              May cause heap objects to be moved.
794   *                              Changes display.
795   *
796   *       Globals:               Reads the application global rgbGray.
797   *
798   *       Return:    void
799   *
800   ***********************************************************************************/
801
802   void draw_frame(iNode)
803
804   iconNodeHdl iNode;
805
806   {
807       Rect        wholeFrame;    /* frame surrounding entire open icon */
808       Rect        close;         /* close box */
809       Boolean     hilite;
810       register iconNodePtr   ip;
811       Boolean     bw;            /* black & white machine: SE or Plus */
812
813   #ifdef DEBUG
814       /* debugwrite("\pdraw_frame"); */
815   #endif
816
817       ip = (*iNode);
818       hilite = ip->hilite;
819       wholeFrame = ip->frame;            /* Get the frame and closebox rects. */
820       close = wholeFrame;
821       close.right = close.left + CLOSEBOXSIZE;
822       close.bottom = close.top + CLOSEBOXSIZE;
823       bw = !environs.hasColorQD;
824
825       if (oneBit)
826           if (hilite)
827               if (bw)
828                   ForeColor(whiteColor);
829               else
830                   RGBForeColor(&RGBWhite); /* In one bit color worlds draw frame in b&w. */
831           else
832               if (bw)
833                   ForeColor(blackColor);
834               else
835                   RGBForeColor(&RGBBlack);
836       else
837           RGBForeColor(&RGBGray);    /* In a color environment, draw frame in 50% gray. */
838
839       FrameRect(&wholeFrame);
840       FrameRect(&close);
841   }
842
843
844
```

11/23/88 5:56 PM                          iconDraw.c                                Page 21

```
845   /*******************************************************************************
846    * Function name:   draw_centerline - draw an opened process icon and its contents
847    *
848    *   Description:   draw_centerline draws the contents of an opened icon:
849    *                  background, centerline, frame and controls.
850    *
851    *       Inputs:    iNode      an icon Node
852    *
853    *       Outputs:   none
854    *
855    *   Side Effects:             May cause heap objects to be moved.
856    *                             Changes display.
857    *
858    *       Return:    void
859    *
860    *******************************************************************************/
861
862   void draw_centerline(iNode)
863
864   iconNodeHdl    iNode;
865
866   {
867       iconNodePtr ip;     /* pointer to an iconNode for quickness */
868       Boolean    split;
869       Rect       frame;
870       Rect       u, v;
871       short      center, middle, hi, lo;
872       iconNodeHdl desc, sNode, dNode;
873
874   #ifdef DEBUG
875       debugwrite("\pdraw_centerline");
876   #endif
877
878       ip = *iNode;        /* copy some stuff to the stack */
879       split = (ip->iKind == iconProcess) && ((*(ip->data.proc))->split);
880       frame = ip->frame;
881       desc = ip->desc;
882
883       center = VCENTER(frame) - 1;   /* Pen hangs below coordinate, so subtract one to center pen. */
884       PenSize(2, 2);
885       MoveTo(frame.left, center);
886       if (!split)
887           LineTo(frame.right-1, center); /* Pen will draw 1 pixel to right of it's X positon. */
888       else
889           {
890               u.right = frame.left + MARGIN;
891               u.bottom = center + 2;
892               u.top = u.bottom - 2*MARGIN;
893               u.left = u.right - 2*MARGIN;
894               v = u;
895
896               FrameArc(&u, 90, 90);
897               OffsetRect(&u, 0, 2*MARGIN - 2);
898               FrameArc(&u, 0, 90);
899
900               OffsetRect(&v, WIDTH(frame), 0);
901               FrameArc(&v, 180, 90);
902               OffsetRect(&v, 0, 2*MARGIN - 2);
903               FrameArc(&v, 270, 90);
904
905               if (desc)
906                   {
907                       sNode = desc;
908                       dNode = sNode;
```

```
909                     hi = 0x7FFF;        /* MaxInt */
910                     lo = 0;
911
912                     do {
913                         middle = VCENTER((*dNode)->outLine) - 1;
914                         u.left = frame.left + MARGIN;
915                         u.right = u.left + 2*MARGIN;
916                         v.right = frame.right - MARGIN;
917                         v.left = v.right - 2*MARGIN;
918                         if (middle < center)    /* up on the left, down to the right */
919                             {
920                                 u.top = middle;
921                                 u.bottom = u.top + MAX(8,MIN(2*MARGIN, center-middle));
922                                 v.top = u.top;
923                                 v.bottom = u.bottom;
924                                 FrameArc(&u, 270, 90);
925                                 FrameArc(&v, 0, 90);
926                                 hi = MIN(hi, u.top + MARGIN);
927                             }
928                         else
929                             {
930                                 u.bottom = middle + 2;
931                                 u.top = u.bottom - MAX(8, MIN(2*MARGIN, middle-center));
932                                 v.top = u.top;
933                                 v.bottom = u.bottom;
934                                 FrameArc(&u, 180, 90);
935                                 FrameArc(&v, 90, 90);
936                                 lo = MAX(lo, u.bottom - MARGIN);
937                             }
938
939                         MoveTo(frame.left + 2*MARGIN, middle);
940                         LineTo(frame.right - 2*MARGIN, middle);
941                         dNode = (*dNode)->next;
942
943                     } while (dNode != sNode);
944
945                     MoveTo(frame.left + MARGIN - 1, hi);
946                     Line(0, lo - hi);
947                     MoveTo(frame.right - MARGIN - 1, hi);
948                     Line(0, lo - hi);
949                 }
950         }
951     PenNormal();
952 }
953
954
955
```

```
11/23/88 5:56 PM                           iconDraw.c                                    Page 2

956   /******************************************************************************
957   * Function name:    draw_open_icon - draw an opened process icon and its contents
958   *
959   *   Description:    draw_open_icon draws the contents of an opened icon:
960   *                   background, centerline, frame and controls.
961   *
962   *       Inputs:     iNode      an icon Node
963   *
964   *       Outputs:    none
965   *
966   *   Side Effects:              May cause heap objects to be moved.
967   *                              Changes display.
968   *
969   *       Return:     void
970   *
971   ******************************************************************************/
972
973   void draw_open_icon(iNode)
974
975   iconNodeHdl iNode;
976
977   {
978       RGBColor    c, d, cl, fColor, hiColor;
979       long        qdc, qdcl, qdhi;
980       Rect        r, s, t, u, v;
981       PicHandle   p;
982       RgnHandle   rgn, clipRgn;
983       iconNodeHdl dNode, sNode;
984       iconNodePtr ip;
985       Boolean     hasColor;
986
987   #ifdef DEBUG
988       /* debugwrite("\pdraw_open_icon"); */
989   #endif
990       hasColor = environs.hasColorQD;
991
992       cl = RGBBlack;       /* Color QuickDraw */
993       qdcl = blackColor;   /* B & W QuickDraw */
994
995       if (oneBit)
996           {
997           hiColor = RGBBlack; /* For color windows. */
998           qdhi = blackColor;  /* For B & W windows. */
999           }
1000      else
1001          hilightcolor(theWPtr, &hiColor);    /* use hilight color for selected node's backgrounds. */
1002
1003      if (hasColor)
1004          GetForeColor(&fColor);
1005
1006      ip = *iNode;         /* While iNode is dereferenced only do non-memory-moving operations. */
1007
1008      r = ip->frame;
1009      s = r;
1010      if (ip->iKind == iconStep)
1011          p = (*(ip->data.panel))->pict;
1012      else
1013          p = nil;
1014
1015      if (ip->hilite)
1016          {
1017          c = hiColor;     /* Draw background in hilite color. */
1018          cl = c;
1019          InvertColor(&cl);   /* Use inverted centerline for hilighted backgrounds. */
```

23/88 5:56 PM                               iconDraw.c                                              Page 24

```
1020            qdc = blackColor;    /* For B&W windows. */
1021            qdcl = whiteColor;
1022        }
1023    else /* Not hilited */
1024        {
1025            if (oneBit)
1026                {
1027                    c = RGBWhite;        /* For color windows. */
1028                    qdc = whiteColor;    /* For B & W windows. */
1029                    qdcl = blackColor;   /* For B & W windows. */
1030                }
1031            else
1032                c = (*((*iNode)->data.proc))->backColor;
1033        }
1034
1035    if (!p)              /* soon to be a handle to a control list and picture. */
1036        {
1037            if (hasColor)
1038                RGBForeColor(&c);
1039            else
1040                ForeColor(qdc);
1041
1042            /* Just painting each background rect is actually faster, though
1043               visually obnoxious when redrawing deeply nested routines.     */
1044            clipRgn = NewRgn();
1045            failnil((char*)clipRgn);
1046            GetClip(clipRgn);
1047            rgn = back_rgn(iNode);
1048            SectRgn(clipRgn, rgn, rgn);
1049            SetClip(rgn);            /* Clip to the background minus the contained icon frames. */
1050            InsetRect(&s, 1, 1);     /* Inset to avoid painting over the frame. */
1051            PaintRect(&s);           /* Paint the background */
1052
1053            if (hasColor)
1054                RGBForeColor(&cl);
1055            else
1056                ForeColor(qdcl);
1057            draw_centerline(iNode);
1058
1059            SetClip(clipRgn);
1060            DisposeRgn(clipRgn);
1061            DisposeRgn(rgn);         /* Reset the clip region. */
1062        }
1063    else
1064        {
1065            t = r;
1066            InsetRect(&t, HILITEWIDTH, HILITEWIDTH);
1067            LoadResource(p);
1068            DrawPicture(p, &t); /*** Soon, draw picture, then draw controls for this icon. */
1069
1070            if (hasColor)
1071                RGBForeColor(&c);
1072            else
1073                ForeColor(qdc);
1074            PenSize(HILITEWIDTH, HILITEWIDTH);
1075            FrameRect(&s);
1076            PenNormal();
1077        }
1078
1079    draw_frame(iNode);           /* Draw the frame and close box. */
1080    if (hasColor)
1081        RGBForeColor(&fColor);
1082    else
1083        ForeColor(blackColor);   /* Reset to the default foreground color. */
```

11/23/88 5:56 PM                  iconDraw.c                            Page 25

1084   }
1085
1086
1087

11/23/88 5:56 PM                    iconDraw.c                              Page 26

```
1088  /******************************************************************************
1089   * Function name:   draw_closed_icon - draws the area contained by the icon frame rectangle
1090   *
1091   *   Description:    draw_closed_icon draws the contents of an closed icon in the correct
1092   *                   hilite state and color.
1093   *
1094   *       Inputs:     iNode       an icon Node
1095   *
1096   *       Outputs:    none
1097   *
1098   *   Side Effects:               May cause heap objects to be moved.
1099   *                               Changes display.
1100   *
1101   *       Return:     void
1102   *
1103   ******************************************************************************/
1104
1105  void draw_closed_icon(iNode)
1106
1107  iconNodeHdl     iNode;
1108
1109  {
1110      BitMap      srcBits;        /* Icon's bitmap for CopyMask call */
1111      BitMap      maskBits;       /* Mask's bitmap for CopyMask call*/
1112      RGBColor    fc, bc, hiColor;
1113      iconNodePtr ip;             /* iNode dereferenced */
1114      Boolean     hilite;         /* And some pertinent fields from iNode */
1115      Rect        frame;
1116      CIconHandle cicn;
1117      iconListHdl theIcon;
1118
1119  #ifdef DEBUG
1120      /* debugwrite("\pdraw_closed_icon"); */
1121  #endif
1122
1123      ip = *iNode;                /* Grab some values from this node. */
1124      hilite = ip->hilite;
1125      frame = ip->frame;
1126      cicn = ip->cicn;
1127      theIcon = (iconListHdl)ip->icon;
1128
1129      if (!environs.hasColorQD)   /* On a black and white machine, just plot the icon. */
1130          {
1131          PlotIcon(&frame, (Handle)theIcon);
1132          if (hilite)
1133              InvertRect(&frame);
1134          }
1135      else                        /* For a color machine, find out if a color icon is there, */
1136          {
1137          GetForeColor(&fc);      /* Preserve the port's current drawing colors. */
1138          GetBackColor(&bc);
1139
1140          if (cicn)               /* and if so, plot it, and invert to hilite. */
1141              {
1142              PlotCIcon(&frame, cicn);
1143              if (hilite)
1144                  InvertRect(&frame);
1145              /*
1146              Neither PlotCIcon, CopyMask, or CopyBits seems to work with the system cicns!
1147              RGBForeColor(&RGBBlack);
1148              RGBBackColor(&RGBWhite);
1149              CopyMask(   (BitMapPtr)&((*cicn)->iconPMap),
1150                          (BitMapPtr)&((*cicn)->iconMask),
1151                          (BitMapPtr)(*(((CGrafPtr)theWPtr)->portPixMap)),
```

```
1152                    &((*cicn)->iconPMap.bounds),
1153                    &((*cicn)->iconMask.bounds), &frame);
1154
1155        CopyBits(   (BitMapPtr)&((*cicn)->iconPMap),
1156                    (BitMapPtr)(*(((CGrafPtr)theWPtr)->portPixMap)),
1157                    &((*cicn)->iconPMap.bounds),
1158                    &frame, srcCopy, nil);
1159        */
1160        }
1161    else                    /* Lacking a color icon, plot the b&w icon using the right */
1162        {                   /* color depending upon the hilite state and user-selected */
1163        hilightcolor(theWPtr, &hiColor);    /* hilite color. */
1164        if (hilite)
1165            {
1166            RGBForeColor((bright(&hiColor) ? &RGBBlack : &RGBWhite));
1167            RGBBackColor(&hiColor);
1168            }
1169        else
1170            {
1171            RGBForeColor(&RGBBlack);
1172            RGBBackColor(&RGBWhite);
1173            }
1174
1175        srcBits.baseAddr = (Ptr)(*theIcon)->icon;    /* Warning: dereferenced & not locked. */
1176        srcBits.rowBytes = 4;
1177        SetRect(&srcBits.bounds, 0, 0, 32, 32); /* Left, Top, Right, Bottom */
1178
1179        maskBits = srcBits;
1180        maskBits.baseAddr = (Ptr)(*theIcon)->mask;   /* Warning: dereferenced & not locked. */
1181
1182        CopyMask(&srcBits, &maskBits, (BitMapPtr)(*(((CGrafPtr)theWPtr)->portPixMap)),
1183            &(srcBits.bounds), &(maskBits.bounds), &frame);
1184
1185        RGBForeColor(&fc);                  /* Reset the port's colors. */
1186        RGBBackColor(&bc);
1187        }
1188    }
1189 }
1190
1191
1192
```

11/23/88 5:56 PM iconDraw.c Page 28

```
1193  /******************************************************************************
1194   * Function name:   draw_icon_node - draws the area contained by the icon frame rectangle
1195   *
1196   *   Description:    draw_open_icon draws icon, opened icon & notes.
1197   *
1198   *       Inputs:     iNode       an icon Node
1199   *
1200   *       Outputs:    none
1201   *
1202   * Side Effects:                 May cause heap objects to be moved.
1203   *                               Changes display.
1204   *
1205   *       Return:     void
1206   *
1207   ******************************************************************************/
1208  void draw_icon_node(iNode)
1209
1210  iconNodeHdl    iNode;
1211
1212  {
1213  #ifdef  DEBUG
1214      /* debugwrite("\pdraw_icon_node");*/
1215  #endif
1216
1217      if ((*iNode)->open)
1218          draw_open_icon(iNode);      /* If it's open, draw its frame. */
1219      else
1220          draw_closed_icon(iNode);    /* if it's closed, draw its icon. */
1221
1222      draw_notes(iNode);              /* Now, draw the top & bottom notes. */
1223  }
1224
1225
1226
```

11/23/88 5:56 PM          iconDraw.c          Page 29

```
1227   /****************************************************************************
1228   * Function name:    draw_icon_list - draws all the icons in a list
1229   *
1230   *    Description:   draw_icon_list recursively draws all the icons that overlap
1231   *                   the rectangle passed in area. At update time the update region's
1232   *                   rgnBBox can be passed in area to speed the redraw time.
1233   *
1234   *    Inputs:        iNode     an icon Node
1235   *                   area      the bounding rect of the area to be drawn
1236   *
1237   *    Outputs:       none
1238   *
1239   * Side Effects:               May cause heap objects to be moved.
1240   *                             Changes display.
1241   *
1242   *    Return:        void
1243   *
1244   ****************************************************************************/
1245
1246   void draw_icon_list(area,iNode)
1247
1248   Rect            *area;
1249   iconNodeHdl     iNode;
1250
1251   {
1252       iconNodeHdl    tNode;  /* temporary copy of iNode */
1253       iconNodeHdl    desc;
1254       iconNodePtr    ip;
1255       Rect           q;
1256
1257   #ifdef DEBUG
1258       debugwrite("\pdraw_icon_list");
1259   #endif
1260
1261       tNode = iNode;
1262       do {
1263           /* Draw this node if it overlaps the update area. */
1264           if (SectRect(area, &((*tNode)->outLine), &q))
1265               {
1266               draw_icon_node(tNode);
1267
1268               /* Recursively draw it's descendents, if any. */
1269               ip = *tNode;
1270               if (ip->open)
1271                  {
1272                  desc = ip->desc;
1273                  if (desc)
1274                      draw_icon_list(area, desc);
1275                  }
1276               }
1277
1278           tNode = (*tNode)->next; /* Draw it's siblings, if any. */
1279
1280       } while (tNode != iNode);   /* Until all siblings and their descendents have been drawn. */
1281   }
1282
1283
1284
```

```
11/23/88 5:56 PM                          iconDraw.c                                       Page 30

1285  /*********************   ,*******************************.   ***********************
1286   * Function name:    remeasure_icons - draws all the icons in a list
1287   *
1288   *   Description:     remeasure_icons recursively draws all the icons that overlap
1289   *                    the rectangle passed in area. At update time the update region's
1290   *                    rgnBBox can be passed in area to speed the redraw time.
1291   *
1292   *      Inputs:       iNode      an icon Node
1293   *                    area       the bounding rect of the area to be drawn
1294   *
1295   *      Outputs:      none
1296   *
1297   *   Side Effects:               May cause heap objects to be moved.
1298   *                               Changes display.
1299   *
1300   *      Return:       void
1301   *
1302   **********************************************************************************/
1303
1304  void remeasure_icons()
1305
1306  {
1307      Rect       r;
1308
1309  #ifdef  DEBUG
1310      debugwrite("\premeasure_icons");
1311  #endif
1312      if(iList != nil)
1313          {
1314          SetRect(&r, 0, 0, 0, 0);        /* Set the topleft corner of the icon list. */
1315          measure_icon_list(iList, &r);   /* Measure the icon rects */
1316          center_icons(iList, &r);
.317
1318          SetImageArea(theWPtr, &r);      /* Adjust the window's image area to fit the new image. */
1319          }
1320      remeasure = false;              /* This window has been remeasured. */
1321  }
1322
1323
1324
```

11/23/88 5:56 PM                          iconDraw.c                          Page 31

```
1325   /******************** ********************************** *************************
1326   * Function name:   draw_icons - draws all the icons in a list
1327   *
1328   *   Description:   draw_icons remeasures the entire icon list, if needed, and
1329   *                  redraws only those nodes that intersect area.
1330   *
1331   *   Inputs:    wPtr     an icon window
1332   *             area     the bounding rect of the area to be drawn
1333   *
1334   *   Outputs:  none
1335   *
1336   * Side Effects:             May cause heap objects to be moved.
1337   *                           Changes display.
1338   *
1339   *   Return:   void
1340   *
1341   ****************************************************************************/
1342
1343   void draw_icons(wPtr, area)
1344
1345   WindowPtr   wPtr;
1346   Rect        *area;
1347
1348   {
1349       Rect        r;
1350       RgnHandle   backRgn;
1351       iconNodePtr ip;
1352
1353   #ifdef DEBUG
1354       debugwrite("\pdraw_icons");
1355   #endif
1356
1357       if (remeasure)             /* Recompute the sizes of the icons if necessary. */
1358           remeasure_icons();
1359
1360       backRgn = NewRgn();
1361       failnil((char*)backRgn);
1362       OpenRgn();
1363
1364       FrameRect(&(wPtr->portRect));
1365
1366       /* Erase the empty space around the first node if it's open. */
1367       SetRect(&r, 0, 0, 0, 0);
1368       if (iList)
1369           {
1370           ip = *iList;
1371           if (ip->open)
1372               r = ip->frame;  /* Erase all but the first icon frame. */
1373           FrameRect(&r);
1374           }
1375
1376       CloseRgn(backRgn);
1377       EraseRgn(backRgn);
1378       DisposeRgn(backRgn);
1379
1380       oneBit = shallow_depth(wPtr);   /* Use only black and white colors in a one bit world. */
1381
1382       if (iList)
1383           draw_icon_list(area, iList);
1384
1385   }
1386
1387
```

```
12/14/88 1:14 PM                        iconaction.h                                Page 1

1    /********************************************************************************
2     *   Copyright ©1988 by Applied Biosystems, Inc. All rights reserved.
3     ********************************************************************************
4     *
5     *    File Name: iconAction.h
6     *
7     *    Description: Header for iconAction.c, Event handling routines for icon windows.
8     *
9     *    Caveats: None.
10    *
11    *    Edit History: 28 October 88 Converted from Pascal by HG
12    *
13    ********************************************************************************/
14
15
16   /********************************************************************************
17    *   Preprocessor Directives
18    */
19   #ifndef __ICONACTION__
20   #define __ICONACTION__
21
22   #define STARTDRAGSLOP   5
23   #define HANDDELAY       10
24
25   /* icon for variable control panel */
26   #define VARICON         3000
27
28   /* System color look up table. */
29   #define SYSTEMCLUT      8
30
31
32
33   /********************************************************************************
34    *   Include Files
35    */
36   #include <strings.h>
37   #include "includes.h"
38   #include "errs.h"
39   #include "scroll.h"
40   #include "iconUtils.h"
41   #include "panels.h"
42   #include "iconDraw.h"
43   #include "TestInit.h"
44
45
46   /********************************************************************************
47    *   Macros
48    *   none
49    */
50
51
52   /********************************************************************************
53    *   Structures and Typedefs
54    */
55
56   typedef struct attribs{
57       short open   : 1;      /* true for opened icon */
58       short hilite : 1;      /* true for selected icon */
59       short FEX    : 14;     /* reserved for future expansion */
60   } attribs;
61
62   enum {inNoIcon,inOpenIcon,inClosedIcon};
63
64
```

12/14/88 1:14 PM                              iconaction.h                                              Page 2

```
65  /*******************************************************************************
66   *    Prototypes
67   */
68  WindowPtr new_icon_window(short id);
69  void do_content(WindowPtr wPtr, EventRecord *event);
70  void cut_icon(WindowPtr wPtr);
71  void copy_icon(WindowPtr wPtr);
72  void paste_icon(WindowPtr wPtr);
73  void clear_icon(WindowPtr wPtr);
74  void set_color(WindowPtr wPtr);
75  void new_icon_node(WindowPtr wPtr, short stepID);
76
77  #endif
```

```
12/21/88 4:37 PM                              iconaction.c                                    Page 1    /*******************************************************************************
2        Copyright ©1988 by Applied Biosystems, Inc. All rights reserved.
3    ********************************************************************************
4    *
5    *       File Name: iconAction.c
6    *
7    *       Description: Event handling routines for icon windows.
8    *
9    *       Caveats: None.
10   *
11   *       Edit History: 28 October 88 Converted from Pascal by HG
12   *
13   *******************************************************************************/
14
15
16   /*******************************************************************************
17   *    Preprocessor Directives
18   *    none
19   */
20
21
22   /*******************************************************************************
23   *    Include Files
24   */
25   #include "iconAction.h"
26
27
28   /*******************************************************************************
29   *    Macros
30   *    none
31   */
32
33
34   /*******************************************************************************
35   *    Structures and Typedefs
36   *    none
37   */
38
39
40   /*******************************************************************************
41   *    Statics
42   */
43   static  long          lastUp;        /* Tick count at last mouse up. (Used to detect double clicks.) */
44   static  Cursor        hand;          /* a copy of the image-dragging cursor */
45   static  iconNodeHdl   topHilited;    /* Lowest node which contains all hilighted nodes. */
46
47
48   /*******************************************************************************
49   *    External References
50   *    none
51   */
52
53
54   /*******************************************************************************
55   *    Function Prototypes -- functions local to this file
56   */
57   void       inval(Rect *r);
58   void       do_list(attribs *modify, attribs *assert, Boolean visible, iconNodeHdl iNode);
59   void       init_icons(void);
60   iconNodeHdl init_icon_window(void);
61   Boolean    in_descendents(Point *p, iconNodeHdl iNode, short *pos);
62   void       find_icon(Point *p, iconNodeHdl *iNode, short *pos, short *outcome);
63   Boolean    track_close(Point *p, iconNodeHdl iNode, Boolean *closeIt);
64   void       unhilite_all(iconNodeHdl iNode);
```

```
12      4:37 PM                        iconaction.c                                    Page 2

65  void      open_icons(Boolean open, WindowPtr wPtr);
66  void      hilite_icon(iconNodeHdl iNode);
67  void      hilite_sublist(iconNodeHdl iNode);
68  void      auto_scroll(WindowPtr wPtr, iconNodeHdl iNode);
69  void      open_icon(WindowPtr wPtr, iconNodeHdl iNode);
70  void      close_icon(WindowPtr wPtr, iconNodeHdl iNode);
71  Boolean   double_click(EventRecord *event);
72  Boolean   dragged(EventRecord *event);
73  void      do_mouse_down(WindowPtr wPtr, EventRecord *event);
74  Boolean   find_top_hilited(iconNodeHdl *iNode);
75  void      hilite_node(iconNodeHdl iNode);
76  void      do_keydown(WindowPtr wPtr, EventRecord *event);
77
78
79
```

```
80   /*****************************************************************************
81    * Function name:    inval -- invalidates a rectangle in image coordinates
82    *
83    * Description:      Offsets the rectangle to screen coordinates, then invalidates the
84    *                   rectangle.
85    *
86    *      Inputs:      r           pointer to the rect
87    *
88    *      Outputs:     none
89    *
90    * Side Effects:                 May cause heap objects to be moved.
91    *                               Changes the current grafports update region.
92    *
93    *      Return:      void
94    *
95    *****************************************************************************/
96
97   void inval(r)
98
99   Rect    *r;
100
101  {
102      Rect    r2;      /* a copy to alter */
103
104      r2 = *r;
105
106      OffsetRect(&r2,-curOrigin.h, -curOrigin.v);
107      InvalRect(&r2);
108  }
109
110
111
```

```
12/21/88 4:37 PM                          iconaction.c                                    Page 4

112  /********************************************************************************
113   * Function name:   do_list -- changes hiliting or open/close state of an icon list.
114   *
115   *   Description:    Do_list changes only those attributes specified in the modify
116   *                   bitfield and changes them to the state indicate in the assert
117   *                   bitfield.
118   *
119   *       Inputs:     modify      Change only the attributes set to true in this bitfield
120   *                   assert      Change the attributes to the state indicated in this bitfield
121   *                   visible
122   *                   iNode       Change this node and all of its descendents
123   *
124   *       Outputs:    none
125   *
126   *   Side Effects:               May cause heap objects to be moved.
127   *                               May change the current grafport's update region.
128   *
129   *       Return:     void
130   *
131   ********************************************************************************/
132
133  void do_list(modify, assert, visible, iNode)
134
135  attribs     *modify;
136  attribs     *assert;
137  Boolean     visible;
138  iconNodeHdl iNode;
139
140  {
141
142      iconNodeHdl t;          /* a handle to the current icon node */
143      iconNodePtr p;          /* t dereferenced */
144      Boolean     open;       /* t's fields */
145      Boolean     hilite;
146      iconNodeHdl desc;
147
148      Boolean     setIt;      /* true when something needs to be set */
149      Boolean     descVisible;/* true when an icon is open */
150
151  #ifdef DEBUG
152      /* debugwrite("\pdo_list"); */
153  #endif
154
155      t = iNode;
156      do {
157          p =*t;              /* Grab the values we need while its dereferenced. */
158          open = p->open;
159          desc = p->desc;
160          hilite = p->hilite;
161
162          if (modify->open)
163              {
164                  setIt = assert->open;
165
166                  /* Opening or closing an icon invalidates the entire port. */
167                  if (open != setIt)
168                      {
169                          InvalRect(&(theWPtr->portRect));
170                          remeasure = true;
171                      }
172
173                  (*t)->open = setIt;
174              }
175
```

12/21/88 4:37 PM                            iconaction.c                                       Page 5

```
176            if (modify->hilite)
177                {
178                setIt = assert->hilite;
179
180                /* Invalidate the frame only if it's visible and its hilighting changes. */
181                if ((visible) && (hilite != setIt))
182                    inval(&((*t)->frame));
183
184                (*t)->hilite = setIt;
185                }
186
187            /* Now do all the descendents of this node. */
188            if (desc)
189                {
190                descVisible = ((visible) && ((*t)->open));
191                do_list(modify, assert, descVisible, desc);
192                }
193
194            /* Now do the next node at the same level, if any. */
195            t = (*t)->next;
196        }while (t != iNode);
197    }
198
199
200
```

```
201   /*******************************************************************************
202    * Function name:    init_icons -- call once at the beginning to initialize icon unit.
203    *
204    *   Description:    Init_icons currently only stores a copy of the hand cursor on
205    *                   the stack.
206    *
207    *      Inputs:      none
208    *
209    *      Outputs:     none
210    *
211    *  Side Effects:                May cause heap objects to be moved.
212    *
213    *      Return:      void
214    *
215    *******************************************************************************/
216
217   void init_icons()
218
219   {
220       CursHandle   h;
221
222       iScrap = nil;           /* start with an empty icon scrap */
223
224       h = GetCursor(HANDCURS);  /* Get the hand cursor & copy to the stack. */
225       failnil((char *) h);
226       hand = **h;
227
228       RGBWhite.red   = 0xFFFF;   /* Set up these frequently used colors once for quickness. */
229       RGBWhite.green = 0xFFFF;
230       RGBWhite.blue  = 0xFFFF;
231
232       RGBGray.red    = 0x8000;
233       RGBGray.green  = 0x8000;
234       RGBGray.blue   = 0x8000;
235
236       RGBBlack.red   = 0;
237       RGBBlack.green = 0;
238       RGBBlack.blue  = 0;
239   }
240
241
242
```

12/21/88 4:37 PM                                iconaction.c                                         Page 7

```
243  /****************************************************************************
244   * Function name:    init_icon_window -- Sets a new window's defaults.
245   *
246   *   Description:    init_icon_window sets the text size, font and style for an icon
247   *                   window.
248   *                   *** Testing only: Gets test data for the window.
249   *
250   *       Inputs:     none
251   *
252   *       Outputs:    iconNodeHdl a reference to iList, the head of the window's icon list.
253   *
254   * Side Effects:               May cause heap objects to be moved.
255   *
256   *       Return:     void
257   *
258   ****************************************************************************/
259
260  iconNodeHdl init_icon_window()
261
262  {
263
264      iconNodeHdl  theList;
265      STR255       s;
266      OSErr        err;
267
268      TextFont(geneva);         /* Set up port's text drawing parameters. */
269      TextSize(9);
270      TextMode(srcOr);
271      TextFace(0);
272      SpaceExtra(0);
273
274  #ifdef DEBUG
275      debugwrite("\pinit_icon_window");
276  #endif
277
278      strcpy(&s, "\pSample Data");
279      err = test_init(&s, &theList);  /*create a demo icon list*/
280      warn(err);
281
282      return(theList);
283  }
284
285
286
```

12/21/88 4:37 PM                                            iconaction.c                                            Page 8

```
287   /***************************************************************************
288    * Function name:    new_icon_window -- creates a new icon window
289    *
290    *   Description:    Init_icons currently only stores a copy of the hand cursor on
291    *                   the stack.
292    *
293    *       Inputs:     none
294    *
295    *       Outputs:    iconNodeHdl a reference to iList, the head of the window's icon list.
296    *
297    * Side Effects:             May cause heap objects to be moved.
298    *
299    *       Return:     void
300    *
301    ***************************************************************************/
302
303   WindowPtr new_icon_window(id)
304
305   short   id;
306
307   {
308       WindowPtr      wPtr;           /* the Newly created icon window */
309       Handle         h;              /* Handle to window's additional data */
310       short          options;        /* Options to the MakeWindow command. */
311
312       CTabHandle     ctab;           /* A color look up table, the source for the palette. */
313       PaletteHandle  palette;        /* The window's palette. */
314
315       h = NewHandle(sizeof(iconWInfc));
316       failnil((char*)h);
317
318       options = HSCROLL + VSCROLL + GROWBOX;
319       wPtr = (WindowPtr) MakeWindow(id, options, ICONWKIND, h);
320       SetPort(wPtr);
321
322       if (environs.hasColorQD)
323           {
324           /* Set up the window's palette. */
325           ctab = GetCTable(SYSTEMCLUT);
326           failnil((char*)ctab);
327
328           palette = NewPalette((*ctab)->ctSize, ctab, pmTolerant, 0x0000);
329           failnil((char*)palette);
330
331           SetPalette(wPtr, palette, true);    /* True means update the window when the color world changes
332           ActivatePalette(wPtr);
333           }
334       set_context(wPtr);
335       iList = init_icon_window();
336       remeasure = true;
337       restore_context();
338
339       return(wPtr);
340   }
341
342
343
```

```
12/21/88 4:37 PM                        iconaction.c                                      Page 9

344   /**********************************************************************************
345   * Function name:   in_descendents -- returns true if a point is inside descendent icon of node
346   *
347   *   Description:   in_descendents returns true if the point passed by p is contained
348   *                  within the bounds of one of the descendent icons belonging to the node
349   *                  indicated by iNode.
350   *
351   *      Inputs:     p         pointer to the Point in question
352   *                  iNode     parent of the descendents
353   *
354   *
355   *      Outputs:    pos       the position of the point as the number of the icon
356   *                            within its parent process frame counting from left to right
357   *
358   * Side Effects:              none
359   *
360   *      Return:     Boolean
361   *
362   **********************************************************************************/
363
364   Boolean in_descendents(p, iNode, pos)
365
366   Point        *p;
367   iconNodeHdl  iNode;
368   short        *pos;
369
370   {
371        iconNodeHdl   n1;      /* starting point in search */
372        iconNodeHdl   n2;      /* current node */
373        Boolean       found;   /* true when the node containing the point is found. */
374        Rect          r;       /* local copy of current node's frame */
375
376   #ifdef DEBUG
377        debugwrite("\pin_descendents");
378   #endif
379
380        found = false;
381        n1 = (*iNode)->desc;    /* Go down a level, if there's one there. */
382        n2 = n1;
383        *pos = 0;
384
385        if (n2)
386            do{
387                r = (*n2)->frame;
388                found = PTINRECT(*p, &r);
389
390                if (!found)
391                    if (p->h > HCENTER(r))
392                        *pos += 1;
393
394                n2 = (*n2)->next;
395            }while((!found) && (n2 != n1));
396
397        return(found);
398   }
399
400
401
402
```

```
12/21/88 4:37 PM                        iconaction.c                                    Page 10

403   /********************************************************************************
404   * Function name:     find_icon -- finds highest level node containing a point
405   *
406   *   Description:     Starting at iNode, find_icon recursively searches for
407   *                    the first node containing the point indicated by p.
408   *
409   *       Inputs:      p           pointer to the Point in question
410   *                    iNode       root of the list
411   *
412   *       Outputs:     pos         the position of the icon in it's list
413   *                    outcome     code indicating the result of the find (notfound inicon inbackground)
414   *                    iNode       icon containing the point
415   *
416   *   Side Effects:                May cause heap objects to be moved.
417   *
418   *       Return:      void
419   *
420   ********************************************************************************/
421   void find_icon(p, iNode, pos, outcome)
422
423   Point         *p;
424   iconNodeHdl   *iNode;
425   short         *pos;
426   short         *outcome;
427
428   {
429
430       iconNodeHdl     aNode;       /* the current icon node */
431       iconNodePtr     ap;          /* aNode dereferenced */
432       iconNodeHdl     desc;        /* aNode's descendent */
433       Boolean         open;        /* aNode's open state */
434       iconNodeHdl     startNode;
435
436       startNode = *iNode;
437       aNode = *iNode;
438       *outcome = inNoIcon;         /* default is that point is in no icon */
439       do {
440           ap = *aNode;             /* Grab some values from aNode */
441           open = ap->open;
442           desc = ap->desc;
443
444           if (PTINRECT(*p, &((*aNode)->frame)))
445               {
446               if (!open)
447                   {
448                   *iNode = aNode;
449                   *outcome = inClosedIcon;
450                   }
451               else
452                   if (!(in_descendents(p, aNode, pos)))
453                       {
454                       *outcome = inOpenIcon;
455                       *iNode = aNode;
456                       }
457                   else
458                       {
459                       if (desc)
460                           {
461                           find_icon(p, &desc, pos, outcome);    /* Recursion happens here. */
462                           if (*outcome != inNoIcon)
463                               *iNode = desc;
464                           }
465                       }
466               }
```

```
 467          aNode = (*aNode)->next;
 468      } while ((*outcome == inNoIcon) && (aNode != startNode));
 469
 470 #ifdef  DEBUG
 471      switch (*outcome){
 472          case inNoIcon:
 473              debugwrite("\pinNoIcon");
 474              break;
 475          case inOpenIcon:
 476              debugwrite("\pinOpenIcon");
 477              break;
 478          case inClosedIcon:
 479              debugwrite("\pinClosedIcon");
 480              break;
 481      }
 482 #endif
 483
 484 }
 485
 486
 487
```

12/21/88 4:37 PM                           iconaction.c                                Page 12

```
488    /*****************************************************************************
489     * Function name:    track_close -- handles the close box for an icon frame
490     *
491     *   Description:    track_close returns true if point p is contained within
492     *                   the icon's close box. CloseIt is set to true iff the mouse
493     *                   is released within the close box. Point p must be in image coordinates.
494     *
495     *       Inputs:     p           pointer to the Point in question
496     *                   iNode       icon in question
497     *
498     *       Outputs:    closeit     set to true if mouse was released within the closebox
499     *                   return      true if point is within the closebox
500     *
501     *   Side Effects:               May cause heap objects to be moved.
502     *
503     *       Return:     Boolean
504     *
505     *****************************************************************************/
506
507    Boolean track_close(p, iNode, closeIt)
508
509    Point       *p;
510    iconNodeHdl iNode;
511    Boolean     *closeIt;
512
513    {
514        Point       upPt;       /* where the mouse came up */
515        Rect        r;          /* closeBox in image coordinates */
516        Rect        q;          /* closeBox in screen coordinates */
517        Boolean     result;     /* function result */
518        RgnHandle   clip;       /* temporary storage for the window's clip region */
519
520    #ifdef  DEBUG
521        debugwrite("\ptrack_close");
522    #endif
523
524        result = false;
525        *closeIt = false;
526
527        r = (*iNode)->frame;    /* make a rectangle equal to the close box */
528        r.right = r.left + CLOSEBOXSIZE;
529        r.bottom = r.top + CLOSEBOXSIZE;
530
531        if (PTINRECT(*p, &r))
532            {
533                q = r;
534                OffsetRect(&q, -curOrigin.h, -curOrigin.v); /* Offset to screen coordinates for drawing. */
535
536                clip = NewRgn();
537                failnil((char*)clip);
538
539                GetClip(clip);      /* Clip to usable area to avoid drawing over scrollbars. */
540                ClipRect(&usable);
541                InvertRect(&q);     /* Hilight close box. */
542
543                while (WaitMouseUp()) /* Wait for him to let go. */
544                    GetMouse(&upPt);
545
546                InvertRect(&q);     /* Unhilight close box and reset the clipRgn. */
547                SetClip(clip);
548                DisposeRgn(clip);
549
550                offset_point(&upPt, curOrigin.h, curOrigin.v); /* Offset to image coordinates. */
551                *closeIt = PTINRECT(upPt, &r);
```

12/21/88 4:37 PM                        iconaction.c                                Page 13

```
552              result = true;
553         }
554      return(result);
555   }
556
557
558
```

```
12/21/88 4:37 PM                        iconaction.c                                    Page 14

559   /**********************************************************************************
560   * Function name:   unhilite_all -- unhilites an icon and all of its descendents.
561   *
562   *   Description:   Uses do_list to set the hilite attribute for an icon list to false.
563   *
564   *       Inputs:    iNode     root of a list of icons
565   *
566   *       Outputs:
567   *
568   *   Side Effects:            May cause heap objects to be moved.
569   *                            May invalidate portions of the window.
570   *
571   *       Return:    void
572   *
573   **********************************************************************************/
574
575   void unhilite_all(iNode)
576
577   iconNodeHdl    iNode;
578
579   {
580       attribs    modify;
581       attribs    assert;
582
583   #ifdef DEBUG
584       debugwrite("\punhilite_all");
585   #endif
586
587       modify.hilite = true;        /* Change only the hilite attribute. */
588       modify.open = false;
589       assert.hilite = false;       /* Change it to unhilited. */
590
591       do_list(&modify, &assert, true, iNode);
592
593       topHilited = nil;            /* Nothing is hilited anymore. */
594   }
595
596
597
```

```
12/21/88 4:37 PM                         iconaction.c                                    Page 15

598  /******************************************************************************
599   * Function name:    open_icons - opens or closes all the icons in a window
600   *
601   *   Description:    use open_icons to open or close an entire list of icons.
602   *                   The flag open tells whether to open or close the icon list.
603   *
604   *       Inputs:     open     flag indicating whether to open or close the icons
605   *                   wPtr     icon window in question
606   *
607   *       Outputs:
608   *
609   * Side Effects:              May cause heap objects to be moved.
610   *                            May invalidate portions of the window.
611   *
612   *       Return:     void
613   *
614   ******************************************************************************/
615
616  void open_icons(open, wPtr)
617
618  Boolean         open;
619  WindowPtr       wPtr;
620
621  {
622
623      attribs    modify, assert;
624
625      set_context(wPtr);
626
627      modify.hilite = false;       /* Change only the open attribute. */
628      modify.open = true;
629      assert.open = open;          /* Change it to whatever was passed in the open parameter. */
630      do_list(&modify, &assert, true, iList);
631
632      restore_context();
633  }
634
635
636
```

```
12/21/88 4:37 PM                        iconaction.c                              Page 16

637  /**********************************************************************************
638   * Function name:    hilite_icon - hilites a single icon & unhilites all the rest.
639   *
640   *   Description:    Hilites a single icon and causes it to be redrawn.
641   *
642   *        Inputs:    iNode     icon to hilite
643   *
644   *        Outputs:
645   *
646   *   Side Effects:             May cause heap objects to be moved.
647   *                             May invalidate portions of the window.
648   *
649   *        Return:    void
650   *
651   **********************************************************************************/
652
653  void hilite_icon(iNode)
654
655  iconNodeHdl    iNode;
656
657  {
658      register iconNodePtr ip;    /* dereference for quickness */
659      Rect            r;
660
661      unhilite_all(iList);        /* unhilite everything */
662      topHilited = iNode;         /* iNode is now the topmost, hilited icon */
663      ip = *iNode;
664      ip->hilite = true;          /* hilite iNode */
665      r = ip->frame;
666      inval(&r);                  /* invalidate its image */
667  }
668
669
670
```

```
671  /**********************************************************************************
672   * Function name:   hilite_sublist - hilites a single icon & unhilites all the rest.
673   *
674   *   Description:   Hilites an icon and its descendents.
675   *
676   *   Inputs:        iNode       icon to hilite
677   *
678   *   Outputs:       none
679   *
680   *   Side Effects:              May cause heap objects to be moved.
681   *                              May invalidate portions of the window.
682   *
683   *   Return:        void
684   *
685   **********************************************************************************/
686
687  void hilite_sublist(iNode)
688
689  iconNodeHdl     iNode;
690
691  {
692       attribs      modify, assert;
693       iconNodeHdl desc;
694       Rect         frame;
695       register iconNodePtr    ip;
696
697  #ifdef DEBUG
698       debugwrite("\philite_sublist");
699  #endif
700
701       unhilite_all(iList);        /* Unhilite everything. */
702
703       ip = *iNode;                /* Grab some values from iNode */
704       ip->hilite = true;
705       desc = ip->desc;
706       frame = ip->frame;
707
708       inval(&frame);              /* Handle iNode as a special case. */
709
710       if (desc)
711           {
712               modify.hilite = true;   /* Now, hilite iNode's descendents. */
713               modify.open = false;
714               assert.hilite = true;
715               do_list(&modify, &assert, true, desc);
716           }
717  }
718
719
720
```

12/21/88 4:37 PM             iconaction.c             Page 18

```c
721  /******************************************************************************
722   * Function name:   auto_scroll - scrolls an icon into view
723   *
724   *   Description:    AutoScroll scrolls the minimum amount necessary to bring as
725   *                   much of iNode into view as possible within the current window size.
726   *
727   *       Inputs:     wPtr        Window containing the icon
728   *                   iNode       icon to scroll
729   *
730   *       Outputs:    none
731   *
732   *  Side Effects:            May cause heap objects to be moved.
733   *                           May invalidate portions of the window.
734   *                           Scrolls the window.
735   *
736   *       Return:     void
737   *
738   ******************************************************************************/
739
740  void auto_scroll(wPtr, iNode)
741
742  WindowPtr       wPtr;
743  iconNodeHdl     iNode;
744
745  {
746      Rect    w, i;
747      short   dh, dv, wHeight, iHeight, wWidth, iWidth;
748
749      i = (*iNode)->outLine;
750      w = usable;
751      InsetRect(&w, MARGIN, MARGIN);
752
753      OffsetRect(&w, curOrigin.h, curOrigin.v);   /* Put window into image coordinates. */
754      wHeight = HEIGHT(w);
755      iHeight = HEIGHT(i);
756      wWidth = WIDTH(w);
757      iWidth = WIDTH(i);
758
759      if (i.left < w.left)                /* If icon is off-screen to the left... */
760          if (iWidth < wWidth)
761              dh = w.left - i.left;       /* ...nudge it to the right. */
762          else
763              dh = w.right - i.right;
764      else
765          if (i.right > w.right)          /* If it's off-screen to the right, nudge it left. */
766              if (iWidth < wWidth)
767                  dh = w.right - i.right;
768              else
769                  dh = w.left - i.left;
770          else
771              dh = 0;                     /* Otherwise, leave it alone. */
772
773      if (i.top < w.top)                  /* If icon is off-screen to the top... */
774          if (iHeight < wHeight)
775              dv = w.top - i.top;         /* ...nudge it down. */
776          else
777              dv = w.bottom - i.bottom;
778      else
779          if (i.bottom > w.bottom)        /* If it's off-screen to the bottom, nudge it up. */
780              if (iHeight < wHeight)
781                  dv = w.bottom - i.bottom;
782              else
783                  dv = w.top - i.top;
784          else
```

12/21/88 4:37 PM iconaction.c Page 19

```
785            dv = 0;
786
787      if ((dh) || (dv))
788          {
789          ScrollTheWindow(wPtr, -dh, -dv);
790          UpdateTheWindow(wPtr);
791          }
792  }
793
794
795
```

12/21/88 4:37 PM                    iconaction.c                                          Page 20

```
796   /******************************************************************************
797   * Function name:    open_icon - opens & hilites an icon and unhilites all the rest
798   *
799   *   Description:    Opens an icon, hilites it and all of its descendents, unhilites
800   *                   everything else, invalidates the whole port, remeasures the iconlist,
801   *                   and autoscrolls the icon into view, if necessary.
802   *
803   *       Inputs:     wPtr     Window containing the icon
804   *                   iNode    icon to scroll
805   *
806   *       Outputs:    none
807   *
808   *   Side Effects:   May cause heap objects to be moved.
809   *                   Invalidates portions of the window.
810   *                   Remeasures the icon list.
811   *                   May scroll the window.
812   *
813   *       Return:     void
814   *
815   ******************************************************************************/
816
817   void open_icon(wPtr, iNode)
818
819   WindowPtr      wPtr;
820   iconNodeHdl    iNode;
821
822   {
823       set_context(wPtr);
824
825       (*iNode)->open = true;
826       hilite_sublist(iNode);             /* Unhilights everything outside, hilights everything inside node i
827       InvalRect(&((wPtr)->portRect));    /* Redraw everything. */
828       remeasure_icons();
829       auto_scroll(wPtr, iNode);
830
831       restore_context();
832   }
833
834
835
```

12/21/88 4:37 PM                        iconaction.c                                        Page 21

```
836   /********************************************************************************
837    * Function name:    close_icon - closes a single icon.
838    *
839    *   Description:    close_icon closes a single icon requests a remeasure and invalidates the
840    *                   whole window.
841    *
842    *       Inputs:     wPtr        Window containing the icon
843    *                   iNode       icon to scroll
844    *
845    *       Outputs:    none
846    *
847    *   Side Effects:               May cause heap objects to be moved.
848    *                               Invalidates the whole window.
849    *                               Sets the remeasure flag to remeasure before the next Draw.
850    *
851    *       Return:     void
852    *
853    ********************************************************************************/
854
855   void close_icon(wPtr,iNode)
856
857   WindowPtr       wPtr;
858   iconNodeHdl     iNode;
859
860   {
861       debugwrite("\pclose_icon");
862
863       set_context(wPtr);
864       (*iNode)->open = false;
865       InvalRect(&(wPtr->portRect));   /* Redraw everything. */
866       remeasure_icons();              /* Remeasure before backpedalling ****/
867       restore_context();
868   }
869
870
871
```

12/21/88 4:37 PM   iconaction.c   Page 22

```
872  /****************************************************************************
873   * Function name:   double_click - returns true if the passed event was a double click.
874   *
875   *   Description:   double_click compares the time of a mouseUp event to the time
876   *                  recorded in lastUp. If the two times are within the range selected by the
877   *                  user as the double click time, double_click returns true.
878   *
879   *       Inputs:    event      EventRecord
880   *
881   *       Outputs:   return     true iff event was second click of a double click
882   *
883   *  Side Effects:              Depends upon the global variable lastUp.
884   *
885   *       Return:    Boolean
886   *
887   ****************************************************************************/
888
889  Boolean double_click(event)
890
891  EventRecord    *event;
892
893  {
894      return((event->what == mouseDown) && (ABS(ABS(event->when) - ABS(lastUp)) < GetDblTime()));
895  }
896
897
898
```

12/21/88 4:37 PM        iconaction.c

```
899   /*******************************************************************************
900    * Function name:   dragged - returns true if the passed event was a drag
901    *
902    *   Description:   dragged returns true if the mouse has been dragged more than
903    *                  the number of pixels specified in STARTDRAGSLOP in either the horizontal or
904    *                  vertical directions. If dragging has taken place or the mouse has been
905    *                  held down for more than double click time, then the cursor is changed
906    *                  into a hand.
907    *
908    *   Inputs:    event      EventRecord
909    *
910    *   Outputs:   return     true iff event was a drag
911    *
912    *   Side Effects:         May cause heap objects to be moved.
913    *                         Hangs multitasking until button is released.
914    *
915    *   Return:    Boolean
916    *
917    *******************************************************************************/
918
919   Boolean dragged(event)
920
921   EventRecord      *event;
922
923   {
924       Point        pt1, pt2;
925       Boolean      moved;
926
927       pt1 = event->where;
928       GlobalToLocal(&pt1);
929
930       moved = false;
931       while ((StillDown() && (!moved)))
932           {
933           GetMouse(&pt2);
934           moved = ((ABS(pt2.h - pt1.h) > STARTDRAGSLOP) || (ABS(pt2.v - pt1.v) > STARTDRAGSLOP));
935
936           if ((moved) || (ABS(event->when - TickCount()) > GetDblTime()))
937               SetCursor(&hand);
938           }
939       return(moved);
940   }
941
942
943
944
```

12/21/88 4:37 PM　　　　　　　　　　　　　　iconaction.c　　　　　　　　　　　　　　Page 24

```
945  /*******************************************************************************
946   * Function name:   do_mouse_down - handles mousedowns for icon windows
947   *
948   *   Description:   do_mouse_down dispatches mousedown events for an icon window
949   *                  to the various actions that can be done.
950   *
951   *      Inputs:     wPtr      the icon window
952   *                  event     a pointer to the mousedown event
953   *
954   *      Outputs:    none
955   *
956   *   Side Effects:            May cause heap objects to be moved.
957   *
958   *      Return:     void
959   *
960   *******************************************************************************/
961
962  void do_mouse_down(wPtr, event)
963
964  WindowPtr       wPtr;
965  EventRecord     *event;
966
967  {
968      GrafPtr     gPtr;
969      Point       p;
970      iconNodeHdl iNode;
971      short       pos;
972      Boolean     closeIt;
973      short       findcode;
974      cPanelHdl   panel;
975
976  #ifdef  DEBUG
977      debugwrite("\pdo_mouse_down");
978  #endif
979
980      GetPort(&gPtr);
981      SetPort(wPtr);
982      p = event->where;                              /* Global coordinates. */
983      GlobalToLocal(&p);                             /* Window coordinates. */
984      offset_point(&p, curOrigin.h, curOrigin.v);    /* Image coordinates. */
985
986      iNode = iList;
987      find_icon(&p, &iNode, &pos, &findcode);
988      switch(findcode) {
989          case inOpenIcon:
990              {
991              if (track_close(&p, iNode, &closeIt))  /* Is it in the close Box? */
992                  {
993                  if (closeIt)
994                      close_icon(wPtr, iNode);       /* Close it, and unhilight its descendents. */
995                  }
996              else
997                  {
998                  if (!(*iNode)->hilite)             /* ((*iNode)->iKind == iconProcess) */
999                      hilite_sublist(iNode);         /* Clicked in opened icon background, hilight icon & */
1000                 else
1001                     if ((*iNode)->iKind == iconStep)
1002                         {
1003                         panel = (*iNode)->data.panel;
1004                         do_panel_mouse_down(panel, event);
1005                         }
1006                 }
1007             }
1008             break;
```

```
1009
1010            case inClosedIcon:
1011                {
1012                if (double_click(event))    /* Was it a double click? */
1013                    open_icon(wPtr, iNode); /* Open this icon. */
1014                else
1015                    hilite_icon(iNode);     /* Hilight this icon. */
1016                }
1017            break;
1018
1019            case inNoIcon:
1020                unhilite_all(iList);        /* Clicked in the background, unhilight all. */
1021            break;
1022            }
1023
1024        /* Update changes, if any, before starting to drag. */
1025        if (!EmptyRgn((((WindowPeek)wPtr)->updateRgn)))
1026            {
1027 #ifdef  DEBUG
1028            debugwrite("\pregion not empty");
1029 #endif
1030            UpdateTheWindow(wPtr);
1031            }
1032
1033        /* if still down and mouse moves a few pixels, turn the cursor into a hand and drag image. */
1034        if (dragged(event))
1035            {
1036            SetCursor(&hand);
1037            DragImage(wPtr,event);
1038            SetCursor(&(QD.arrow));
1039            }
1040        SetPort(gPtr);
1041 }
1042
1043
1044
```

```
2/21/88 4:37 PM                          iconaction.c                                    Page 26

1045  /******************************************************************************
1046   * Function name:   find_top_hilited - finds the topmost, hilited icon
1047   *
1048   * Description:     do_mouse_down dispatches mousedown events for an icon window
1049   *                  to the various
1050   *
1051   *      Inputs:      iNode      root of the list
1052   *
1053   *      Outputs:     iNode      top hilited icon
1054   *                   return     true iff a hilited icon could be found.
1055   *
1056   * Side Effects:               May cause heap objects to be moved.
1057   *
1058   *      Return:      Boolean
1059   *
1060   ******************************************************************************/
1061
1062  Boolean find_top_hilited(iNode)
1063
1064  iconNodeHdl     *iNode;
1065
1066  {
1067      iconNodeHdl     jHdl;
1068      iconNodeHdl     start;
1069      Boolean         found;
1070
1071      iconNodePtr     ip;        /* jHdl dereferenced */
1072      iconNodeHdl     desc;      /* jHdl's fields */
1073      Boolean         open;
1074      Boolean         hilite;
1075
1076      start = *iNode;
1077      jHdl = *iNode;
1078      found = false;
1079
1080      do{
1081          ip = *jHdl;            /* Grab some fields from jHdl */
1082          hilite = ip->hilite;
1083          open = ip->open;
1084          desc = ip->desc;
1085
1086          if (hilite)
1087              {
1088              *iNode = jHdl;
1089              found = true;
1090              }
1091          else
1092              {
1093              if ((open) && (desc))
1094                  {
1095                  *iNode = desc;
1096                  found = find_top_hilited(iNode);
1097                  }
1098              }
1099          jHdl = (*jHdl)->next;
1100      }while ((!found) && (jHdl != start));
1101
1102      if (!found)
1103          *iNode = nil,
1104          SysBeep(1);
1105      return(found);
1106  }
1107
1108
```

12/21/88 4:37 PM					iconaction.c					Page 27

1109

```
12/21/88  4:37 PM                          iconaction.c                                            Page 28

1110  /*******************************************************************************
1111   * Function name:   hilite_node - hilites closed node or open node and sublist
1112   *
1113   *   Description:   hilite_node dispatches mousedown events for an icon window
1114   *                  to the various
1115   *
1116   *   Inputs:        iNode     icon to be hilited
1117   *
1118   *   Outputs:       none
1119   *
1120   * Side Effects:              May cause heap objects to be moved.
1121   *                            May invalidate portions of the window.
1122   *
1123   *   Return:        void
1124   *
1125   *******************************************************************************/
1126
1127  void hilite_node(iNode)
1128
1129  iconNodeHdl     iNode;
1130
1131  {
1132      if ((*iNode)->open)
1133          hilite_sublist(iNode);
1134      else
1135          hilite_icon(iNode);
1136  }
1137
1138
1139
```

12/21/88 4:37 PM                          iconaction.c

```
1140  /*****************************************************************************
1141   * Function name:    do_keydown - interprets keydown events for icon windows
1142   *
1143   * Description:      Handles arrow key presses and interprets them as instructions
1144   *                   about hiliting, opening and closing icons.
1145   *
1146   *     Inputs:       iNode      icon to be hilited
1147   *
1148   *     Outputs:      none
1149   *
1150   * Side Effects:                May cause heap objects to be moved.
1151   *                              May invalidate portions of the window.
1152   *
1153   *     Return:       void
1154   *
1155   *****************************************************************************/
1156
1157  void do_keydown(wPtr, event)
1158
1159  WindowPtr       wPtr;
1160  EventRecord     *event;
1161
1162  {
1163      short       c;
1164      Boolean     optionDown;
1165
1166      iconNodeHdl iNode;
1167      register iconNodePtr    ip;      /* iNode dereferenced */
1168      Boolean     open;                /* iNode's fields */
1169      iconNodeHdl desc;
1170      iconNodeHdl moma;
1171
1172
1173      iNode = iList;
1174      c = event->message & charCodeMask;       /* Get the ascii code of the key pressed. */
1175      optionDown = event->modifiers & optionKey; /* Was the option key down? */
1176      switch (c){
1177          case DOWNKEY:
1178              if (find_top_hilited(&iNode))
1179                  if (!(*iNode)->open)
1180                      open_icon(wPtr,iNode);
1181                  else
1182                      if ((*iNode)->desc != nil)
1183                          hilite_node((*iNode)->desc);
1184              break;
1185
1186          case UPKEY:
1187              if (find_top_hilited(&iNode))
1188                  if (((*iNode)->open) && (((*iNode)->desc == nil) || optionDown))  /* If it's open, close */
1189                      close_icon(wPtr,iNode);
1190                  else
1191                      if ((*iNode)->moma != nil)  /* If it's closed, hilight the parent, if any. */
1192                          hilite_sublist((*iNode)->moma);
1193              break;
1194
1195          case LEFTKEY:
1196              if (find_top_hilited(&iNode))
1197                  {
1198                  iNode = (*iNode)->prev;
1199                  hilite_node(iNode);
1200                  auto_scroll(wPtr, iNode);
1201                  }
1202              break;
1203
```

```
12/21/88 4:37 PM                         iconaction.c                              Page 30

1204            case RIGHTKEY:
1205                if (find_top_hilited(&iNode))
1206                    {
1207                    iNode = (*iNode)->next;
1208                    hilite_node(iNode);
1209                    auto_scroll(wPtr, iNode);
1210                    }
1211            break;
1212
1213            default:
1214                do_panel_key(event);
1215            } /* end switch */
1216    }
1217
1218
1219
```

12/21/88 4:37 PM    iconaction.c    Page 31

```
1220  /******************************************************************************
1221   * Function name:    do_content - dispatches all events that belong to an icon window
1222   *
1223   *   Description:
1224   *
1225   *       Inputs:     wPtr        the icon window
1226   *                   event       the event to be handled
1227   *
1228   *       Outputs:    none
1229   *
1230   *   Side Effects:               May cause heap objects to be moved.
1231   *                               May invalidate portions of the window.
1232   *
1233   *       Return:     void
1234   *
1235   ******************************************************************************/
1236
1237  void do_content(wPtr, event)
1238
1239  WindowPtr       wPtr;
1240  EventRecord     *event;
1241
1242  {
1243      Point   p;          /* mouse location in window's coordinates. */
1244      Rect    r;          /* Window's useable area. */
1245
1246      set_context(wPtr);
1247
1248      p = event->where;
1249      r = usable;
1250      GlobalToLocal(&p);
1251      switch (event->what) {
1252          case mouseUp:
1253              if (PTINRECT(p, &r))
1254                  lastUp = event->when;
1255              break;
1256
1257          case mouseDown:
1258              if (PTINRECT(p, &r))
1259                  do_mouse_down(wPtr, event);
1260              else
1261                  DoControls(wPtr, event);    /* Let the scroll bar handlers do it. */
1262              break;
1263
1264          case keyDown:
1265          case autoKey:
1266              do_keydown(wPtr, event);
1267              break;
1268      }
1269
1270      restore_context();
1271  }
1272
1273
1274
```

```
1275  /*****************************************************************************
1276   * Function name:    cut_icon - cuts hilited material and saves it to scrap
1277   *
1278   *   Description:
1279   *
1280   *      Inputs:     wPtr        the icon window
1281   *
1282   *      Outputs:    none
1283   *
1284   *   Side Effects:              May cause heap objects to be moved.
1285   *                              May invalidate portions of the window.
1286   *                              Replaces contents of iScrap.
1287   *
1288   *      Return:     void
1289   *
1290   *****************************************************************************/
1291
1292  void cut_icon(wPtr)
1293
1294  WindowPtr       wPtr;
1295
1296  {
1297      iconNodeHdl     iNode;
1298
1299      set_context(wPtr);
1300      iNode = iList;
1301      if (find_top_hilited(&iNode))
1302          {
1303              /* Destroy previous contents of the icon scrap.*/
1304              if (iScrap)
1305                  kill_list(&iScrap);
1306
1307              /* Detach the node and its descendents from the list and put in the scrap heap. */
1308              detach_node(iNode);
1309              iScrap = iNode;
1310          }
1311      InvalRect(&(wPtr->portRect));
1312      remeasure = true;
1313      restore_context();
1314  }
1315
1316
1317
```

```
12/21/88 4:37 PM                        iconaction.c                                Page 33

1318  /****  ***********************************************************************
1319   * Function name:   copy_icon - copies hilited material to icon scrap
1320   *
1321   *   Description:
1322   *
1323   *       Inputs:     wPtr        the icon window
1324   *
1325   *       Outputs:    none
1326   *
1327   *   Side Effects:               May cause heap objects to be moved.
1328   *                               Replaces contents of iScrap.
1329   *
1330   *       Return:     void
1331   *
1332   ****************************************************************************/
1333
1334  void copy_icon(wPtr)
1335
1336  WindowPtr      wPtr;
1337
1338  {
1339
1340       iconNodeHdl    iNode;
1341       iconNodeHdl    newList;
1342
1343       set_context(wPtr);
1344       iNode = iList;
1345       if (find_top_hilited(&iNode))
1346           {
1347               newList = copy_list(iNode);
1348               unhilite_all(newList);
1349
1350               if (iScrap)
1351                   kill_list(&iScrap);
1352
1353               iScrap = newList;
1354           }
1355       /*InvalRect(wPtr^.portRect);???*/
1356       remeasure = true;
1357       restore_context();
1358  }
1359
1360
1361
```

```
12/21/88 4:37 PM                          iconaction.c                                    Page 34

1362   /*****************************************************************************
1363   * Function name:    paste_icon - pastes contents of icon scrap after top hilited icon.
1364   *
1365   *   Description:
1366   *
1367   *       Inputs:     wPtr        the icon window
1368   *
1369   *       Outputs:    none
1370   *
1371   *   Side Effects:               May cause heap objects to be moved.
1372   *                               Replaces contents of iScrap.
1373   *
1374   *       Return:     void
1375   *
1376   *****************************************************************************/
1377
1378   void paste_icon(wPtr)
1379
1380   WindowPtr   wPtr;
1381
1382   {
1383
1384       iconNodeHdl     iNode;
1385       iconNodeHdl     newList;
1386
1387       set_context(wPtr);
1388       iNode = iList;
1389       if (find_top_hilited(&iNode))
1390           {
1391               newList = (iconNodeHdl) copy_list(iScrap);
1392               attach_after(iNode, newList);
1393               hilite_node(newList);
1394           }
1395       InvalRect(&(wPtr->portRect));
1396       remeasure = true;
1397       restore_context();
1398   }
1399
1400
1401
```

```
12/21/88 4:37 PM                          iconaction.c                                    Page 1402  /*****************************************************************************
1403   * Function name:   clear_icon - clears hilited icon sublist. doesn't affect icon scrap
1404   *
1405   *   Description:
1406   *
1407   *       Inputs:     wPtr        the icon window
1408   *
1409   *       Outputs:    none
1410   *
1411   *   Side Effects:               May cause heap objects to be moved.
1412   *                               Replaces contents of iScrap.
1413   *
1414   *       Return:     void
1415   *
1416   *****************************************************************************/
1417
1418  void clear_icon(wPtr)
1419
1420  WindowPtr       wPtr;
1421
1422  {
1423
1424      iconNodeHdl     iNode;
1425
1426      set_context(wPtr);
1427      iNode = iList;
1428      if (find_top_hilited(&iNode))
1429          {
1430          /* Detach the node and its descendents from the list and dispose. */
1431          detach_node(iNode);
1432          kill_list(&iNode);
1433          }
1434      InvalRect(&(wPtr->portRect));
1435      remeasure = true;
1436      restore_context();
1437  }
1438
1439
1440
```

12/21/88 4:37 PM                                iconaction.c                                        Page 36

```
1441  /*******************************************************************************
1442   * Function name:   set_color - sets the background color for the hilited icon
1443   *
1444   *   Description:
1445   *
1446   *       Inputs:     wPtr      the icon window
1447   *
1448   *       Outputs:    none
1449   *
1450   *   Side Effects:             May cause heap objects to be moved.
1451   *                             Replaces contents of iScrap.
1452   *
1453   *       Return:     void
1454   *
1455   *******************************************************************************/
1456
1457  void set_color(wPtr)
1458
1459  WindowPtr       wPtr;
1460
1461  {
1462      iconNodeHdl     i;
1463      RGBColor        c, d;
1464      Point           p;
1465
1466      set_context(wPtr);
1467      i = iList;
1468      if ((find_top_hilited(&i)) && ((*i)->iKind == iconProcess))
1469          {
1470          p.h = 25;
1471          p.v = 45;
1472          c = (*(*i)->data.proc)->backColor;
1473          if (GETCOLOR(p, "\pPick a color:", &c, &d))
1474              {
1475              (*(*i)->data.proc)->backColor = d;
1476              inval(&((*i)->frame));
1477              }
1478          }
1479      restore_context();
1480  }
1481
1482
1483
```

```
/**********************************************************************
 * Function name:   new_icon_node - sets the background color for the hilited icon
 *
 *   Description:
 *
 *       Inputs:    wPtr        the icon window
 *                  stepID      the identifier of this step
 *
 *       Outputs:   none
 *
 *   Side Effects:              May cause heap objects to be moved.
 *                              Replaces contents of iScrap.
 *
 *       Return:    void
 *
 **********************************************************************/ void new_icon_node(wPtr, stepID)

WindowPtr   wPtr;
short       stepID;

{

/* stepRange = 1000;    1000..1999 reserved for step icons. */
    /* PROCRANGE = 2000;    2000..2999 reserved for procedure icons. */
    /* VARICON  = 3000;     3000..3999 reserved for structural icons.*/ iconNodeHdl iNode, newIcon, desc;
    Handle      h, hd;
    short       range, sIndex, kind;
    Str255      str;
    PicHandle   p;
    cPanelHdl   panel;

set_context(wPtr);
    iNode = iList;
    if (find_top_hilited(&iNode))
        {
        range = (stepID / 1000) * 1000;
        sIndex = stepID % 1000;
        if (range == PROC_ICON_RANGE)
            kind = iconProcess;
        else
            kind = iconStep;

newIcon = add_node(kind, nil);
        failnil((char*)newIcon);

(*newIcon)->stepID = stepID;
        h = (Handle) GetResource('ICN#', stepID);
        failnil((char*)h);

(*newIcon)->icon = h;

attach_after(iNode, newIcon);

/* Range = 2000 means it's a procedure, add the vars icon as its sole descendent. */
        if (range == PROC_ICON_RANGE)
            {
                desc = add_node(iconStep, nil);
                failnil((char*)desc);
                (*desc)->stepID = VARICON;
                hd = (Handle) GetResource('ICN#',VARICON);  /* Get its icon. */
```

12/21/88 4:37 PM                            iconaction.c                                    Page 38

```
1548                failnil((char*)hd);
1549                (*desc)->icon = hd;
1550
1551                load_panel(VARICON, &panel, desc);
1552                (*desc)->data.panel = panel;
1553
1554                (*newIcon)->desc = desc;         /* Attach descendent node. */
1555                (*desc)->moma = newIcon;
1556
1557                (*newIcon)->iKind = iconProcess;     /* Yes Virginia, it is a procedure. */
1558            }
1559
1560        /* Get default icon name if a name wasn't supplied. */
1561        if (GetHandleSize((*newIcon)->bNote) == 0)
1562            {
1563                GetIndString(&str, range, sIndex);
1564                /* set_text((*newIcon)->bNote, &str);*/
1565                SetString((*newIcon)->bNote, &str);
1566            }
1567
1568        /* Get Default Picture, if one wasn't supplied. */
1569        if (range == 1000)
1570            {
1571                (*newIcon)->iKind = iconStep;
1572                load_panel(VARICON, &panel, newIcon);
1573                (*newIcon)->data.panel = panel;
1574            }
1575
1576        hilite_node(newIcon);                /* Hilight the newly added icon. */
1577        InvalRect(&(wPtr->portRect));
1578        remeasure = true;
1579
1580        }
1581    restore_context();
1582    remeasure_icons();
1583    auto_scroll(wPtr, newIcon);              /* Move it into view. */
1584 }
1585
1586
```

11/16/88 3:57 PM  TestInit.h  Page 1

```
1   /******************************************************************************
2    *   Copyright ©1988 by Applied Biosystems, Inc. All rights reserved.
3    ******************************************************************************
4    *
5    *       File Name: TestInit.h
6    *
7    *       Description: Header for testInit.c, early file handling routines
8    *
9    *       Caveats: None.
10   *
11   *       Edit History: 16 Novemeber 88 Converted from Pascal by HG
12   *
13   ******************************************************************************/
14
15
16   /******************************************************************************
17    *   Preprocessor Directives
18    */
19   #ifndef __TESTINIT__
20   #define __TESTINIT__
21
22
23   /******************************************************************************
24    *   Include Files
25    */
26   #include "includes.h"
27   #include "misc.h"
28   #include "iconUtils.h"
29
30
31   /******************************************************************************
32    *   Macros
33    *   none
34    */
35
36
37   /******************************************************************************
38    *   Structures and Typedefs
39    *   none
40    */
41
42
43   /******************************************************************************
44    *   Scope Declarations
45    *   none
46    */
47
48
49   /******************************************************************************
50    *   Function Prototypes
51    */
52   OSErr test_init(STR255 *fName, iconNodeHdl *iList);
53
54
55
56   #endif
```

11/23/88 2:48 PM                                TestInit.c                                    Page 1

```
1   /***********************************************************************************
2    *  Copyright ©1988 by Applied Biosystems, Inc. All rights reserved.
3    ***********************************************************************************
4    *
5    *   File Name: TestInit.c
6    *
7    *   Description: Early file I/O routines for proto
8    *
9    *   Caveats: None.
10   *
11   *   Edit History: 16 November 88 Converted from Pascal by HG
12   *
13   ***********************************************************************************/
14
15
16  /***********************************************************************************
17   *  Preprocessor Directives
18   */
19  #define LINEBUFCHARS 255
20  #define LINEBUFSIZE (LINEBUFCHARS + 1)
21
22
23  /***********************************************************************************
24   *  Include Files
25   */
26  #include "misc.h"
27  #include "iconUtils.h"
28
29
30  /***********************************************************************************
31   *  External References
32   *   none
33   */
34
35
36  /***********************************************************************************
37   *  Structures and Typedefs
38   *   none
39   */
40
41
42  /***********************************************************************************
43   *  Static Objects
44   */
45  static char aLine[LINEBUFSIZE];                      /* buffer for line being parsed. */
46  static short index;                                  /* index to aLine */
47  static char blanks[] = {(char)TAB, (char)SPACE, '\0'}; /* characters seen as white space. */
48  static char digits[] = "0123456789";                 /* decimal digits */
49  static char hexdigits[] = "0123456789AaBbCcDdEeFf";  /* hexadecimal digits */
50
51
52
53
```

11/23/88 2:48 PM                           TestInit.c                                         Page 2

```
54   /************************************************************************************
55    *   Function Prototypes
56    */
57   static  OSErr       get_test_data(STR255 *fName, short vRef, Handle *buf);
58   static  Handle      get_icon_list(short id);
59   static  CIconHandle get_CICN(short id);
60   static  long        skip_blanks(void);
61   static  Boolean     next_param(char *c);
62   static  char*       get_text(char *s);
63   static  void        HexStringToNum(char *s, long *n);
64   static  long        get_hex_num(void);
65   static  void        get_color(RGBColor *the_color);
66   static  long        get_int(void);
67   static  PicHandle   get_pict(void);
68   static  Boolean     superfluous();
69   static  void        str2text(char *s, Handle t);
70   static  void        get_params(iconNodeHdl inh);
71   static  OSErr       set_defaults(iconNodeHdl inh);
72   static  OSErr       parse_line(Handle buf, long offset, long count, iconNodeHdl *iNode, short *depth);
73   static  iconNodeHdl find_ancestor(iconNodeHdl iNode, short depth);
74   static  void        add_desc(iconNodeHdl parent, iconNodeHdl child);
75   static  OSErr       parse_node(iconNodeHdl *theNode, short *depth, Handle buf, long offset, long count);
76   static  OSErr       process_lines(Handle buf, iconNodeHdl *iList);
77
78
79
80
81
82
```

11/23/88 2:48 PM  TestInit.c  Page 3

```
83  /************************************************************************
84   * Function name:    get_test_data - reads test data into memory.
85   *
86   *   Description:    Creates a buffer sufficient to hold the entire text of the file.
87   *                   Reads the file into the buffer and returns a handle to the
88   *                   buffer.
89   *
90   *       Inputs:     *fName    String pointer to file's full name.
91   *                   vRef      file's volume reference number.
92   *
93   *       Outputs:    *buf      a handle to the data
94   *
95   *       Globals:
96   *
97   * Side Effects:               Large blocks of memory allocated. Can move heap objects.
98   *
99   *       Return:     OSErr     File I/O error code.
100  *
101  ************************************************************************/
102
103  OSErr get_test_data(fName, vRef, buf)
104
105  STR255  *fName;
106  short   vRef;
107  Handle  *buf;       /* Our buffer */
108
109  {
110      OSErr   err;    /* File I/O error code. */
111      OSErr   err2;   /* An error code just for closing the file. */
112      short   fRef;   /* File's reference number */
113      long    eof;    /* End-of-file = file size = buffer size */
114
115      err = FSOPEN(fName, vRef, &fRef);      /* Open Data file */
116      if (!err)
117          {
118          err = GetEOF(fRef, &eof);          /* Find it's size. */
119          if (!err)
120              {
121              *buf = NewHandle(eof);         /* Create a buffer for it. */
122              err = MemError();
123              if (!err)
124                  {
125                  HLock(*buf);
126                  err = FSRead(fRef, &eof, **buf);/* Read it into its buffer. */
127                  HUnlock(*buf);
128                  }
129              }
130          }
131      err2 = FSClose(fRef);                  /* Close it. */
132      fRef = 0;
133
134      err = ((!err) ? err2 : err );          /* Any file I/O problem is terminal. */
135      if (err)
136          {
137          DisposHandle(&buf);                /* On error, throw away the buffer. */
138          *buf = nil;
139          warn(err);
140          }
141
142      return err;                            /* Return the error code. */
143  }
144
145
146
```

```
11/23/88 2:48 PM                        TestInit.c                                   Page 4

147  /****************************************************************************
148  * Function name:    get_icon_list - loads an ICN# resource
149  *
150  *    Description:    Takes an ICN# resource id number and attempts to load that
151  *                    iconlist. If that iconlist cannot be loaded then the default
152  *                    iconlist, a blank procedure icon, is loaded.
153  *
154  *        Inputs:     id          resource id for the desired icon
155  *
156  *       Outputs:                 Handle to an icon list.
157  *
158  *       Globals:
159  *
160  *  Side Effects:                 May allocate memory.
161  *
162  *        Return:     Handle      a handle to the icon list or nil
163  *
164  ****************************************************************************/
165
166  Handle get_icon_list(id)
167
168  short id;
169
170  {
171      Handle h;
172
173      h = GetResource('ICN#', id);              /* Requested icon */
174      if (h == nil)
175          h = GetResource('ICN#', DEFAULT_ICON); /* Default icon */
176
177      failnil(h);
178      return h;
179  }
180
181
182
```

11/23/88 2:48 PM                          TestInit.c                                    Page 5

```
183  /*******************************************************************************
184   * Function name:    get_CICN - loads an CICN (color icon) resource
185   *
186   *   Description:    Takes an CICN resource id number and attempts to load that
187   *                   iconlist. If that iconlist cannot be loaded then nil is returned.
188   *
189   *       Inputs:     id          resource id for the desired icon
190   *
191   *       Outputs:    (return)
192   *
193   *       Globals:
194   *
195   * Side Effects:                 May allocate memory.
196   *
197   *       Return:     CIconHandle A handle to a color icon or nil.
198   *
199   *******************************************************************************/
200
201  CIconHandle get_CICN(id)
202
203  short id;
204
205  {
206      CIconHandle cicn;
207      short       err;
208
209      cicn = (CIconHandle) GetResource('cicn', id);
210
211      err = ResError();   /* Check for resource errors. */
212      if (err)
213          cicn = nil;
214
215      return cicn;
216  }
217
218
219
```

```
220  /*******************************************************************************
221   * Function name:   skip_blanks skips runs of tabs and/or spaces in input stream
222   *
223   * Description:     Moves index to next non-blank character or to end of line.
224   *
225   *       Inputs:    void
226   *
227   *      Outputs:    void
228   *
229   *      Globals:    aLine      the line buffer
230   *                  index      the offset into the buffer to current char
231   *
232   * Side Effects:    index      the index is moved to the first non-blank char
233   *
234   *       Return:    long       the new value of index
235   *
236   *******************************************************************************/
237
238  long skip_blanks()
239  {
240      /* strspn returns first char NOT in the set of blanks. */
241      index += strspn(&aLine[index], blanks);
242      return index;
243  }
244
245
246
```

```
247  /***************************************************************************
248   * Function name:   next_param - finds the next parameter in the input line.
249   *
250   *    Description:   next_param moves the index to the first blank space following
251   *                   a word following a hyphen or the end of the line. The first char
252   *                   following the hyphen is output via *c. The function result is
253   *                   true iff a parameter is found.
254   *
255   *         Inputs:   void
256   *
257   *        Outputs:   *c        the first char of the parameter
258   *
259   *        Globals:   aLine     the line buffer
260   *                   index     the offset into the buffer to current char
261   *
262   *   Side Effects:   index     the index is moved to the first non-blank char
263   *
264   *         Return:   Boolean   true iff a parameter is found.
265   *
266   ***************************************************************************/
267
268  Boolean next_param(c)
269
270  char *c;
271
272  {
273       static char minus[2] = "-";
274       Boolean found;
275
276       /* strcspn returns first char that IS in the set of "-". */
277       index += strcspn(&aLine[index], minus); /* find the next minus sign or end of string */
278       found = (aLine[index] != 0);
279       if (found)
280          {
281             index++;              /* Step past the minus sign. */
282             *c = aLine[index];    /* get first char of descriptor */
283
284             index += strcspn(&aLine[index], blanks); /* skip the rest of the descriptor. */
285             skip_blanks();        /* Step past any white space. */
286          }
287       return found;
288  }
289
290
291
```

```
292  /*****************************************************************************
293   * Function name:    get_text - returns a copy of the next quoted string in the input line.
294   *
295   *   Description:    Finds a single-quoted string in the input string and copies it.
296   *                   Converts pipe characters, "|", to carriage returns.
297   *
298   *        Inputs:    void
299   *
300   *       Outputs:    *s        the text
301   *
302   *       Globals:    aLine     the line buffer
303   *                   index     the offset into the buffer to current char
304   *
305   *  Side Effects:    index     the index is moved to first char past the close quote
306   *
307   *        Return:    char*     same as s
308   *
309   *****************************************************************************/
310
311  char* get_text(s)
312
313  char *s;
314
315  {
316      static char quote[2] = "'";            /* Initialize to a string of a single single quote. */
317      short   len;
318      long    start;
319      short   i;
320
321      /* strcspn returns first char that IS in the set. */
322      index += strcspn(&aLine[index], quote); /* Find the open quote and_ */
323      index++;                                /* step past it. */
324      start = index;                          /* Start of text. */
325      index += strcspn(&aLine[index], quote); /* Find the close quote. */
326
327      len = index - start;
328      len = MIN(len, LINEBUFCHARS);           /* Stay within bounds. */
329      index++;                                /* Step past the quote. */
330
331      strncpy(s, &aLine[start], len);         /* Make a copy of the string. */
332      s[len] = '\0';                          /* Add the terminating null character. */
333
334      /* Now replace any "|" chars in the copy with carriage returns */
335      for (i = 0; (i <= len) ; i++)
336          if (s[i] == '|')
337              s[i] = (char) CR;
338
339      return s;
340  }
```

11/23/88 2:48 PM                            TestInit.c                                      Page 9

```
345   /*****************************************************************************
346    * Function name:    HexStringToNum - converts a ascii string of hex digits to a number.
347    *
348    * Description:      Converts a number represented as ascii hexadecimal into a long integer.
349    *                   Recognizes the chars '0'..'9', 'A'..'F', 'a'..'f' as hex digits.
350    *
351    *     Inputs:       void
352    *
353    *     Outputs:      void
354    *
355    *     Globals:      aLine      the line buffer
356    *                   index      the offset into the buffer to current char
357    *
358    * Side Effects:     index      the index is moved to the first non-blank char
359    *
360    *     Return:       long       the new value of index
361    *
362    *****************************************************************************/
363
364   void HexStringToNum(s, n)
365
366   char *s;
367   long *n;
368
369   {
370
371       short i;
372       short x;
373       char  c;
374       short len;
375
376       *n = 0L;
377       len = strlen(s);
378       for ( i = 0 ; i < len ; i++)
379       {
380           c = s[i];
381           if (('0' <= c) && (c <= '9'))
382               x = (short) c - (short) '0';
383           else
384               if (('a' <= c) && (c <= 'f'))
385                   x = 10 + (short) c - (short) 'a';
386               else
387                   if (('A' <= c) && (c <= 'F'))
388                       x = 10 + (short) c - (short) 'A';
389
390           *n = (*n << 4) + x;
391       }
392
393   }
394
395
396
```

11/23/88 2:48 PM    TestInit.c    Page 10

```
397   /*******************************************************************************
398    * Function name:    get_hex_num - tries to interpret a hexadecimal number in the input string.
399    *
400    *   Description:    get_hex_num attempts to find a string of hexadecimal digits in the
401    *                   input line and, if found, converts them to a long int.
402    *
403    *        Inputs:    void
404    *
405    *       Outputs:    void
406    *
407    *       Globals:    aLine      the line buffer
408    *                   index      the offset into the buffer to current char
409    *
410    *  Side Effects:    index      the index to the line is advanced to next white space
411    *
412    *        Return:    long       the number
413    *
414    *******************************************************************************/
415
416   long get_hex_num()
417
418   {
419   #define FEW_CHARS 19
420   #define FEW_CHARS_LEN (1 + FEW_CHARS)
421
422       char       nStr[FEW_CHARS_LEN];
423       short      i, len;
424       long       n, start;
425
426       /* Skip blanks. */
427       start = skip_blanks();
428
429       /* Find the extent of the hex string. */
430       index += strspn(&aLine[index], hexdigits);   /* Index now points to first non-hexdigit */
431       len = index - start;
432       len = MIN(len, FEW_CHARS);                   /* stay within bounds */
433
434       strncpy(nStr, &aLine[start], len);           /* make a copy of the number string */
435
436       HexStringToNum(nStr, &n);                    /* Convert the numeric string to a number. */
437
438       return n;
439
440   #undef FEW_CHARS
441   #undef FEW_CHARS_LEN
442   }
443
444
445
```

```
446  /******************************************************************************
447  * Function name:   get_color - tries to interpret a hexadecimal number in the input string.
448  *
449  *    Description:   Tries to find three consecutive hexadecimal strings
450  *                   separated by white space. First hex number is red, then
451  *                   green, then blue.
452  *
453  *         Inputs:   void
454  *
455  *        Outputs:   *the_color   a pointer to an RGBColor.
456  *
457  *        Globals:   aLine        the line buffer
458  *                   index        the offset into the buffer to current char
459  *
460  *   Side Effects:   index        changes the index to aLine
461  *
462  *         Return:   void
463  *
464  ******************************************************************************/
465
466  void get_color(the_color)
467
468  RGBColor *the_color;
469
470  {
471      the_color->red   = LOWORD(get_hex_num());   /* Take the hex value of each color component. */
472      the_color->green = LOWORD(get_hex_num());
473      the_color->blue  = LOWORD(get_hex_num());
474  }
475
476
477
```

11/23/88 2:48 PM  TestInit.c  Page 12

```
478  /*******************************************************************************
479   * Function name:   get_int -- pulls an integer out of the input string or zero
480   *
481   *   Description:   get_int expects to find an integer in ascii format as the next
482   *                  item in the input stream. get_in skips all tabs and spaces
483   *                  then copies all digits into a local buffer from which
484   *                  the integer equivalent is derived.
485   *
486   *       Inputs:    void
487   *
488   *      Outputs:    return     the integer
489   *
490   *      Globals:    aLine      pointer to current string
491   *                  index      start of current line in buffer
492   *
493   * Side Effects:               Can move heap objects.
494   *
495   *       Return:    long       the integer or zero
496   *
497   *******************************************************************************/
498
499  long get_int()
500
501  {
502  #define FEW_CHARS 19
503  #define FEW_CHARS_LEN (1 + FEW_CHARS)
504
505       char     nStr[FEW_CHARS_LEN];       /* Allows for 20 digit ints, which is more than maxlongint.
506       short    i;
507       short    len;
508       long     n, start;
509
510       start = skip_blanks();              /* Merrily skip past the white space. */
511
512       /* Find the end of the numeric string. */
513       index += strspn(&aLine[index], digits);   /* Index now points to first non-digit */
514       len = index - start;
515       len = MIN(len, FEW_CHARS);          /* Stay within string's bounds. */
516
517       strncpy(nStr, &aLine[start], len);  /* make a copy of the number string */
518
519       /* Convert the numeric string to a number. */
520  #ifdef THINK_C
521       StringToNum(CtoPstr(nStr), &n);
522  #else
523       StringToNum(nStr, &n); /**** STRINGTONUM doesn't work on MPW 2.0!!! ****/
524  #endif
525
526       return n;
527
528  #undef FEW_CHARS
529  #undef FEW_CHARS_LEN
530  }
531
532
533
```

11/23/88 2:48 PM                    TestInit.c                                    Page 13

```
534   /******************************************************************************
535   * Function name:    get_pict    gets a pict corresponding to a number in the input line
536   *
537   *    Description:              Attempts to find the next number in the input line. If
538   *                              the number is non-zero, requests the PICT resource
539   *                              with id number. Returns the handle to the picture or nil.
540   *
541   *        Outputs:
542   *
543   *    Side Effects:             Can move heap objects.
544   *
545   *        Return:     PicHandle  the handle to the picture or nil.
546   *
547   ******************************************************************************/
548
549   PicHandle get_pict()
550
551   {
552       PicHandle   ph = nil;
553       short       id;
554
555       id = LOWORD(get_int());
556       if (id)
557           ph = GetPicture(id);
558
559       return ph;
560   }
561
562
563
```

11/23/88 2:48 PM　　　　　　　　　　　　　　　　TestInit.c　　　　　　　　　　　　　　　　Page 14

```
564   /***********************************************************************************
565    * Function name:    superfluous - tells if a line has no content.
566    *
567    *   Description:    Comment lines are lines beginning with '#' or lines which contain
568    *                   only white space. Comment lines are superfluous.
569    *
570    *        Inputs:    aLine      pointer to current string
571    *                   index      start of current line in buffer
572    *
573    *       Outputs:    return
574    *
575    *  Side Effects:
576    *
577    *        Return:    Boolean    true if this line needs no further interpretation
578    *
579    ***********************************************************************************/
580
581   Boolean superfluous()
582
583   {
584       /* Is it an explicit comment?
585        * (aLine[0] == '#')
586        *
587        * Are there no non-blank chars on this line?
588        * (strlen(aLine) == strcspn(aLine, blanks))
589        */
590       return ((aLine[0] == '#') || (strlen(aLine) == strcspn(aLine, blanks)));
591   }
592
593
594
```

```
595  /************************************************************************
596   * Function name:    str2text - makes a text handle out of a C string
597   *
598   *   Description:    str2text sets a previously allocated text handle to the
599   *                   C string passed in s.
600   *
601   *       Inputs:     t         an allocated handle containing zero or more bytes
602   *                   s         a C string
603   *
604   *       Outputs:    t         the contents of handle t are changed
605   *
606   * Side Effects:               Allocates memory. May move heap objects.
607   *
608   *       Return:     void
609   *
610   ************************************************************************/
611
612  void str2text(s, t)
613
614  char      *s;
615  Handle    t;
616
617  {
618      long   len;
619
620      failnil(t);           /* Don't bother proceeding if handle is empty. */
621      len = strlen(s);      /* Find string's length. */
622
623      SetHandleSize(t, len); /* Size the handle to fit the string. */
624      warn(MemError());     /* Out of memory? */
625
626      HLock(t);
627          BlockMove(s, *t, len); /* Copy the string into the handle. */
628      HUnlock(t);
629  }
630
631
632
```

```
633   /***********************************************************************************
634   * Function name:    get_params --  interprets optional parameters for the node
635   *
636   *   Description:    parse_line copies count chars starting at offset from the text
637   *                   in the text buffer. The line is ignored if it's a comment, otherwise
638   *                   parse_line attempts to find the node id number as the first text in the
639   *                   line. The icon node is allocated. Additional parameters are
640   *                   interpreted if they exist.
641   *
642   *       Inputs:     buf         handle to buffer contain entire contents of text file
643   *                   offset      start of current line in buffer
644   *                   count       number of chars in this line
645   *
646   *       Globals:    aLine       text line to be interpreted
647   *                   index       index to aLine
648   *
649   *       Outputs:    *iNode      node created from information in text line
650   *                   *depth      depth from root of iNode
651   *
652   *   Side Effects:               index is may be advanced
653   *                               Fields of iconNodeHdl inh are altered.
654   *                               Allocates memory; can move heap objects.
655   *
656   *       Return:     void
657   *
658   ***********************************************************************************/
659
660   void get_params(inh)
661
662   iconNodeHdl     inh;
663
664   {
665       char        c;                  /* First char of a param name. */
666       char        s[LINEBUFSIZE];     /* Holding place for text strings. */
667
668       while (next_param(&c))
669           {
670           switch (c)
671               {
672               case 't':
673               case 'T':
674                   str2text(get_text(s), (*inh)->tNote);
675                   break;
676               case 'b':
677               case 'B':
678                   str2text(get_text(s), (*inh)->bNote);
679                   break;
680               case 'c':
681               case 'C':
682                   if ((*inh)->iKind == iconProcess)
683                       get_color(&((*(*inh)->data.proc)->backColor));
684                   break;
685               case 'p':
686               case 'P':
687                   if ((*inh)->iKind == iconStep)
688                       (*(*inh)->data.panel)->pict = get_pict();   /* Get a non-default picture. */
689                   break;
690               case 's':
691               case 'S':
692                   if ((*inh)->iKind == iconProcess)
693                       (*(*inh)->data.proc)->split = true;
694                   break;
695               default:
696                   break;
```

11/23/88 2:48 PM  Testlnit.c  Page 17

```
697             } /* end switch */
698         } /* end while */
699    }
700
701
702
```

```
703  /*****************************************************************************
704   * Function name:    set_defaults -- sets defaults for an icon node
705   *
706   * Description:      set_defaults sets the default string and picture if these
707   *                   fields weren't already specified.
708   *
709   *     Inputs:       inh       a handle to an iconNode
710   *
711   *     Globals:      aLine     text line to be interpreted
712   *                   index     index to aLine
713   *
714   *     Outputs:
715   *
716   *     Side Effects:           Fields of iconNodeHdl inh are altered.
717   *                             May allocate memory; can move heap objects.
718   *
719   *     Return:       OSErr     Resource error encountered.
720   *
721   *****************************************************************************/
722
723  OSErr set_defaults(inh)
724
725  iconNodeHdl inh;
726
727  {
728      short       id;
729      short       range;
730      short       sIndex;
731      panelHdl    ph;
732      PicHandle   pict;
733      OSErr       err = 0;
734      Rect        r;
735      STR255      str;
736
737      id = (*inh)->stepID;                    /* Get the id. */
738
739      /* Get name if a name wasn't supplied. */
740      if (GetHandleSize((*inh)->bNote) == 0)
741          {
742          range = (id / 1000) * 1000;
743          sIndex = id % 1000;
744          if (sIndex != 0)
745              {
746              GETINDSTRING(&str, range, sIndex);
747              set_text((*inh)->bNote, &str);
748              }
749          }
750
751      /* Get Default Picture, if one wasn't supplied. */
752      if ((*inh)->iKind == iconStep)
753          {
754          ph = (*inh)->data.panel;
755          SetRect(&((*ph)->pBox), 0, 0, 48, 48); /* default panel dimensions. */
756          if ((*ph)->pict == nil)
757              {
758              pict = GetPicture(id);
759              err = ResError();
760              if ((err == noErr) && (pict != nil))
761                  {
762                  (*ph)->pict = pict;
763                  r = (*pict)->picFrame;
764                  InsetRect(&r, -HILITEWIDTH, -HILITEWIDTH);
765                  OffsetRect(&r, -r.left, -r.top);
766                  (*ph)->pBox = r;
```

```
767              }
768          }
769      }
770     return err;
771 }
772
773
774
```

11/23/88 2:48 PM                           TestInit.c                                Page 20

```
775   /****************************************************************************
776   * Function name:    parse_line -- converts a line of text into an iconNode
777   *
778   *   Description:    parse_line copies count chars starting at offset from the text
779   *                   in the text buffer. The line is ignored if it's a comment, otherwise
780   *                   parse_line attempts to find the node id number as the first text in the
781   *                   line. The icon node is allocated. Additional parameters are
782   *                   interpreted if they exist.
783   *
784   *       Inputs:     buf        handle to buffer contain entire contents of text file
785   *                   offset     start of current line in buffer
786   *                   count      number of chars in this line
787   *
788   *       Outputs:    *iNode     node created from information in text line
789   *                   *depth     depth from root of iNode
790   *
791   * Side Effects:                Allocates memory; can move heap objects.
792   *
793   *       Return:     OSErr
794   *
795   ****************************************************************************/
796
797   OSErr parse_line(buf, offset, count, iNode, depth)
798
799   Handle      buf;
800   long        offset;
801   long        count;
802   iconNodeHdl *iNode;
803   short       *depth;
804
805   {
806
807       short       len, kind, id;
808       long        p,n,start,last;
809       Handle      icon;
810       CIconHandle cicn;
811       iconNodeHdl inh;
812       OSErr       err = noErr;
813   #ifdef DEBUG
814       STR255  dStr;
815   #endif
816
817       len = MIN(count, LINEBUFCHARS);        /* Copy to a c string on the stack. */
818
819       BlockMove(((char*)*buf+offset), aLine, len);
820       aLine[len] = '\0';
821       index = 0;
822
823   #ifdef DEBUG
824       strcpy((char*)&dStr, aLine);
825       debugwrite(CtoPstr((char*)&dStr));
826   #endif
827
828       *depth = 0;
829       *iNode = nil;
830
831       if (!superfluous())
832           {
833           while (aLine[index] == (char)TAB)    /* Count the tabs. */
834               index++;
835           *depth = index;
836           id = LOWORD(get_int());              /* Get node's icon id number. */
837
838           /* What kind of icon is it? */
```

```
839            if ((PROC_ICON_RANGE <= id) && (id < STRUC_ICON_RANGE))
840                kind = iconProcess;
841            else
842                kind = iconStep;
843
844            *iNode = inh = add_node(kind, nil); /* Allocate a node. */
845
846            (*inh)->stepID = id;
847            cicn = get_CICN(id);
848            (*inh)->cicn = cicn;
849            icon = get_icon_list(id);
850            (*inh)->icon = icon;
851
852            get_params(inh);          /* interpret any optional parameters. */
853            err = set_defaults(inh);  /* Fill in default values for unspecified parameters. */
854            }
855     return err;
856 }
857
858
859
```

11/23/88 2:48 PM　　　　　　　　　　　　TestInit.c　　　　　　　　　　　　　　　　　　Page 22

```
860  /*****************************************************************************
861   * Function name:   find_ancestor -- finds ancestor node n generations back
862   *
863   *   Description:   Taking an iconNode and the depth in the tree, find_ancestor finds
864   *                  the node at depth generations back from iNode. If iNode happens
865   *                  to be the root, iNode is returned.
866   *
867   *
868   *       Inputs:    iNode      the node in question
869   *                  depth      nesting level of ancestor
870   *
871   *       Outputs:   (return)   ancestor depth generations back
872   *
873   * Side Effects:               none
874   *
875   *       Return:    iconNodeHdl the ancestor
876   *
877   *****************************************************************************/
878
879  iconNodeHdl find_ancestor(iNode, depth)
880
881  iconNodeHdl iNode;
882  short       depth;
883
884  {
885
886      short        n;
887      iconNodeHdl  moma = iNode;
888
889      for (n = 1; n <= depth; n++)
890          {
891          moma = (*iNode)->moma;
892          if (moma != nil)
893              iNode = moma;
894          else
895              break;
896          }
897      return moma;
898  }
899
900
901
```

```
 902   /***************************************************************************
 903   * Function name:    add_desc --  Makes child node a descendent of parent node.
 904   *
 905   *    Description:   If parent node has no descendents, add_desc adds child as the first
 906   *                   descendent node and changes parent node's kind to reflect that fact.
 907   *                   if parent node already has some descendents, add_desc adds the child
 908   *                   node as the last node in the descendent list.
 909   *
 910   *    Inputs:        parent    node to receive child as a descendent node
 911   *                   child     node to be added to parent's descendent list
 912   *
 913   *    Outputs:       none
 914   *
 915   * Side Effects:               Splices child node into iconlist.
 916   *
 917   *    Return:        void
 918   *
 919   ***************************************************************************/
 920
 921   void add_desc(parent, child)
 922
 923   iconNodeHdl parent;
 924   iconNodeHdl child;
 925
 926   {
 927       register iconNodePtr ip;
 928       iconNodeHdl     desc;
 929
 930       ip = *parent;
 931       desc = ip->desc;
 932
 933       if (desc == nil)
 934           {
 935               ip->iKind = iconProcess;    /* parent must be a procedure. */
 936               ip->desc = child;
 937               (*child)->moma = parent;
 938           }
 939       else
 940           /* Make new child the last of the offspring. */
 941           attach_after((*desc)->prev, child);
 942   }
 943
 944
 945
```

```
946  /*******************************************************************************
947   * Function name:   parse_node -- Creates an icon node from a text description.
948   *
949   *   Description:   Attempts to interpret a line of text as a description of an
950   *                  icon node. Returns an error message if a memory error is
951   *                  encountered.
952   *
953   *       Inputs:    *theNode    last previously created icon node or nil if this is the first.
954   *                  *depth      current nesting level
955   *                  buf         buffer containing entire contents of description text file
956   *                  offset      start of information about this icon node
957   *                  count       number of chars pertainting to this node
958   *
959   *      Outputs:    *theNode    newly created icon node
960   *                  *depth      depth of the new node
961   *
962   * Side Effects:                Causes memory to be allocated; may move heap objects.
963   *
964   *       Return:    OSErr       error code encountered during parsing
965   *
966   *******************************************************************************/
967
968  OSErr parse_node(theNode, depth, buf, offset, count)
969
970  iconNodeHdl     *theNode;
971  short           *depth;
972  Handle          buf;
973  long            offset;
974  long            count;
975
976  {
977      OSErr       err = noErr;
978      short       newDepth = 0;
979      iconNodeHdl newNode;
980      iconNodeHdl ancestor;
981
982      err = parse_line(buf, offset, count, &newNode, &newDepth);
983
984      if ((!err) && (newNode != nil))
985          {
986              /* Can't attach to anything if there's nothing to attach to. */
987              if (*theNode != nil)
988                  {
989                  if (newDepth == *depth)
990                      attach_after(*theNode, newNode);
991                  else
992                      if (newDepth < *depth)
993                          {
994                          ancestor = find_ancestor(*theNode, *depth - newDepth);
995                          attach_after(ancestor, newNode);
996                          }
997                      else /* (newDepth > *depth) */
998                          add_desc(*theNode, newNode);
999                  }
1000
1001             *theNode = newNode;
1002             *depth = newDepth;
1003         }
1004
1005     return err;
1006  }
1007
1008
1009
```

```
11/23/88 2:48 PM                          TestInit.c                                          Page 25

1010   /****************************************************************************************
1011   * Function name:    process_lines -- parses the file and creates the icon nodes
1012   *
1013   *   Description:    process_lines divides the text buffer into carriage-return
1014   *                   or end of text delimited lines and sends each line to parse_node
1015   *                   which attempts to interpret the line as a description of an
1016   *                   icon node. Returns the head of the list in iList. Returns an
1017   *                   error message if a memory error is encountered.
1018   *
1019   *       Inputs:     buf     Handle to the file's text
1020   *                   iList   pointer to a handle to hold the head of the list
1021   *
1022   *       Outputs:    *iList  head of the list or nil if unsuccessful
1023   *
1024   *       Return:     OSErr   error code
1025   *
1026   ****************************************************************************************/
1027
1028   OSErr process_lines(buf, iList)
1029
1030   Handle      buf;
1031   iconNodeHdl *iList;
1032
1033   {
1034       long        p, last, count;
1035       long        start = 0;
1036       char        c = CR;
1037       OSErr       err = noErr;
1038       iconNodeHdl iNode = nil;
1039       short       depth = 0;
1040       Boolean     first = true;
1041
1042       last = GetHandleSize(buf);
1043       err = MemError();
1044       if (!err)
1045           {
1046               do{
1047                   /* Starting at the current position in the text,
1048                    * find the next carriage return, if any.
1049                    */
1050                   p = Munger(buf, start, &c, 1, nil, 0);
1051
1052                   /* If a carriage return was found, or there was some text after the
1053                    * last carriage return, try to interpret the text as a line of
1054                    * icon description text
1055                    */
1056                   if ((p > 0) || (start < last))
1057                       {
1058                           /* If p is positive, then return-char-terminated line was found,
1059                            * and the number of chars in this line is p-start. If no return
1060                            * char can be found, p will be negative and the length of the line
1061                            * is last-start, since the last line in the text might not be terminated
1062                            * with a carriage return.
1063                            */
1064                           count = ((p > 0) ? p : last) - start;
1065
1066                           /* Now that we have a line of text, let's create the icon node
1067                            * that the text describes, if any.
1068                            */
1069                           err = parse_node(&iNode, &depth, buf, start, count);
1070
1071                           /* If the parsing was successful and the line described a node
1072                            * and this is the first icon in the list, then record it as
1073                            * the head of the list.
```

| | | |
|---|---|---|
| 11/23/88 2:48 PM | TestInit.c | Page 26 |

```
1074                        */
1075                        if ((first) && (!err) && (iNode))
1076                        {
1077                            *iList = iNode;
1078                            first = false;
1079                        }
1080                }
1081                start = p + 1;  /* Skip the return character. */
1082            }while((!err) && (p >= 0));    /* Munger returns a negative when it can't find the CR. */
1083        }
1084    return err;
1085 }
1086
1087
1088
1089
```

```
1090  /************************************************************************
1091   * Function name:   test_init creates an icon list from an icon list description file.
1092   *
1093   *   Description:   test_init takes the name of a file and returns an icon list handle.
1094   *
1095   *
1096   *      Inputs:      fName      The name of the icon description file.
1097   *                   iList      pointer to handle to receive the new icon list
1098   *
1099   *      Outputs:     *iList     changed to new list or nil if unsuccessful
1100   *
1101   *  Side Effects:              Large chunks of memory may be allocated by this routine.
1102   *                             Heap objects may be moved.
1103   *
1104   *      Return:      OSErr     File I/O error code
1105   *
1106   ************************************************************************/
1107
1108  OSErr test_init(fName, iList)
1109
1110  STR255      *fName;
1111  iconNodeHdl *iList;
1112
1113  {
1114      OSErr   err;
1115      Handle  buf;       /* A (possibly large) buffer containing file's entire contents. */
1116
1117  #ifdef DEBUG
1118      debugwrite("\pTEST_INIT");
1119  #endif
1120
1121      *iList = nil;      /* Default to nil. */
1122
1123      err = get_test_data(fName, 0, &buf);   /* Allocate and fill the buffer with the file's contents. */
1124
1125      if ( (buf) && (!err) )
1126              err = process_lines(buf, iList);/* Parse the text and create the icon list. */
1127
1128      if (buf)
1129              DisposHandle(buf);             /* Get rid of the in-memory copy of the file. */
1130
1131      return err;
1132  }
1133
1134
1135  /************************************************************************
1136   *   Closing Preprocessor Directives
1137   */
1138  #undef  LINEBUFCHARS
1139  #undef  LINEBUFSIZE
```

Proto.h

```
1   /*******************************************************************************
2                   Applied Biosystems, Inc. All rights reserved.
3   ********************************************************************************
4   *
5   *       File Name: Proto.h
6   *
7   *       Description: Header for proto.c, Main unit of proto.
8   *
9   *       Caveats: None.
10  *
11  *
12  *
13  *******************************************************************************/
14
15
16  /********************************************************************************
17  *   Preprocessor Directives
18  */
19  #ifndef __PROTO__
20  #define __PROTO__
21
22
23  /********************************************************************************
24  *   Include Files
25  */
26  #include "includes.h"
27  #include "misc.h"
28  #include "iconUtils.h"
29  #include "iconAction.h"
30  #include "RezIDs.h"
31
32
33  /********************************************************************************
34  *   Scope
35  */
36  extern MenuHandle   MyMenus[menuCount];  /* The menu handles */
37  extern Boolean      DoneFlag;            /* Becomes TRUE when File/Quit chosen */
38  extern WindowPtr    mainWPtr;            /* Main window */
39
40
41
42  #endif
```

Proto.c                                                                       Page 1

```
1   /******************************************************************************
2    *          © by Applied Biosystems, Inc. All rights reserved.
3    ******************************************************************************
4    *
5    *       File Name: Proto.c
6    *
7    *       Description: Main unit of Front End prototype
8    *
9    *          Caveats: None.
10   *
11   *       Edit History: 17 Nov 88 updated by HG
12   *
13   ******************************************************************************/
14
15
16   /******************************************************************************
17    *   Preprocessor Directives
18    *   none
19    */
20
21
22   /******************************************************************************
23    *   Include Files
24    */
25   #include "Proto.h"
26
27
28   /******************************************************************************
29    *   Externals
30    */
31   #ifdef MPW
32   extern _DataInit();
33   #endif
34
35
36   /******************************************************************************
37    *   Globals
38    */
39   MenuHandle  MyMenus[menuCount];  /* The menu handles */
40   Boolean     DoneFlag;            /* Becomes TRUE when File/Quit chosen */
41   WindowPtr   mainWPtr;            /* Main window */
42
43
44   /*
45    * Draw dispaches update events to various window's updating mechanisms.
46    */
47   void Draw(wPtr, updateArea)
48   WindowPtr   wPtr;
49   Rect        *updateArea;
50   {
51       if (((WindowPeek) wPtr)->windowKind == ICONWKIND)
52           draw_icons(wPtr,updateArea);
53   }
54
55
56
57   /******************************************************************************
58    *
59    *   do_dummy_dialog
60    *
61    ******************************************************************************/
62
63   void do_dummy_dialog(id)
64
```

Proto.c                                                                                         Page 2

```
 65  short    id;
 66
 67  {
 68      DialogPtr   dPtr;
 69      short       theItem;
 70
 71      dPtr = GetNewDialog(id, nil, (WindowPtr)-1L);
 72      do{
 73          ModalDialog(nil, &theItem);
 74      }while(!theItem);
 75
 76      DisposDialog(dPtr);
 77  }
 78
 79
 80
 81
 82  /***********************************************************************************
 83   *
 84   *   doCommand
 85   *
 86   ***********************************************************************************/
 87
 88  void doCommand(mResult)
 89      long    mResult;
 90  {
 91      short               id;
 92      int                 theMenu, theItem;
 93      char                daName[256];
 94      GrafPtr             savePort;
 95      extern MenuHandle   MyMenus[];
 96      extern Boolean      DoneFlag;
 97      extern void         showAboutMeDialog();
 98      WindowPtr           wPtr;
 99
100      theItem = LOWORD(mResult);
101      theMenu = HIWORD(mResult);      /* This is the resource ID */
102      wPtr = FrontWindow();
103
104      switch (theMenu) {
105          case appleMENU:
106              if (theItem == aboutMeCommand) {
107                  showAboutMeDialog();
108              } else {
109                  GetItem(MyMenus[appleMenu], theItem, daName);
110                  GetPort(&savePort);
111                  (void) OpenDeskAcc(daName);
112                  SetPort(savePort);
113              }
114              break;
115
116          case fileMENU:
117              switch (theItem) {
118                  case newCommand: ;
119                      break;
120                  case openCommand:
121                      open_icons(true, mainWPtr);
122                      break;
123                  case closeCommand:
124                      open_icons(false, mainWPtr);
125                      break;
126                  case saveCommand:
127                      break;
128                  case saveAsCommand: ;
```

Proto.c                                                                        Page 3

```
129              break;
130          case saveCopyCommand: ;
131              break;
132          case revertCommand: ;
133              break;
134          case pageSetUpCommand: ;
135              break;
136          case printCommand: ;
137              break;
138          case quitCommand:
139              DoneFlag = true;           /* Request exit */
140              break;
141          default:
142              break;
143      }
144      break;
145
146  case editMENU:
147      /*
148       * If this is for a 'standard' edit item,
149       * run it through SystemEdit first.
150       * SystemEdit will return FALSE if it's not a system window.
151       */
152      if ((theItem <= clearCommand) && SystemEdit(theItem-1)) {
153          break;
154      }
155      /*
156       * Otherwise, it's my window.
157       * Handle Cut/Copy/Paste properly
158       * between the TEScrap and the Clipboard.
159       */
160      switch (theItem) {
161          case undoCommand:
162              /* can't undo */
163              break;
164          case cutCommand: if (wPtr == mainWPtr) {
165                  cut_icon(wPtr);
166              };
167              break;
168          case copyCommand:if (wPtr == mainWPtr) {
169                  copy_icon(wPtr);
170              };
171              break;
172          case pasteCommand:if (wPtr == mainWPtr) {
173                  paste_icon(wPtr);
174              };
175              break;
176          case clearCommand:if (wPtr == mainWPtr) {
177                  clear_icon(wPtr);
178              };
179              break;
180          case setColorCommand:if (wPtr == mainWPtr) {
181                  set_color(wPtr);
182              };
183              break;
184          default:
185              break;
186      } /*endsw theItem*/
187      break;
188  case viewMENU: if (wPtr == mainWPtr){
189      };
190      break;
191  case checkMENU: if (wPtr == mainWPtr){
192      };
```

Proto.c                                                                 Page 4

```
193             break;
194     case runMENU: if (wPtr == mainWPtr){
195             switch(theItem){
196                     case ITEM_START:
197                             break;
198                     case ITEM_SUSPEND:
199                             break;
200                     case ITEM_RESUME:
201                             break;
202                     case ITEM_ABORT:
203                             break;
204                     default:
205                             break;
206                     }; /* endswitch theItem */
207             }; /* endif the right window */
208             break;
209     case toolsMENU: if (wPtr == mainWPtr){
210             switch(theItem){
211                     case mixCommand:
212                             new_icon_node(wPtr,mix);
213                             break;
214                     case spinCommand:
215                             new_icon_node(wPtr,spin);
216                             break;
217                     case tempCommand:
218                             new_icon_node(wPtr,temp);
219                             break;
220                     case absorbanceCommand:
221                             new_icon_node(wPtr,absorbance);
222                             break;
223                     case dryCommand:
224                             new_icon_node(wPtr,dry);
225                             break;
226                     case waitCommand:
227                             new_icon_node(wPtr,wait);
228                             break;
229                     case notebookCommand:
230                             new_icon_node(wPtr,notebook);
231                             break;
232                     case checklistCommand:
233                             new_icon_node(wPtr,checklist);
234                             break;
235                     default :
236                             break;
237                     }; /* endswitch theItem */
238             }; /* endif the right window */
239             break;
240     case setupMENU: if (wPtr == mainWPtr){
241             switch(theItem){
242                     case ITEM_GROUPSAMPLES:
243                             do_dummy_dialog(PICK_SAMPLES);
244                             break;
245                     case ITEM_PICKRESTRICTION:
246                             do_dummy_dialog(PICK_RESTRICTION);
247                             break;
248                     case ITEM_PICKPROBES:
249                             do_dummy_dialog(PICK_PROBE);
250                             break;
251                     default :
252                             break;
253                     }; /* endswitch theItem */
254             }; /* endif the right window */
255             break;
256     default:
```

Proto.c                                                                                        Page 5

```
257            break;
258        }/*endsw theMenu*/
259
260        HiliteMenu(0);
261
262 #ifdef DEBUG
263        debugwrite("\pBye-Bye.");
264        debugwrite("\p");
265        closedebug();
266 #endif
267
268        return;
269 }
270
271
272 /*
273  *
274  * This code is execute-once, so we toss it in the "Initialize"
275  * segment so that main() can unload it after it's called.
276  *
277  */
278 /*
279  * Set the segment to Initialize.  BEWARE: leading and trailing white space
280  * would be part of the segment name!
281  */
282 #ifdef MPW
283 #define __SEG__ Initialize
284 #endif
285
286
287 /******************************************************************************
288  *
289  *     setupMenus
290  *
291  ******************************************************************************/
292
293 void setupMenus()
294 {
295     extern      MenuHandle   MyMenus[];
296     register    MenuHandle   *pMenu;
297     int         j;
298
299     /*
300      * Get the menu resources and fill out the menu array.
301      */
302     for ( j = 0; j < menuCount ; ++j) MyMenus[appleMenu+j] = GetMenu(appleMENU+j);
303
304     /*
305      * Set up the desk accessories menu.
306      * The "About Proto..." item, followed by a grey line,
307      * is presumed to be already in the resource.  We then
308      * append the desk accessory names from the 'DRVR' resources.
309      */
310     AddResMenu(MyMenus[appleMenu], (ResType) 'DRVR');
311
312     /*
313      * Now insert all of the application menus in the menu bar.
314      *
315      * "Real" C programmers never use array indices
316      * unless they're constants :-)
317      */
318     for (pMenu = &MyMenus[appleMenu]; pMenu < &MyMenus[menuCount]; ++pMenu) {
319         InsertMenu(*pMenu, 0);
320     }
```

Proto.c                                                                    Page 6

```
321
322        DrawMenuBar();
323        return;
324   }
325
326
327   /*
328    * Back to the Main segment.
329    */
330   #ifdef MPW
331   #define __SEG__ Main
332   #endif
333
334
335
336   /*******************************************************************************
337    *
338    *   showAboutMeDialog
339    *
340    *******************************************************************************/
341
342   void showAboutMeDialog()
343   {
344        GrafPtr       savePort;
345        DialogPtr     theDialog;
346        short         itemType;
347        Handle        itemHdl;
348        Rect          itemRect;
349        short         itemHit;
350
351        GetPort(&savePort);
352        theDialog = GetNewDialog(aboutMeDLOG, nil, (WindowPtr) -1);
353        SetPort(theDialog);
354
355        GetDItem(theDialog, authorItem, &itemType, &itemHdl, &itemRect);
356        SetIText(itemHdl, "Harry Guiremand");
357        GetDItem(theDialog, languageItem, &itemType, &itemHdl, &itemRect);
358        SetIText(itemHdl, "C");
359
360        do
361        {
362             ModalDialog(nil, &itemHit);
363        }
364        while (itemHit != okButton);
365
366        CloseDialog(theDialog);
367
368        SetPort(savePort);
369        return;
370   }
371
372
373
374   /*******************************************************************************
375    *
376    *   main
377    *
378    *******************************************************************************/
379
380   int main()
381   {
382        Rect              screenRect;
383        Rect              dragRect;
384        Rect              growRect;
```

Proto.c                                                                 Page 7

```
385       short                windowLoc;
386       Point                mousePt;
387       EventRecord          myEvent;
388       WindowPtr            theActiveWindow;
389       WindowPtr            whichWindow;
390       WindowPtr            wPtr;
391       register  WindowPtr  myWindow;        /* Referenced often */
392       WindowRecord         wRecord;
393       CCrsrHandle          cArrow;
394       Rect                 r;
395       RgnHandle            vRgn;
396       RgnPtr               vPtr;
397
398       /*
399        * Initialization traps
400        */
401
402  #ifdef MPW
403       UnloadSeg(_DataInit);
404  #endif
405
406       MaxApplZone();
407       MoreMasters();
408       MoreMasters();
409       MoreMasters();
410       MoreMasters();
411       MoreMasters();
412       InitGraf(&(QD thePort));
413       InitFonts();
414       FlushEvents(everyEvent, 0);
415       InitWindows();
416       InitMenus();
417       TEInit();
418       InitDialogs(nil);
419       InitCursor();
420       if (init_environs() != noErr)
421           ExitToShell();
422
423       InitScroll();                  /* Initialize the scrolling unit */
424       init_icons();                  /* Initialize the icon window handling unit */
425       if (environs.hasColorQD)
426           cArrow = GetCCursor(Arrow_crsr);
427
428  #ifdef DEBUG
429       opendebug();
430       debugwrite("\pHello.");
431  #endif
432
433       /*
434        * setupMenus is execute-once code, so we can unload it now.
435        */
436       setupMenus();         /* Local procedure, below */
437
438  #ifdef MPW
439       UnloadSeg(setupMenus);  /* MPW handles segmentation differently. */
440  #endif
441
442       /*
443        * Calculate the drag rectangle in advance.
444        * This will be used when dragging a window frame around.
445        * It constrains the area to within 4 pixels from the screen edge
446        * and below the menu bar, which is 20 pixels high.
447        */
448       screenRect = QD screenBits.bounds;
```

Proto.c                                                                                                         Page 8

```
449      /*SetRect(&dragRect, 4, 20 + 4, screenRect.right-4, screenRect.bottom-4);*/
450      SETRECT(&dragRect, 4, 20 + 4, screenRect.right-4, screenRect.bottom-4);
451
452      growRect = dragRect;                    /* Maximum widht and height of a window. */
453      growRect.top = growRect.left = 80;  /* Minimum width and height of a window. */
454      /*
455       * Create our one and only window from the WIND resource.
456       * If the WIND resource isn't there, we die.
457       */
458      myWindow = new_icon_window(mainWIND);
459      mainWPtr = myWindow;
460
461      /*
462       * Ready to go.
463       * Start with a clean event slate, and cycle the main event loop
464       * until the File/Quit menu item sets DoneFlag.
465       *
466       * It would not be good practice for the doCommand() routine to
467       * simply ExitToShell() when it saw the QuitItem -- to ensure
468       * orderly shutdown, satellite routines should set global state,
469       * and let the main event loop handle program control.
470       */
471      DoneFlag = false;
472      for ( ;; ) {
473          if (DoneFlag)
474              {
475              /*
476               * Quit has been requested, by the File/Quit menu, or perhaps
477               * by a fatal error somewhere else (missing resource, etc).
478               * Here we could put up a Save Changes? DLOG, which would also
479               * allow the Cancel button to set DoneFlag to false.
480               */
481              break;      /* from main event loop */
482              }
483          /*
484           * Main Event tasks:
485           */
486          SystemTask();
487
488          theActiveWindow = FrontWindow();         /* Used often, avoid repeated calls */
489          /*
490           * Things to do on each pass through the event loop
491           * when we are the active window:
492           *      [1] Track the mouse, and set the cursor appropriately:
493           *          (IBeam if in content region, Arrow if outside)
494           *      [2] TEIdle our textedit window, so the insertion bar blinks.
495           */
496          if (myWindow == theActiveWindow) {
497              GetMouse(&mousePt);
498              if (PTINRECT(mousePt, &myWindow->portRect))
499                  {
500                  if (environs.hasColorQD)
501                      SetCCursor(cArrow);
502                  }
503              else
504                  SetCursor(&(QD arrow));
505          }
506          /*
507           * Handle the next event.
508           * In a more complex application, this switch statement
509           * would probably call satellite routines to handle the
510           * major cases (mouseDown, keyDown, etc), but our actions
511           * are simple here and it suffices to perform the code in-line.
512           */
```

Proto.c                                                                 Page 9

```
513         if (!GetNextEvent(everyEvent, &myEvent)) {
514             /*
515              * A null or system event, not for me.
516              * Here is a good place for heap cleanup and/or
517              * segment unloading if I want to.
518              */
519             continue;
520         }
521         /*
522          * In the unlikely case that the active desk accessory does not
523          * handle mouseDown, keyDown, or other events, GetNextEvent() will
524          * give them to us!  So before we perform actions on some events,
525          * we check to see that the affected window in question is really
526          * our window.
527          */
528         switch (myEvent.what) {
529             case mouseUp: {
530                 switch (FINDWINDOW(myEvent.where, &whichWindow)) {
531                     case inContent:
532                         if (whichWindow == myWindow) {
533                             do_content(myWindow,&myEvent);
534                         }
535                         break;
536                     default:
537                         break;
538                 }/*endsw FindWindow*/
539             }
540             break;
541             case mouseDown:
542             {
543                 windowLoc = FINDWINDOW(myEvent.where, &whichWindow);
544                 switch (windowLoc) {
545                     case inSysWindow:
546                         SystemClick(&myEvent, whichWindow);
547                         break;
548
549                     case inMenuBar:
550                         doCommand(MENUSELECT(myEvent.where));
551                         break;
552
553                     case inDrag:
554                         DRAGWINDOW(whichWindow, myEvent.where, &dragRect);
555                         break;
556
557                     case inGrow:
558                         if (((WindowPeek) whichWindow)->windowKind == ICONWKIND)
559                             GrowTheWindow(whichWindow, &(myEvent.where), &growRect);
560                         break;
561
562                     case inContent:
563                         if (whichWindow != theActiveWindow) {
564                             SelectWindow(whichWindow);
565                         } else if (whichWindow == myWindow) {
566                             do_content(myWindow,&myEvent);
567                         }
568                         break;
569
570                     case inZoomIn:
571                     case inZoomOut:
572                         if (TRACKBOX(whichWindow, myEvent.where, windowLoc))
573                         {
574                             ZoomWindow(whichWindow, windowLoc, true);
575                             ZoomTheWindow(whichWindow);
576                         }
```

Proto.c                                                                Page 10

```
577                    break;
578
579                default:
580                    break;
581            }/*endsw FindWindow*/
582        } /* end mouseDown case */
583        break;
584
585    case keyDown:
586    case autoKey:
587        if (myWindow == theActiveWindow) {
588            if (myEvent.modifiers & cmdKey) {
589                doCommand(MenuKey(myEvent.message & charCodeMask));
590            } else {
591                do_content(myWindow,&myEvent);
592            }
593        }
594        break;
595
596    case activateEvt:
597        if ((WindowPtr) myEvent.message == myWindow) {
598            if (myEvent.modifiers & activeFlag) {
599                DisableItem(MyMenus[editMenu], undoCommand);
600                SetPort((WindowPtr) myEvent.message);
601                if (environs.hasColorQD)
602                    ActivatePalette((WindowPtr) myEvent.message);
603            } else
604            {
605                /* Inactivate window */
606            }
607        }
608        break;
609
610    case updateEvt:
611        {
612            wPtr = (WindowPtr) myEvent.message;
613            UpdateTheWindow(wPtr);
614        }
615        break;
616
617    default:
618        break;
619
620    }/*endsw myEvent.what*/
621
622    }/*endfor Main Event loop*/
623    /*
624     * Cleanup here.
625     */
626    CloseWindow(myWindow);
627
628    return 0;    /* Return from main() to allow C runtime cleanup */
629 }
630
631
``` panels.r                                                                                               Page 1

```
1    /*********************************************************************************
2                        Applied Biosystems, Inc. All rights reserved.
3    **********************************************************************************
4    *
5    *       File Name: panels.r
6    *
7    *       Description: Resource definition files for control panels.
8    *
9    *       Caveats: None.
10   *
11   *    Edit History: 13 December 88 Created by HG
12   *
13   *********************************************************************************/
14
15
16
17   type 'Panl' {
18        Rect;                          /* boundary of item */
19        pstring;                       /* step's name */
20        align word;
21        integer;                       /* step opCode number */
22        integer;                       /* step's resource id */
23        integer = $$CountOf(items);    /* number of items in this control panel */
24        wide array items {
25            Rect;                      /* boundary of item */
26            switch {
27                case Picture:
28                    key literal longint = 'pict';     /* Template signature */
29                    integer;                          /* PICT resource id   */
30
31                case Rectangle:
32                    key literal longint = 'rect';     /* Frame Rect in current ForeColor */
33
34                case Menu:
35                    key literal longint = 'menu';
36                    integer;                          /* menu id */
37
38                case EditText:
39                    key literal longint = 'edit';
40                    pstring;                          /* pre string text */
41                    align word;
42                    pstring;                          /* intial edit text */
43                    align word;
44                    pstring;                          /* post string text, often "µl" */
45                    align word;
46
47                case Text:
48                    key literal longint = 'text';     /* static text */
49                    pstring;
50                    align word;
51            };
52        };
53   };
```

```
                                              proto.r                                          Page 1

1   /*******************************************************************************
2                       Applied Biosystems, Inc. All rights reserved.
3   ********************************************************************************
4   *
5   *       File Name: proto.r
6   *
7   *       Description: Resource definition files for control panels.
8   *
9   *       Caveats: None.
10  *
11  *       Edit History: 13 December 88 Created by HG
12  *
13  *******************************************************************************/
14
15  #include "panels.r";
16  #include "Types.r"
17
18  #define kAspirate 1013
19
20  #define kPopUp              235
21  #define kSourceMenu         11500
22  #define kDestinationMenu    11501
23  #define kPumpRateMenu       11502
24  #define kAscendMenu         11503
25  #define kDescendMenu        11504
26  #define kLevelMenu          11505
27
28  resource 'Panl' (kAspirate, "Aspirate") {
29          { 0, 0, 210, 364}, "Aspirate", 100, 1013, {
30
31                  {   8,  16,  26,  76 }, Picture    { 1013 };
32                  {  27,  14,  28, 350 }, Rectangle  { };
33                  {  34,  16,  56, 150 }, EditText   { "Volume", "0", "µl" };
34                  {  34, 170,  54, 350 }, Menu       { kSourceMenu };
35                  {  60,  16,  80, 150 }, Menu       { kPumpRateMenu };
36                  {  60, 170,  80, 350 }, Menu       { kLevelMenu };
37                  {  88,  14,  89, 350 }, Rectangle  { };
38                  {  96,  16, 116, 168 }, Menu       { kAscendMenu };
39                  { 120,  16, 140, 168 }, Menu       { kDescendMenu };
40                  { 144,  16, 166, 168 }, EditText   { "Predispense", "0", "µl" };
41                  { 168,  16, 190, 168 }, EditText   { "Airgap", "0", "µl" }
42
43          };
44  };
45
46  resource 'MENU' (kSourceMenu, "source") {
47      kPopUp,
48      textMenuProc,
49      allEnabled,
50      enabled,
51      "Source",
52      {   "none",         noIcon, "", "", plain,
53          "Diluent",      noIcon, "", "", plain,
54          "Samples...",   noIcon, "", "", plain,
55          "Reagents...",  noIcon, "", "", plain,
56          "Washes...",    noIcon, "", "", plain,
57          "Reaction...",  noIcon, "", "", plain,
58          "Separation...",noIcon, "", "", plain
59      }
60  };
61
62  resource 'MENU' (kDestinationMenu, "destination") {
63      kPopUp,
64      textMenuProc,
``` proto.r                                                                                        Page 2

```
 65        allEnabled,
 66        enabled,
 67        "Destination",
 68      {  "none",          noIcon, "", "", plain,
 69         "Waste",         noIcon, "", "", plain,
 70         "Samples…",      noIcon, "", "", plain,
 71         "Reaction…",     noIcon, "", "", plain,
 72         "Separation…",   noIcon, "", "", plain
 73      }
 74    };
 75
 76    resource 'MENU' (kPumpRateMenu, "rate") {
 77        kPopUp,
 78        textMenuProc,
 79        allEnabled,
 80        enabled,
 81        "Pump Rate",
 82      {  "max",   noIcon, "", "", plain,
 83         "9",     noIcon, "", "", plain,
 84         "8",     noIcon, "", "", plain,
 85         "7",     noIcon, "", "", plain,
 86         "6",     noIcon, "", "", plain,
 87         "5",     noIcon, "", "", plain,
 88         "4",     noIcon, "", "", plain,
 89         "3",     noIcon, "", "", plain,
 90         "2",     noIcon, "", "", plain,
 91         "min",   noIcon, "", "", plain
 92      }
 93    };
 94
 95    resource 'MENU' (kAscendMenu, "ascend") {
 96        kPopUp,
 97        textMenuProc,
 98        allEnabled,
 99        enabled,
100        "Ascend Speed",
101      {  "max",   noIcon, "", "", plain,
102         "9",     noIcon, "", "", plain,
103         "8",     noIcon, "", "", plain,
104         "7",     noIcon, "", "", plain,
105         "6",     noIcon, "", "", plain,
106         "5",     noIcon, "", "", plain,
107         "4",     noIcon, "", "", plain,
108         "3",     noIcon, "", "", plain,
109         "2",     noIcon, "", "", plain,
110         "min",   noIcon, "", "", plain
111      }
112    };
113
114    resource 'MENU' (kDescendMenu, "descend") {
115        kPopUp,
116        textMenuProc,
117        allEnabled,
118        enabled,
119        "Descend Speed",
120      {  "max",   noIcon, "", "", plain,
121         "9",     noIcon, "", "", plain,
122         "8",     noIcon, "", "", plain,
123         "7",     noIcon, "", "", plain,
124         "6",     noIcon, "", "", plain,
125         "5",     noIcon, "", "", plain,
126         "4",     noIcon, "", "", plain,
127         "3",     noIcon, "", "", plain,
128         "2",     noIcon, "", "", plain,
```

```
                                    proto.r                                  Page 3
129          "min",   noIcon, "", "", plain
130       }
131  );
132
133
134  resource 'MENU' (kLevelMenu, "level") {
135      kPopUp,
136      textMenuProc,
137      allEnabled,
138      enabled,
139      "Level",
140      {   "Above Surface...",   noIcon, "", "", plain,
141          "At Surface",         noIcon, "", "", plain,
142          "Below Surface...",   noIcon, "", "", plain
143      }
144  };
```

What is claimed is:

1. A computerized control system for operating a machine, comprising:
   a general-purpose computer apparatus;
   a display monitor coupled to the computer apparatus;
   an interactive display presented on the display monitor, the interactive display comprising connected pictorial icons representing sequences of actions performable by the machine;
   input apparatus coupled to the general-purpose computer for a user to interact with the display; and
   an I/O subsystem connected to the computer and connectable to the machine for sending, in response to a user initiation input, data and commands to the machine for performing the sequences of actions in the order of connection of the pictorial icons, and for receiving signals from the machine;
   wherein a connected sequence of icons may be collapsed in place to show a higher-level icon representing the connected sequence of icons, the higher-level icon then occupying the place of the uncollapsed connected sequence of icons, and individual higher-level icons may be expended in place to show lower-level connected sequences of icons representing individual sequences of actions making up the sequence of actions represented by the individual higher-level icon.

2. A computerized control system as in claim 1 wherein expansion in place results in a bounding box surrounding the lower-level sequence of icons, the bounding box labeled to identify the higher-level icon, and the bounding box connected in the overall sequence of icons in the place occupied by the higher-level icon before expansion in place.

3. A control system as in claim 1 wherein the pictorial icons provide pictorial association with the sequences of actions.

4. A control system as in claim 1 comprising a graphic tool enabling a user to select individual ones of the pictorial icons representing sequences of actions performable by the machine and to arrange copies of the selected pictorial icons in connected serial sequences to represent combined serial sequences of actions performable by the machine.

5. A control system as in claim 4 wherein selected pictorial icons may be connected to provide parallel paths as well as serial sequences, and a user may select alternative parallel paths to be followed in response to a command to perform the serial sequences of actions.

6. A control system as in claim 1 wherein control flow is indicated in the display as a machine operates in response to commands sent via the I/O subsystem, by highlighting individual icons while the machine is commanded to perform the sequence of actions represented by the individual icons.

7. A control system as in claim 1 wherein each connected series of icons may be collapsed in place until only one pictorial icon remains, the one pictorial icon being a top-level icon representing an overall sequence of actions performable by the machine.

8. A control system as in claim 1 wherein expansion in place is operable to the level of fundamental icons representing fundamental action sequences, fundamental action sequences arbitrarily defined in the control system as action sequences not further expandable into component actions represented by icons.

9. A control system as in claim 8 wherein a fundamental icon may be converted, in response to a user input, into an interactive input control panel having fields for accepting values for control variables specific to the fundamental action sequence represented by the fundamental icon.

10. A control system as in claim 9 wherein the interactive input control panel is connected in the icon sequence in place of the icon with which it is associated.

11. A control system as in claim 1 wherein the machine is an automated laboratory for performing chemical procedures.

12. A method for operating a machine comprising the steps of:
   (a) selecting pictorial icons from selectable pictorial icons in an interactive display of a computerized control system connected to the machine, individual ones of the selectable pictorial icons representing one of specific actions and sequences of actions performable by the machine;
   (b) arranging copies of the pictorial icons in connected sequences representing sequences of actions to be performed by the machine;
   (c) providing an initiation input to the computerized control system to initiate operation of the machine; and
   (d) controlling the order of actions of the machine by routing action commands from the computerized control system to the machine in the order of the connected sequence of icons;
   wherein a connected sequence of icons may be collapsed in place to show a higher-level icon representing the connected sequence of icons, the higher-level icon then occupying the place of the uncollapsed connected sequence of icons, and individual higher-level icons may be expanded in place to show lower-level connected sequences of icons representing individual sequences of actions making up the sequence of actions represented by the individual higher-level icon.

13. The method of claim 12 wherein expansion in place results in a bounding box surrounding the lower-level sequence of icons, the bounding box labeled to identify the higher-level icon, and the bounding box connected in the overall sequence of icons in the place occupied by the higher-level icon before expansion in place.

14. The method of claim 12 wherein the pictorial icons provide pictorial association to the sequences of actions they represent.

15. The method of claim 12 further comprising a step for selecting individual ones of the pictorial icons representing sequences of actions performable by the machine and arranging copies of the selected pictorial icons in connected serial sequences to represent combined serial sequences of actions performable by the machine.

16. The method of claim 15 wherein icons may be arranged in parallel as well as sequential paths, and comprising steps for selecting alternates among parallel paths for control to follow in response to the initiating input.

17. The method of claim 12 wherein the step for controlling the order of actions comprises highlighting icons in the connected sequence as commands related to the icons are sent to the machine, for indicating to a user which action sequence commands in the connected sequence are being sent to the machine.

18. The method of claim 12 wherein the collapsing is operable to the extent that a connected series of icons may be collapsed in place to present higher-level icons until only one pictorial icon remains, the one icon then being a top-level icon representing all of the sequence of actions represented by the sequence of uncollapsed icons.

19. The method of claim 12 wherein expansion in place is operable to the level of fundamental icons representing fundamental action sequences, fundamental action sequences arbitrarily defined in the control system as action sequences not further expandable into component actions represented by icons.

20. The method of claim 19 wherein a fundamental icon may be converted, in response to a user input, into an interactive input control panel having fields for accepting values for control variables specific to the fundamental action sequence represented by the fundamental icon.

21. The method of claim 20 wherein the interactive input control panel is connected in the icon sequence in place of the icon with which it is associated.

22. The method of claim 12 wherein the machine is an automated laboratory for performing chemical procedures.

23. In a computerized control system, a robotic interface for controlling a machine, comprising:
  connected pictorial icons in an interactive display, individual ones of the icons representing one of an action and a sequence of actions performable by the machine, the overall sequence of icons representing an overall sequence of actions in the order of connection;
  a user-operable input apparatus;
  command code associated with each icon for commanding the machine to perform the action and sequence of actions represented by the icon; and
  a user-operable initiating signal for initiating operation to send command code to the machine in the order of the sequential connection of the icons;
    wherein a connected sequence of icons may be collapsed in place to show a higher-level icon representing the connected sequence of icons, the higher-level icon then occupying the place of the uncollapsed connected sequence of icons, and individual higher-level icons may be expended in place to show lower-level connected sequences of icons representing individual sequences of actions making up the sequence of actions represented by the individual higher-level icon.

24. A robotic interface as in claim 23 wherein expansion in place results in a bounding box surrounding the lower-level sequence of icons, the bounding box labeled to identify the higher-level icon, and the bounding box connected in the overall sequence of icons in the place occupied by the higher-level icon before expansion in place.

25. A robotic interface as in claim 23 wherein the pictorial icons provide pictorial association to the sequences of actions they represent.

26. A robotic interface as in claim 23 further comprising a graphic tool for selecting individual ones of the pictorial icons representing sequences of actions performable by the machine and arranging copies of the selected pictorial icons in connected serial sequences to represent combined serial sequences of actions performable by the machine.

27. A robotic interface as in claim 26 wherein icons may be arranged in parallel as well as sequential paths, and comprising a function for selecting alternates among parallel paths for control to follow in response to the initiating signal.

28. A robotic interface as in claim 23 wherein the robotic interface is configured for highlighting icons in the connected sequence as commands related to the icons are sent to the machine, for indicating to a user which action sequence commands in the connected sequence are being sent to the machine.

29. A robotic interface as in claim 23 wherein the operation of collapsing is operable to the extent that a connected series of icons may be collapsed in place to present higher-level icons until only one pictorial icon remains, the one icon then being a top-level icon representing all of the sequence of actions represented by the sequence of uncollapsed icons.

30. A robotic interface as in claim 23 wherein expansion in place is operable to the level of fundamental icons representing fundamental action sequences, fundamental action sequences arbitrarily defined in the control system as action sequences not further expandable into component actions represented by icons.

31. A robotic interface as in claim 30 wherein a fundamental icon may be converted, in response to a user input, into an interactive input control panel having fields for accepting values for control variables specific to the fundamental action sequence represented by the fundamental icon.

32. A robotic interface as in claim 31 wherein the interactive input control panel is connected in the icon sequence in place of the icon with which it is associated.

33. A robotic interface as in claim 23 wherein the machine is an automated laboratory for performing chemical procedures.

34. An automated machine comprising:
  a computerized control system having an interactive display and input apparatus, the interactive display comprising connected pictorial icons representing sequences of actions performable by the machine, the system configured to transmit commands and data associated with the pictorial icons to operate the machine in the connected order of the pictorial icons in response to an initiating input signal;
  actuators responsive to the commands and data transmitted from the control system for initiating specific actions performable by the machine; and
  sensors positioned to sense actions and configured to report action status to the control system;
    wherein a connected sequence of icons in the interactive display may be collapsed in place to show a higher-level icon representing the connected sequence of icons, the higher-level icon then occupying the place of the uncollapsed connected sequence of icons, and individual higher-level icons may be expended in place to show lower-level connected sequences of icons representing individual sequences of actions making up the sequence of actions represented by the individual higher-level icon.

35. An automated machine as in claim 34 wherein expansion in place results in a bounding box surrounding the lower-level sequence of icons, the bounding box labeled to identify the higher-level icon, and the bounding box connected in the overall sequence of icons in the place occupied by the higher-level icon before expansion in place.

36. An automated machine as in claim 34 wherein the pictorial icons provide pictorial association to the sequences of actions they represent.

37. An automated machine as in claim 34 further comprising a graphic tool for selecting individual ones of the pictorial icons representing sequences of actions performable by the machine and arranging copies of the selected pictorial icons in connected serial sequences to represent combined serial sequences of actions performable by the machine.

38. An automated machine as in claim 37 wherein icons may be arranged in parallel as well as sequential paths, and comprising a function for selecting alternates among parallel paths for control to follow in response to the initiating signal.

39. An automated machine as in claim 34 wherein the interactive display is configured for highlighting icons in the connected sequence as commands related to the icons are sent to the machine, for indicating to a user which action sequence commands in the connected sequence are being sent to the machine.

40. An automated machine as in claim 34 wherein the operation of collapsing is operable to the extent that a connected series of icons may be collapsed in place to present higher-level icons until only one pictorial icon remains, the one icon then being a top-level icon representing all of the sequence of actions represented by the sequence of uncollapsed icons.

41. An automated machine as in claim 34 wherein expansion in place is operable to the level of fundamental icons representing fundamental action sequences, fundamental action sequences arbitrarily defined in the control system as action sequences not further expandable into component actions represented by icons.

42. An automated machine as in claim 41 wherein a fundamental icon may be converted, in response to a user input, into an interactive input control panel having fields for accepting values for control variables specific to the fundamental action sequence represented by the fundamental icon.

43. An automated machine as in claim 42 wherein the interactive input control panel is connected in the icon sequence in place of the icon with which it is associated.

44. An automated machine as in claim 34 wherein the machine is an automated laboratory for performing chemical procedures.

45. A computer programming system comprising:
an interactive display on a monitor of a general-purpose computer, the interactive display having user-selectable pictorial icons associated with specific code sequences, the icons selectable by a user and arrangeable as copies in connected sequences representing program flow; and
input apparatus coupled to the general-purpose computer for a user to provide input and make selections in the interactive display;
wherein individual connected sequences of icons in the interactive display may be collapsed in place to show a higher-level icon representing the collapsed connected sequence of icons, the higher-level icon then occupying the place of the uncollapsed connected sequence of icons, and individual higher-level icons may be expended in place to show lower-level connected sequences of icons.

46. A computer programming system as in claim 45 wherein, in response to a user initiation input, a program formed as a connected sequence of icons may be executed in the order of connection.

47. A computer programming system as in claim 46 wherein icons may be arranged in parallel as well as sequential paths, and comprising a function for selecting alternates among parallel paths for control to follow in response to the initiating input.

48. A computer programming system as in claim 46 wherein the interactive display is configured for highlighting icons in the connected sequence as code related to the icons is executed, for indicating to a user which code sequences are being executed.

49. A computer programming system as in claim 45 wherein expansion in place results in a bounding box surrounding the lower-level sequence of icons, the bounding box labeled to identify the higher-level icon, and the bounding box connected in the overall sequence of icons in the place occupied by the higher-level icon before expansion in place.

50. A computer programming system as in claim 45 wherein the pictorial icons provide pictorial association to the code sequences they represent.

51. A computer programming system as in claim 45 wherein the operation of collapsing is operable to the extent that a connected series of icons may be collapsed in place to present higher-level icons until only one pictorial icon remains, the one icon then being a top-level icon representing all of the sequence of code represented by a program.

52. A computer programming system as in claim 45 wherein expansion in place is operable to the level of fundamental icons representing fundamental code sequences, fundamental code sequences arbitrarily defined in the programming system as code sequences not further expandable into component code sequences represented by icons.

53. A computer programming system as in claim 52 wherein a fundamental icon may be converted, in response to a user input, into an interactive input control panel having fields for accepting values for control variables specific to the fundamental code sequence represented by the fundamental icon.

54. A computer programming system as in claim 53 wherein the interactive input control panel is connected in the icon sequence in place of the icon with which it is associated.

* * * * *